(12) United States Patent
Numajiri et al.

(10) Patent No.: US 10,662,156 B2
(45) Date of Patent: May 26, 2020

(54) GUANIDINE DERIVATIVE AND MEDICAL USE THEREOF

(71) Applicant: Toray Industries, Inc., Tokyo (JP)

(72) Inventors: Yoshitaka Numajiri, Kanagawa (JP);
Keiichi Okimura, Kanagawa (JP);
Yuki Matsumura, Kanagawa (JP);
Kennunettsu Asaba, Kanagawa (JP);
Tomohide Masuda, Kanagawa (JP);
Kazuyuki Tokumaru, Kanagawa (JP);
Yasufumi Goto, Kanagawa (JP);
Shigeo Fujii, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/317,350

(22) PCT Filed: Jul. 28, 2017

(86) PCT No.: PCT/JP2017/027395
§ 371 (c)(1),
(2) Date: Jan. 11, 2019

(87) PCT Pub. No.: WO2018/021520
PCT Pub. Date: Feb. 1, 2018

(65) Prior Publication Data
US 2019/0233376 A1 Aug. 1, 2019

(30) Foreign Application Priority Data

Jul. 29, 2016 (JP) .................................. 2016-150467
Feb. 28, 2017 (JP) .................................. 2017-036506

(51) Int. Cl.
| | | |
|---|---|---|
| C07D 213/36 | (2006.01) |
| C07D 213/57 | (2006.01) |
| C07D 401/12 | (2006.01) |
| C07D 405/12 | (2006.01) |
| C07D 409/12 | (2006.01) |
| C07D 417/12 | (2006.01) |
| C07D 213/61 | (2006.01) |
| C07D 213/63 | (2006.01) |
| C07D 239/26 | (2006.01) |
| A61P 37/02 | (2006.01) |
| A61P 17/06 | (2006.01) |

(Continued)

(52) U.S. Cl.
CPC .......... *C07D 213/36* (2013.01); *A61K 31/443* (2013.01); *A61K 31/444* (2013.01); *A61K 31/4418* (2013.01); *A61K 31/4436* (2013.01); *A61K 31/4439* (2013.01); *A61K 31/505* (2013.01); *A61P 17/06* (2018.01); *A61P 37/02* (2018.01); *A61P 37/06* (2018.01); *A61P 37/08* (2018.01); *A61P 43/00* (2018.01); *C07D 213/57* (2013.01); *C07D 213/61* (2013.01); *C07D 213/63* (2013.01); *C07D 213/81* (2013.01); *C07D 213/84* (2013.01); *C07D 239/26* (2013.01); *C07D 401/12* (2013.01); *C07D 405/12* (2013.01); *C07D 409/12* (2013.01); *C07D 417/12* (2013.01)

(58) Field of Classification Search
CPC .. C07D 213/36; C07D 213/57; C07D 401/12; C07D 405/12; C07D 409/12; C07D 213/61; C07D 213/63; C07D 417/12; A61P 37/08; A61P 37/02; A61P 17/06
See application file for complete search history.

(56) References Cited

U.S. PATENT DOCUMENTS

| 3,313,813 A | 4/1967 | Cragoe, Jr. |
| 2003/0119877 A1 | 6/2003 | Ishida et al. |

(Continued)

FOREIGN PATENT DOCUMENTS

| JP | 2004-517870 A | 6/2004 |
| WO | 02/088084 A1 | 11/2002 |

(Continued)

OTHER PUBLICATIONS

Coornaert, B. et al., "T cell antigen receptor stimulation induces MALT1 paracaspase—mediated cleavage of the NF-κB inhibitor A20," *Nature Immunology*, 2008, vol. 9, No. 3, pp. 263-271.

(Continued)

*Primary Examiner* — Alexander R Pagano
*Assistant Examiner* — Ebenezer O Sackey
(74) *Attorney, Agent, or Firm* — DLA Piper LLP (US)

(57) ABSTRACT

A compound has a guanidine skeleton that inhibits the protease activity of MALT1 and exerts a therapeutic or prophylactic effect on autoimmune disease such as psoriasis or allergic disease such as atopic dermatitis. The guanidine derivative is typified by the following formula or a pharmacologically acceptable salt thereof.

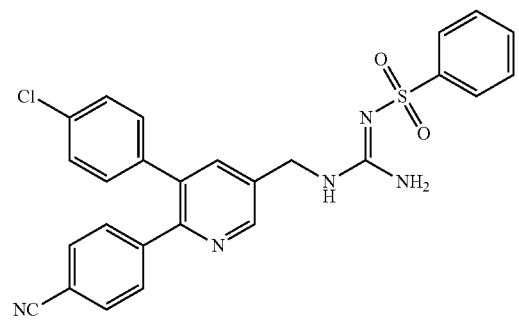

13 Claims, 2 Drawing Sheets

(51) Int. Cl.
  *A61P 37/08* (2006.01)
  *A61K 31/444* (2006.01)
  *A61K 31/505* (2006.01)
  *A61K 31/4418* (2006.01)
  *C07D 213/84* (2006.01)
  *C07D 213/81* (2006.01)
  *A61P 43/00* (2006.01)
  *A61K 31/4439* (2006.01)
  *A61K 31/443* (2006.01)
  *A61P 37/06* (2006.01)
  *A61K 31/4436* (2006.01)

(56) References Cited

U.S. PATENT DOCUMENTS

2004/0102436 A1 5/2004 Asaki et al.
2008/0021070 A1 1/2008 Barre et al.

FOREIGN PATENT DOCUMENTS

| WO | 2006/042955 | A1 | | 4/2006 |
| WO | 2009/065897 | A2 | | 5/2009 |
| WO | 2013/017637 | A1 | | 2/2013 |
| WO | 2015/181747 | A1 | | 12/2015 |
| WO | 2018159650 | A1 | * | 7/2018 |

OTHER PUBLICATIONS

Staal, J. et al., "T-cell receptor-induced JNK activation requires proteolytic inactivation of CYLD by MALT1," *The EMBO Journal*, 2011, vol. 30, pp. 1742-1752.

Ngo, V. N. et al., "A loss-of-function RNA interference screen for molecular targets in cancer," *Nature*, 2006, vol. 441, pp. 106-110.

Brüstle, A. et al., "The NF-κB regulator MALT1 determines the encephalitogenic potential of Th17 cells," *The Journal of Clinical Investigation*, 2012, vol. 122, No. 12, pp. 4698-4709.

Lee, E. G. et al., "Failure to Regulate TNF-Induced NF-κB and Cell Death Responses in A20-Deficient Mice," *Science*, 2000, vol. 289, pp. 2350-2354.

Klemm, S. et al., "The Bcl10—Malt1 complex segregates FcεRI-mediated nuclear factor κB activation and cytokine production from mast cell degranulation," *The Journal of Experimental Medicine*, 2006, vol. 203, No. 2, pp. 337-347.

Rebeaud, F. et al., "The proteolytic activity of the paracaspase MALT1 is key in T cell activation," *Nature Immunology*, 2008, vol. 9, No. 3, pp. 272-281.

Fontan, L. et al., "MALT1 Small Molecule Inhibitors Specifically Suppress ABC-DLBCL In Vitro and In Vivo," *Cancer Cell*, 2012, vol. 22, pp. 812-824.

Lim, S. M. et al., "Identification of β-Lapachone Analogs as Novel MALT1 Inhibitors to Treat an Aggressive Subtype of Diffuse Large B-Cell Lymphoma," *Journal of Medicinal Chemistry*, 2015, vol. 58, pp. 8491-8502.

* cited by examiner

GUANIDINE DERIVATIVE AND MEDICAL USE THEREOF

TECHNICAL FIELD

This disclosure relates to a guanidine derivative and medical use thereof.

BACKGROUND

Mucosa-associated lymphoid tissue lymphoma translocation protein 1 (hereinafter, referred to as MALT1) is cysteine protease, and activates the signal transduction of nuclear factor kappa-light-chain-enhancer of activated B cells (hereinafter, referred to as NF-κB) by decomposing proteins such as A20 and CYLD, responsible for the negative feedback mechanism of the transcriptional activity of the NF-κB (Beyaert et al., Nature Immunology, 2008, Vol. 9, p. 263-271 and Beyaert et al., The EMBO Journal, 2011, Vol. 30, p. 1742-1752).

NF-κB signals control immune responses such as the survival, differentiation, and activation of B cells and T cells. It is known that excessive activation of NF-κB signals by the increased protease activity of MALT1 may cause various types of autoimmune disease. For example, in MALT lymphoma or activated B-cell-like diffuse large B-cell lymphoma (ABC-DLBCL), the protease activity of MALT1 is increased and involved in the occurrence of diseases involving immunological abnormality (Staudt et al., Nature, 2006, Vol. 441, p. 106-110).

It has been reported as to experimental autoimmune encephalomyelitis models, which are typical animal models of multiple sclerosis, that deficiency in MALT1 gene (mucosa-associated lymphoid tissue lymphoma translocation gene 1; hereinafter, referred to as MALT1 gene) completely suppresses the pathological condition thereof. Therefore, it has also been reported that the inhibition of the protease activity of MALT1 is effective for the treatment or prevention of multiple sclerosis (Mak et al., The Journal of Clinical Investigation, 2012, Vol. 122, p. 4698-4709).

The association of autoimmune disease with proteins such as A20 and CYLD, which are decomposed and deactivated by MALT1 has also been reported. For example, it has been reported that autoimmune disease-like pathological conditions such as rheumatism, psoriasis, and colitis occur spontaneously in mice deficient in a gene encoding A20 (Ma et al., Science, 2000, Vol. 289, p. 2350-2354).

It has been reported as to dinitrofluorobenzene-induced dermatitis models, which are typical animal models of contact dermatitis, that deficiency in MALT1 gene remarkably suppresses the pathological condition thereof; thus the inhibition of the protease activity of MALT1 can be expected to produce therapeutic and prophylactic effects on contact dermatitis (Klemm et al., The Journal of Experimental Medicine, 2006, Vol. 203, p. 337-347).

For example, an oligopeptide compound Z-VRPR-fmk (Thome et al., Nature Immunology, 2008, Vol. 9, p. 272-281), phenylfuran derivatives (International Publication No. WO 2009/065897), phenothiazine derivatives (International Publication No. WO 2013/017637), triazole derivatives (Melnick et al., Cancer Cell, 2012, Vol. 22, p. 812-824), β-lapachone derivatives (Lim et al., Journal of Medicinal Chemistry, 2015, Vol. 58, p. 8491-8502) and pyrazolopyrimidine derivatives (International Publication No. WO 2015/181747) are known as compounds inhibiting the protease activity of MALT1.

On the other hand, for example, diphenylpyridine derivatives (JP Patent Publication (Kohyo) No. 2004-517870 A (2004)) as compounds having a cyclooxygenase inhibitory effect, selexipag; N-(2-(4-N-(5,6-diphenylpyrazin-2-yl)-N-isopropylamino)butoxy)acetyl)methanesulfonamide (International Publication No. WO 2002/088084) as a compound having prostaglandin 12 receptor agonism, N-((5,6-diphenylpyridin-3-yl)methylamine derivatives (International Publication No. WO 2006/042955) as compounds having a cannabinoid 1 receptor antagonistic effect, and pyrazine carbonyl guanidine derivatives (U.S. Pat. No. 3,313,813) as compounds having a diuretic effect have been reported as compounds having a diphenylpyridine, diphenylpyrimidine, diphenylpyridazine or diphenylpyrazine skeleton.

However, International Publication No. WO 2009/065897, International Publication No. WO 2013/017637, International Publication No. WO 2015/181747, JP Patent Publication (Kohyo) No. 2004-517870 A (2004), International Publication No. WO 2002/088084, International Publication No. WO 2006/042955 and U.S. Pat. No. 3,313,813 and Beyaert et al., Nature Immunology, 2008, Vol. 9, p. 263-271, Beyaert et al., The EMBO Journal, 2011, Vol. 30, p. 1742-1752, Staudt et al., Nature, 2006, Vol. 441, p. 106-110, Mak et al., The Journal of Clinical Investigation, 2012, Vol. 122, p. 4698-4709, Ma et al., Science, 2000, Vol. 289, p. 2350-2354, Klemm et al., The Journal of Experimental Medicine, 2006, Vol. 203, p. 337-347, Thome et al., Nature Immunology, 2008, Vol. 9, p. 272-281, Melnick et al., Cancer Cell, 2012, Vol. 22, p. 812-824 and Lim et al., Journal of Medicinal Chemistry, 2015, Vol. 58, p. 8491-8502 neither disclose that nor suggest the possibility that a guanidine derivative having a diphenylheteroaryl skeleton inhibits the protease activity of MALT1.

Accordingly, it could be helpful to provide a compound that inhibits the protease activity of MALT1 and exerts a therapeutic or prophylactic effect on autoimmune disease such as psoriasis or allergic disease such as atopic dermatitis.

SUMMARY

We found a novel guanidine derivative having an effect of inhibiting the protease activity of MALT1.

Specifically, we provide a guanidine derivative represented by general formula (I) or a pharmacologically acceptable salt thereof:

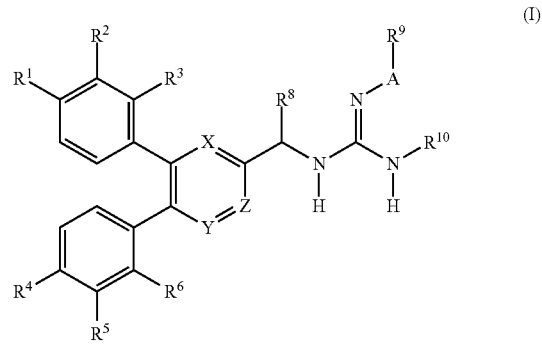

wherein $R^1$ to $R^6$ each independently represent a hydrogen atom, a halogen atom, an alkyl group having 1 to 3 carbon atoms, an alkoxy group having 1 to 3 carbon atoms, a cyano group, a methoxycarbonyl group or a hydroxy group, wherein in each of the alkyl group having 1 to 3 carbon atoms and the alkoxy group having 1 to 3 carbon atoms, 1 to 5 hydrogen atoms are optionally replaced, each independently, with a halogen atom; X and Y each independently represent N or CH, and Z represents N or $CR^7$, with the proviso that X, Y and Z neither represent N at the same time nor represent the group other than N at the same time; $R^7$ represents a hydrogen atom, a halogen atom, an alkyl group having 1 to 3 carbon atoms, an alkoxy group having 1 to 3 carbon atoms or a hydroxy group; $R^8$ represents a hydrogen atom or an alkyl group having 1 to 3 carbon atoms; A represents $S(=O)_2$, $C(=O)$ or $CH_2$; $R^9$ represents an alkoxy group having 1 to 3 carbon atoms; an amino group; a dimethylamino group; an alkyl group having 1 to 6 carbon atoms in which 1 to 3 hydrogen atoms are optionally replaced, each independently, with a halogen atom, a methoxy group or a phenyl group; a cycloalkyl group having 3 to 6 carbon atoms in which 1 to 3 hydrogen atoms are optionally replaced, each independently, with a halogen atom; an aryl group in which 1 or 2 hydrogen atoms are optionally replaced, each independently, with a halogen atom, a trifluoromethyl group, an alkoxy group having 1 to 3 carbon atoms, a hydroxy group or a cyano group; or a heteroaryl group in which one hydrogen atom is optionally replaced with a halogen atom, a methyl group or a cyano group; and $R^{10}$ represents a hydrogen atom, an alkyl group having 1 to 3 carbon atoms, a hydroxy group or an amino group.

In this context, the phrase "an alkoxy group having 1 to 3 carbon atoms; an amino group; a dimethylamino group; an alkyl group having 1 to 6 carbon atoms in which 1 to 3 hydrogen atoms are optionally replaced, each independently, with a halogen atom, a methoxy group or a phenyl group; a cycloalkyl group having 3 to 6 carbon atoms in which 1 to 3 hydrogen atoms are optionally replaced, each independently, with a halogen atom; an aryl group in which 1 or 2 hydrogen atoms are optionally replaced, each independently, with a halogen atom, a trifluoromethyl group, an alkoxy group having 1 to 3 carbon atoms, a hydroxy group or a cyano group; or a heteroaryl group in which one hydrogen atom is optionally replaced with a halogen atom, a methyl group or a cyano group" is used interchangeably with an alkoxy group having 1 to 3 carbon atoms, an amino group, a dimethylamino group, an alkyl group having 1 to 6 carbon atoms (in the alkyl group, 1 to 3 hydrogen atoms are optionally replaced, each independently, with a halogen atom, a methoxy group or a phenyl group), a cycloalkyl group having 3 to 6 carbon atoms (in the cycloalkyl group, 1 to 3 hydrogen atoms are optionally replaced, each independently, with a halogen atom), an aryl group (in the aryl group, 1 or 2 hydrogen atoms are optionally replaced, each independently, with a halogen atom, a trifluoromethyl group, an alkoxy group having 1 to 3 carbon atoms, a hydroxy group or a cyano group), or a heteroaryl group (in the heteroaryl group, one hydrogen atom is optionally replaced with a halogen atom, a methyl group or a cyano group).

In the guanidine derivative represented by general formula (I), preferably, $R^1$ and $R^4$ are each independently a hydrogen atom, a fluorine atom, a chlorine atom, a methyl group, a trifluoromethyl group, a methoxy group, an isopropoxy group, a trifluoromethoxy group or a cyano group; $R^2$, $R^3$, $R^5$ and $R^6$ are each independently a hydrogen atom, a fluorine atom or a chlorine atom; the combination of X to Z is X=CH, Y=N, and Z=$CR^7$, X=CH, Y=CH, and Z=N, X=N, Y=CH, and Z=CH, or X=N, Y=CH, and Z=N; $R^7$ is a hydrogen atom, a fluorine atom, a methyl group, a methoxy group or a hydroxy group; $R^8$ is a hydrogen atom or a methyl group; A is $S(=O)_2$; $R^9$ is a dimethylamino group; a benzyl group; a cycloalkyl group having 3 to 6 carbon atoms; a phenyl group in which one hydrogen atom is optionally replaced with a halogen atom, an alkoxy group having 1 to 3 carbon atoms, a hydroxy group or a cyano group; or a heteroaryl group in which one hydrogen atom is optionally replaced with a halogen atom, a methyl group or a cyano group; and $R^{10}$ is a hydrogen atom, a methyl group, a hydroxy group or an amino group, $R^1$ and $R^4$ are each independently a hydrogen atom, a fluorine atom, a chlorine atom, a methyl group, a trifluoromethyl group, a methoxy group, a trifluoromethoxy group or a cyano group; each of $R^2$, $R^3$, $R^5$ and $R^6$ is a hydrogen atom; the combination of X to Z is X=CH, Y=N, and Z=$CR^7$, X=CH, Y=CH, and Z=N, X=N, Y=CH, and Z=CH, or X=N, Y=CH, and Z=N; $R^7$ is a hydrogen atom, a fluorine atom, a methyl group, a methoxy group or a hydroxy group; $R^8$ is a hydrogen atom; A is $S(=O)_2$; $R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group; and $R^{10}$ is a hydrogen atom, a methyl group, a hydroxy group or an amino group, $R^1$ and $R^4$ are each independently a hydrogen atom, a fluorine atom, a chlorine atom, a methyl group, a trifluoromethyl group, a methoxy group, a trifluoromethoxy group or a cyano group; each of $R^2$, $R^3$, $R^5$ and $R^6$ is a hydrogen atom; the combination of X to Z is X=CH, Y=N, and Z=$CR^7$, or X=CH, Y=CH, and Z=N; $R^7$ is a hydrogen atom; $R^8$ is a hydrogen atom; A is $C(=O)$; $R^9$ is an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group; and $R^{10}$ is a hydrogen atom, each of $R^1$ and $R^4$ is a chlorine atom; each of $R^2$, $R^3$, $R^5$ and $R^6$ is a hydrogen atom; the combination of X to Z is X=CH, Y=N, and Z=$CR^7$, or X=CH, Y=CH, and Z=N; $R^7$ is a hydrogen atom; $R^8$ is a hydrogen atom; A is $C(=O)$; $R^9$ is an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloallkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group; and $R^{10}$ is a hydrogen atom, or each of $R^1$ and $R^4$ is a chlorine atom; each of $R^2$, $R^3$, $R^5$ and $R^6$ is a hydrogen atom; X is CH; Y is N; Z is $CR^1$; $R^7$ is a hydrogen atom; $R^8$ is a hydrogen atom; A is $C(=O)$; $R^9$ is an ethoxy group; an amino group; a dimethylamino group; a 2-thiazolyl group; a 4-thiazolyl group; a 2-thienyl group;

a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group; and $R^{10}$ is a hydrogen atom.

In this example, high MALT1 inhibitory activity can be expected.

In the guanidine derivative represented by general formula (I), more preferably, each of $R^1$ and $R^4$ is a chlorine atom; each of $R^2$, $R^3$, $R^5$ and $R^6$ is a hydrogen atom; the combination of X to Z is X=CH, Y=N, and Z=CR$^7$, X=CH, Y=CH, and Z=N, X=N, Y=CH, and Z=CH, or X=N, Y=CH, and Z=N; $R^7$ is a hydrogen atom, a fluorine atom, a methyl group, a methoxy group or a hydroxy group; $R^8$ is a hydrogen atom; A is S(=O)$_2$; $R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group; and $R^{10}$ is a hydrogen atom, a methyl group, a hydroxy group or an amino group, or $R^1$ and $R^4$ are each independently a hydrogen atom, a fluorine atom, a chlorine atom, a methyl group, a trifluoromethyl group, a methoxy group, a trifluoromethoxy group or a cyano group; each of $R^2$, $R^3$, $R^5$ and $R^6$ is a hydrogen atom; X is CH; Y is N; Z is CR$^7$; $R^7$ is a hydrogen atom or a fluorine atom; $R^8$ is a hydrogen atom; A is S(=O)$_2$; $R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, a methoxy group, an ethoxy group, a hydroxy group or a cyano group; and $R^{1'}$ is a hydrogen atom.

In this example, high MALT1 inhibitory activity can be expected and, furthermore, an excellent therapeutic or prophylactic effect on autoimmune disease or allergic disease can be expected.

We also provide a medicament and a MALT1 inhibitor comprising a guanidine derivative represented by general formula (I) or a pharmacologically acceptable salt thereof as an active ingredient.

The medicament is preferably a therapeutic or prophylactic agent for autoimmune disease, and the therapeutic or prophylactic agent for autoimmune disease is more preferably a therapeutic or prophylactic agent for psoriasis. Alternatively, the medicament is preferably a therapeutic or prophylactic agent for allergic disease, and the therapeutic or prophylactic agent for allergic disease is more preferably a therapeutic or prophylactic agent for atopic dermatitis.

The guanidine derivative or the pharmacologically acceptable salt thereof has an effect of strongly inhibiting the protease activity of MALT1 and as such, can exert a therapeutic or prophylactic effect on autoimmune disease such as psoriasis or allergic disease such as atopic dermatitis.

DETAILED DESCRIPTION

Figure 1:
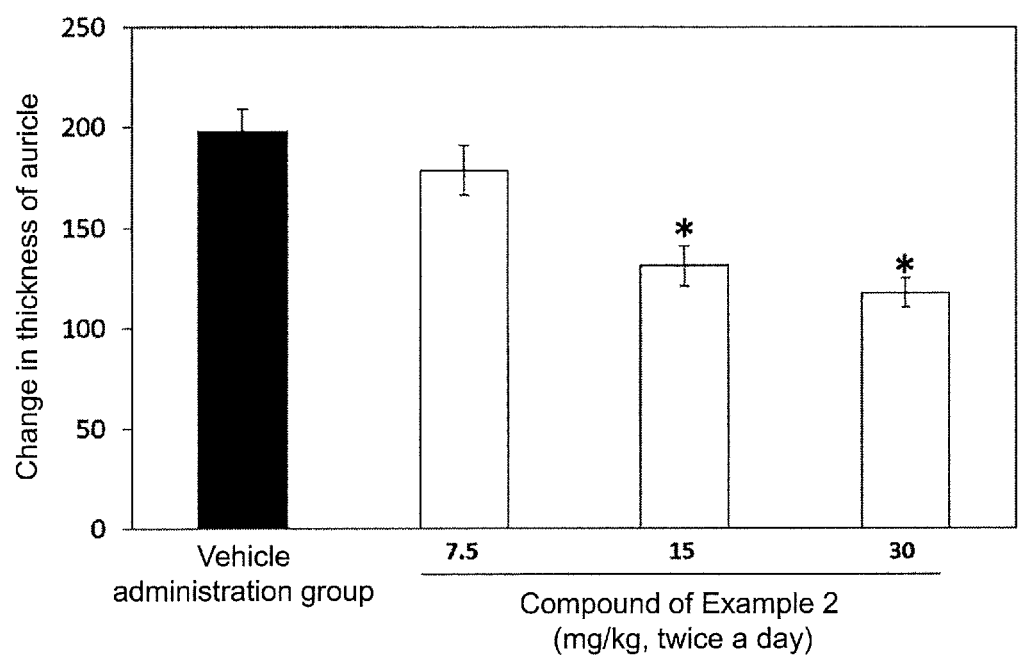
FIG. 1 is a diagram showing the effect of the compound of Example 2 on the thickness of the auricle in imiquimod-induced psoriasis mouse models.

The guanidine derivative is represented by general formula (I)

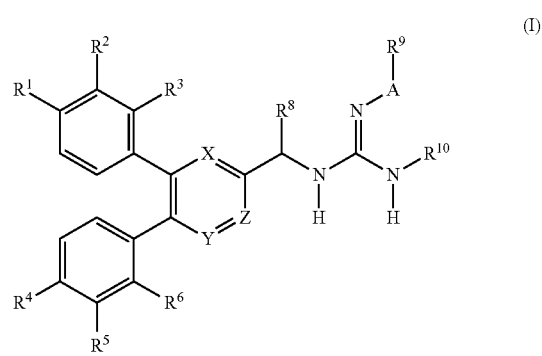

wherein $R^1$ to $R^6$ each independently represent a hydrogen atom, a halogen atom, an alkyl group having 1 to 3 carbon atoms, an alkoxy group having 1 to 3 carbon atoms, a cyano group, a methoxycarbonyl group or a hydroxy group, wherein in each of the alkyl group having 1 to 3 carbon atoms and the alkoxy group having 1 to 3 carbon atoms, 1 to 5 hydrogen atoms are optionally replaced, each independently, with a halogen atom;

X and Y each independently represent N or CH, and Z represents N or CR$^7$, with the proviso that X, Y and Z neither represent N at the same time nor represent the group other than N at the same time;

$R^7$ represents a hydrogen atom, a halogen atom, an alkyl group having 1 to 3 carbon atoms, an alkoxy group having 1 to 3 carbon atoms or a hydroxy group;

$R^8$ represents a hydrogen atom or an alkyl group having 1 to 3 carbon atoms;

A represents S(=O)$_2$, C(=O) or CH$_2$;

$R^9$ represents an alkoxy group having 1 to 3 carbon atoms; an amino group; a dimethylamino group; an alkyl group having 1 to 6 carbon atoms in which 1 to 3 hydrogen atoms are optionally replaced, each independently, with a halogen atom, a methoxy group or a phenyl group; a cycloalkyl group having 3 to 6 carbon atoms in which 1 to 3 hydrogen atoms are optionally replaced, each independently, with a halogen atom; an aryl group in which 1 or 2 hydrogen atoms are optionally replaced, each independently, with a halogen atom, a trifluoromethyl group, an alkoxy group having 1 to 3 carbon atoms, a hydroxy group or a cyano group; or a heteroaryl group in which one hydrogen atom is optionally replaced with a halogen atom, a methyl group or a cyano group; and $R^{10}$ represents a hydrogen atom, an alkyl group having 1 to 3 carbon atoms, a hydroxy group or an amino group.

The following terms are as defined below unless otherwise specified.

The "halogen atom" means a fluorine atom, a chlorine atom, a bromine atom or an iodine atom.

The "alkyl group having 1 to 3 carbon atoms" means a methyl group, an ethyl group, a propyl group or an isopropyl group.

The "alkyl group having 1 to 3 carbon atoms in which 1 to 5 hydrogen atoms are optionally replaced, each independently, with a halogen atom" means a group in which 1 to 5 hydrogen atoms of the "alkyl group having 1 to 3 carbon atoms" described above are optionally replaced, each independently, with a halogen atom. Examples thereof include a methyl group, a chloromethyl group, a fluoromethyl group, a trifluoromethyl group, an ethyl group, a 2,2,2-trifluoroethyl group, a pentafluoroethyl group, a propyl group and an isopropyl group.

The "alkyl group having 2 to 5 carbon atoms" means a linear or branched hydrocarbon group having 2 to 5 carbon atoms. Examples thereof include an ethyl group, a propyl group, an isopropyl group, a butyl group, an isobutyl group, a sec-butyl group, a tert-butyl group, a pentyl group, an isopentyl group, a sec-pentyl group, a tert-pentyl group and a neopentyl group.

The "alkyl group having 1 to 6 carbon atoms" means a linear or branched hydrocarbon group having 1 to 6 carbon atoms. Examples thereof include a methyl group, an ethyl group, a propyl group, an isopropyl group, a butyl group, an isobutyl group, a sec-butyl group, a tert-butyl group, a pentyl group, an isopentyl group, a sec-pentyl group, a tert-pentyl group, a neopentyl group, a 1-methylpentyl group, a hexyl group, an isohexyl group, a sec-hexyl group, a tert-hexyl group and a neohexyl group.

The "cycloalkyl group having 3 to 6 carbon atoms" means, for example, a cyclopropyl group, a cyclobutyl group, a cyclopentyl group or a cyclohexyl group.

The "cycloalkyl group having 3 to 6 carbon atoms in which 1 to 3 hydrogen atoms are optionally replaced, each independently, with a halogen atom" means a group in which 1 to 3 hydrogen atoms of the "cycloalkyl group having 3 to 6 carbon atoms" described above are optionally replaced, each independently, with a halogen atom. Examples thereof include a cyclopropyl group, a 2-chlorocyclopropyl group, a 2-fluorocyclopropyl group, a 2,2-difluorocyclopropyl group, a cyclobutyl group, a 3,3-difluorocyclobutyl group, a cyclopentyl group, a cyclohexyl group and a 4,4-difluorocyclohexyl group.

The "alkoxy group having 1 to 3 carbon atoms" means a methoxy group, an ethoxy group, a propoxy group or an isopropoxy group.

The "alkoxy group having 1 to 3 carbon atoms in which 1 to 5 hydrogen atoms are optionally replaced, each independently, with a halogen atom" means a group in which 1 to 5 hydrogen atoms of the "alkoxy group having 1 to 3 carbon atoms" described above are optionally replaced, each independently, with a halogen atom. Examples thereof include a methoxy group, a fluoromethoxy group, a difluoromethoxy group, a trifluoromethoxy group, an ethoxy group, a 2-chloroethoxy group, a 2,2,2-trifluoroethoxy group, a pentafluoroethoxy group, a propoxy group and an isopropoxy group.

The "alkyl group having 1 to 6 carbon atoms in which 1 to 3 hydrogen atoms are optionally replaced, each independently, with a halogen atom, a methoxy group or a phenyl group" means a group in which 1 to 3 hydrogen atoms of the "alkyl group having 1 to 6 carbon atoms" described above are optionally replaced, each independently, with a halogen atom, a methoxy group or a phenyl group. Examples thereof include a methyl group, a fluoromethyl group, a chloromethyl group, a methoxymethyl group, a benzyl group, an ethyl group, a 2,2,2-trifluoroethyl group, a 2-phenylethyl group, a propyl group, an isopropyl group, a 2-phenylpropan-2-yl group, a butyl group, an isobutyl group, a tert-butyl group, a 4-phenylbutyl group, a pentyl group, an isopentyl group, a hexyl group, a sec-hexyl group and a tert-hexyl group.

The "alkyl group having 2 to 5 carbon atoms in which 1 to 3 hydrogen atoms are optionally replaced, each independently, with a fluorine atom, a methoxy group or a phenyl group" means a group in which 1 to 3 hydrogen atoms of the "alkyl group having 2 to 5 carbon atoms" described above are optionally replaced, each independently, with a fluorine atom, a methoxy group or a phenyl group. Examples thereof include an ethyl group, a 2,2,2-trifluoroethyl group, a 2-methoxyethyl group, a 2-phenylethyl group, a propyl group, an isopropyl group, a 2-phenylpropan-2-yl group, a butyl group, an isobutyl group, a tert-butyl group, a 4-phenylbutyl group, a pentyl group and an isopentyl group.

The "aryl group" means a monocyclic or dicyclic aromatic hydrocarbon group. Examples thereof include a phenyl group and naphthyl groups (e.g., a 1-naphthyl group and a 2-naphthyl group).

The "heteroaryl group" means a 4- to 7-membered monocyclic aromatic heterocyclic group or condensed aromatic heterocyclic group containing 1 to 4 heteroatoms selected from a nitrogen atom, an oxygen atom and an optionally oxidized sulfur atom as ring-constituting atoms. Examples thereof include furyl groups (e.g., a 2-furyl group and a 3-furyl group), thienyl groups (e.g., a 2-thienyl group and a 3-thienyl group), pyridyl groups (e.g., a 2-pyridyl group, a 3-pyridyl group and a 4-pyridyl group), pyrimidinyl groups (e.g., a 2-pyrimidinyl group, a 4-pyrimidinyl group, a 5-pyrimidinyl group and a 6-pyrimidinyl group), pyrrolyl groups (e.g., a 1-pyrrolyl group, a 2-pyrrolyl group and a 3-pyrrolyl group), imidazolyl groups (e.g., a 1-imidazolyl group, a 2-imidazolyl group, a 4-imidazolyl group and a 5-imidazolyl group), pyrazolyl groups (e.g., a 1-pyrazolyl group, a 3-pyrazolyl group and a 4-pyrazolyl group), thiazolyl groups (e.g., a 2-thiazolyl group, a 4-thiazolyl group and a 5-thiazolyl group), isothiazolyl group (e.g., a 3-isothiazolyl group, a 4-isothiazolyl group and a 5-isothiazolyl group), oxazolyl groups (e.g., a 2-oxazolyl group, a 4-oxazolyl group and a 5-oxazolyl group), isoxazolyl groups (e.g., a 3-isoxazolyl group, a 4-isoxazolyl group and a 5-isoxazolyl group), oxadiazolyl groups (e.g., a 1,2,4-oxadiazol-5-yl group and a 1,3,4-oxadiazol-2-yl group), thiadiazolyl groups (e.g., a 1,3,4-thiadiazol-2-yl group), triazolyl (e.g., a 1,2,4-triazol-1-yl group, a 1,2,4-triazol-3-yl group, a 1,2,3-triazol-1-yl group, a 1,2,3-triazol-2-yl group and a 1,2,3-triazol-4-yl group), tetrazolyl groups (e.g., a tetrazol-1-yl group and a tetrazol-5-yl group), triazinyl groups (e.g., a 1,2,4-triazin-1-yl group and a 1,2,4-triazin-3-yl group), quinolyl groups (e.g., a 2-quinolyl group, a 3-quinolyl group, a 4-quinolyl group and a 6-quinolyl group), isoquinolyl groups (e.g., a 3-isoquinolyl group), quinazolyl groups (e.g., a 2-quinazolyl group and a 4-quinazolyl group), benzofuryl groups (e.g., a 2-benzofuryl group and a 3-benzofuryl group), benzothienyl groups (e.g., a 2-benzothienyl group and a 3-benzothienyl group), benzoxazolyl groups (e.g., a 2-benzoxazolyl group), benzothiazolyl groups (e.g., a 2-benzothiazolyl group), benzimidazolyl groups (e.g., a benzimidazol-1-yl group, a benzimidazol-2-yl group and a benzimidazol-5-yl group), indolyl groups (e.g., an indol-1-yl group, an indol-2-yl group, an indol-3-yl group and an indol-5-yl group), indazolyl groups (e.g., a 1H-indazol-3-yl group), pyrrolopyrazinyl groups (e.g., a 1H-pyrrolo[2,3-b]pyrazin-2-yl group and a 1H-pyrrolo[2,3-b]pyrazin-6-yl group), imidazopyridyl groups (e.g., a 1H-imidazo[4,5-b]pyridin-2-yl group, a 1H-imidazo[4,5-c]pyridin-2-yl group and a 2H-imidazo[1,2-a]pyridin-3-yl group), imidazopyrazinyl groups (e.g., a 1H-imidazo[4,5-b]

pyrazin-2-yl group), pyrazolopyridyl groups (e.g., a 1H-pyrazolo[4,3-c]pyridin-3-yl group) and pyrazolothienyl groups (e.g., a 2H-pyrazolo[3,4-b]thiophen-2-yl group).

The "aryl group in which 1 or 2 hydrogen atoms are optionally replaced, each independently, with a halogen atom, a trifluoromethyl group, an alkoxy group having 1 to 3 carbon atoms, a hydroxy group or a cyano group" means a group in which 1 or 2 hydrogen atoms of the "aryl group" described above are optionally replaced, each independently, with a halogen atom, a trifluoromethyl group, an alkoxy group having 1 to 3 carbon atoms, a hydroxy group or a cyano group. Examples thereof include a phenyl group, naphthyl groups (e.g., a 1-naphthyl group and a 2-naphthyl group), fluorophenyl groups (e.g., a 2-fluorophenyl group, a 3-fluorophenyl group and a 4-fluorophenyl group), chlorophenyl groups (e.g., a 2-chlorophenyl group and a 3-chlorophenyl group), bromophenyl groups (e.g., a 2-bromophenyl group), iodophenyl groups (e.g., an 2-iodophenyl group), difluorophenyl groups (e.g., a 2,3-difluorophenyl group, a 3,4-difluorophenyl group and a 2,5-difluorophenyl group), dichlorophenyl groups (e.g., a 2,3-dichlorophenyl group, a 3,4-dichlorophenyl group and a 2,5-dichlorophenyl group), chlorofluorophenyl groups (e.g., a 4-chloro-3-fluorophenyl group), trifluoromethylphenyl groups (e.g., a 2-trifluoromethylphenyl group, a 3-trifluoromethylphenyl group, and a 4-trifluoromethylphenyl group), methoxyphenyl groups (e.g., a 2-methoxyphenyl group, a 3-methoxyphenyl group and a 4-methoxyphenyl group), ethoxyphenyl groups (e.g., a 2-ethoxyphenyl group and a 3-methoxyphenyl group), propoxyphenyl groups (e.g., a 2-propoxyphenyl group), isopropoxyphenyl groups (e.g., a 2-isopropoxyphenyl group and a 3-isopropoxyphenyl group), chloromethoxyphenyl groups (e.g., a 3-chloro-4-methoxyphenyl group), fluoromethoxyphenyl groups (e.g., a 3-fluoro-4-methoxyphenyl group), hydroxyphenyl groups (e.g., a 2-hydroxyphenyl group and a 3-hydroxyphenyl group), cyanophenyl groups (e.g., a 2-cyanophenyl group, a 3-cyanophenyl group and a 4-cyanophenyl group), cyanofluorophenyl groups (e.g., a 4-cyano-3-fluorophenyl group), fluoronaphthyl groups (e.g., a 2-fluoronaphthalen-1-yl group and a 1-fluoronaphthalen-2-yl group), chloronaphthyl groups (e.g., a 2-chloronaphthalen-1-yl group), bromonaphthyl groups (e.g., a 2-bromonaphthalen-1-yl group), methoxynaphthyl groups (e.g., a 2-methoxynaphthalen-1-yl group) and ethoxynaphthyl groups (e.g., a 2-ethoxynaphthalen-1-yl group).

The "phenyl group in which one hydrogen atom is optionally replaced with a halogen atom, an alkoxy group having 1 to 3 carbon atoms, a hydroxy group or a cyano group" means a group in which one hydrogen atom of a phenyl group is optionally replaced with a halogen atom, an alkoxy group having 1 to 3 carbon atoms, a hydroxy group or a cyano group. Examples thereof include a phenyl group, fluorophenyl groups (e.g., a 2-fluorophenyl group, a 3-fluorophenyl group and a 4-fluorophenyl group), chlorophenyl groups (e.g., a 2-chlorophenyl group and a 3-chlorophenyl group), bromophenyl groups (e.g., a 2-bromophenyl group), iodophenyl groups (e.g., a 2-iodophenyl group), methoxyphenyl groups (e.g., a 2-methoxyphenyl group, a 3-methoxyphenyl group and a 4-methoxyphenyl group), ethoxyphenyl groups (e.g., a 2-ethoxyphenyl group and a 3-methoxyphenyl group), propoxyphenyl groups (e.g., a 2-propoxyphenyl group), isopropoxyphenyl groups (e.g., a 2-isopropoxyphenyl group and a 3-isopropoxyphenyl group), hydroxyphenyl groups (e.g., a 2-hydroxyphenyl group and a 3-hydroxyphenyl group), and cyanophenyl groups (e.g., a 2-cyanophenyl group, a 3-cyanophenyl group and a 4-cyanophenyl group).

The "heteroaryl group in which one hydrogen atom is optionally replaced with a halogen atom, a methyl group or a cyano group" means a group in which one hydrogen atom of the "heteroaryl group" described above is optionally replaced with a halogen atom, a methyl group or a cyano group. Examples thereof include furyl groups (e.g., a 2-furyl group and a 3-furyl group), thienyl groups (e.g., a 2-thienyl group and a 3-thienyl group), pyridyl groups (e.g., a 2-pyridyl group, a 3-pyridyl group and a 4-pyridyl group), pyrimidinyl groups (e.g., a 2-pyrimidinyl group, a 4-pyrimidinyl group, a 5-pyrimidinyl group and a 6-pyrimidinyl group), pyrrolyl groups (e.g., a 1-pyrrolyl group, a 2-pyrrolyl group and a 3-pyrrolyl group), imidazolyl groups (e.g., a 1-imidazolyl group, a 2-imidazolyl group, a 4-imidazolyl group and a 5-imidazolyl group), pyrazolyl groups (e.g., a 1-pyrazolyl group, a 3-pyrazolyl group and a 4-pyrazolyl group), thiazolyl groups (e.g., a 2-thiazolyl group, a 4-thiazolyl group and a 5-thiazolyl group), isothiazolyl groups (e.g., a 3-isothiazolyl group, a 4-isothiazolyl group and a 5-isothiazolyl group), oxazolyl groups (e.g., a 2-oxazolyl group, a 4-oxazolyl group and a 5-oxazolyl group), isoxazolyl groups (e.g., a 3-isoxazolyl group, a 4-isoxazolyl group and a 5-isoxazolyl group), oxadiazolyl groups (e.g., a 1,2,4-oxadiazol-5-yl group and a 1,3,4-oxadiazol-2-yl group), thiadiazolyl groups (e.g., a 1,3,4-thiadiazol-2-yl group), triazolyl (e.g., a 1,2,4-triazol-1-yl group, a 1,2,4-triazol-3-yl group, a 1,2,3-triazol-1-yl group, a 1,2,3-triazol-2-yl group and a 1,2,3-triazol-4-yl group), tetrazolyl groups (e.g., a tetrazol-1-yl group and a tetrazol-5-yl group), triazinyl groups (e.g., a 1,2,4-triazin-1-yl group and a 1,2,4-triazin-3-yl group), quinolyl groups (e.g., a 2-quinolyl group, a 3-quinolyl group, a 4-quinolyl group and a 6-quinolyl group), isoquinolyl groups (e.g., a 3-isoquinolyl group), quinazolyl groups (e.g., a 2-quinazolyl group and a 4-quinazolyl group), benzofuryl groups (e.g., a 2-benzofuryl group and a 3-benzofuryl group), benzothienyl groups (e.g., a 2-benzothienyl group and a 3-benzothienyl group), benzoxazolyl groups (e.g., a 2-benzoxazolyl group), benzothiazolyl groups (e.g., a 2-benzothiazolyl group), benzimidazolyl groups (e.g., a benzimidazol-1-yl group, a benzimidazol-2-yl group and a benzimidazol-5-yl group), indolyl groups (e.g., an indol-1-yl group, an indol-2-yl group, an indol-3-yl group and an indol-5-yl group), indazolyl groups (e.g., a 1H-indazol-3-yl group), pyrrolopyrazinyl groups (e.g., a 1H-pyrrolo[2,3-b]pyrazin-2-yl group and a 1H-pyrrolo[2,3-b]pyrazin-6-yl group), imidazopyridyl groups (e.g., a 1H-imidazo[4,5-b]pyridin-2-yl group, a 1H-imidazo[4,5-c]pyridin-2-yl group and a 2H-imidazo[1,2-a]pyridin-3-yl group), imidazopyrazinyl groups (e.g., a 1H-imidazo[4,5-b]pyrazin-2-yl group), pyrazolopyridyl groups (e.g., a 1H-pyrazolo[4,3-c]pyridin-3-yl group), pyrazolothienyl groups (e.g., a 2H-pyrazolo[3,4-b]thiophen-2-yl group), chlorofuryl groups (e.g., a 3-chlorofuran-2-yl group, a 4-chlorofuran-2-yl group and a 5-chlorofuran-2-yl group), chlorothienyl groups (e.g., a 3-chlorothiophen-2-yl group, a 4-chlorothiophen-2-yl group, and a 5-chlorothiophen-2-yl group), fluoropyridyl groups (e.g., a 3-fluoropyridin-2-yl group, a 4-fluoropyridin-2-yl group, a 5-fluoropyridin-2-yl group and a 6-fluoropyridin-2-yl group), chloropyridyl groups (e.g., a 3-chloropyridin-2-yl group), chloropyrimidinyl groups (e.g., a 2-chloropyrimidin-4-yl group), chloroquinolyl groups (e.g., a 3-chloroquinolin-2-yl group), methylpyrazolyl groups (e.g., a 1-methyl-1H-pyrazol-4-yl group), methylfuryl groups (e.g., a 3-methylfuran-2-yl group), methylpyridyl groups (2-methylpyridin-4-yl group) and cyanopyridyl groups (2-cyanopyridin-4-yl group).

The "phenyl group in which one hydrogen atom is optionally replaced with a halogen atom, a methoxy group, an ethoxy group, a hydroxy group or a cyano group" means a group in which one hydrogen atom of a phenyl group is optionally replaced with a halogen atom, a methoxy group, an ethoxy group, a hydroxy group or a cyano group. Examples thereof include a phenyl group, fluorophenyl groups (e.g., a 2-fluorophenyl group, a 3-fluorophenyl group and a 4-fluorophenyl group), chlorophenyl groups (e.g., a 2-chlorophenyl group and a 3-chlorophenyl group), bromophenyl groups (e.g., a 2-bromophenyl group), iodophenyl groups (e.g., a 2-iodophenyl group), methoxyphenyl groups (e.g., a 2-methoxyphenyl group, a 3-methoxyphenyl group and a 4-methoxyphenyl group), ethoxyphenyl groups (e.g., a 2-ethoxyphenyl group and a 3-methoxyphenyl group), hydroxyphenyl groups (e.g., a 2-hydroxyphenyl group and a 3-hydroxyphenyl group), and cyanophenyl groups (e.g., a 2-cyanophenyl group, a 3-cyanophenyl group and a 4-cyanophenyl group).

The "cycloalkyl group having 3 to 6 carbon atoms in which 1 or 2 hydrogen atoms are optionally replaced with fluorine atom(s)" means a group in which 1 or 2 hydrogen atoms of the "cycloalkyl group having 3 to 6 carbon atoms" described above are optionally replaced with fluorine atom(s). Examples thereof include a cyclopropyl group, a 2-fluorocyclopropyl group, a 2,2-difluorocyclopropyl group, a cyclobutyl group, a 3,3-difluorocyclobutyl group, a cyclopentyl group, a cyclohexyl group and a 4,4-difluorocyclohexyl group.

The "phenyl group in which one hydrogen atom is optionally replaced with a fluorine atom, a chlorine atom, a trifluoromethyl group, a methoxy group or a cyano group" means a group in which one hydrogen atom of a phenyl group is optionally replaced with a fluorine atom, a chlorine atom, a trifluoromethyl group, a methoxy group or a cyano group. Examples thereof include a phenyl group, fluorophenyl groups (e.g., a 2-fluorophenyl group, a 3-fluorophenyl group and a 4-fluorophenyl group), chlorophenyl groups (e.g., a 2-chlorophenyl group and a 3-chlorophenyl group), trifluoromethylphenyl groups (e.g., a 2-trifluoromethylphenyl group, a 3-trifluoromethylphenyl group, and a 4-trifluoromethylphenyl group), methoxyphenyl groups (e.g., a 2-methoxyphenyl group, a 3-methoxyphenyl group and a 4-methoxyphenyl group), and cyanophenyl groups (e.g., a 2-cyanophenyl group, a 3-cyanophenyl group and a 4-cyanophenyl group).

The phrase "X and Y each independently represent N or CH, and Z represents N or $CR^7$, with the proviso that X, Y and Z neither represent N at the same time nor represent the group other than N at the same time" means that the combination of X to Z is X=N, Y=N, and Z=$CR^7$, X=CH, Y=N, and Z=$CR^7$, X=N, Y=CH, and Z=$CR^7$, X=CH, Y=CH, and Z=N, X=N, Y=CH, and Z=N, or X=CH, Y=N, and Z=N.

In the guanidine derivative represented by general formula (I), $R^1$ and $R^4$ are each independently preferably a hydrogen atom, a fluorine atom, a chlorine atom, a methyl group, a trifluoromethyl group, a methoxy group, an isopropoxy group, a trifluoromethoxy group or a cyano group, more preferably a chlorine atom.

$R^2$, $R^3$, $R^5$ and $R^6$ are each independently preferably a hydrogen atom, a fluorine atom or a chlorine atom, more preferably a hydrogen atom.

The combination of X to Z is preferably X=CH, Y=N, and Z=$CR^7$, X=CH, Y=CH, and Z=N, X=N, Y=CH, and Z=CH, or X=N, Y=CH, and Z=N.

$R^7$ is preferably a hydrogen atom, a fluorine atom, a methyl group, a methoxy group or a hydroxy group, more preferably a hydrogen atom or a fluorine atom.

$R^8$ is preferably a hydrogen atom or a methyl group, more preferably a hydrogen atom.

A is preferably $S(=O)_2$.

$R^9$ is preferably a dimethylamino group; a benzyl group; a cycloalkyl group having 3 to 6 carbon atoms; a phenyl group in which one hydrogen atom is optionally replaced with a halogen atom, an alkoxy group having 1 to 3 carbon atoms, a hydroxy group or a cyano group; or a heteroaryl group in which one hydrogen atom is optionally replaced with a halogen atom, a methyl group or a cyano group, more preferably a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group. In this context, the phrase "a dimethylamino group; a benzyl group; a cycloalkyl group having 3 to 6 carbon atoms; a phenyl group in which one hydrogen atom is optionally replaced with a halogen atom, an alkoxy group having 1 to 3 carbon atoms, a hydroxy group or a cyano group; or a heteroaryl group in which one hydrogen atom is optionally replaced with a halogen atom, a methyl group or a cyano group" is used interchangeably with a dimethylamino group, a benzyl group, a cycloalkyl group having 3 to 6 carbon atoms, a phenyl group (in the phenyl group, one hydrogen atom is optionally replaced with a halogen atom, an alkoxy group having 1 to 3 carbon atoms, a hydroxy group or a cyano group,), or a heteroaryl group (in the heteroaryl group, one hydrogen atom is optionally replaced with a halogen atom, a methyl group or a cyano group). The phrase "a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group" is used interchangeably with a dimethylamino group, a cycloalkyl group having 3 to 6 carbon atoms, a 2-thienyl group, a 5-chloro-2-thienyl group, a 3-thienyl group, a 2-furyl group, a 3-furyl group, a 2-benzothienyl group, or a phenyl group (in the phenyl group, one hydrogen atom is optionally replaced with a halogen atom, an alkoxy group having 1 to 3 carbon atoms, a hydroxy group or a cyano group). In another example, $R^9$ is preferably an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group. In this context, the phrase "an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group" is used interchangeably with an ethoxy group, an amino group, a dimethylamino group, a 2-thiazolyl group, a 4-thiazolyl group, a 2-thienyl group, a 3-thienyl group, a 2-pyridyl group, a 2-furyl group, an alkyl group having 2 to 5 carbon atoms (in the alkyl group, 1 to 3 hydrogen atoms are optionally replaced, each independently, with a fluorine atom, a methoxy group or a phenyl group), a cycloalkyl group having 3 to 6 carbon atoms (in the cycloalkyl group, 1 or 2 hydrogen atoms are optionally replaced with fluorine atom(s)), or a phenyl group (in the phenyl group, one hydrogen atom is optionally replaced with a fluorine atom, a chlorine atom, a trifluoromethyl group, a methoxy group or a cyano group).

$R^{10}$ is preferably a hydrogen atom, a methyl group, a hydroxy group or an amino group, more preferably a hydrogen atom.

Preferred examples may be arbitrarily combined.

Specific examples of compounds preferred as the guanidine derivative represented by general formula (I) are shown in Tables 1-1 to 1-6. However, this disclosure is not limited by these compounds.

TABLE 1-1

Structural formula

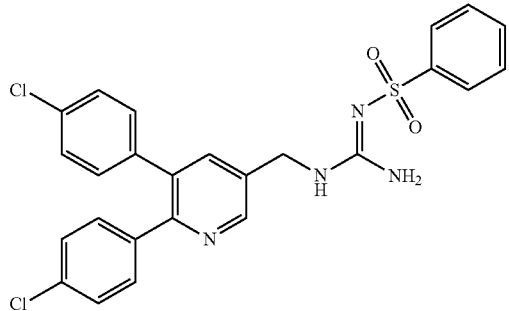 [SMILES: N/C(=N\S(=O)(=O)c1ccccc1)NCc1cnc(-c2ccc(Cl)cc2)c(-c2ccc(Cl)cc2)c1]

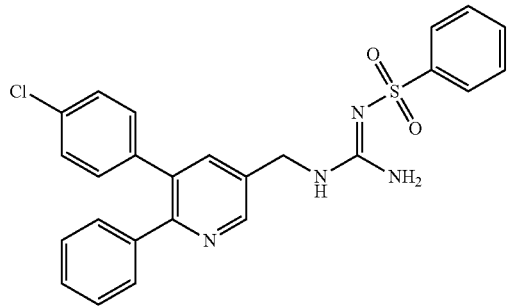 [SMILES: N/C(=N\S(=O)(=O)c1ccccc1)NCc1cnc(-c2ccccc2)c(-c2ccc(Cl)cc2)c1]

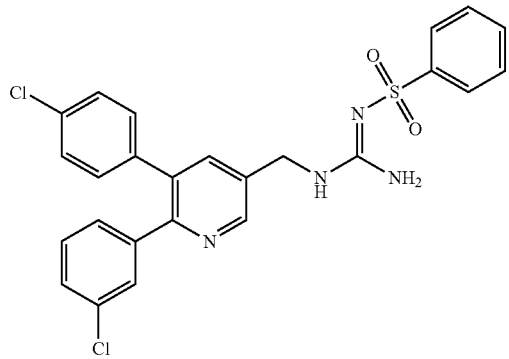 [SMILES: N/C(=N\S(=O)(=O)c1ccccc1)NCc1cnc(-c2cccc(Cl)c2)c(-c2ccc(Cl)cc2)c1]

TABLE 1-1-continued

Structural formula

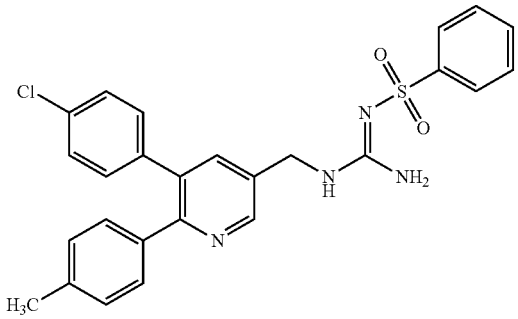

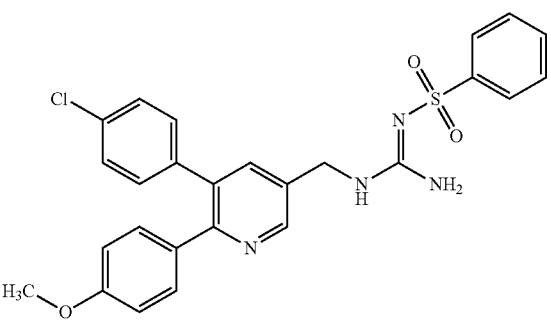 [SMILES: COc1ccc(-c2ncc(CN/C(N)=N/S(=O)(=O)c3ccccc3)cc2-c2ccc(Cl)cc2)cc1]

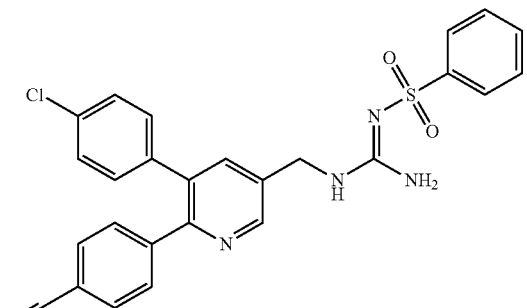

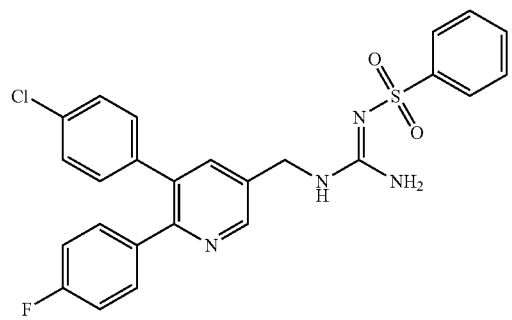

TABLE 1-1-continued

Structural formula

TABLE 1-1-continued
Structural formula
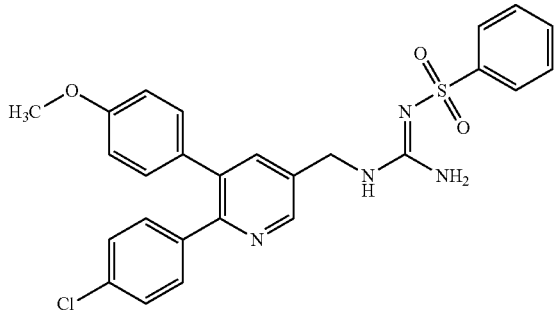 [SMILES: COc1ccc(-c2cc(CN/C(N)=N/S(=O)(=O)c3ccccc3)cnc2-c2ccc(Cl)cc2)cc1]
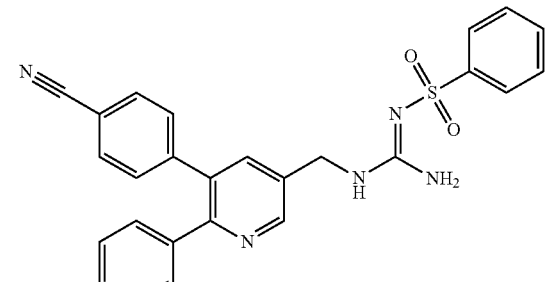
TABLE 1-2
Structural formula
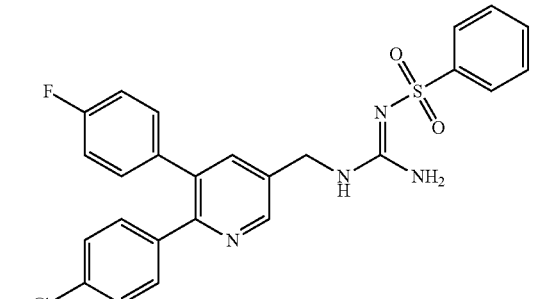
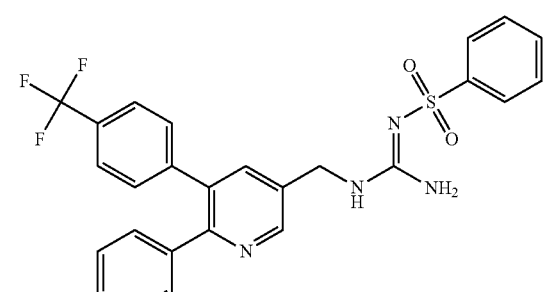
TABLE 1-2-continued
Structural formula
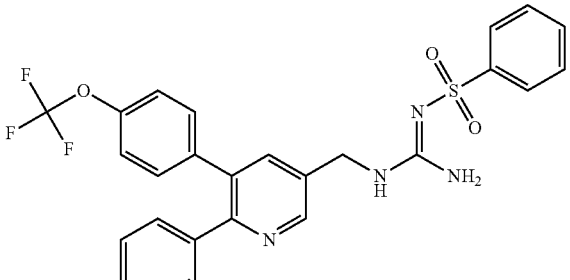
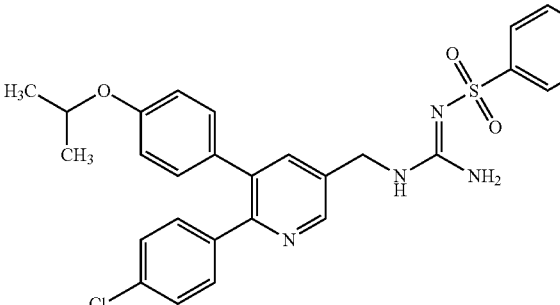
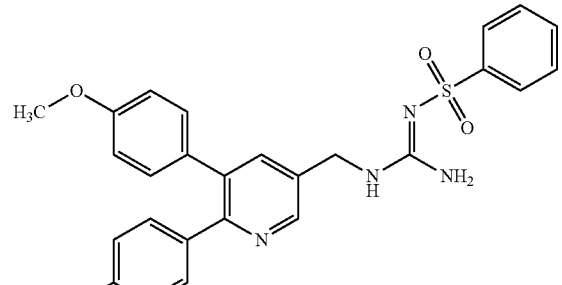
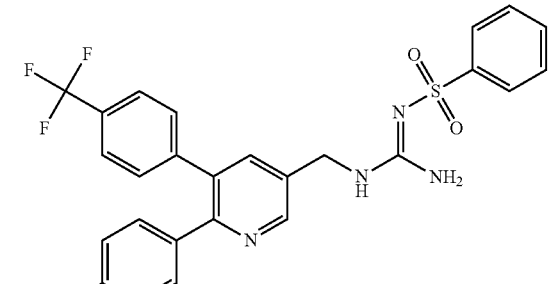
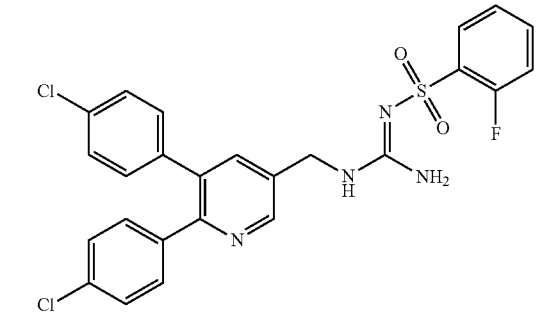 [SMILES: N/C(=N\S(=O)(=O)c1ccccc1F)NCc1cnc(-c2ccc(Cl)cc2)c(-c2ccc(Cl)cc2)c1]

TABLE 1-2-continued

Structural formula (chemical structures)

TABLE 1-2-continued

Structural formula

[Chemical structure: 5-(4-chlorophenyl)-6-(4-chloro-2-fluorophenyl)pyridin-3-yl-methyl guanidine with phenylsulfonyl group]

[Chemical structure: 5-(3-fluoro-4-methoxyphenyl)-6-(4-chlorophenyl)pyridin-3-yl-methyl guanidine with phenylsulfonyl group]

TABLE 1-3

Structural formula

[Chemical structure: 5,6-bis(4-chlorophenyl)pyridin-3-yl-methyl hydrazinecarboximidamide with phenylsulfonyl group]

[Chemical structure: 5,6-bis(4-chlorophenyl)pyridin-3-yl-methyl N-hydroxyguanidine with phenylsulfonyl group]

TABLE 1-3-continued

Structural formula

[Chemical structure: 5,6-bis(4-chlorophenyl)pyridin-3-yl-methyl N-methylguanidine with phenylsulfonyl group]

[Chemical structure: 5,6-bis(4-chlorophenyl)pyridin-3-yl-methyl guanidine with carbamoyl group]

[Chemical structure: 4,5-bis(4-chlorophenyl)pyridin-2-yl-methyl guanidine with phenylsulfonyl group]

[Chemical structure: 4,5-bis(4-chlorophenyl)pyridin-2-yl-methyl guanidine with thiophene-2-sulfonyl group]

[Chemical structure: 4,5-bis(4-chlorophenyl)pyridin-2-yl-methyl guanidine with benzoyl group]

TABLE 1-3-continued
Structural formula
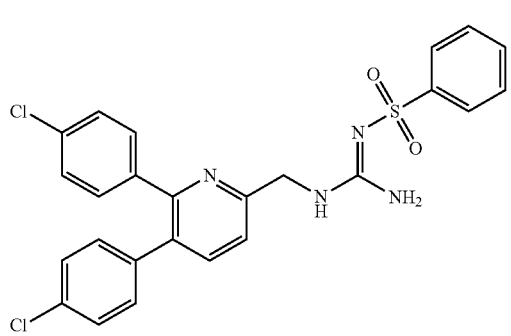 [SMILES: N/C(=N\S(=O)(=O)c1ccccc1)NCc1ccc(-c2ccc(Cl)cc2)c(-c2ccc(Cl)cc2)n1]
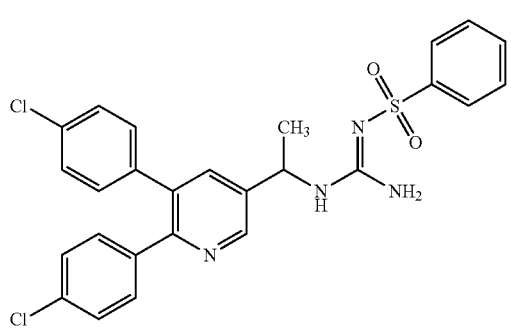 [SMILES: CC(N/C(N)=N/S(=O)(=O)c1ccccc1)c1cnc(-c2ccc(Cl)cc2)c(-c2ccc(Cl)cc2)c1]
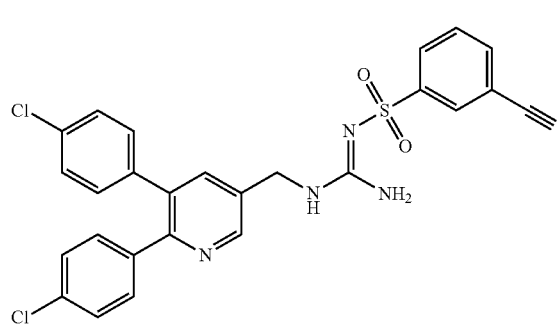
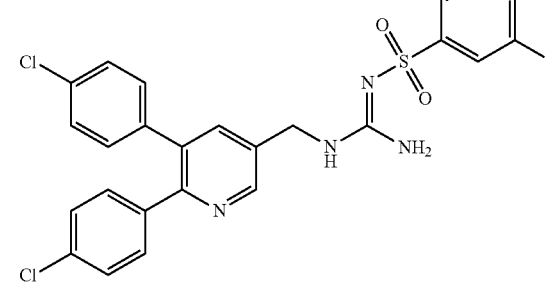
TABLE 1-3-continued
Structural formula
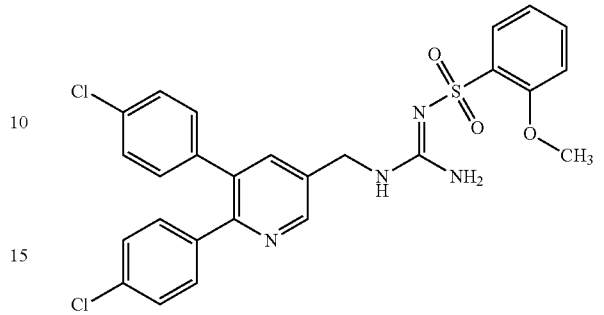
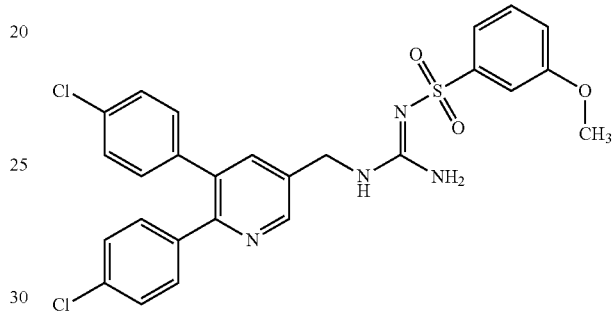
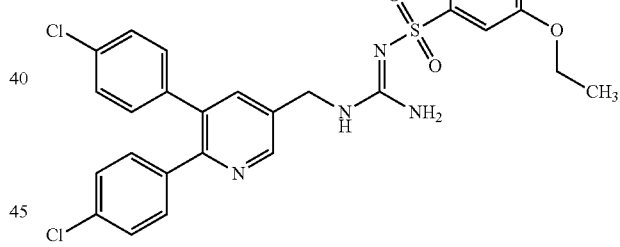
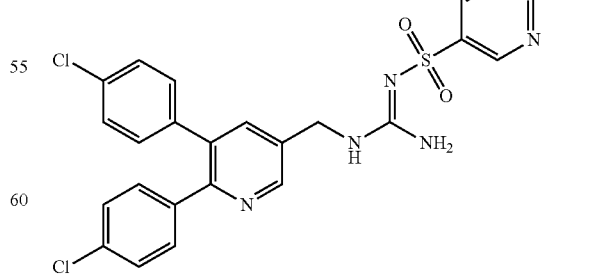

TABLE 1-3-continued

Structural formula

TABLE 1-4-continued

Structural formula

TABLE 1-4

Structural formula

TABLE 1-4-continued
Structural formula
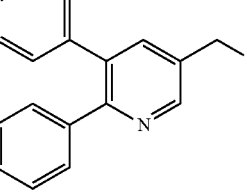

TABLE 1-4-continued
Structural formula
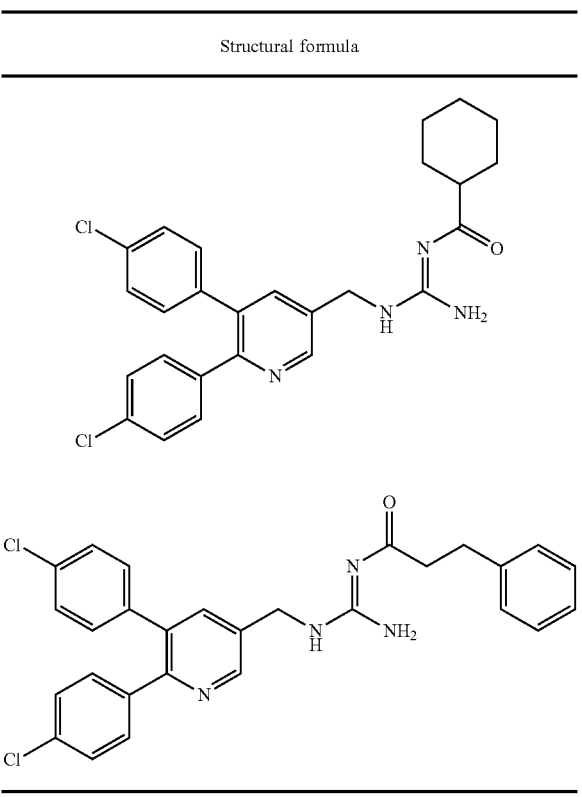
TABLE 1-5
Structural formula
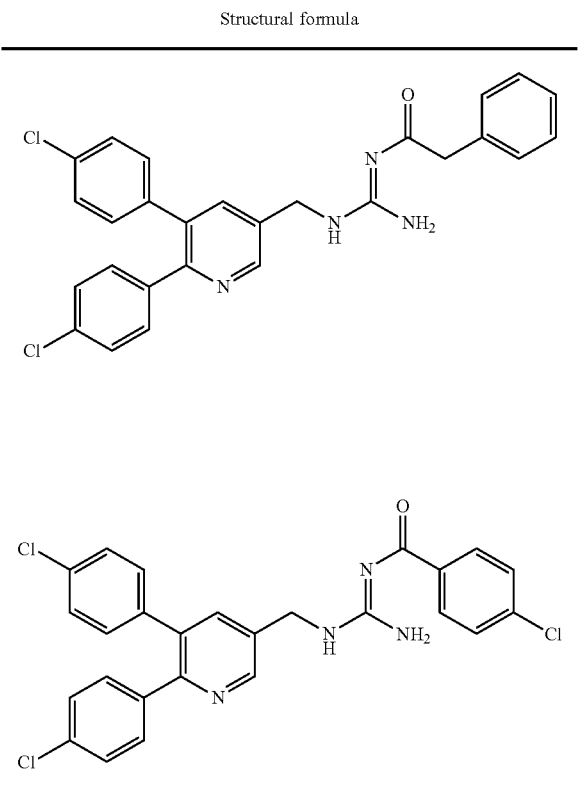
TABLE 1-5-continued
Structural formula
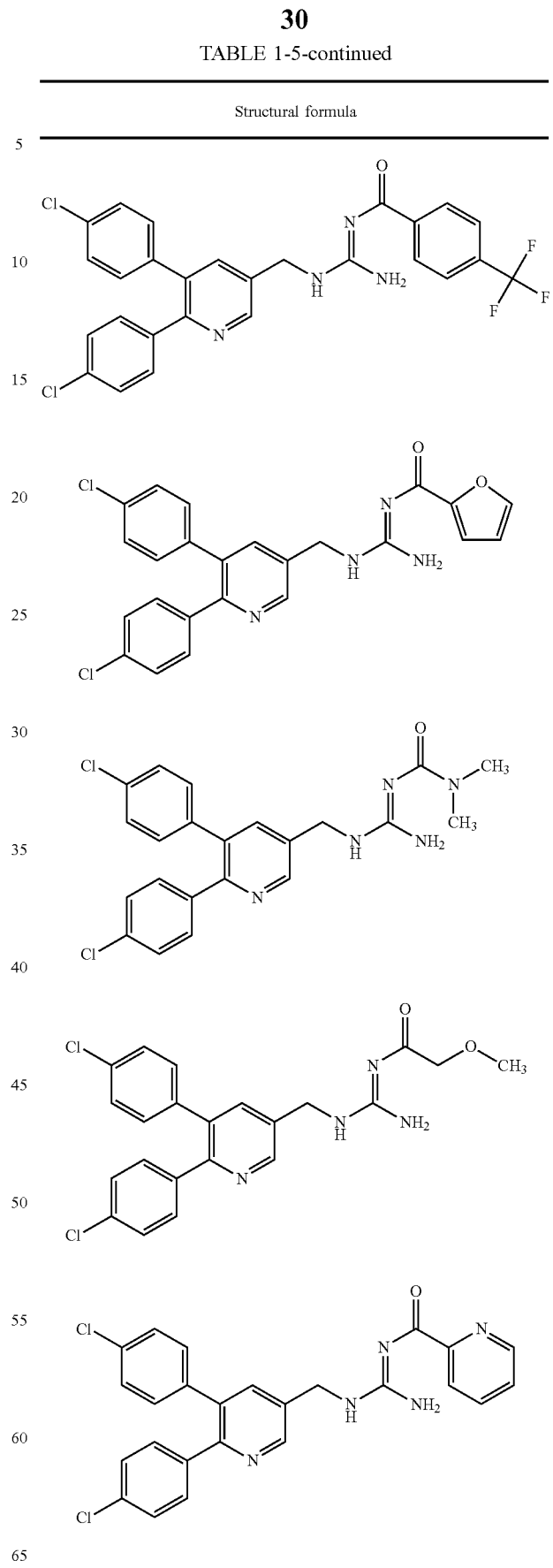

TABLE 1-5-continued
Structural formula
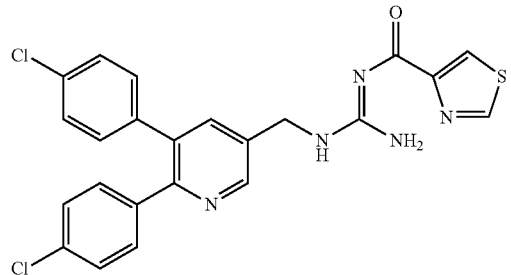 [SMILES: N/C(=N\C(=O)c1cscn1)NCc1cnc(-c2ccc(Cl)cc2)c(-c2ccc(Cl)cc2)c1]
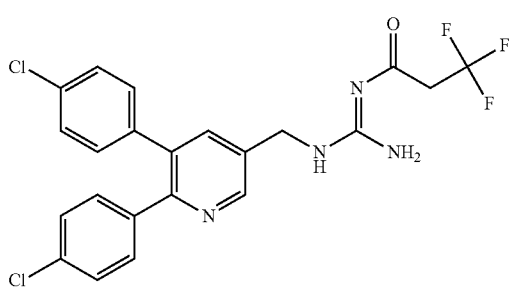 [SMILES: N/C(=N\C(=O)CC(F)(F)F)NCc1cnc(-c2ccc(Cl)cc2)c(-c2ccc(Cl)cc2)c1]
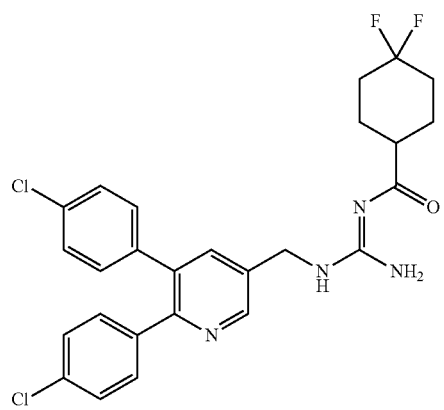 [SMILES: N/C(=N\C(=O)C1CCC(F)(F)CC1)NCc1cnc(-c2ccc(Cl)cc2)c(-c2ccc(Cl)cc2)c1]
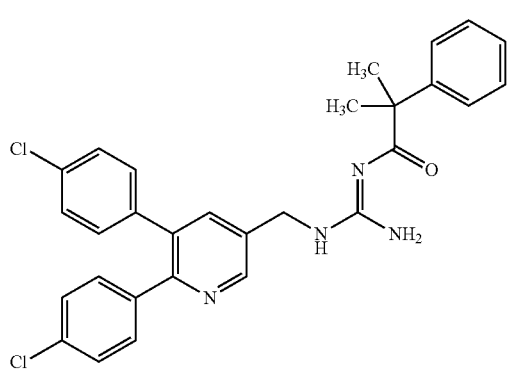 [SMILES: CC(C)(C(=O)/N=C(\N)NCc1cnc(-c2ccc(Cl)cc2)c(-c2ccc(Cl)cc2)c1)c1ccccc1]
TABLE 1-5-continued
Structural formula
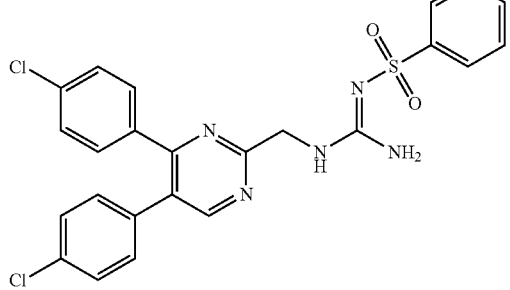
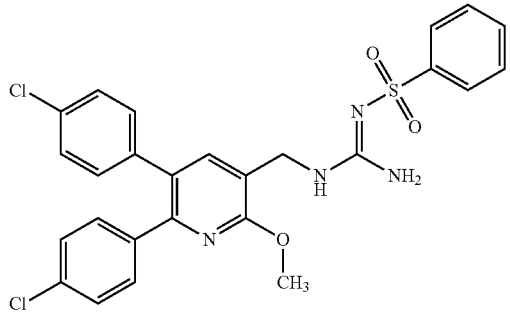 [SMILES: COc1nc(-c2ccc(Cl)cc2)c(-c2ccc(Cl)cc2)cc1CN/C(N)=N/S(=O)(=O)c1ccccc1]
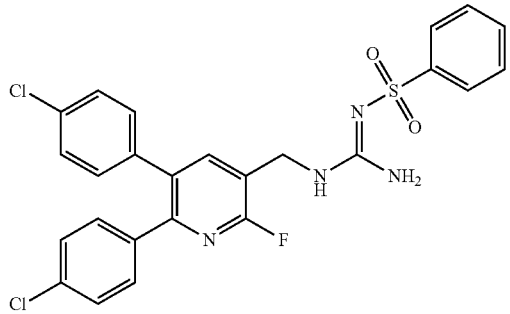 [SMILES: N/C(=N\S(=O)(=O)c1ccccc1)NCc1cc(-c2ccc(Cl)cc2)c(-c2ccc(Cl)cc2)nc1F]
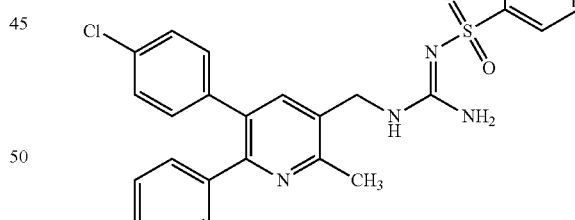
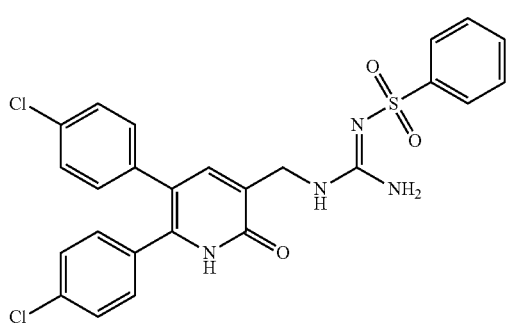 [SMILES: N/C(=N\S(=O)(=O)c1ccccc1)NCc1cc(-c2ccc(Cl)cc2)c(-c2ccc(Cl)cc2)[nH]c1=O]
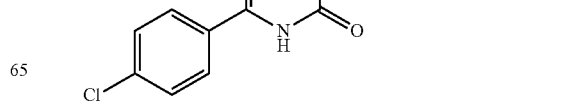

TABLE 1-5-continued

Structural formula

TABLE 1-6

Structural formula

TABLE 1-6-continued

Structural formula

The compounds described in Tables 1-1 to 1-6 also include pharmacologically acceptable salts thereof.

The guanidine derivative represented by general formula (I) may have optical isomers or diastereomers. The guanidine derivative represented by general formula (I) includes not only a single isomer but a racemate and a diastereomer mixture.

The guanidine derivative represented by general formula (I) may have other tautomers or geometric isomers, depending on the type of a substituent. These isomers may be described as only one form of an isomer. However, this disclosure also includes these isomers and also includes separated isomers and mixtures of the isomers. For example, the guanidine derivative represented by general formula (I) may have three isomers differing in the position of the double bond shown in scheme 1 given below at the guanidine site. Each isomer may further have an E-isomer and a Z-isomer based on the geometry of the double bond. This disclosure includes all of these isomers.

Scheme 1

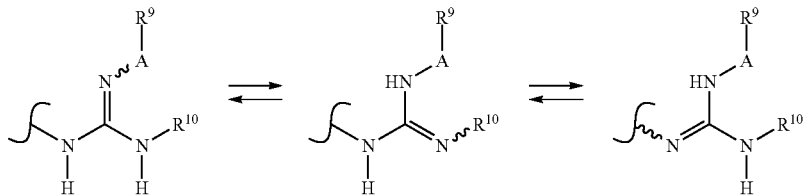

wherein the structure partially represents the guanidine site of the guanidine derivative represented by general formula (I); and the bond indicated by the wavy line represents that any of an E-configuration and a Z-configuration can be adopted.

Furthermore, this disclosure includes a prodrug of the guanidine derivative represented by general formula (I). The prodrug of the guanidine derivative represented by general formula (I) is a compound that is converted enzymatically or chemically in vivo to the guanidine derivative represented by general formula (I). The active pharmaceutical ingredient of the prodrug of the guanidine derivative represented by general formula (I) is the guanidine derivative represented by general formula (I). However, the prodrug of the guanidine derivative represented by general formula (I) may have activity in itself.

Examples of the group that forms the prodrug of the guanidine derivative represented by general formula (I) include groups described in known literatures (e.g., "IYAKUHIN no KAIHATSU (Development of Pharmaceuticals in English)", Hirokawa-Shoten Ltd., 1990, Vol. 7, p. 163-198; and Progress in Medicine, Vol. 5, 1985, p. 2157-2161).

Examples of the "pharmacologically acceptable salt" of the guanidine derivative represented by general formula (I) include: inorganic acid salts such as hydrochloride, sulfate, nitrate, hydrobromide, hydroiodide and phosphate; and organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate and cinnamate. Hydrochloride, sulfate, hydrobromide, maleate, benzoate or methanesulfonate is preferred.

The guanidine derivative represented by general formula (I) may be crystals. Both a single crystal form and a mixture of crystal forms are included in the guanidine derivative represented by general formula (I).

The guanidine derivative represented by general formula (I) may be a pharmaceutically acceptable cocrystal or cocrystal salt. In this context, the cocrystal or the cocrystal salt means a crystalline substance that is constituted at room temperature by two or more unique solids differing in physical properties (e.g., structure, melting point, heat of fusion, hygroscopicity, solubility or stability). The cocrystal or the cocrystal salt can be produced according to a cocrystallization known method.

The guanidine derivative represented by general formula (I) or the pharmacologically acceptable salt thereof may form an anhydride, a hydrate or a solvate.

The guanidine derivative represented by general formula (I) may be labeled with one or more isotopes. Examples of the labeling isotope include $^{2}H$, $^{3}H$, $^{13}C$, $^{14}C$, $^{15}N$, $^{15}O$, $^{17}O$, $^{18}O$ and/or $^{125}I$.

The guanidine derivative represented by general formula (I) can be produced by a suitable method based on characteristics derived from the backbone thereof or the type of a substituent. A starting material and a reagent for use in the production of such a compound can be generally purchased or can be produced by a known method.

The guanidine derivative represented by general formula (I) and an intermediate and a starting material for use in the production thereof can each be isolated and purified by a known approach. Examples of the known approach for isolation and purification include solvent extraction, recrystallization and chromatography.

When the guanidine derivative represented by general formula (I) contains optical isomers or stereoisomers, each individual isomer can be obtained as a single compound by a known method. Examples of the known method include crystallization, enzymatic resolution and chiral chromatography.

Hereinafter, typical methods of producing the compound will be described. The compounds in the schemes given below may form a salt. For example, the same as the salt of the guanidine derivative represented by general formula (I) is used as such a salt. The production method is not limited by the following examples.

Production Method 1

Guanidine derivative (I-a) in which each of $R^{8}$ and $R^{10}$ in the guanidine derivative represented by general formula (I) (hereinafter, referred to as guanidine derivative (I)) is a hydrogen atom can be obtained by, for example, a method described in scheme 2.

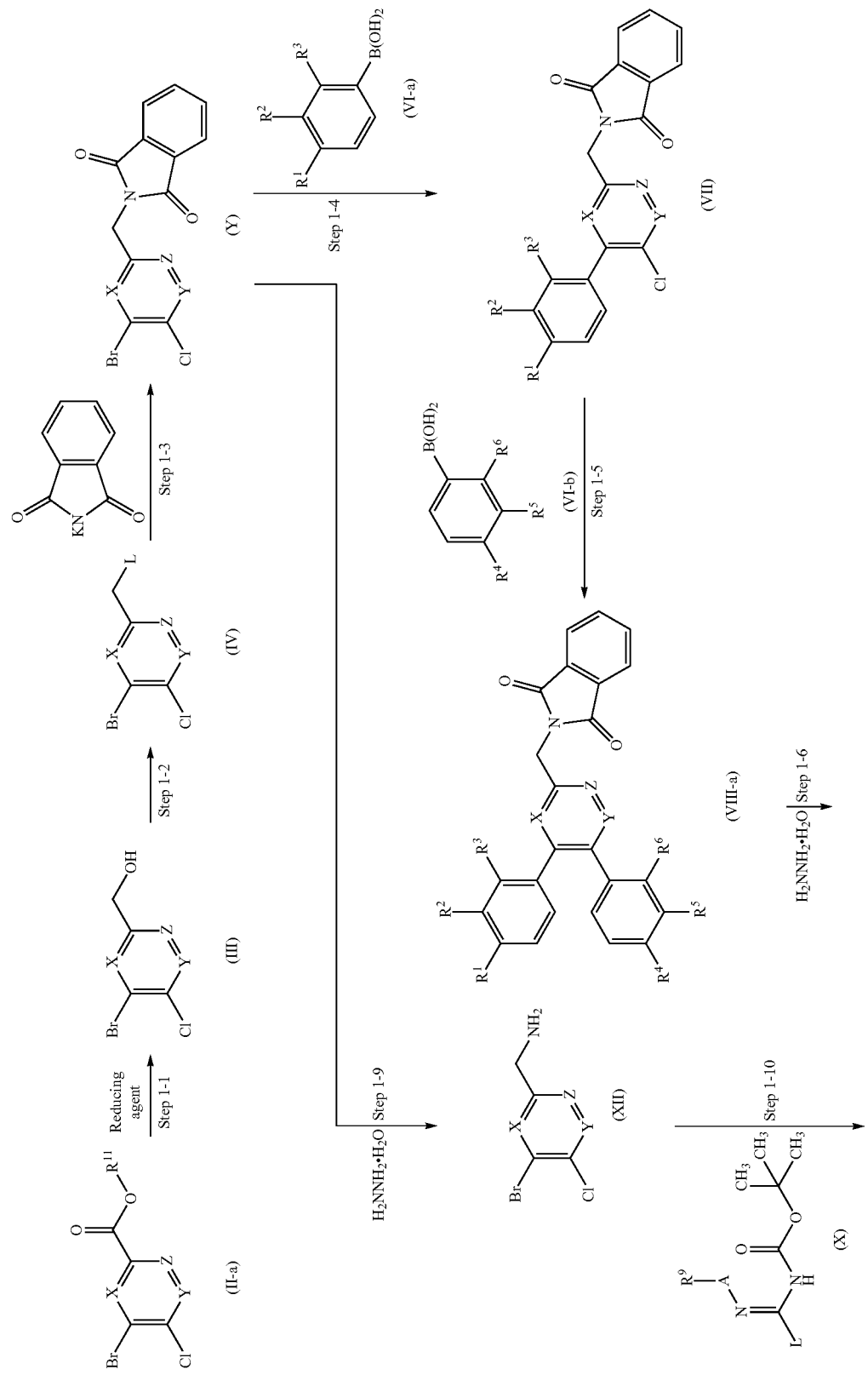

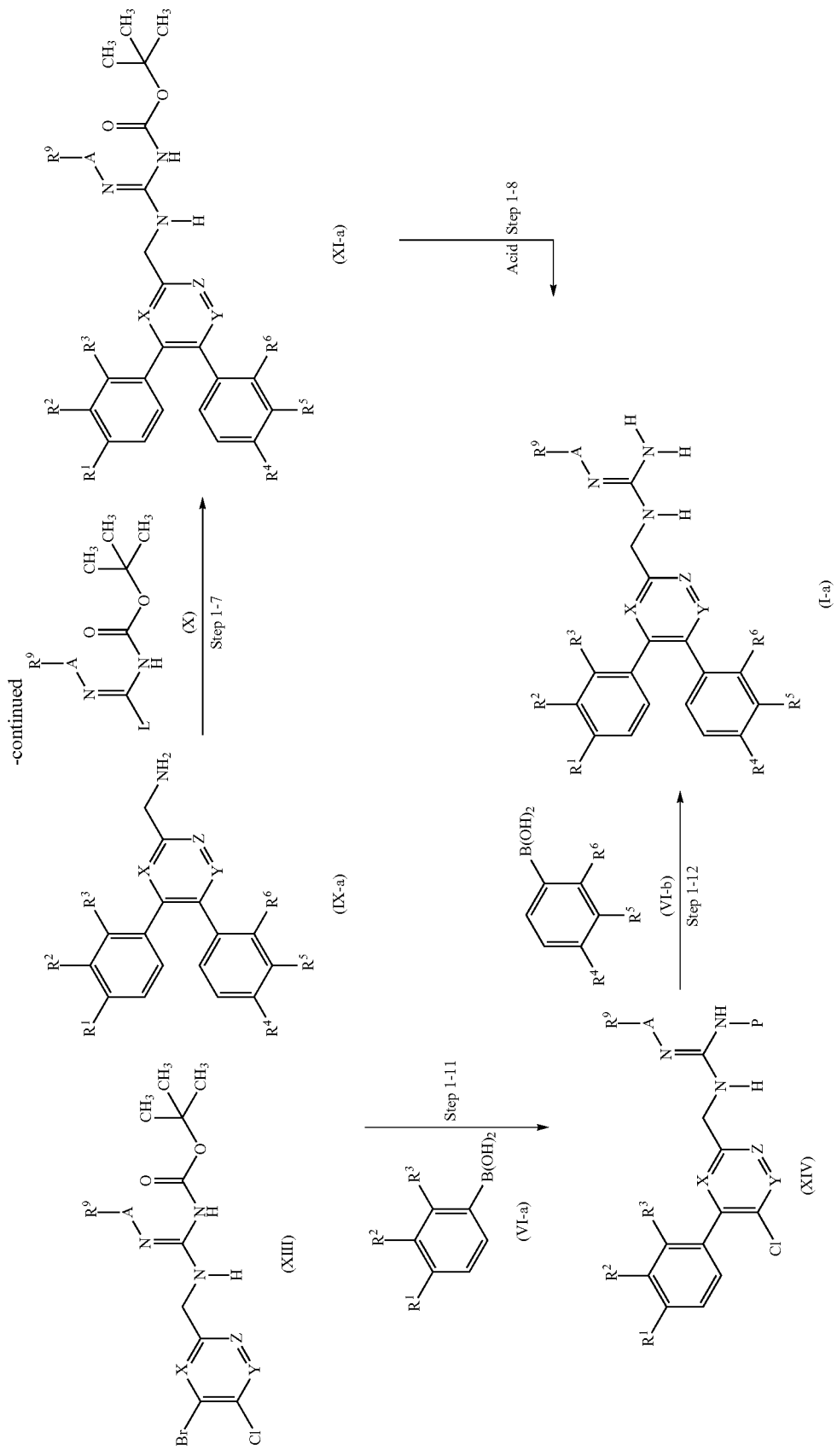

wherein $R^{11}$ represents a protective group for the carboxyl group; each L independently represents a leaving group; P represents a tert-butoxycarbonyl group or a hydrogen atom; and each of the other symbols is as defined above.

$R^{11}$ is a protective group for the carboxyl group. Examples thereof include a methyl group, an ethyl group, a propyl group, an isopropyl group, a tert-butyl group and a benzyl group.

L is a leaving group. Examples thereof include: halogen atoms such as a fluorine atom, a chlorine atom, a bromine atom and an iodine atom; alkylthio groups having 1 to 12 carbon atoms such as a methylthio group, an ethylthio group and a dodecylthio group; aryloxy groups such as a phenoxy group; alkylsulfonyloxy groups such as a methanesulfonyloxy group, an ethanesulfonyloxy group and a trifluoromethanesulfonyloxy group; alkylsulfonylamino groups such as a trifluoromethanesulfonylamino group; and azolyl groups such as an imidazol-1-yl group and a pyrazol-1-yl group.

Step 1-1

The heteroarylmethyl alcohol derivative (III) can be obtained through the reduction reaction of heteroaryl ester derivative (II-a).

Examples of the reducing agent for use in the reduction reaction include: aluminum reducing agents such as lithium aluminum hydride and diisobutyl aluminum hydride; and boron reducing agents such as sodium borohydride and lithium borohydride. An aluminum reducing agent such as lithium aluminum hydride or diisobutyl aluminum hydride is preferred.

The amount of the reducing agent used in the reduction reaction is preferably 0.3 to 100 equivalents, more preferably 0.5 to 20 equivalents, with respect to the heteroaryl ester derivative (II-a).

The reaction solvent for use in the reduction reaction is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; aprotic polar solvents such as N,N-dimethylformamide (hereinafter, referred to as DMF), N,N-dimethylacetamide (hereinafter, referred to as DMA) and dimethyl sulfoxide (hereinafter, referred to as DMSO); ether solvents such as diethyl ether, tetrahydrofuran, dimethoxyethane and 1,4-dioxane; aromatic hydrocarbon solvents such as toluene and xylene; and mixed solvents thereof. An ether solvent such as diethyl ether, tetrahydrofuran, dimethoxyethane or 1,4-dioxane, or an aromatic hydrocarbon solvent such as toluene or xylene is preferred.

The reaction temperature of the reduction reaction is preferably −100° C. to 200° C., more preferably −50° C. to 50° C.

The reaction time of the reduction reaction differs depending on reaction conditions and is preferably 1 to 30 hours.

The heteroaryl ester derivative (II-a) for use in the reduction reaction can be purchased or can be produced by a known method or a method equivalent thereto.

Step 1-2

The heteroaryl derivative (IV) can be obtained through the halogenation reaction of heteroarylmethyl alcohol derivative (III). In another method, the heteroaryl derivative (IV) can also be obtained through the sulfonylation reaction of heteroarylmethyl alcohol derivative (III).

Examples of the halogenating agent for use in the halogenation reaction include thionyl chloride, thionyl bromide, oxalyl chloride, phosphorus pentachloride and phosphoryl chloride. Thionyl chloride is preferred.

The amount of the halogenating agent used in the halogenation reaction is preferably 0.5 to 1000 equivalents, more preferably 0.8 to 100 equivalents, with respect to the heteroarylmethyl alcohol derivative (III).

The halogenation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The halogenation reaction may employ a reaction solvent, if desired. The reaction solvent used is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; basic solvents such as pyridine and 2,6-lutidine; chlorine solvents such as dichloromethane, chloroform and 1,2-dichloroethane; and mixed solvents thereof.

The reaction temperature of the halogenation reaction is preferably −100° C. to 200° C., more preferably −20° C. to 150° C.

The reaction time of the halogenation reaction differs depending on reaction conditions and is preferably 1 to 30 hours.

Examples of the sulfonylating agent for use in the sulfonylation reaction include methanesulfonyl chloride, p-toluenesulfonyl chloride and trifluoromethanesulfonic anhydride. Methanesulfonyl chloride is preferred.

The amount of the sulfonylating agent used in the sulfonylation reaction is preferably 0.5 to 100 equivalents, more preferably 0.8 to 10 equivalents, with respect to the heteroarylmethyl alcohol derivative (III).

The sulfonylation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The reaction solvent for use in the sulfonylation reaction is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; basic solvents such as pyridine and 2,6-lutidine; and mixed solvents thereof. A basic solvent such as pyridine or 2,6-lutidine is preferred.

The reaction temperature of the sulfonylation reaction is preferably −100° C. to 200° C., more preferably −50° C. to 50° C.

The reaction time of the sulfonylation reaction differs depending on reaction conditions and is preferably 1 to 30 hours.

Step 1-3

The N-(heteroarylmethyl)phthalimide derivative (V) can be obtained through the substitution reaction of heteroaryl derivative (IV) with potassium phthalimide.

The amount of the potassium phthalimide used in the substitution reaction is preferably 0.5 to 100 equivalents, more preferably 0.8 to 10 equivalents, with respect to the heteroaryl derivative (IV).

The reaction solvent for use in the substitution reaction is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; and mixed solvents thereof. An aprotic polar solvent such as DMA or DMSO is preferred.

The reaction temperature of the substitution reaction is preferably −30° C. to 300° C., more preferably 0° C. to 150° C.

The reaction time of the substitution reaction differs depending on reaction conditions and is preferably 1 to 30 hours.

Step 1-4

The phenylheteroaryl derivative (VII) can be obtained through the coupling reaction of N-(heteroarylmethyl)phthalimide derivative (V) with phenylboronic acid derivative (VI-a) in the presence of a metal catalyst and a base.

The amount of the phenylboronic acid derivative (VI-a) used in the coupling reaction is preferably 0.5 to 10 equivalents, more preferably 1 to 3 equivalents, with respect to the N-(heteroarylmethyl)phthalimide derivative (V).

Examples of the metal catalyst for use in the coupling reaction include 1,1'-bis(diphenylphosphino)ferrocenedichloropalladium(II) dichloromethane adduct, palladium(II) chloride, palladium(II) acetate, bis(dibenzylideneacetone)palladium(0), tetrakistriphenylphosphinepalladium(0) and dichlorobistriphenylphosphinepalladium(0). 1,1'-Bis(diphenylphosphino)ferrocenedichloropalladium(II) dichloromethane adduct or tetrakistriphenylphosphinepalladium(0) is preferred.

The amount of the metal catalyst used in the coupling reaction is preferably 0.01 to 5 equivalents, more preferably 0.025 to 0.5 equivalents, with respect to the N-(heteroarylmethyl)phthalimide derivative (V).

The coupling reaction may further employ a ligand. Examples of the ligand used include triphenylphosphine, tert-butylphosphine and 2,2'-bis(diphenylphosphino)-1,1'-binaphthyl.

Examples of the base for use in the coupling reaction include: organic bases such as triethylamine and N,N-diisopropylethylamine; inorganic bases such as sodium carbonate, potassium carbonate and cesium carbonate; lithium amides such as lithium hexamethyldisilazide and lithium diisopropylamide; metal alkoxides such as sodium tert-butoxide and potassium tert-butoxide; and mixtures thereof. An inorganic base such as sodium carbonate, potassium carbonate or cesium carbonate is preferred.

The amount of the base used in the coupling reaction is preferably 0.5 to 10 equivalents, more preferably 1 to 3 equivalents, with respect to the N-(heteroarylmethyl)phthalimide derivative (V).

The reaction solvent for use in the coupling reaction is appropriately selected according to the type of the reagent used and the like and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; water; and mixed solvents thereof. An ether solvent such as tetrahydrofuran, 1,4-dioxane, ethylene glycol dimethyl ether or dimethoxyethane, or an aromatic hydrocarbon solvent such as benzene or toluene is preferred.

The reaction temperature of the coupling reaction is preferably 0 to 200° C., more preferably 50 to 150° C.

The reaction time of the coupling reaction is appropriately selected according to conditions such as the reaction temperature and is preferably 1 to 30 hours.

The phenylboronic acid derivative (VI-a) for use in the coupling reaction can be purchased or can be produced by a known method or a method equivalent thereto.

Step 1-5

The diphenylheteroaryl derivative (VIII-a) can be obtained through the coupling reaction of phenylheteroaryl derivative (VII) with phenylboronic acid derivative (VI-b) in the presence of a metal catalyst and a base. The conditions of the reagent, the catalyst, the ligand, the base, the reaction solvent and the reaction temperature in this step are the same as in the step 1-4.

The phenylboronic acid derivative (VI-b) for use in the coupling reaction can be purchased or can be produced by a known method or a method equivalent thereto.

Step 1-6

The diphenylheteroarylmethylamine derivative (IX-a) can be obtained through the deprotection reaction of diphenylheteroaryl derivative (VIII-a) in the presence of hydrazine monohydrate.

The amount of the hydrazine monohydrate used in the deprotection reaction is preferably 0.5 to 100 equivalents, more preferably 0.8 to 10 equivalents, with respect to the diphenylheteroaryl derivative (VIII-a).

The reaction solvent for use in the deprotection reaction is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; and mixed solvents thereof. An alcohol solvent such as methanol, ethanol, isopropyl alcohol or tert-butyl alcohol is preferred.

The reaction temperature of the deprotection reaction is preferably −30° C. to 300° C., more preferably 0° C. to 150° C.

The reaction time of the deprotection reaction differs depending on reaction conditions and is preferably 1 to 30 hours.

Step 1-7

The guanidine derivative (XI-a) can be obtained through the guanidination reaction of diphenylheteroarylmethylamine derivative (IX-a) with guanidinating agent (X).

The amount of the guanidinating agent (X) used in the guanidination reaction is preferably 0.5 to 10 equivalents, more preferably 1 to 3 equivalents, with respect to the diphenylheteroarylmethylamine derivative (IX-a).

The guanidination reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The reaction solvent for use in the guanidination reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; and mixed solvents thereof. An ether solvent such as diethyl ether, tetrahydrofuran, dimethoxyethane or 1,4-dioxane is preferred.

The reaction temperature of the guanidination reaction is preferably 0 to 300° C., more preferably 30 to 200° C.

The reaction time of the guanidination reaction differs depending on reaction conditions and is preferably 1 to 30 hours The guanidinating agent (X) for use in the guanidination reaction can be purchased or can be produced by a known method (e.g., Nikola et al., ChemMedChem, 2011, Vo. 6, 1727-1738) or a method equivalent thereto.

Step 1-8

The guanidine derivative (I-a) can be obtained through the deprotection reaction of guanidine derivative (XI-a) in the presence of an acid.

Examples of the acid for use in the deprotection reaction include hydrochloric acid, a solution of 10% by weight of hydrogen chloride in methanol, a 4 mol/L solution of hydrogen chloride in ethyl acetate, trifluoroacetic acid and hydrofluoric acid. A 4 mol/L solution of hydrochloric acid in ethyl acetate or trifluoroacetic acid is preferred.

The amount of the acid used in the deprotection reaction is preferably 0.5 to 1000 equivalents, more preferably 1 to 100 equivalents, with respect to the guanidine derivative (XI-a).

The reaction solvent for use in the deprotection reaction is appropriately selected according to the type of the reagent used and the like and is not particularly limited as long as the solvent does not inhibit the reaction. Examples thereof include: ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; alcohol solvents such as methanol and ethanol; and mixed solvents thereof. An ester solvent such as ethyl acetate or propyl acetate, or a chlorine solvent such as dichloromethane, chloroform or 1,2-dichloroethane is preferred.

The reaction temperature of the deprotection reaction is preferably −78 to 200° C., more preferably −20 to 100° C.

The reaction time of the deprotection reaction differs depending on reaction conditions and is preferably 1 to 50 hours.

Step 1-9

The heteroarylmethylamine derivative (XII) can be obtained through the deprotection reaction of N-(heteroarylmethyl)phthalimide derivative (V) in the presence of hydrazine monohydrate. The conditions of the reagent, the reaction solvent and the reaction temperature in this step are the same as in the step 1-6.

Step 1-10

The guanidine derivative (XIII) can be obtained through the guanidination reaction of heteroarylmethylamine derivative (XII) with guanidinating agent (X). The conditions of the reagent, the base, the reaction solvent and the reaction temperature in this step are the same as in the step 1-7.

Step 1-11

The phenylheteroaryl derivative (XIV) can be obtained through the coupling reaction of guanidine derivative (XIII) with phenylboronic acid derivative (VI-a) in the presence of a metal catalyst and a base. The conditions of the reagent, the catalyst, the ligand, the base, the reaction solvent and the reaction temperature in this step are the same as in the step 1-4. The deprotection reaction of the tert-butoxycarbonyl group may progress in this step.

Step 1-12

The guanidine derivative (I-a) can be obtained through the coupling reaction of phenylheteroaryl derivative (XIV) with phenylboronic acid derivative (VI-b) in the presence of a metal catalyst and a base. The conditions of the reagent, the catalyst, the ligand, the base, the reaction solvent and the reaction temperature in this step are the same as in the step 1-5. The deprotection reaction of the tert-butoxycarbonyl group may progress in this step.

Production Method 2

Guanidine derivative (I-b), (I-c), (I-d) or (I-e) in which $R^1$ is $R^4$, $R^2$ is $R^5$ and $R^3$ is $R^6$ in the guanidine derivative (I) can be obtained by, for example, a method described in scheme 3.

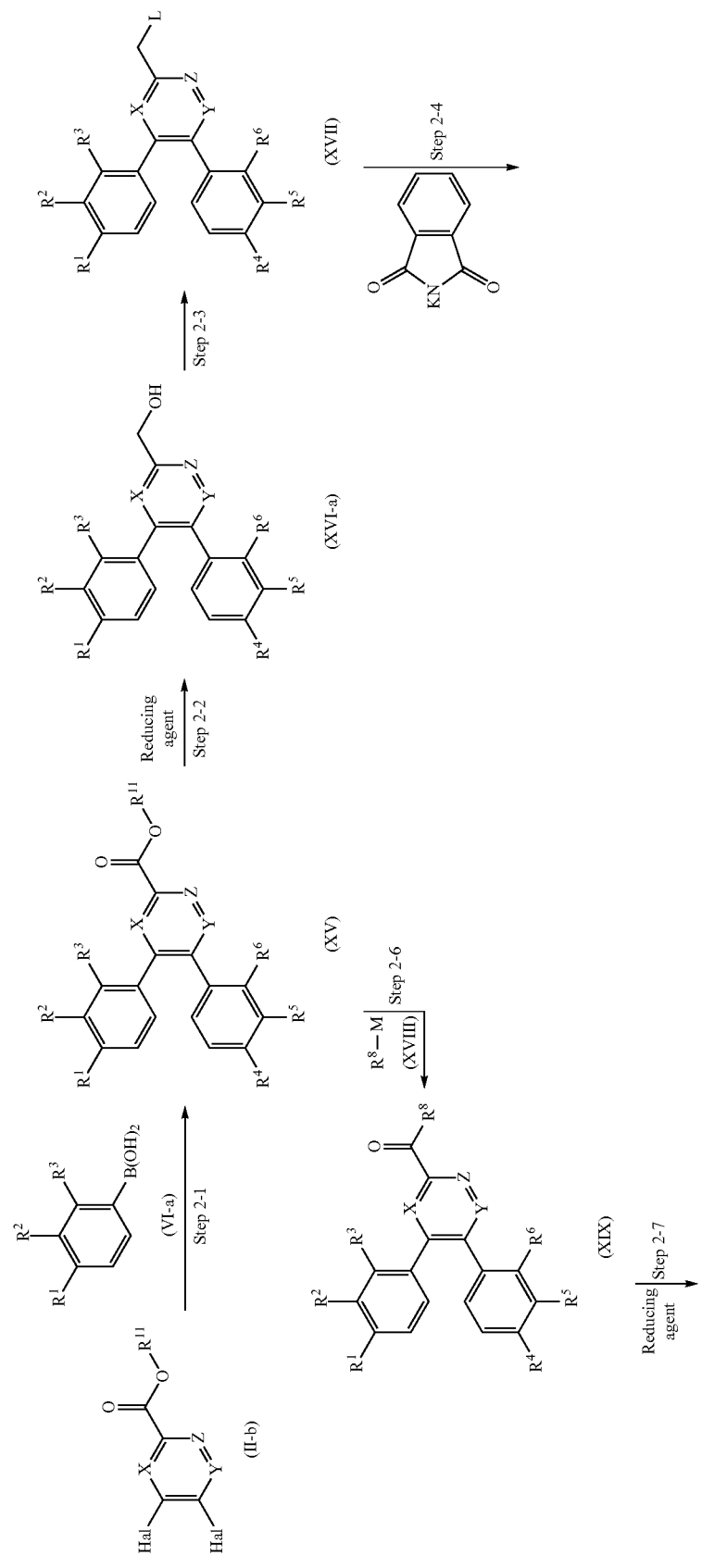

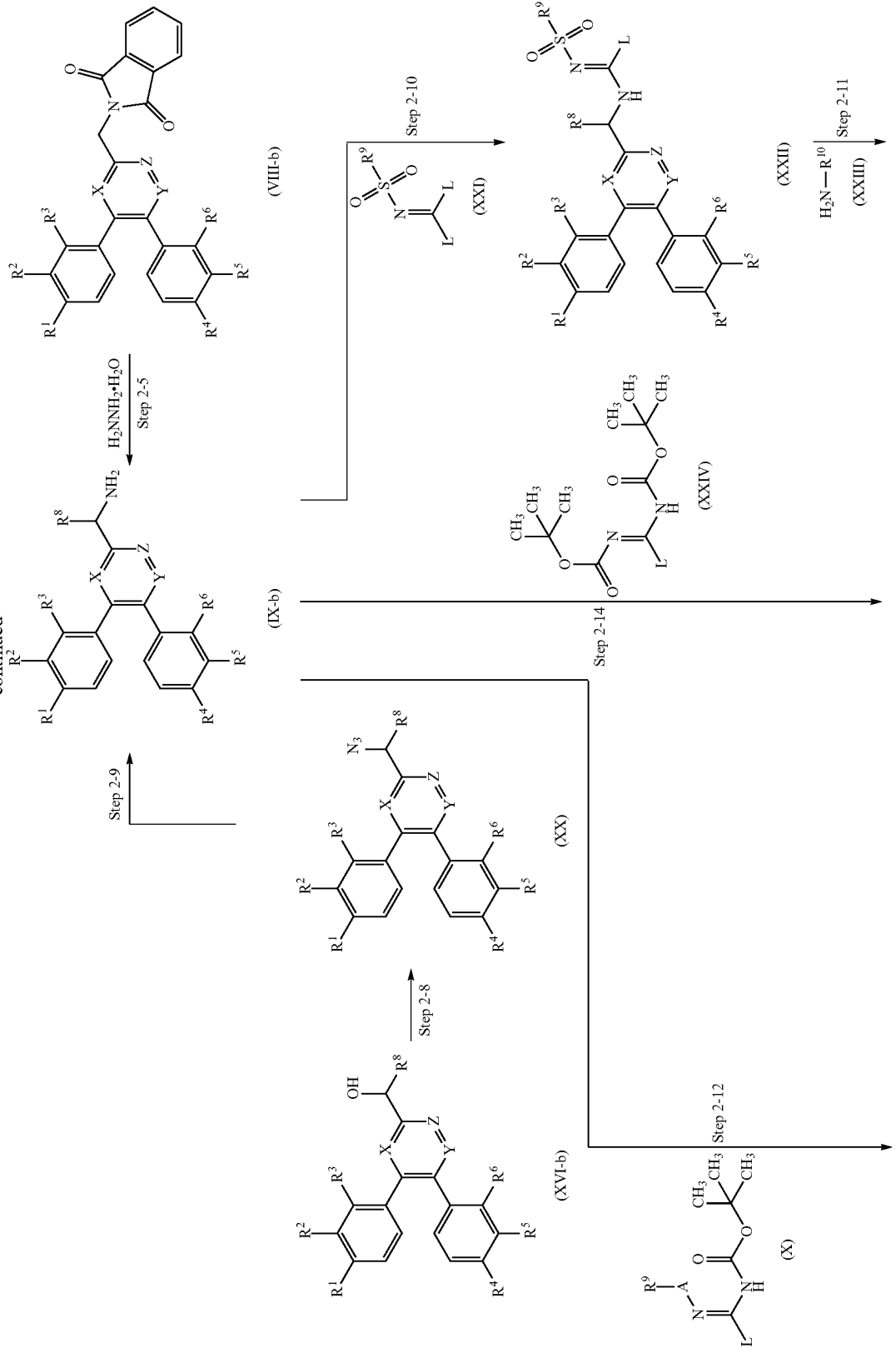

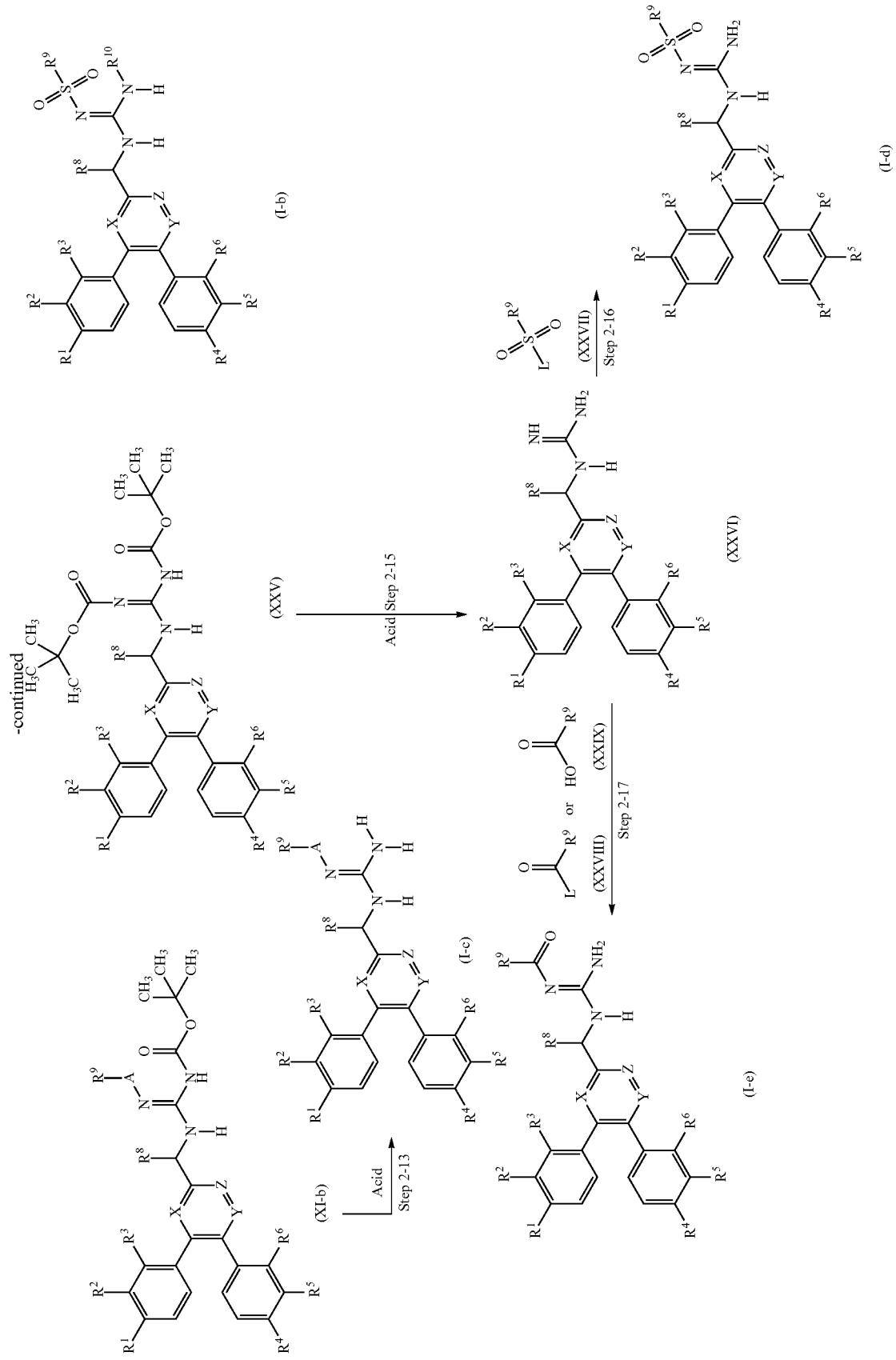

wherein Hal represents a halogen atom; $R^8$-M represents an alkyl metal reagent; and each of the other symbols is as defined above.

Examples of $R^8$-M include alkyllithium, alkylsodiunm, alkylmagnesium halide and alkylaluminum.

Step 2-1

The diphenylheteroaryl derivative (XV) can be obtained through the coupling reaction of heteroaryl ester derivative (II-b) with phenylboronic acid derivative (VI-a) in the presence of a metal catalyst and a base.

The amount of the phenylboronic acid derivative (VI-a) used in the coupling reaction is preferably 0.5 to 10 equivalents, more preferably 2 to 5 equivalents, with respect to the heteroaryl ester derivative (II-b).

Examples of the metal catalyst for use in the coupling reaction include 1,1'-bis(diphenylphosphino)ferrocenedichloropalladium(II) dichloromethane adduct, palladium(II) chloride, palladium(II) acetate, bis(dibenzylideneacetone)palladium(0), tetrakistriphenylphosphinepalladium(0) and dichlorobistriphenylphosphinepalladium(0). 1,1'-Bis(diphenylphosphino)ferrocenedichloropalladium(II) dichloromethane adduct or tetrakistriphenylphosphinepalladium(0) is preferred.

The amount of the metal catalyst used in the coupling reaction is preferably 0.01 to 5 equivalents, more preferably 0.025 to 0.5 equivalents, with respect to the heteroaryl ester derivative (II-b).

The coupling reaction can further employ a ligand. Examples of the ligand used include triphenylphosphine, tert-butylphosphine and 2,2'-bis(diphenylphosphino)-1,1'-binaphthyl.

Examples of the base for use in the coupling reaction include: organic bases such as triethylamine and N,N-diisopropylethylamine; inorganic bases such as sodium carbonate, potassium carbonate and cesium carbonate; lithium amides such as lithium hexamethyldisilazide and lithium diisopropylamide; metal alkoxides such as sodium tert-butoxide and potassium tert-butoxide; and mixtures thereof. An inorganic base such as sodium carbonate, potassium carbonate or cesium carbonate is preferred.

The amount of the base used in the coupling reaction is preferably 0.5 to 10 equivalents, more preferably 2 to 5 equivalents, with respect to the heteroaryl ester derivative (II-b).

The reaction solvent for use in the coupling reaction is appropriately selected according to the type of the reagent used and the like and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; water; and mixed solvents thereof. An ether solvent such as tetrahydrofuran, 1,4-dioxane, ethylene glycol dimethyl ether or dimethoxyethane, or an aromatic hydrocarbon solvent such as benzene or toluene is preferred.

The reaction temperature of the coupling reaction is preferably 0 to 200° C., more preferably 50 to 150° C.

The reaction time of the coupling reaction is appropriately selected according to conditions such as the reaction temperature and is preferably 1 to 30 hours.

The heteroaryl ester derivative (II-b) for use in the coupling reaction can be purchased or can be produced by a known method or a method equivalent thereto.

Step 2-2

The diphenylheteroaryl alcohol derivative (XVI-a) can be obtained through the reduction reaction of diphenylheteroaryl derivative (XV). The conditions of the reagent, the reaction solvent, the reaction temperature and the reaction time in this step are the same as in the step 1-1.

Step 2-3

The diphenylheteroaryl derivative (XVII) can be obtained through the halogenation reaction of diphenylheteroaryl alcohol derivative (XVI-a). In another method, the diphenylheteroaryl derivative (XVII) can also be obtained through the sulfonylation reaction of diphenylheteroaryl alcohol derivative (XVI-a). The conditions of the reagent, the reaction solvent, the reaction temperature and the reaction time in this step are the same as in the step 1-2.

Step 2-4

The diphenylheteroaryl derivative (VIII-b) can be obtained through the substitution reaction of diphenylheteroaryl derivative (XVII) with potassium phthalimide. The conditions of the reagent, the reaction solvent, the reaction temperature and the reaction time in this step are the same as in the step 1-3.

Step 2-5

The diphenylheteroarylmethylamine derivative (IX-b) can be obtained through the deprotection reaction of diphenylheteroaryl derivative (VIII-b) in the presence of hydrazine monohydrate. The conditions of the reagent, the reaction solvent, the reaction temperature and the reaction time in this step are the same as in the step 1-6.

Step 2-6

The diphenylheteroaryl ketone derivative (XIX) can be obtained through the nucleophilic addition reaction of alkyl metal reagent (XVIII) to diphenylheteroaryl derivative (XV) in the presence of N,O-dimethylhydroxylamine hydrochloride.

The amount of the N,O-dimethylhydroxylamine hydrochloride used in the nucleophilic addition reaction is preferably 0.2 to 30 equivalents, more preferably 0.5 to 5 equivalents, with respect to the diphenylheteroaryl derivative (XV).

The amount of the alkyl metal reagent (XVIII) used in the nucleophilic addition reaction is preferably 0.5 to 30 equivalents, more preferably 1.5 to 20 equivalents, with respect to the diphenylheteroaryl derivative (XV).

The reaction solvent for use in the nucleophilic addition reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; aromatic hydrocarbon solvents such as benzene and toluene; and mixed solvents thereof. An ether solvent such as tetrahydrofuran, 1,4-dioxane, ethylene glycol dimethyl ether or dimethoxyethane is preferred.

The reaction temperature of the nucleophilic addition reaction is preferably −78° C. to 100° C., more preferably −30° C. to 50° C.

The reaction time of the nucleophilic addition reaction differs depending on reaction conditions and is preferably 10 minutes to 10 hours.

The alkyl metal reagent (XVIII) for use in the nucleophilic addition reaction can be purchased or can be produced by a known method or a method equivalent thereto.

Step 2-7

The diphenylheteroaryl alcohol derivative (XVI-b) can be obtained through the reduction reaction of diphenylheteroaryl ketone derivative (XIX).

Examples of the reagent for use in the reduction reaction include lithium aluminum hydride, diisobutyl aluminum hydride, sodium borohydride, lithium borohydride, lithium triethylborohydride and a borane-tetrahydrofuran complex. Sodium borohydride is preferred.

The amount of the reagent used in the reduction reaction is preferably 0.25 to 100 equivalents, more preferably 0.5 to 10 equivalents, with respect to the diphenylheteroaryl ketone derivative (XIX).

The reaction solvent for use in the reduction reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; aromatic hydrocarbon solvents such as benzene and toluene; alcohol solvents such as methanol and ethanol; water; and mixed solvents thereof. An alcohol solvent such as methanol or ethanol is preferred.

The reaction temperature of the reduction reaction is preferably −78° C. to 100° C., more preferably −30° C. to 50° C.

The reaction time of the reduction reaction differs depending on reaction conditions and is preferably 10 minutes to 10 hours.

Step 2-8

The alkyl azide derivative (XX) can be obtained through the azidation reaction of diphenylheteroaryl alcohol derivative (XVI-b) with diphenylphosphoryl azide in the presence of diazabicycloundecene.

The amount of the diazabicycloundecene used in the azidation reaction is preferably 0.5 to 10 equivalents, more preferably 2 to 5 equivalents, with respect to the diphenylheteroaryl alcohol derivative (XVI-b).

The amount of the diphenylphosphoryl azide used in the azidation reaction is preferably 0.5 to 10 equivalents, more preferably 2 to 5 equivalents, with respect to the diphenylheteroaryl alcohol derivative (XVI-b).

The reaction solvent for use in the azidation reaction is appropriately selected according to the type of the reagent used and the like and is not particularly limited as long as the solvent does not inhibit the reaction. Examples thereof include: ether solvents such as tetrahydrofuran, 1,4-dioxane, ethylene glycol dimethyl ether and dimethoxyethane; aromatic hydrocarbon solvents such as benzene and toluene; and mixed solvents thereof. An aromatic hydrocarbon solvent such as benzene or toluene is preferred.

The reaction temperature of the azidation reaction is preferably 0 to 200° C., more preferably 20 to 100° C.

The reaction time of the azidation reaction is appropriately selected according to conditions such as the reaction temperature and is preferably 1 to 30 hours.

Step 2-9

The diphenylheteroarylmethylamine derivative (IX-b) can be obtained through the reduction reaction of alkyl azide derivative (XX).

Examples of the reagent for use in the reduction reaction include lithium aluminum hydride, triphenylphosphine and tributylphosphine. Triphenylphosphine is preferred.

The amount of the reagent used in the reduction reaction is preferably 0.25 to 100 equivalents, more preferably 0.5 to 10 equivalents, with respect to the alkyl azide derivative (XX).

The reaction solvent for use in the reduction reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; aromatic hydrocarbon solvents such as benzene and toluene; alcohol solvents such as methanol and ethanol; water; and mixed solvents thereof. A mixed solvent of an ether solvent such as tetrahydrofuran, 1,4-dioxane, ethylene glycol dimethyl ether or dimethoxyethane and water is preferred.

The reaction temperature of the reduction reaction is preferably 0 to 200° C., more preferably 10 to 100° C.

The reaction time of the reduction reaction differs depending on reaction conditions and is preferably 1 to 30 hours.

Step 2-10

The carbamimidic acid derivative (XXII) can be obtained through the carbamimidation reaction of diphenylheteroarylmethylamine derivative (IX-b) with carbonimidic acid derivative (XXI).

The amount of the carbonimidic acid derivative (XXI) used in the carbamimidation reaction is preferably 0.5 to 10 equivalents, more preferably 1 to 3 equivalents, with respect to the diphenylheteroarylmethylamine derivative (IX-b).

The carbamimidation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The reaction solvent for use in the carbamimidation reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; and mixed solvents thereof. An ether solvent such as diethyl ether, tetrahydrofuran, dimethoxyethane or 1,4-dioxane is preferred.

The reaction temperature of the carbamimidation reaction is preferably 0 to 300° C., more preferably 30 to 200° C.

The reaction time of the carbamimidation reaction differs depending on reaction conditions and is preferably 1 to 30 hours.

The carbonimidic acid derivative (XXI) for use in the carbamimidation reaction can be purchased or can be produced by a known method or a method equivalent thereto.

Step 2-11

The guanidine derivative (I-b) can be obtained through the guanidination reaction of carbamimidic acid derivative (XXII) with amine derivative (XXIII).

The amount of the amine derivative (XXIII) used in the guanidination reaction is preferably 0.5 to 100 equivalents, more preferably 1 to 20 equivalents, with respect to the carbamimidic acid derivative (XXII).

The reaction solvent for use in the guanidination reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; and mixed solvents thereof. A nitrile solvent such as acetonitrile or propionitrile is preferred.

The reaction temperature of the guanidination reaction is preferably 0 to 300° C., more preferably 30 to 200° C.

The reaction time of the guanidination reaction differs depending on reaction conditions and is preferably 1 to 30 hours.

The amine derivative (XXIII) for use in the guanidination reaction can be purchased or can be produced by a known method or a method equivalent thereto.

Step 2-12

The guanidine derivative (XI-b) can be obtained through the guanidination reaction of diphenylheteroarylmethylamine derivative (IX-b) with guanidinating agent (X). The conditions of the reagent, the reaction solvent, the reaction temperature and the reaction time in this step are the same as in the step 1-7.

Step 2-13

The guanidine derivative (I-c) can be obtained through the deprotection reaction of guanidine derivative (XI-b) in the presence of an acid. The conditions of the reagent, the reaction solvent, the reaction temperature and the reaction time in this step are the same as in the step 1-8.

Step 2-14

The guanidine derivative (XXV) can be obtained through the guanidination reaction of diphenylheteroarylmethylamine derivative (IX-b) with guanidinating agent (XXIV).

The amount of the guanidinating agent (XXIV) used in the guanidination reaction is preferably 0.5 to 10 equivalents, more preferably 1 to 3 equivalents, with respect to the diphenylheteroarylmethylamine derivative (IX-b).

The guanidination reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The reaction solvent for use in the guanidination reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; and mixed solvents thereof. An ether solvent such as diethyl ether, tetrahydrofuran, dimethoxyethane or 1,4-dioxane is preferred.

The reaction temperature of the guanidination reaction is preferably 0 to 300° C., more preferably 30 to 200° C.

The reaction time of the guanidination reaction differs depending on reaction conditions and is preferably 1 to 30 hours.

The guanidinating agent (XXIV) for use in the guanidination reaction can be purchased or can be produced by a known method or a method equivalent thereto.

Step 2-15

The guanidine derivative (XXVI) can be obtained through the deprotection reaction of guanidine derivative (XXV) in the presence of an acid. The conditions of the reagent, the reaction solvent, the reaction temperature and the reaction time in this step are the same as in the step 1-8.

Step 2-16

The guanidine derivative (I-d) can be obtained through the sulfonylation reaction of guanidine derivative (XXVI) with sulfonylating agent (XXVII).

The amount of the sulfonylating agent (XXVII) used in the sulfonylation reaction is preferably 0.5 to 10 equivalents, more preferably 1 to 3 equivalents, with respect to the guanidine derivative (XXVI).

The sulfonylation reaction may employ a base, if desired. Examples of the base used include: organic bases such as triethylamine, N,N-diisopropylethylamine and pyridine; alkali metal hydroxides such as sodium hydroxide, potassium hydroxide and lithium hydroxide; alkali metal bicarbonates such as sodium bicarbonate and potassium bicarbonate; alkali metal carbonates such as sodium carbonate and potassium carbonate; and mixtures thereof. An alkali metal hydroxide such as sodium hydroxide, potassium hydroxide or lithium hydroxide is preferred.

The guanidine derivative (XXVI) for use in the sulfonylation reaction may be a free form or may be a salt such as hydrochloride.

The reaction solvent for use in the sulfonylation reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; ketone solvents such as acetone and methyl ethyl ketone; water; and mixed solvents thereof. A mixed solvent of an ether solvent such as diethyl ether, tetrahydrofuran, dimethoxyethane or 1,4-dioxane and water is preferred.

The reaction temperature of the sulfonylation reaction is preferably −78° C. to 100° C., more preferably −20° C. to 50° C.

The reaction time of the sulfonylation reaction differs depending on reaction conditions and is preferably 1 to 30 hours.

The sulfonylating agent (XXVII) for use in the sulfonylation reaction can be purchased or can be produced by a known method or a method equivalent thereto.

Step 2-17

The guanidine derivative (I-e) can be obtained through the acylation reaction of guanidine derivative (XXVI) with acylating agent (XXVIII). In another method, the guanidine derivative (I-e) can be obtained through the condensation reaction of guanidine derivative (XXVI) with carboxylic acid (XXIX).

The amount of the acylating agent (XXVIII) used in the acylation reaction is preferably 0.5 to 10 equivalents, more preferably 1 to 3 equivalents, with respect to the guanidine derivative (XXVI).

The acylation reaction may employ a base, if desired. Examples of the base used include: organic bases such as triethylamine, N,N-diisopropylethylamine and pyridine; alkali metal hydroxides such as sodium hydroxide, potassium hydroxide and lithium hydroxide; alkali metal bicarbonates such as sodium bicarbonate and potassium bicarbonate; alkali metal carbonates such as sodium carbonate and potassium carbonate; and mixtures thereof. An alkali metal hydroxide such as sodium hydroxide, potassium hydroxide or lithium hydroxide is preferred.

The guanidine derivative (XXVI) for use in the acylation reaction may be a free form or may be a salt such as hydrochloride.

The reaction solvent for use in the acylation reaction is appropriately selected according to the type of the reagent used and is not particularly limited as long as the solvent does not inhibit the reaction. Examples thereof include: nitrile solvents such as acetonitrile and propionitrile; aprotic polar solvents such as DMF, DMA and DMSO; ether solvents such as diethyl ether, tetrahydrofuran, dimethoxyethane and 1,4-dioxane; ester solvents such as ethyl acetate and propyl acetate; ketone solvents such as acetone and methyl ethyl ketone; water; and mixed solvents thereof. A mixed solvent of an ether solvent such as diethyl ether, tetrahydrofuran, dimethoxyethane or 1,4-dioxane and water is preferred.

The reaction temperature of the acylation reaction is preferably −78° C. to 100° C., more preferably −20° C. to 50° C.

The reaction time of the acylation reaction differs depending on reaction conditions and is preferably 1 to 30 hours.

The acylating agent (XXVIII) for use in the acylation reaction can be purchased or can be produced by a known method or a method equivalent thereto.

The amount of the carboxylic acid (XXIX) used in the condensation reaction is preferably 0.5 to 10 equivalents, more preferably 1 to 3 equivalents, with respect to the guanidine derivative (XXVI).

Examples of the condensing agent for use in the condensation reaction include N,N'-dicyclohexylcarbodiimide, N-ethyl-N'-3-dimethylaminopropylcarbodiimide hydrochloride (hereinafter, referred to as EDC.HCl), N,N'-carbodiimidazole, {{[(I-cyano-2-ethoxy-2-oxoethylidene)amino]oxy}-4-morpholinomethylene}dimethylammonium hexafluorophosphate (hereinafter, referred to as COMU), O-(7-azabenzotriazol-1-yl)-1,1,3,3-tetramethyluronium hexafluorophosphate (hereinafter, referred to as HATU) and O-(benzotriazol-1-yl)-N,N,N',N'-tetramethyluronium hexafluorophosphate (hereinafter, referred to as HBTU). COMU or HATU is preferred.

The amount of the condensing agent used in the condensation reaction is preferably 0.5 to 10 equivalents, more preferably 1 to 3 equivalents, with respect to the guanidine derivative (XXVI).

Examples of the base for use in the condensation reaction include: organic bases such as triethylamine and N,N-diisopropylethylamine; inorganic bases such as sodium bicarbonate and potassium carbonate; metal hydride compounds such as sodium hydride, potassium hydride and calcium hydride; alkyllithiums such as methyllithium and butyllithium; lithium amides such as lithium hexamethyldisilazide and lithium diisopropylamide; and mixtures thereof. An organic base such as triethylamine or N,N-diisopropylethylamine is preferred.

The amount of the base used in the condensation reaction is preferably 0.5 to 10 equivalents, more preferably 1 to 5 equivalents, with respect to the guanidine derivative (XXVI).

The guanidine derivative (XXVI) for use in the condensation reaction may be a free form or may be a salt such as hydrochloride.

The reaction solvent for use in the condensation reaction is appropriately selected according to the type of the reagent used and the like and is not particularly limited as long as the solvent does not inhibit the reaction. Examples thereof include: ether solvents such as tetrahydrofuran, 1,4-dioxane, ethylene glycol dimethyl ether and dimethoxyethane; halogen solvents such as dichloromethane, chloroform and 1,2-dichloroethane; aprotic polar solvents such as DMF, DMA and DMSO; and nitrile solvents such as acetonitrile and propionitrile. A halogen solvent such as dichloromethane, chloroform or 1,2-dichloroethane, or an aprotic polar solvent such as DMF, DMA or DMSO is preferred.

The reaction temperature of the condensation reaction is preferably 0 to 200° C., more preferably 20 to 100° C.

The reaction time of the condensation reaction is appropriately selected according to conditions such as the reaction temperature and is preferably 1 to 100 hours.

The carboxylic acid (XXIX) for use in the condensation reaction can be purchased or can be produced by a known method or a method equivalent thereto.

Production Method 3

Guanidine derivative (I-f) or (I-g) in which $R^8$ is H in the guanidine derivative (I) can be obtained by, for example, a method described in scheme 4.

Scheme 4
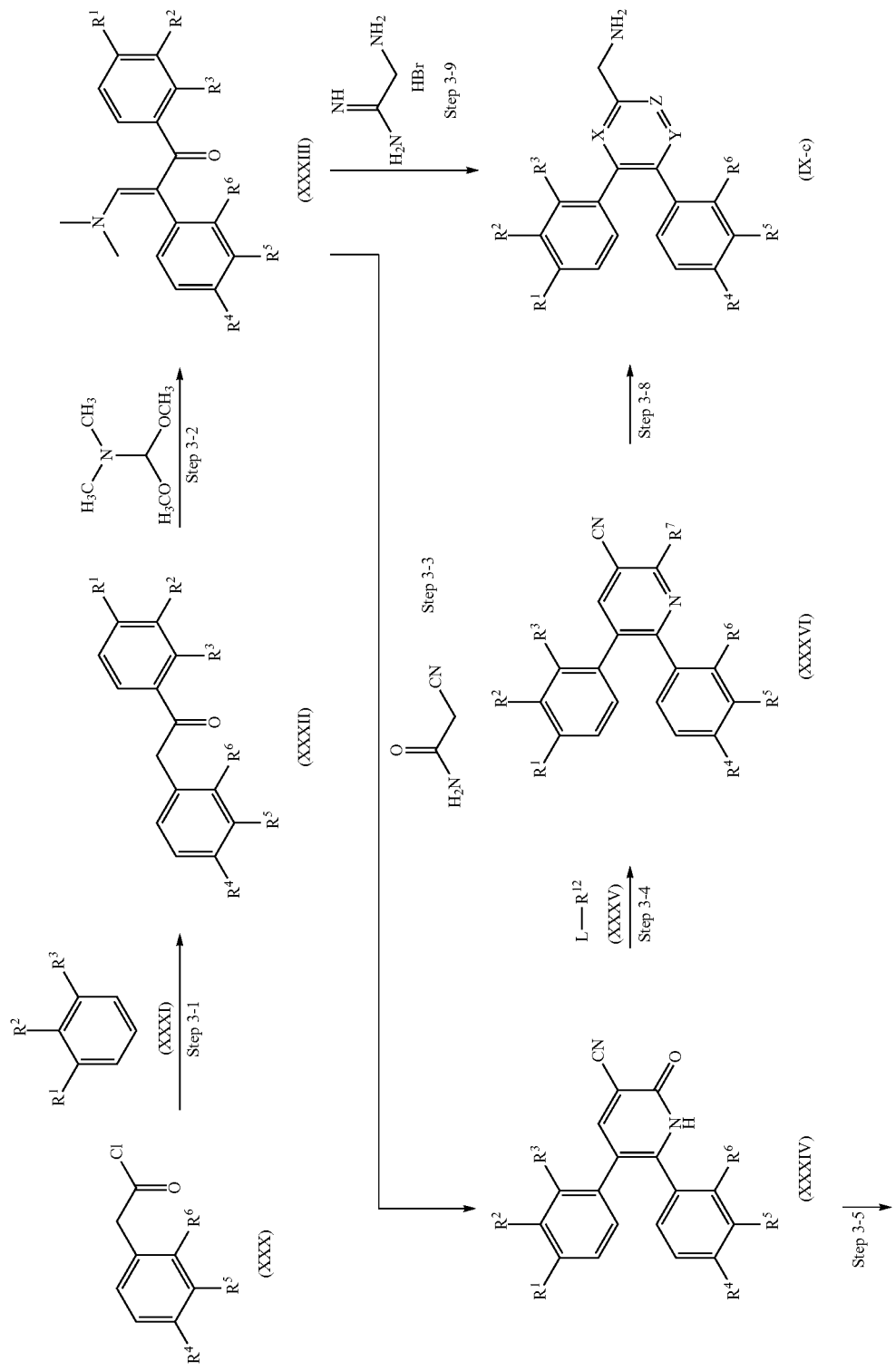

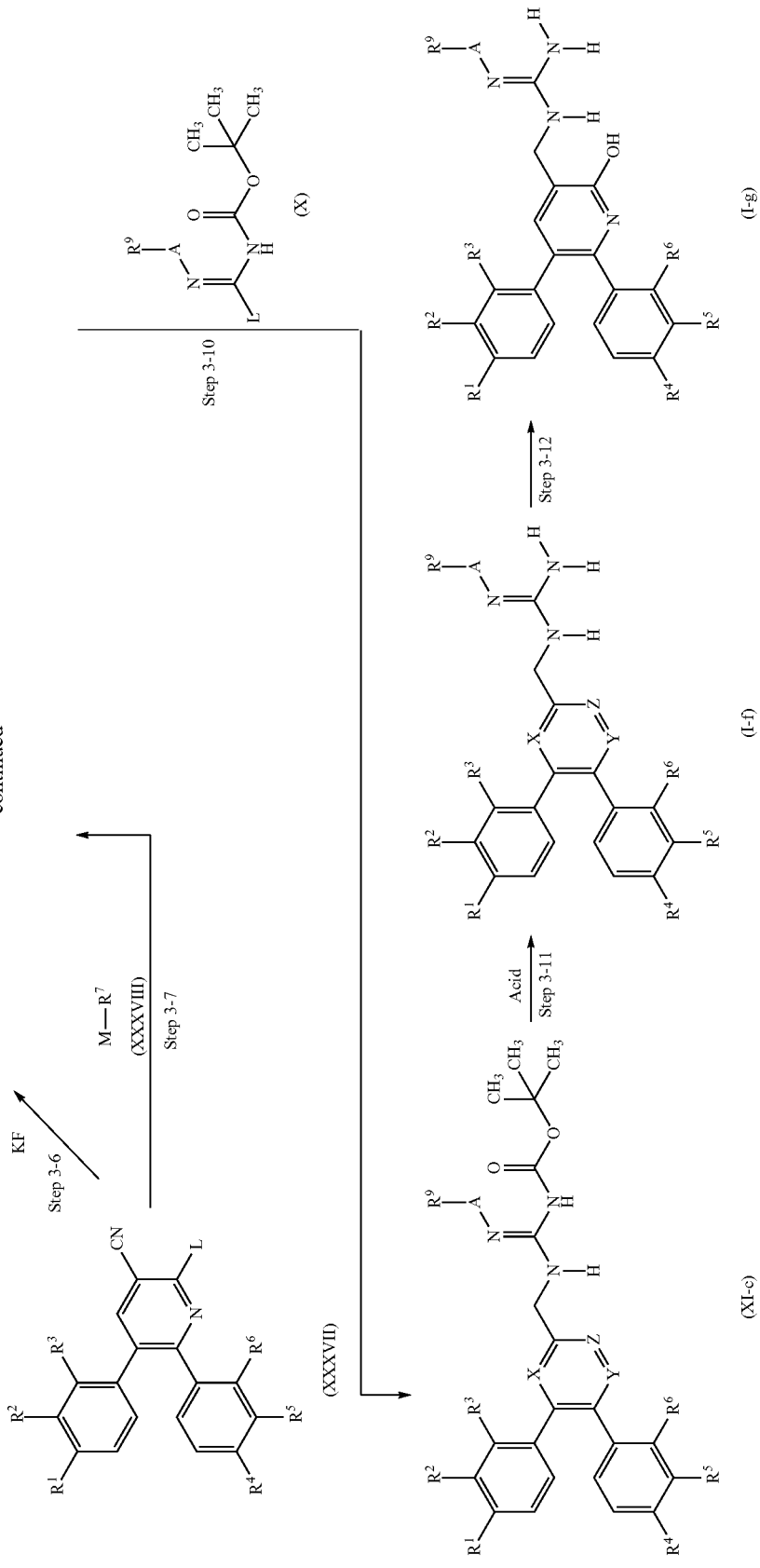

wherein R² represents an alkyl group having 1 to 3 carbon atoms; and each of the other symbols presence of a Lewis acid.

The amount of the benzene derivative (XXXI) used in the Friedel-Crafts reaction is preferably 0.5 to 100 equivalents, more preferably 1 to 10 equivalents, with respect to the phenylacetic acid chloride derivative (XXX).

Examples of the Lewis acid for use in the Friedel-Crafts reaction include aluminum chloride, iron chloride, zinc chloride, lanthanum trifluoromethanesulfonate, scandium trifluoromethanesulfonate, sulfuric acid, phosphoric acid and polyphosphoric acid. Aluminum chloride or iron chloride is preferred.

The Friedel-Crafts reaction may employ a reaction solvent, if desired. The reaction solvent used is appropriately selected according to the type of the reagent used and is not particularly limited as long as the solvent does not inhibit the reaction. Examples thereof include: aprotic polar solvents such as nitromethane, nitroethane and nitrobenzene; chlorine solvents such as dichloromethane, chloroform and 1,2-dichloroethane; and mixed solvents thereof. A chlorine solvent such as dichloromethane, chloroform or 1,2-dichloroethane is preferred.

The reaction temperature of the Friedel-Crafts reaction is preferably 0 to 300° C., more preferably 10 to 150° C.

The reaction time of the Friedel-Crafts reaction differs depending on reaction conditions and is preferably 1 to 30 hours.

The phenylacetic acid chloride derivative (XXX) for use in the Friedel-Crafts reaction can be purchased or can be produced by a known method or a method equivalent thereto.

The benzene derivative (XXXI) for use in the Friedel-Crafts reaction can be purchased or can be produced by a known method or a method equivalent thereto.

Step 3-2

The enamine derivative (XXXIII) can be obtained through the condensation reaction of diphenylethanone derivative (XXXII) with N,N-dimethylformamide dimethyl acetal.

The amount of the N,N-dimethylformamide dimethyl acetal used in the condensation reaction is preferably 0.5 to 100 equivalents, more preferably 1 to 10 equivalents, with respect to the diphenylethanone derivative (XXXII).

The reaction solvent for use in the condensation reaction is appropriately selected according to reaction conditions and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; and mixed solvents thereof. An aprotic polar solvent such as DMF, DMA or DMSO is preferred.

The reaction temperature of the condensation reaction is preferably 0 to 250° C., more preferably 30 to 150° C.

The reaction time of the condensation reaction differs depending on reaction conditions and is preferably 1 to 30 hours.

Step 3-3

The cyanopyridone derivative (XXXIV) can be obtained through the cycloaddition reaction of enamine derivative (XXXIII) with 2-cyanoacetamide in the presence of a base.

The amount of the 2-cyanoacetamide used in the cycloaddition reaction is preferably 0.5 to 100 equivalents, more preferably 1 to 10 equivalents, with respect to the enamine derivative (XXXIII).

Examples of the base for use in the cycloaddition reaction include: organic bases such as triethylamine, N,N-diisopropylethylamine and pyridine; inorganic bases such as sodium bicarbonate and potassium carbonate; metal alkoxides such as sodium methoxide, sodium ethoxide and potassium tert-butoxide; metal hydrides such as sodium hydride and potassium hydride; and mixtures thereof. A metal alkoxide such as sodium ethoxide or potassium tert-butoxide, or a metal hydride such as sodium hydride or potassium hydride is preferred.

The reaction solvent for use in the cycloaddition reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; and mixed solvents thereof. An aprotic polar solvent such as DMF, DMA or DMSO is preferred.

The reaction temperature of the cycloaddition reaction is preferably −30° C. to 200° C., more preferably 0° C. to 80° C.

The reaction time of the cycloaddition reaction differs depending on reaction conditions and is preferably 1 to 30 hours.

Step 3-4

The diphenylpyridine derivative (XXXVI) can be obtained through the alkylation reaction of cyanopyridone derivative (XXXIV) with alkylating agent (XXXV).

The amount of the alkylating agent (XXXV) used in the alkylation reaction is preferably 0.5 to 100 equivalents, more preferably 1 to 10 equivalents, with respect to the cyanopyridone derivative (XXXIV).

The alkylation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An inorganic base such as sodium bicarbonate or potassium carbonate is preferred.

The reaction solvent for use in the alkylation reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; and mixed solvents thereof. An aprotic polar solvent such as DMF, DMA or DMSO is preferred.

The reaction temperature of the alkylation reaction is preferably 0 to 200° C., more preferably 10 to 100° C.

The reaction time of the alkylation reaction differs depending on reaction conditions and is preferably 1 to 30 hours.

The alkylating agent (XXXV) for use in the alkylation reaction can be purchased or can be produced by a known method or a method equivalent thereto.

Step 3-5

The cyanopyridine derivative (XXXVII) can be obtained through the halogenation reaction of cyanopyridone derivative (XXXIV). In another method, the cyanopyridine derivative (XXXVII) can also be obtained through the sulfonylation reaction of cyanopyridone derivative (XXXIV).

Examples of the halogenating agent for use in the halogenation reaction include thionyl chloride, thionyl bromide, oxalyl chloride, phosphorus pentachloride, phosphorus tribromide and phosphoryl chloride. Phosphorus pentachloride or phosphoryl chloride is preferred.

The amount of the halogenating agent used in the halogenation reaction is preferably 0.5 to 1000 equivalents, more preferably 0.8 to 100 equivalents, with respect to the cyanopyridone derivative (XXXIV).

The halogenation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The halogenation reaction may employ a reaction solvent, if desired. The reaction solvent used is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; basic solvents such as pyridine and 2,6-lutidine; chlorine solvents such as dichloromethane, chloroform and 1,2-dichloroethane; and mixed solvents thereof.

The reaction temperature of the halogenation reaction is preferably −100° C. to 200° C., more preferably −20° C. to 150° C.

The reaction time of the halogenation reaction differs depending on reaction conditions and is preferably 1 to 30 hours.

Examples of the sulfonylating agent for use in the sulfonylation reaction include methanesulfonyl chloride, p-toluenesulfonyl chloride and trifluoromethanesulfonic anhydride.

The amount of the sulfonylating agent used in the sulfonylation reaction is preferably 0.5 to 100 equivalents, more preferably 0.8 to 10 equivalents, with respect to the cyanopyridone derivative (XXXIV).

The sulfonylation reaction may employ a base, if desired. Examples of the base used include: organic bases such as triethylamine, N,N-diisopropylethylamine and pyridine; inorganic bases such as sodium bicarbonate and potassium carbonate; and mixtures thereof. An organic base such as triethylamine, N,N-diisopropylethylamine or pyridine is preferred.

The reaction solvent for use in the sulfonylation reaction is appropriately selected according to the type of the reagent used and is not particularly limited as long as the solvent does not inhibit the reaction. Examples thereof include: aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; chlorine solvents such as dichloromethane, chloroform and 1,2-dichloroethane; basic solvents such as pyridine and 2,6-lutidine; and mixed solvents thereof. A chlorine solvent such as dichloromethane, chloroform or 1,2-dichloroethane is preferred.

The reaction temperature of the sulfonylation reaction is preferably −100° C. to 200° C., more preferably −50° C. to 50° C.

The reaction time of the sulfonylation reaction differs depending on reaction conditions and is preferably 1 to 30 hours.

Step 3-6

The diphenylpyridine derivative (XXXVI) can be obtained through the fluorination reaction of cyanopyridine derivative (XXXVII) with potassium fluoride.

The amount of the potassium fluoride used in the fluorination reaction is preferably 0.5 to 1000 equivalents, more preferably 0.8 to 100 equivalents, with respect to the cyanopyridine derivative (XXXVII).

The fluorination reaction may employ a base, if desired. Examples of the base used include: organic bases such as triethylamine, N,N-diisopropylethylamine and pyridine; inorganic bases such as sodium bicarbonate and potassium carbonate; and mixtures thereof. An inorganic base such as sodium bicarbonate or potassium carbonate is preferred.

The reaction solvent for use in the fluorination reaction is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; aprotic polar solvents such as DMF, DMA and DMSO; ether solvents such as diethyl ether, tetrahydrofuran, dimethoxyethane and 1,4-dioxane; aromatic hydrocarbon solvents such as toluene and xylene; basic solvents such as pyridine and 2,6-lutidine; chlorine solvents such as dichloromethane, chloroform and 1,2-dichloroethane; and mixed solvents thereof.

The reaction temperature of the fluorination reaction is preferably −100° C. to 300° C., more preferably 0° C. to 200° C.

The reaction time of the fluorination reaction differs depending on reaction conditions and is preferably 1 to 30 hours.

Step 3-7

The diphenylpyridine derivative (XXXVI) can be obtained through the coupling reaction of cyanopyridine derivative (XXXVII) with alkyl metal derivative (XXXVIII) in the presence of a metal catalyst and a base.

The amount of the alkyl metal derivative (XXXVIII) used in the coupling reaction is preferably 0.5 to 10 equivalents, more preferably 2 to 5 equivalents, with respect to the cyanopyridine derivative (XXXVII).

Examples of the metal catalyst for use in the coupling reaction include 1,1'-bis(diphenylphosphino)ferrocenedichloropalladium(II) dichloromethane adduct, palladium(II) chloride, palladium(II) acetate, bis(dibenzylideneacetone)palladium(0), tetrakistriphenylphosphinepalladium(0) and dichlorobistriphenylphosphinepalladium(0). 1,1'-Bis(diphenylphosphino)ferrocenedichloropalladium(II) dichloromethane adduct or tetrakistriphenylphosphinepalladium (0) is preferred.

The amount of the metal catalyst used in the coupling reaction is preferably 0.01 to 5 equivalents, more preferably 0.025 to 0.5 equivalents, with respect to the cyanopyridine derivative (XXXVII).

Examples of the base for use in the coupling reaction include: organic bases such as triethylamine and N,N-diisopropylethylamine; inorganic bases such as sodium carbonate, potassium carbonate and cesium carbonate; lithium amides such as lithium hexamethyldisilazide and lithium diisopropylamide; metal alkoxides such as sodium tert-butoxide and potassium tert-butoxide; and mixtures thereof.

An inorganic base such as sodium carbonate, potassium carbonate or cesium carbonate is preferred.

The amount of the base used in the coupling reaction is preferably 0.5 to 10 equivalents, more preferably 2 to 5 equivalents, with respect to the cyanopyridine derivative (XXXVII).

The reaction solvent for use in the coupling reaction is appropriately selected according to the type of the reagent used and the like and is not particularly limited as long as the solvent does not inhibit the reaction. Examples thereof include: ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; water; and mixed solvents thereof. An ether solvent such as tetrahydrofuran, 1,4-dioxane, ethylene glycol dimethyl ether or dimethoxyethane is preferred.

The reaction temperature of the coupling reaction is preferably 0 to 200° C., more preferably 50 to 150° C.

The reaction time of the coupling reaction is appropriately selected according to conditions such as the reaction temperature and is preferably 1 to 30 hours.

The alkyl metal derivative (XXXVIII) for use in the coupling reaction can be purchased or can be produced by a known method or a method equivalent thereto.

Step 3-8

The diphenylheteroarylmethylamine derivative (IX-c) can be obtained through the reduction reaction of diphenylpyridine derivative (XXXVI).

Examples of the reagent for use in the reduction reaction include lithium aluminum hydride, a borane-tetrahydrofuran complex, the combination of cobalt chloride and sodium borohydride and the combination of nickel chloride and sodium borohydride.

The amount of the reagent used in the reduction reaction is preferably 0.25 to 100 equivalents, more preferably 0.5 to 10 equivalents, with respect to the diphenylpyridine derivative (XXXVI).

The reaction solvent for use in the reduction reaction is appropriately selected according to the type of the reagent used and is not particularly limited as long as the solvent does not inhibit the reaction. Examples thereof include: ether solvents such as tetrahydrofuran, 1,4-dioxane, ethylene glycol dimethyl ether and dimethoxyethane; aromatic hydrocarbon solvents such as benzene and toluene; alcohol solvents such as methanol and ethanol; water; and mixed solvents thereof. An alcohol solvent such as methanol or ethanol is preferred.

The reaction temperature of the reduction reaction is preferably −78° C. to 100° C., more preferably −30° C. to 50° C.

The reaction time of the reduction reaction differs depending on reaction conditions and is preferably 10 minutes to 10 hours.

Step 3-9

The diphenylheteroarylmethylamine derivative (IX-c) can be obtained through the cycloaddition reaction of enamine derivative (XXXIII) with aminoacetamidine hydrobromide in the presence of a base.

The amount of the aminoacetamidine hydrobromide used in the cycloaddition reaction is preferably 0.5 to 100 equivalents, more preferably 1 to 10 equivalents, with respect to the enamine derivative (XXXIII).

Examples of the base for use in the cycloaddition reaction include: organic bases such as triethylamine, N,N-diisopropylethylamine and pyridine; inorganic bases such as sodium bicarbonate and potassium carbonate; metal alkoxides such as sodium methoxide, sodium ethoxide and potassium tert-butoxide; metal hydrides such as sodium hydride and potassium hydride; and mixtures thereof. A metal alkoxide such as sodium ethoxide or potassium tert-butoxide is preferred.

The reaction solvent for use in the cycloaddition reaction is appropriately selected according to the type of the reagent used and is not particularly limited as long as the solvent does not inhibit the reaction. Examples thereof include: alcohol solvents such as methanol, ethanol, isopropyl alcohol and tert-butyl alcohol; ether solvents such as tetrahydrofuran, 1,4-dioxane, ethylene glycol dimethyl ether and dimethoxyethane; nitrile solvents such as acetonitrile and propionitrile; aromatic hydrocarbon solvents such as benzene and toluene; aprotic polar solvents such as DMF, DMA and DMSO; and mixed solvents thereof. An alcohol solvent such as methanol, ethanol, isopropyl alcohol or tert-butyl alcohol is preferred.

The reaction temperature of the cycloaddition reaction is preferably −30° C. to 200° C., more preferably 0° C. to 100° C.

The reaction time of the cycloaddition reaction differs depending on reaction conditions and is preferably 1 to 30 hours.

Step 3-10

The guanidine derivative (XI-c) can be obtained through the guanidination reaction of diphenylheteroarylmethylamine derivative (IX-c) with guanidinating agent (X). The conditions of the reagent, the reaction solvent, the reaction temperature and the reaction time in this step are the same as in the step 1-7.

Step 3-11

The guanidine derivative (I-f) can be obtained through the deprotection reaction of guanidine derivative (XI-c) in the presence of an acid. The conditions of the reagent, the reaction solvent, the reaction temperature and the reaction time in this step are the same as in the step 1-8.

Step 3-12

The guanidine derivative (I-g) can be obtained through the hydration reaction of guanidine derivative (I-f) in the presence of an acid.

Examples of the acid for use in the hydration reaction include hydrochloric acid, a solution of 10% by weight of hydrogen chloride in methanol, a 4 mol/L solution of hydrogen chloride in ethyl acetate, a 4 mol/L solution of hydrogen chloride in 1,4-dioxane, trifluoroacetic acid and hydrofluoric acid.

The amount of the acid used in the hydration reaction is preferably 0.5 to 1000 equivalents, more preferably 1 to 100 equivalents, with respect to the guanidine derivative (I-f).

The reaction solvent for the hydration reaction is appropriately selected according to the type of the reagent used and the like and is not particularly limited as long as the solvent does not inhibit the reaction. Examples thereof include: ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; alcohol solvents such as methanol and ethanol; and mixed solvents thereof. An ester solvent such as ethyl acetate or propyl acetate, or an ether solvent such as diethyl ether, tetrahydrofuran, dimethoxyethane or 1,4-dioxane is preferred.

The reaction temperature of the hydration reaction is preferably −78° C. to 200° C., more preferably −20° C. to 100° C.

The reaction time of the hydration reaction differs depending on reaction conditions and is preferably 1 to 50 hours.

Production Method 4

Guanidine derivative (I-i) in which each of $R^1$ to $R^3$ in the guanidine derivative (I) is a hydrogen atom, or guanidine derivative (I-j) in which each of $R^4$ to $R^6$ in the guanidine derivative (I) is a hydrogen atom can be obtained by, for example, a method described in scheme 5.

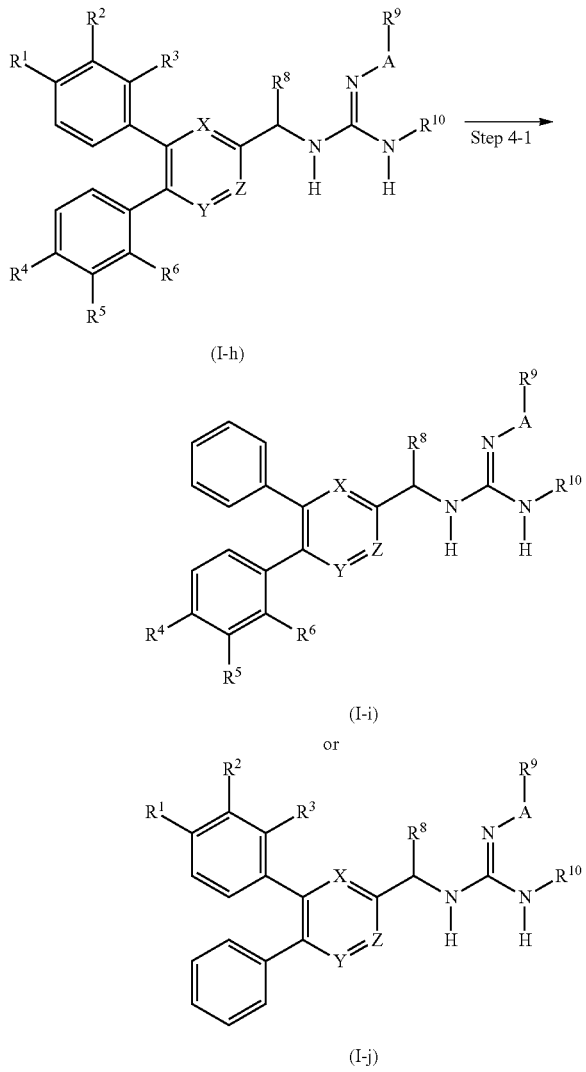

wherein each symbol is as defined above.

Step 4-1

The guanidine derivative (I-i) or the guanidine derivative (I-j) can be obtained through the reduction reaction of guanidine derivative (I-h) (wherein each of $R^1$ to $R^3$ is a hydrogen atom or a halogen atom, or each of $R^1$ to $R^6$ is a hydrogen atom or a halogen atom).

Examples of the catalyst for use in the reduction reaction include palladium carbon and platinum oxide.

The amount of the catalyst used in the reduction reaction is preferably 0.01 to 3 equivalents, more preferably 0.05 to 0.5 equivalents, with respect to the guanidine derivative (I-h).

The reaction solvent for use in the reduction reaction is appropriately selected according to the type of the reagent used and is not particularly limited as long as the solvent does not inhibit the reaction. Examples thereof include: protic polar solvents such as methanol, ethanol, isopropanol and tert-butanol; ether solvents such as diethyl ether, tetrahydrofuran, dimethoxyethane and 1,4-dioxane; ester solvents such as ethyl acetate and propyl acetate; chlorine solvents such as dichloromethane, chloroform and 1,2-dichloroethane; and mixed solvents thereof. A protic polar solvent such as methanol, ethanol, isopropanol or tert-butanol is preferred.

The reaction temperature of the reduction reaction is preferably 0 to 300° C., more preferably 10 to 70° C.

The reaction time of the reduction reaction differs depending on reaction conditions and is preferably 1 to 50 hours.

The medicament and the MALT1 inhibitor comprises the guanidine derivative (I) or the pharmacologically acceptable salt thereof as an active ingredient.

The "inhibition of MALT1" means the inhibition of the protease activity of MALT1.

The "MALT1 inhibitor" means a compound having an effect of inhibiting the protease activity of MALT1 and thereby deleting or attenuating the activity.

The "autoimmune disease" is a generic term for diseases in which due to excessive response of the immune system, the immune system of the body attacks even its own normal cells or tissues, causing symptoms. Examples thereof include psoriasis, multiple sclerosis, rheumatism, inflammatory bowel disease (e.g., ulcerative colitis), systemic lupus erythematosus, ankylosing spondylitis, uveitis and polymyalgia rheumatica.

The "allergic disease" is a generic term for diseases in which the immune system excessively responds to a particular antigen, causing symptoms. Examples thereof include contact dermatitis, atopic dermatitis, allergic dermatitis, allergic rhinitis, allergic conjunctivitis, allergic gastroenteritis, bronchial asthma, childhood asthma and food allergy.

The "psoriasis" is an inflammatory disease of the skin involving the invasion and activation of immunocytes, and acanthosis in association therewith. Typically, thickened white scales on red eruptions are widespread throughout the body, leading to a symptom called desquamation of peeling away the scales. Examples of the psoriasis include plaque psoriasis, pustular psoriasis, arthropathic psoriasis, guttate psoriasis and erythrodermic psoriasis.

The "atopic dermatitis" is a skin disease, most of patients of which have atopic disposition. The atopic dermatitis is characterized by systemic bilaterally symmetric eczema recurrent with exacerbation and remission. Examples thereof include diffuse neurodermatitis, atopic eczema, atopic neurodermatitis, acute infantile eczema, eczema at the bend, eczema on arms and legs in children, dry form of eczema in children, eczema in children, atopic dermatitis in adults, endogenous eczema, infantile dermatitis, and chronic infantile eczema.

The guanidine derivative (I) or the pharmacologically acceptable salt thereof suppresses the function of MALT1 by inhibiting the protease activity, i.e., substrate cleaving activity, of MALT1. Thus, the guanidine derivative (I) or the pharmacologically acceptable salt thereof can be used as a medicament for a disease in which the inhibition of the protease activity of MALT can be expected to achieve amelioration of its pathological condition or remission of its symptoms, particularly, as a therapeutic or prophylactic agent for autoimmune disease or allergic disease. The therapeutic or prophylactic agent for autoimmune disease can be suitably used as a therapeutic or prophylactic agent for psoriasis, multiple sclerosis or ulcerative colitis and can be more suitably used as a therapeutic or prophylactic agent for psoriasis. The therapeutic or prophylactic agent for allergic disease can be suitably used as a therapeutic or prophylactic agent for contact dermatitis or atopic dermatitis and can be more suitably used as a therapeutic or prophylactic agent for atopic dermatitis.

The effect of inhibiting the protease activity of MALT1 by the guanidine derivative (I) or the pharmacologically acceptable salt thereof can be evaluated by use of an in vitro test. Examples of the in vitro test include a method of evaluating the cleavage of a substrate (e.g., BCL10 protein) by MALT (Cancer Cell, 2012, Vol. 22, p. 825-837). Also, a NF-κB transcriptional activity inhibitory effect caused by the inhibition of the protease activity of MALT1 can be evaluated by use of reporter gene assay (International Publication No. WO 2009/065897).

The suppression of the function of MALT1 by the guanidine derivative (I) or the pharmacologically acceptable salt thereof can be evaluated by using the amount of IL-2 (interleukin-2) produced as an index in a lymphocyte line (e.g., Jurkat T cells). Examples of the method using IL-2 production as an index include a method of measuring IL-2 production induced in a MALT1-dependent manner by the co-stimulation of Jurkat T cells with phorbol 12-myristate 13-acetate and ionomycin or with CD3 and CD28 (Cancer Cell, 2012, Vol. 22, p. 825-837).

The effectiveness of the guanidine derivative (I) or the pharmacologically acceptable salt thereof for the treatment or prevention of autoimmune disease can be evaluated by use of a pathological model. Examples of the pathological model include imiquimod-induced psoriasis models (The Journal of Dermatological Science, 2013, Vol. 71, No. 1, p. 29-36), experimental autoimmune encephalomyelitis models (Journal of Neuroscience Research, 2006, Vol. 84, p. 1225-1234), collagen arthritis models (Annual Review of Immunology, 1984, Vol. 2, p. 199-218), sodium dextran sulfate-induced colitis models (Laboratory Investigation, 1993, Vol. 69, p. 238-249), spontaneous models of systemic lupus erythematosus (Nature, 2000, Vol. 404, p. 995-999), ankylosing spondylitis models (Arthritis Research & Therapy, 2012, Vol. 14, p. 253-265) and experimental autoimmune uveitis models (Journal of Immunology, 2006, Vol. 36, p. 3071-3081).

The effectiveness of the guanidine derivative (I) or the pharmacologically acceptable salt thereof for the treatment or prevention of allergic disease can be evaluated by use of a pathological model. Examples of the pathological model include oxazolone-induced atopic dermatitis models (Plos One, 2013, Vol. 8, No. 7, e6614; Journal of Investigative Dermatology, 2011, Vol. 131, No. 9, p. 1845-1852; and Journal of Allergy and Clinical Immunology, 2009, Vol. 124, No. 3, p. 496-506), dinitrofluorobenzene-induced contact dermatitis models (The Journal of Experimental Medicine, 2006, Vol. 203, p. 337-347), pollen-induced allergy models (Vaccine, 2003, Vol. 22, p. 87-95) and ovalbumin-induced asthma models (Nature Protocols, 2006, Vol. 1, p. 840-847). The oxazolone-induced atopic dermatitis models are general models of atopic dermatitis.

The effectiveness of the guanidine derivative (I) or the pharmacologically acceptable salt thereof for the treatment or prevention of autoimmune disease or allergic disease can be evaluated according to the in vitro test described above by using, as an index, for example, reduction in the protease activity of MALT1, reduction in NF-κB transcriptional activity caused by the inhibition of the protease activity of MALT, or reduction in the amount of IL-2 produced serving as an index for the function of MALT1. The effectiveness thereof for the treatment or prevention of psoriasis, one type of autoimmune disease, can be evaluated by use of the imiquimod-induced psoriasis models described above and can be evaluated by using, as an index, for example, reduction in the thickness of the auricle increased with the progression of symptoms in the psoriasis models. Also, the effectiveness thereof for the treatment or prevention of atopic dermatitis, one type of allergic disease, can be evaluated by use of the oxazolone-induced atopic dermatitis models described above and can be evaluated by using, as an index, for example, reduction in the thickness of the skin such as the auricle increased with the progression of symptoms in the atopic dermatitis models (Plos One, 2013, Vol. 8, No. 7, e6614; Journal of Investigative Dermatology, 2011, Vol. 131, No. 9, p. 1845-1852; and Journal of Allergy and Clinical Immunology, 2009, Vol. 124, No. 3, p. 496-506). The increased thickness of the skin such as the auricle reflects the hyperplasia of epidermal cells or the invasion of inflammatory cells. Therefore, the degree of the thickness of the skin such as the auricle indicates the degree of inflammation and the severity of atopic dermatitis.

The guanidine derivative (I) or the pharmacologically acceptable salt thereof can be used as a useful medicament (particularly, therapeutic or prophylactic agent for autoimmune disease or allergic disease) when administered to a mammal (e.g., a mouse, a rat, a hamster, a rabbit, a dog, a cat, a monkey, cattle, sheep or a human), particularly, a human. For clinical use of the guanidine derivative (I) or the pharmacologically acceptable salt thereof as a medicament, the guanidine derivative (I) or the pharmacologically acceptable salt thereof can be administered directly or as a pharmaceutical composition supplemented with a pharmacologically acceptable carrier. The medicament may be appropriately mixed, if necessary, with an additive such as a binder, an excipient, a lubricant, a disintegrant, a sweetener, a stabilizer, a corrigent, a flavor, a colorant, a fluidizer, a preservative, a buffer, a solubilizer, an emulsifier, a surfactant, a suspending agent, a diluent or a tonicity agent. Examples of the pharmacologically acceptable carrier include these additives. The medicament can be produced by a usual method appropriately using these pharmacologically acceptable carriers. Examples of the dosage form of the medicament include: oral formulations based on tablets, capsules, granules, powders and syrups; parenteral formulations based on inhalants, injections, suppositories and solutions; and ointments, creams and patches for local administration. Alternatively, a known sustained-release preparation may be prepared.

The medicament contains preferably 0.00001 to 90% by weight, more preferably 0.01 to 70% by weight, of the guanidine derivative (I) or the pharmacologically acceptable salt thereof. The dose is appropriately selected according to the symptoms, age and body weight of a patient, and an administration method. The amount of the active ingredient per day in an adult is preferably 0.1 µg to 1 g for an injection, 1 µg to 10 g for an oral formulation, or 1 µg to 10 g for a patch, each which can be administered once or several divided times.

Examples of the binder include syrup, gelatin, gum arabic, sorbitol, polyvinyl chloride and tragacanth.

Examples of the excipient include sugar, lactose, corn starch, calcium phosphate, sorbitol and glycine.

Examples of the lubricant include magnesium stearate, calcium stearate, polyethylene glycol, talc and silica.

Examples of the disintegrant include starch and calcium carbonate.

Examples of the sweetener include glucose, fructose, inverted sugar, sorbitol, xylitol, glycerin and simple syrup.

The medicament may be supplemented with or used in combination with an appropriate amount of an additional drug to complement or enhance the therapeutic or prophylactic effect thereof or to reduce the dose.

EXAMPLES

Hereinafter, our methods and derivatives will be described in detail with reference to Examples and Reference Examples. However, this disclosure is not limited by the examples.

Commercially available compounds were used as compounds used in the synthesis of compounds of Examples unless their synthesis methods are described. In Examples and Reference Examples given below, the term "room temperature" usually denotes approximately 10 to approximately 35° C. The name of a solvent described in NMR data denotes the solvent used in measurement. 400 MHz NMR spectra were measured using a nuclear magnetic resonance apparatus model JNM-ECS400 or a nuclear magnetic resonance apparatus model JNM-ECZ400S (JEOL Ltd.). Chemical shifts were indicated by δ (unit: ppm) based on tetramethylsilane. Signals were each indicated by s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), or tt (triple triplet). In $^1$H-NMR, data was not described if a proton of a hydroxy group, an amino group, a carboxyl group, or the like exhibited a very gentle peak. ESI-MS spectra were measured using Agilent Technologies 1200 Series, G6130A (Agilent Technologies, Inc.). The silica gel used was silica gel 60 (Merck KGaA). The aminesilica gel used was aminesilica gel DM1020 (Fuji Silysia Chemical Ltd.). The flash chromatography used was YFLCW-prep2XY (Yamazen Corp.). The microwave synthesis apparatus used was Monowave 300 (Anton Paar GmbH).

Reference Example 1 Synthesis of (5-bromo-6-chloropyridin-3-yl)methanol

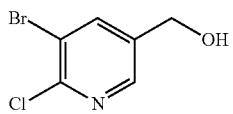

Methyl 5-bromo-6-chloronicotinate (15.0 g) was dissolved in tetrahydrofuran (150 mL). To the solution, a 1 mol/L solution of diisobutyl aluminum hydride in toluene (150 mL) was then gradually added at −78° C. The reaction mixture was warmed to 0° C. and then stirred for 1.5 hours. Under ice cooling, a saturated aqueous solution of potassium sodium tartrate (150 mL) was added to the reaction mixture, and the mixture was stirred at room temperature for 1 hour. The reaction mixture was concentrated under reduced pressure, followed by extraction with ethyl acetate. The organic layer was washed with saturated saline, dried over anhydrous sodium sulfate, and then concentrated under reduced pressure to obtain the title compound (13.0 g) as a white solid.

$^1$H-NMR (DMSO-$d_6$) δ: 4.54 (2H, d, J=5.0 Hz), 5.52 (1H, t, J=5.0 Hz), 8.15-8.16 (1H, m), 8.37-8.38 (1H, m).

MS (ESI) [M+H]+: 222.

Reference Example 2 Synthesis of 3-bromo-2-chloro-5-(chloromethyl)pyridine

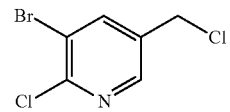

(5-Bromo-6-chloropyridin-3-yl)methanol (13.0 g) synthesized in Reference Example 1 was dissolved in dichloromethane (100 mL). To the solution, thionyl chloride (13.1 mL) was then added at 0° C. The reaction mixture was warmed to room temperature, stirred for 3 hours, and then concentrated under reduced pressure. Toluene was added to the residue, and the mixture was concentrated again under reduced pressure to obtain the title compound (14.1 g) as a white solid.

$^1$H-NMR (CDCl$_3$) δ: 4.55 (2H, s), 8.01 (1H, d, J=2.3 Hz), 8.35 (1H, d, J=2.3 Hz).

MS (ESI) [M+H]$^+$: 240.

Reference Example 3 Synthesis of 2-((5-bromo-6-chloro-pyridin-3-yl)methyl)isoindoline-1,3-dione

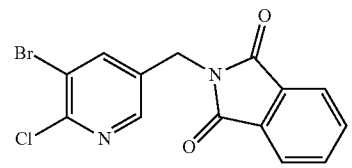 [SMILES: O=C1c2ccccc2C(=O)N1Cc1cnc(Cl)c(Br)c1]

3-Bromo-2-chloro-5-(chloromethyl)pyridine (14.1 g) synthesized in Reference Example 2 and potassium phthalimide (12.2 g) were dissolved in DMF (100 mL), and then, the solution was stirred at 40° C. for 1 hour. The reaction mixture was cooled to room temperature, and then, water was added thereto. The precipitated solid was filtered and washed with n-hexane/ethyl acetate (1/1, v/v). The obtained solid was dried under reduced pressure in the presence of diphosphorus pentoxide to obtain the title compound (18.6 g) as a white solid.

$^1$H-NMR (CDCl$_3$) δ: 4.82 (2H, s), 7.74-7.78 (2H, m), 7.87-7.89 (2H, m), 8.03 (1H, d, J=2.3 Hz), 8.45 (1H, d, J=2.3 Hz).

MS (ESI) [M+H]$^+$: 351.

Reference Example 4 Synthesis of 2-((6-chloro-5-(4-chlorophenyl)pyridin-3-yl)methyl)isoindoline-1, 3-dione

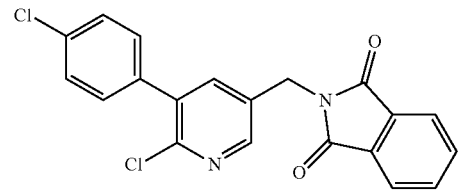 [SMILES: O=C1c2ccccc2C(=O)N1Cc1cnc(Cl)c(-c2ccc(Cl)cc2)c1]

2-((5-Bromo-6-chloro-pyridin-3-yl)methyl)isoindoline-1,3-dione (14.0 g) synthesized in Reference Example 3, 4-chlorophenylboronic acid (6.9 g), potassium carbonate (33.0 g) and [1,1'-bis(diphenylphosphino)ferrocene]palladium(II) dichloride dichloromethane adduct (0.65 g) were suspended in 1,4-dioxane (200 mL). The system was purged with argon, and then, the suspension was stirred at 80° C. for 7 hours. The reaction mixture was cooled to room temperature and then filtered through celite, and the filtrate was concentrated under reduced pressure. The obtained crude product was dissolved in a small amount of chloroform, and then, the solution was recrystallized by addition of n-hexane/ethyl acetate (1/1, v/v) with stirring to obtain the title compound (14.2 g) as a white solid.

$^1$H-NMR (CDCl$_3$) δ: 4.88 (2H, s), 7.36 (2H, d, J=8.6 Hz), 7.42 (2H, d, J=8.6 Hz), 7.73-7.76 (3H, m), 7.84-7.89 (2H, m), 8.50 (1H, d, J=2.3 Hz).

MS (ESI) [M+H]$^+$: 383.

Reference Example 5 Synthesis of 2-((6-chloro-5-phenylpyridin-3-yl)methyl)isoindoline-1,3-dione

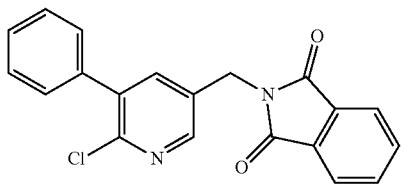 [SMILES: O=C1c2ccccc2C(=O)N1Cc1cnc(Cl)c(-c2ccccc2)c1]

The title compound (0.14 g) was obtained in the same way as in Reference Example 4 using 2-((5-bromo-6-chloro-pyridin-3-yl)methyl)isoindoline-1,3-dione (0.20 g) synthesized in Reference Example 3 and phenylboronic acid (0.076 g).

$^1$H-NMR (CDCl$_3$) δ: 4.88 (2H, s), 7.41-7.45 (5H, m), 7.74 (2H, m), 7.75 (1H, d, J=2.4 Hz), 7.86 (2H, m), 8.49 (1H, d, J=2.4 Hz).

MS (ESI) [M+H]$^+$: 349.

Reference Example 6 Synthesis of 2-((6-chloro-5-(3-chlorophenyl)pyridin-3-yl)methyl)isoindoline-1,3-dione

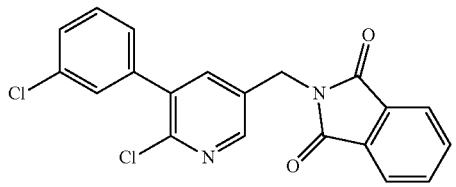 [SMILES: O=C1c2ccccc2C(=O)N1Cc1cnc(Cl)c(-c2cccc(Cl)c2)c1]

The title compound (0.17 g) was obtained in the same way as in Reference Example 4 using 2-((5-bromo-6-chloro-pyridin-3-yl)methyl)isoindoline-1,3-dione (0.20 g) synthesized in Reference Example 3 and 3-chlorophenylboronic acid (0.093 g).

$^1$H-NMR (CDCl$_3$) δ: 4.88 (2H, s), 7.29-7.32 (1H, m), 7.38-7.41 (3H, m), 7.73-7.75 (3H, m), 7.87 (2H, m), 8.52 (1H, d, J=2.4 Hz).

MS (ESI) [M+H]$^+$: 383.

Reference Example 7 Synthesis of 2-((6-chloro-5-(2-chlorophenyl)pyridin-3-yl)methyl)isoindoline-1,3-dione

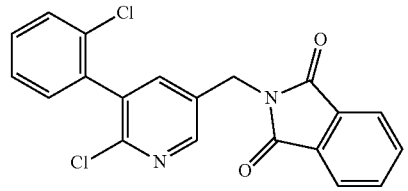 [SMILES: O=C1c2ccccc2C(=O)N1Cc1cnc(Cl)c(-c2ccccc2Cl)c1]

The title compound (0.20 g) was obtained in the same way as in Reference Example 4 using 2-((5-bromo-6-chloro-pyridin-3-yl)methyl)isoindoline-1,3-dione (0.20 g) synthesized in Reference Example 3 and 2-chlorophenylboronic acid (0.093 g).

$^1$H-NMR (CDCl$_3$) δ: 4.89 (2H, s), 7.24-7.26 (1H, m), 7.31-7.39 (2H, m), 7.49 (1H, m), 7.72 (1H, d, J=2.2 Hz), 7.74 (2H, m), 7.87 (2H, m), 8.55 (1H, d, J=2.4 Hz).

MS (ESI) [M+H]$^+$: 383.

Reference Example 8 Synthesis of 2-((6-chloro-5-(4-methylphenyl)pyridin-3-yl)methyl)isoindoline-1,3-dione

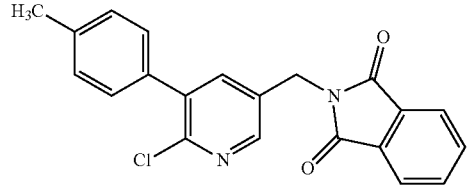 [SMILES: Cc1ccc(-c2cc(CN3C(=O)c4ccccc4C3=O)cnc2Cl)cc1]

The title compound (0.51 g) was obtained in the same way as in Reference Example 4 using 2-((5-bromo-6-chloro-pyridin-3-yl)methyl)isoindoline-1,3-dione (0.80 g) synthesized in Reference Example 3 and 4-methylphenylboronic acid (0.37 g).

$^1$H-NMR (CDCl$_3$) δ: 2.41 (3H, s), 4.88 (2H, s), 7.25 (2H, d, J=8.2 Hz), 7.33 (2H, d, J=8.2 Hz), 7.73 (3H, m), 7.86 (2H, dd, J=5.4, 3.2 Hz), 8.47 (1H, d, J=2.3 Hz).

MS (ESI) [M+H]$^+$: 363.

Reference Example 9 Synthesis of 2-((6-chloro-5-(4-methoxyphenyl)pyridin-3-yl)methyl)isoindoline-1,3-dione

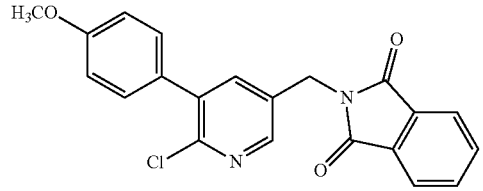 [SMILES: COc1ccc(-c2cc(CN3C(=O)c4ccccc4C3=O)cnc2Cl)cc1]

The title compound (0.84 g) was obtained in the same way as in Reference Example 4 using 2-((5-bromo-6-chloro-pyridin-3-yl)methyl)isoindoline-1,3-dione (1.0 g) synthesized in Reference Example 3 and 4-methoxyphenylboronic acid (0.45 g).

$^1$H-NMR (CDCl$_3$) δ: 3.86 (3H, s), 4.87 (2H, s), 6.97 (2H, d, J=8.8 Hz), 7.37 (2H, d, J=8.8 Hz), 7.73 (3H, dd, J=5.4, 3.2 Hz), 7.86 (2H, dd, J=5.4, 3.2 Hz), 8.46 (1H, d, J=2.4 Hz).
MS (ESI) [M+H]$^+$: 379.

Reference Example 10 Synthesis of 2-((6-chloro-5-(4-cyanophenyl)pyridin-3-yl)methyl)isoindoline-1,3-dione

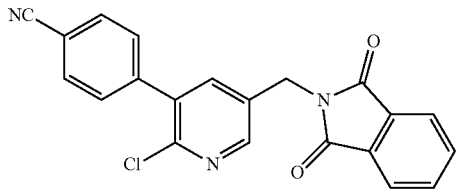 [SMILES: N#Cc1ccc(-c2cc(CN3C(=O)c4ccccc4C3=O)cnc2Cl)cc1]

The title compound (0.30 g) was obtained in the same way as in Reference Example 4 using 2-((5-bromo-6-chloropyridin-3-yl)methyl)isoindoline-1,3-dione (0.80 g) synthesized in Reference Example 3 and 4-cyanophenylboronic acid (0.37 g).
$^1$H-NMR (CDCl$_3$) δ: 4.89 (2H, s), 7.55 (2H, d, J=8.6 Hz), 7.74-7.76 (5H, m), 7.87 (2H, dd, J=5.4, 3.2 Hz), 8.56 (1H, d, J=2.7 Hz).
MS (ESI) [M+H]$^+$: 374.

Reference Example 11 Synthesis of 2-((6-chloro-5-(4-fluorophenyl)pyridin-3-yl)methyl)isoindoline-1,3-dione

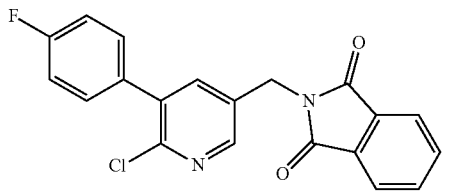 [SMILES: O=C1c2ccccc2C(=O)N1Cc1cnc(Cl)c(-c2ccc(F)cc2)c1]

The title compound (0.32 g) was obtained in the same way as in Reference Example 4 using 2-((5-bromo-6-chloropyridin-3-yl)methyl)isoindoline-1,3-dione (0.50 g) synthesized in Reference Example 3 and 4-fluorophenylboronic acid (0.22 g).
$^1$H-NMR (CDCl$_3$) δ: 4.88 (2H, s), 7.11-7.16 (2H, m), 7.38-7.42 (2H, m), 7.73-7.76 (3H, m), 7.84-7.88 (2H, m), 8.49 (1H, d, J=2.7 Hz).
MS (ESI) [M+H]$^+$: 367.

Reference Example 12 Synthesis of 2-((6-chloro-5-(4-(trifluoromethyl)phenyl)pyridin-3-yl)methyl)isoindoline-1,3-dione

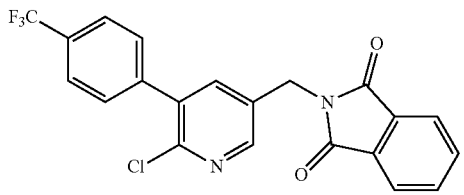 [SMILES: O=C1c2ccccc2C(=O)N1Cc1cnc(Cl)c(-c2ccc(C(F)(F)F)cc2)c1]

The title compound (1.7 g) was obtained in the same way as in Reference Example 4 using 2-((5-bromo-6-chloropyridin-3-yl)methyl)isoindoline-1,3-dione (2.0 g) synthesized in Reference Example 3 and 4-trifluoromethylphenylboronic acid (1.2 g).
$^1$H-NMR (CDCl$_3$) δ:4.89 (2H, s), 7.55 (2H, d, J=8.2 Hz), 7.71 (2H, d, J=8.2 Hz), 7.73-7.76 (3H, m), 7.87 (2H, dd, J=5.7, 2.9 Hz), 8.54 (1H, d, J=2.3 Hz).
MS (ESI) [M+H]$^+$: 417.

Reference Example 13 Synthesis of 2-((6-chloro-5-(4-(trifluoromethoxy)phenyl)pyridin-3-yl)methyl)isoindoline-1,3-dione

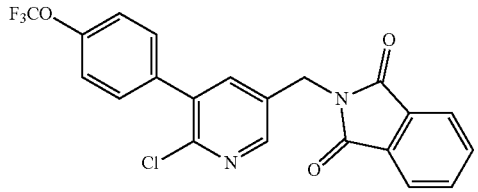 [SMILES: O=C1c2ccccc2C(=O)N1Cc1cnc(Cl)c(-c2ccc(OC(F)(F)F)cc2)c1]

The title compound (0.34 g) was obtained in the same way as in Reference Example 4 using 2-((5-bromo-6-chloropyridin-3-yl)methyl)isoindoline-1,3-dione (0.50 g) synthesized in Reference Example 3 and 4-trifluoromethoxyphenylboronic acid (0.32 g).
$^1$H-NMR (CDCl$_3$) δ: 4.88 (2H, s), 7.29 (2H, d, J=8.6 Hz), 7.46 (2H, d, J=8.6 Hz), 7.73-7.76 (3H, m), 7.85-7.88 (2H, m), 8.51 (1H, d, J=2.3 Hz).
MS (ESI) [M+H]$^+$: 433.

Reference Example 14 Synthesis of 2-((6-chloro-5-(4-isopropoxyphenyl)pyridin-3-yl)methyl)isoindoline-1,3-dione

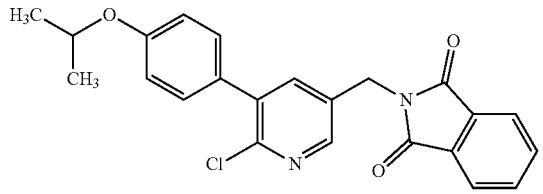 [SMILES: CC(C)Oc1ccc(-c2cc(CN3C(=O)c4ccccc4C3=O)cnc2Cl)cc1]

The title compound (0.31 g) was obtained in the same way as in Reference Example 4 using 2-((5-bromo-6-chloropyridin-3-yl)methyl)isoindoline-1,3-dione (0.50 g) synthesized in Reference Example 3 and 4-isopropoxyphenylboronic acid (0.28 g).
$^1$H-NMR (CDCl$_3$) δ:1.37 (6H, d, J=7.8), 4.57-4.63 (1H, m), 4.87 (2H, s), 6.94 (2H, dt, J=9.4, 2.5 Hz), 7.35 (2H, dt, J=9.4, 2.5 Hz), 7.71-7.76 (3H, m), 7.84-7.88 (2H, m), 8.45 (1H, d, J=2.3 Hz).
MS (ESI) [M+H]$^+$: 407.

Reference Example 15 Synthesis of 2-((5,6-bis(4-chlorophenyl)pyridin-3-yl)methyl)isoindoline-1,3-dione

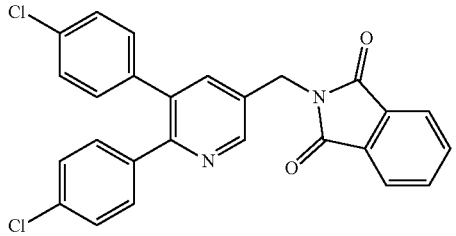

2-((6-Chloro-5-(4-chlorophenyl)pyridin-3-yl)methyl)isoindoline-1,3-dione (1.0 g) synthesized in Reference Example 4, 4-chlorophenylboronic acid (0.82 g), potassium carbonate (1.1 g) and tetrakistriphenylphosphinepalladium (0) (0.30 g) were suspended in 1,4-dioxane (26 mL). The system was purged with argon, and then, the suspension was stirred at 100° C. for 16 hours. The reaction mixture was cooled to room temperature and then filtered through celite, and the filtrate was concentrated under reduced pressure. The obtained crude product was purified by silica gel column chromatography (n-hexane/ethyl acetate) to obtain the title compound (1.0 g).

$^1$H-NMR (CDCl$_3$) δ: 4.94 (2H, s), 7.07 (2H, d, J=8.2 Hz), 7.20-7.28 (6H, m), 7.73-7.75 (3H, m), 7.85-7.89 (2H, m), 8.78 (1H, d, J=2.3 Hz).

MS (ESI) [M+H]$^+$: 459.

Reference Example 16 Synthesis of 2-((5-(4-chlorophenyl)-6-phenylpyridin-3-yl)methyl)isoindoline-1,3-dione

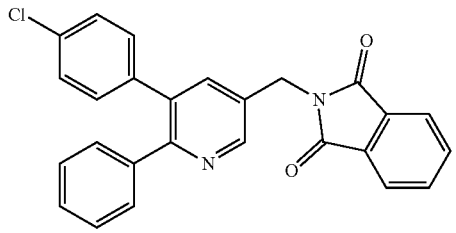

2-((6-Chloro-5-(4-chlorophenyl)pyridin-3-yl)methyl)isoindoline-1,3-dione (0.10 g) synthesized in Reference Example 4, phenylboronic acid (0.064 g), potassium carbonate (0.11 g) and [1,1'-bis(diphenylphosphino)ferrocene]palladium(II) dichloride dichloromethane adduct (0.021 g) were suspended in 1,4-dioxane (1.3 mL). The system was purged with argon, and then, the suspension was stirred at 100° C. for 17 hours. The reaction mixture was cooled to room temperature and then filtered through celite, and the filtrate was concentrated under reduced pressure. The obtained crude product was purified by silica gel column chromatography (n-hexane/ethyl acetate) to obtain the title compound (0.060 g).

$^1$H-NMR (CDCl$_3$) δ:4.95 (2H, s), 7.08 (2H, dd, J=6.6, 2.0 Hz), 7.22-7.31 (6H, m), 7.72-7.76 (3H, m), 7.85-7.88 (2H, m), 8.79 (1H, d, J=2.2 Hz).

MS (ESI) [M+H]$^+$: 425.

Reference Example 17 Synthesis of 2-((6-(3-chlorophenyl)-5-(4-chlorophenyl)pyridin-3-yl)methyl)isoindoline-1,3-dione

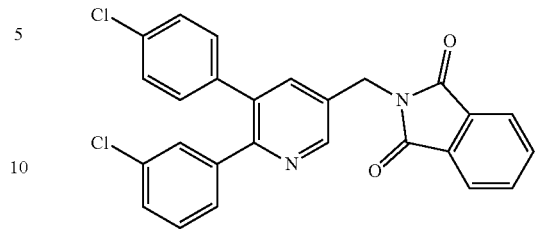

The title compound (0.10 g) was obtained in the same way as in Reference Example 15 using 2-((6-chloro-5-(4-chlorophenyl)pyridin-3-yl)methyl)isoindoline-1,3-dione (0.10 g) synthesized in Reference Example 4 and 3-chlorophenylboronic acid (0.082 g).

$^1$H-NMR (CDCl$_3$) δ: 4.95 (2H, s), 7.03-7.14 (4H, m), 7.22-7.28 (3H, m), 7.43 (1H, t, J=1.8 Hz), 7.73-7.77 (3H, m), 7.86-7.89 (2H, m), 8.78 (1H, d, J=2.3 Hz).

MS (ESI) [M+H]$^+$: 459.

Reference Example 18 Synthesis of 2-((5-(4-chlorophenyl)-6-(4-methylphenyl)pyridin-3-yl)methyl)isoindoline-1,3-dione

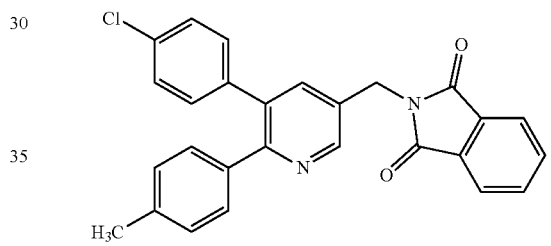

The title compound (0.22 g) was obtained in the same way as in Reference Example 15 using 2-((6-chloro-5-(4-chlorophenyl)pyridin-3-yl)methyl)isoindoline-1,3-dione (0.20 g) synthesized in Reference Example 4 and 4-methylphenylboronic acid (0.14 g).

$^1$H-NMR (CDCl$_3$) δ: 2.31 (3H, s), 4.93 (2H, s), 7.04 (2H, d, J=7.8 Hz), 7.09 (2H, dt, J=8.9, 2.3 Hz), 7.16-7.20 (2H, m), 7.22-7.25 (2H, m), 7.71-7.75 (3H, m), 7.87 (2H, ddd, J=11.5, 6.1, 2.2 Hz), 8.77 (1H, d, J=2.2 Hz).

MS (ESI) [M+H]$^+$: 439.

Reference Example 19 Synthesis of 2-((5-(4-chlorophenyl)-6-(4-methoxyphenyl)pyridin-3-yl)methyl)isoindoline-1,3-dione

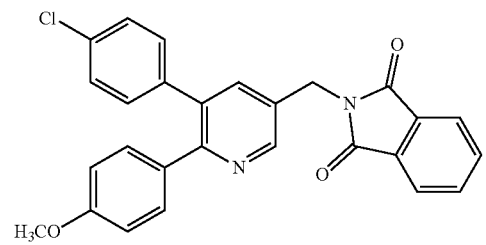

The title compound (0.046 g) was obtained in the same way as in Reference Example 15 using 2-((6-chloro-5-(4-chlorophenyl)pyridin-3-yl)methyl)isoindoline-1,3-dione (0.050 g) synthesized in Reference Example 4 and 4-methoxyphenylboronic acid (0.040 g).

$^1$H-NMR (CDCl$_3$) δ: 3.78 (3H, s), 4.93 (2H, s), 6.77 (2H, d, J=8.2 Hz), 7.09 (2H, d, J=7.7 Hz), 7.23-7.26 (4H, m), 7.71-7.75 (3H, m), 7.85-7.88 (2H, m), 8.75 (1H, d, J=1.8 Hz).

MS (ESI) [M+H]$^+$: 455.

Reference Example 20 Synthesis of 2-((5-(4-chlorophenyl)-6-(4-cyanophenyl)pyridin-3-yl)methyl)isoindoline-1,3-dione

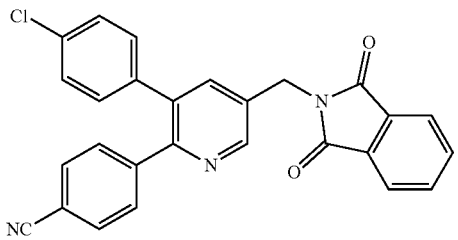

The title compound (0.12 g) was obtained in the same way as in Reference Example 15 using 2-((6-chloro-5-(4-chlorophenyl)pyridin-3-yl)methyl)isoindoline-1,3-dione (0.30 g) synthesized in Reference Example 4 and 4-cyanophenylboronic acid (0.17 g).

$^1$H-NMR (CDCl$_3$) δ: 4.94 (2H, s), 7.03 (2H, d, J=8.6 Hz), 7.25 (2H, d, J=8.2 Hz), 7.40 (2H, d, J=8.6 Hz), 7.52 (2H, d, J=8.2 Hz), 7.72 (2H, m), 7.77 (1H, d, J=2.3 Hz), 7.85 (2H, m), 8.78 (1H, d, J=2.3 Hz).

MS (ESI) [M+H]$^+$: 450.

Reference Example 21 Synthesis of 2-((5-(4-chlorophenyl)-6-(4-fluorophenyl)pyridin-3-yl)methyl)isoindoline-1,3-dione

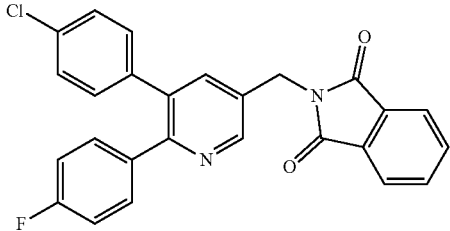

The title compound (0.32 g) was obtained in the same way as in Reference Example 15 using 2-((6-chloro-5-(4-chlorophenyl)pyridin-3-yl)methyl)isoindoline-1,3-dione (0.30 g) synthesized in Reference Example 4 and 4-fluorophenylboronic acid (0.16 g).

$^1$H-NMR (CDCl$_3$) δ:4.94 (2H, s), 6.91-6.95 (2H, m), 7.07 (2H, dt, J=8.8, 2.3 Hz), 7.24-7.30 (4H, m), 7.72-7.75 (3H, m), 7.85-7.88 (2H, m), 8.77 (1H, d, J=1.8 Hz).

MS (ESI) [M+H]$^+$: 443.

Reference Example 22 Synthesis of 2-((5-(4-chlorophenyl)-6-(3-fluorophenyl)pyridin-3-yl)methyl)isoindoline-1,3-dione

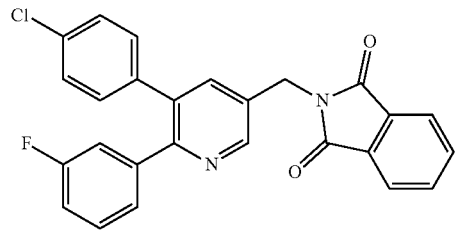 [SMILES: O=C1c2ccccc2C(=O)N1Cc1cnc(-c2cccc(F)c2)c(-c2ccc(Cl)cc2)c1]

The title compound (0.12 g) was obtained in the same way as in Reference Example 15 using 2-((6-chloro-5-(4-chlorophenyl)pyridin-3-yl)methyl)isoindoline-1,3-dione (0.10 g) synthesized in Reference Example 4 and 3-fluorophenylboronic acid (0.073 g).

$^1$H-NMR (CDCl$_3$) δ: 4.95 (2H, s), 6.96 (1H, m), 7.01 (1H, m), 7.06-7.10 (3H, m), 7.16-7.21 (1 H, m), 7.24-7.27 (2H, m), 7.72-7.77 (3H, m), 7.88 (2H, dd, J=5.4, 2.7 Hz), 8.78 (1H, d, J=2.3 Hz).

MS (ESI) [M+H]$^+$: 443.

Reference Example 23 Synthesis of 2-((5-(4-chlorophenyl)-6-(4-(trifluoromethyl)phenyl)pyridin-3-yl)methyl)isoindoline-1,3-dione

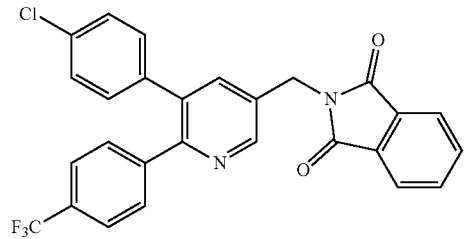

The title compound (0.32 g) was obtained in the same way as in Reference Example 15 using 2-((6-chloro-5-(4-chlorophenyl)pyridin-3-yl)methyl)isoindoline-1,3-dione (0.51 g) synthesized in Reference Example 4 and 4-trifluoromethylphenylboronic acid (0.38 g).

$^1$H-NMR (CDCl$_3$) δ: 4.96 (2H, s), 7.05-7.09 (2H, m), 7.25-7.28 (2H, m), 7.43 (2H, d, J=7.6 Hz), 7.51 (2H, d, J=8.3 Hz), 7.72-7.78 (3H, m), 7.85-7.89 (2H, m), 8.80 (1H, d, J=2.0 Hz).

MS (ESI) [M+H]$^+$: 493.

Reference Example 24 Synthesis of 2-((5-(4-chlorophenyl)-6-(4-(trifluoromethoxy)phenyl)pyridin-3-yl)methyl)isoindoline-1,3-dione

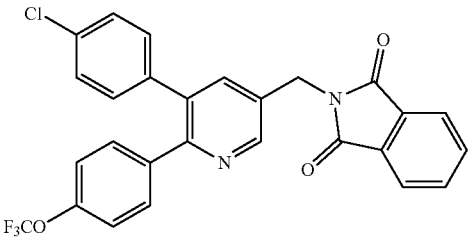

The title compound (0.62 g) was obtained in the same way as in Reference Example 15 using 2-((6-chloro-5-(4-chlorophenyl)pyridin-3-yl)methyl)isoindoline-1,3-dione (0.60 g) synthesized in Reference Example 4 and 4-trifluoromethoxyphenylboronic acid (0.65 g).

$^1$H-NMR (CDCl$_3$) δ: 4.95 (2H, s), 7.08-7.15 (4H, m), 7.24-7.27 (2H, m), 7.32-7.35 (2H, m), 7.74 (2H, m), 7.76 (1H, d, J=1.8 Hz), 7.87 (2H, m), 8.78 (1H, d, J=1.8 Hz).
MS (ESI) [M+H]$^+$: 509.

Reference Example 25 Synthesis of 2-((5-(4-chlorophenyl)-6-(3-fluoro-4-methylphenyl)pyridin-3-yl)methyl)isoindoline-1,3-dione

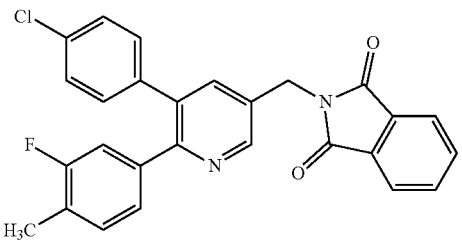 [SMILES: O=C1c2ccccc2C(=O)N1Cc1cnc(-c2ccc(C(F)(F)F)cc2)c(-c2ccc(Cl)cc2)c1]

The title compound (0.19 g) was obtained in the same way as in Reference Example 15 using 2-((6-chloro-5-(4-chlorophenyl)pyridin-3-yl)methyl)isoindoline-1,3-dione (0.20 g) synthesized in Reference Example 4 and 3-fluoro-4-methylphenylboronic acid (0.16 g).

$^1$H-NMR (CDCl$_3$) δ: 2.23 (3H, d, J=1.4 Hz), 4.94 (2H, s), 6.90 (1H, dd, J=7.8, 1.4 Hz), 7.02 (2H, m), 7.09 (2H, m), 7.24-7.27 (2H, m), 7.74 (3H, m), 7.85-7.88 (2H, m), 8.77 (1H, d, J=2.3 Hz).
MS (ESI) [M+H]$^+$: 457.

Reference Example 26 Synthesis of 2-((5-(4-chlorophenyl)-6-(2-fluoro-4-methylphenyl)pyridin-3-yl)methyl)isoindoline-1,3-dione

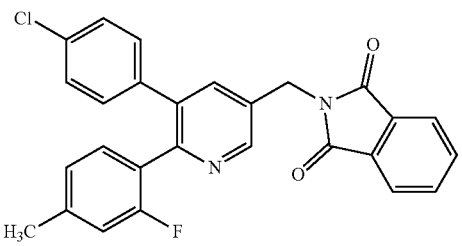 [SMILES: Cc1ccc(-c2ncc(CN3C(=O)c4ccccc4C3=O)cc2-c2ccc(Cl)cc2)c(F)c1]

The title compound (0.24 g) was obtained in the same way as in Reference Example 15 using 2-((6-chloro-5-(4-chlorophenyl)pyridin-3-yl)methyl)isoindoline-1,3-dione (0.20 g) synthesized in Reference Example 4 and 2-fluoro-4-methylphenylboronic acid (0.16 g).

$^1$H-NMR (CDCl$_3$) δ: 2.32 (3H, s), 4.95 (2H, s), 6.68 (1H, d, J=11.0 Hz), 6.95 (1H, dd, J=7.8, 0.9 Hz), 7.07 (2H, m), 7.21 (2H, m), 7.29 (1H, d, J=7.8 Hz), 7.72-7.76 (2H, m), 7.78 (1H, d, J=2.3 Hz), 7.85-7.89 (2H, m), 8.79 (1H, d, J=2.3 Hz).
MS (ESI) [M+H]$^+$: 457.

Reference Example 27 Synthesis of 2-((6-(4-chloro-2-methoxyphenyl)-5-(4-chlorophenyl)pyridin-3-yl)methyl)isoindoline-1,3-dione

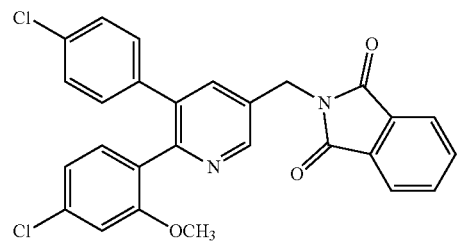 [SMILES: COc1cc(Cl)ccc1-c1ncc(CN2C(=O)c3ccccc3C2=O)cc1-c1ccc(Cl)cc1]

The title compound (0.32 g) was obtained in the same way as in Reference Example 15 using 2-((6-chloro-5-(4-chlorophenyl)pyridin-3-yl)methyl)isoindoline-1,3-dione (0.40 g) synthesized in Reference Example 4 and 4-chloro-2-methoxyphenylboronic acid (0.39 g).

$^1$H-NMR (CDCl$_3$) δ: 3.28 (3H, s), 4.95 (2H, s), 6.66 (1H, d, J=1.8 Hz), 6.99 (1H, dd, J=8.2, 1.8 Hz), 7.03 (2H, m), 7.20 (2H, m), 7.32 (1H, d, J=8.2 Hz), 7.72-7.77 (3H, m), 7.87 (2H, m), 8.77 (1H, d, J=2.3 Hz).
MS (ESI) [M+H]$^+$: 489.

Reference Example 28 Synthesis of 2-((6-(4-chlorophenyl)-5-phenylpyridin-3-yl)methyl)isoindoline-1,3-dione

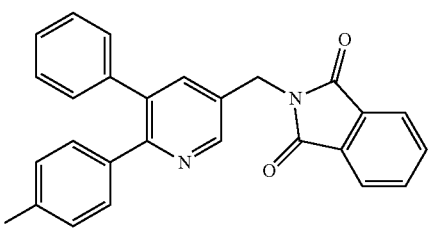

The title compound (0.15 g) was obtained in the same way as in Reference Example 15 using 2-((6-chloro-5-phenylpyridin-3-yl)methyl)isoindoline-1,3-dione (0.13 g) synthesized in Reference Example 5 and 4-chlorophenylboronic acid (0.12 g).

$^1$H-NMR (CDCl$_3$) δ: 4.95 (2H, s), 7.14 (2H, dd, J=6.6, 2.9 Hz), 7.18 (2H, d, J=8.8 Hz), 7.24-7.29 (5H, m), 7.73 (2H, dd, J=5.5, 3.0 Hz), 7.77 (1H, d, J=2.2 Hz), 7.87 (2H, dd, J=5.5, 3.0 Hz), 8.77 (1H, d, J=2.0 Hz).
MS (ESI) [M+H]$^+$: 425.

Reference Example 29 Synthesis of 2-((5-(3-chlorophenyl)-6-(4-chlorophenyl)pyridin-3-yl)methyl)isoindoline-1,3-dione

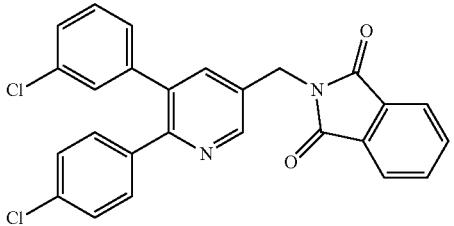 [SMILES: O=C1c2ccccc2C(=O)N1Cc1cnc(-c2ccc(Cl)cc2)c(-c2cccc(Cl)c2)c1]

The title compound (0.083 g) was obtained in the same way as in Reference Example 15 using 2-((6-chloro-5-(3-chlorophenyl)pyridin-3-yl)methyl)isoindoline-1,3-dione (0.12 g) synthesized in Reference Example 6 and 4-chlorophenylboronic acid (0.088 g).

$^1$H-NMR (CDCl$_3$) δ: 4.95 (2H, s), 6.95 (1H, dt, J=7.6, 1.3 Hz), 7.16-7.28 (7H, m), 7.73-7.76 (3H, m), 7.86-7.89 (2H, m), 8.79 (1H, d, J=2.0 Hz).

MS (ESI) [M+H]$^+$: 459.

Reference Example 30 Synthesis of 2-((5-(2-chlorophenyl)-6-(4-chlorophenyl)pyridin-3-yl)methyl)isoindoline-1,3-dione

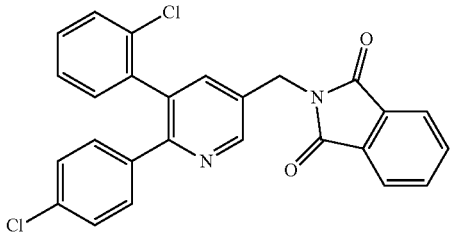 [SMILES: O=C1c2ccccc2C(=O)N1Cc1cnc(-c2ccc(Cl)cc2)c(-c2ccccc2Cl)c1]

The title compound (0.046 g) was obtained in the same way as in Reference Example 15 using 2-((6-chloro-5-(2-chlorophenyl)pyridin-3-yl)methyl)isoindoline-1,3-dione (0.040 g) synthesized in Reference Example 7 and 4-chlorophenylboronic acid (0.033 g).

$^1$H-NMR (CDCl$_3$) δ: 4.95 (2H, s), 7.09 (1H, dd, J=7.7, 1.8 Hz), 7.17 (3H, t, J=8.6 Hz), 7.22-7.26 (3H, m), 7.36 (1H, d, J=8.2 Hz), 7.73-7.75 (3H, m), 7.88 (2H, dd, J=5.2, 3.4 Hz), 8.82 (1H, d, J=2.3 Hz).

MS (ESI) [M+H]: 459.

Reference Example 31 Synthesis of 2-((6-(4-chlorophenyl)-5-(4-methylphenyl)pyridin-3-yl)methyl)isoindoline-1,3-dione

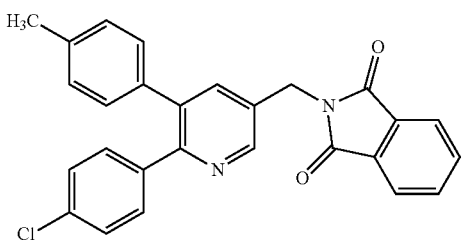 [SMILES: Cc1ccc(-c2cc(CN3C(=O)c4ccccc4C3=O)cnc2-c2ccc(Cl)cc2)cc1]

The title compound (0.056 g) was obtained in the same way as in Reference Example 15 using 2-((6-chloro-5-(4-methylphenyl)pyridin-3-yl)methyl)isoindoline-1,3-dione (0.050 g) synthesized in Reference Example 8 and 4-chlorophenylboronic acid (0.043 g).

$^1$H-NMR (CDCl$_3$) δ: 2.34 (3H, s), 4.94 (2H, d, J=5.9 Hz), 7.02 (2H, d, J=8.2 Hz), 7.08 (2H, d, J=8.2 Hz), 7.19 (2H, d, J=8.8 Hz), 7.27 (2H, d, J=8.5 Hz), 7.73 (2H, dd, J=5.4, 3.2 Hz), 7.75 (1H, d, J=2.3 Hz), 7.86 (2H, dd, J=5.7, 2.9 Hz), 8.74 (1H, d, J=2.3 Hz).

MS (ESI) [M+H]$^+$: 439.

Reference Example 32 Synthesis of 2-((6-(4-chlorophenyl)-5-(4-methoxyphenyl)pyridin-3-yl)methyl)isoindoline-1,3-dione

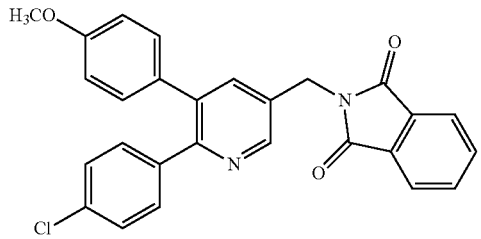 [SMILES: COc1ccc(-c2cc(CN3C(=O)c4ccccc4C3=O)cnc2-c2ccc(Cl)cc2)cc1]

The title compound (0.11 g) was obtained in the same way as in Reference Example 15 using 2-((6-chloro-5-(4-methoxyphenyl)pyridin-3-yl)methyl)isoindoline-1,3-dione (0.13 g) synthesized in Reference Example 9 and 4-chlorophenylboronic acid (0.080 g).

$^1$H-NMR (CDCl$_3$) δ: 3.80 (3H, s), 4.93 (2H, s), 6.81 (2H, d, J=9.5 Hz), 7.05 (2H, d, J=9.4 Hz), 7.20 (2H, d, J=8.9 Hz), 7.27 (2H, d, J=8.9 Hz), 7.73 (2H, dd, J=5.5, 3.0 Hz), 7.75 (1H, d, J=2.2 Hz), 7.87 (2H, dd, J=5.5, 3.0 Hz), 8.73 (1H, d, J=2.2 Hz).

MS (ESI) [M+H]$^+$: 455.

Reference Example 33 Synthesis of 2-((6-(4-chlorophenyl)-5-(4-cyanophenyl)pyridin-3-yl)methyl)isoindoline-1,3-dione

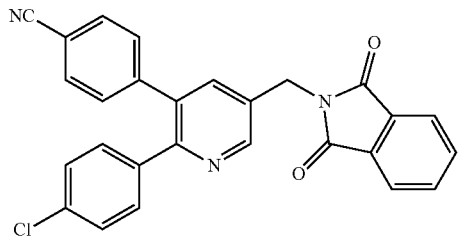 [SMILES: N#Cc1ccc(-c2cc(CN3C(=O)c4ccccc4C3=O)cnc2-c2ccc(Cl)cc2)cc1]

The title compound (0.20 g) was obtained in the same way as in Reference Example 15 using 2-((6-chloro-5-(4-cyanophenyl)pyridin-3-yl)methyl)isoindoline-1,3-dione (0.30 g) synthesized in Reference Example 10 and 4-chlorophenylboronic acid (0.19 g).

$^1$H-NMR (CDCl$_3$) δ: 4.96 (2H, s), 7.22 (4H, d, J=1.4 Hz), 7.24-7.27 (2H, m), 7.58 (2H, d, J=8.6 Hz), 7.74 (2H, dd, J=5.4, 3.2 Hz), 7.78 (1H, d, J=2.3 Hz), 7.88 (2H, dd, J=5.7, 2.9 Hz), 8.82 (1H, d, J=2.3 Hz).

MS (ESI) [M+H]$^+$: 450.

Reference Example 34 Synthesis of 2-((6-(4-chloro-phenyl)-5-(4-fluorophenyl)pyridin-3-yl)methyl)isoindoline-1,3-dione

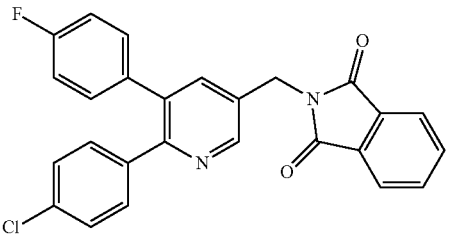 [SMILES: O=C1c2ccccc2C(=O)N1Cc1cnc(-c2ccc(Cl)cc2)c(-c2ccc(F)cc2)c1]

The title compound (0.30 g) was obtained in the same way as in Reference Example 15 using 2-((6-chloro-5-(4-fluorophenyl)pyridin-3-yl)methyl)isoindoline-1,3-dione (0.32 g) synthesized in Reference Example 11 and 4-chlorophenylboronic acid (0.21 g).

$^1$H-NMR (CDCl$_3$) δ: 4.94 (2H, s), 6.95-7.00 (2H, m), 7.08-7.12 (2H, m), 7.19-7.26 (4H, m), 7.72-7.77 (3H, m), 7.87 (2H, dd, J=5.4, 3.2 Hz), 8.77 (1H, d, J=2.3 Hz).

MS (ESI) [M+H]$^+$: 443.

Reference Example 35 Synthesis of 2-((6-(4-chloro-phenyl)-5-(4-(trifluoromethyl)phenyl)pyridin-3-yl)methyl)isoindoline-1,3-dione

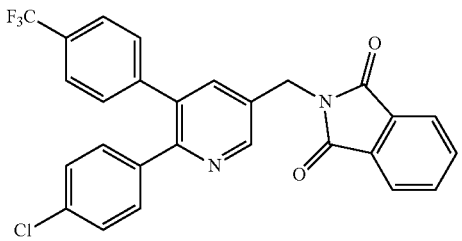 [SMILES: O=C1c2ccccc2C(=O)N1Cc1cnc(-c2ccc(Cl)cc2)c(-c2ccc(C(F)(F)F)cc2)c1]

The title compound (0.45 g) was obtained in the same way as in Reference Example 15 using 2-((6-chloro-5-(4-(trifluoromethyl)phenyl)pyridin-3-yl)methyl)isoindoline-1,3-dione (0.40 g) synthesized in Reference Example 12 and 4-chlorophenylboronic acid (0.23 g).

$^1$H-NMR (CDCl$_3$) δ: 4.96 (2H, s), 7.20-7.32 (6H, m), 7.55 (2H, d, J=8.2 Hz), 7.73-7.76 (2H, m), 7.78 (1H, d, J=2.3 Hz), 7.85-7.88 (2H, m), 8.81 (1H, d, J=1.8 Hz).

MS (ESI) [M+H]$^+$: 493.

Reference Example 36 Synthesis of 2-((6-(4-chloro-phenyl)-5-(4-(trifluoromethoxy)phenyl)pyridin-3-yl)methyl)isoindoline-1,3-dione

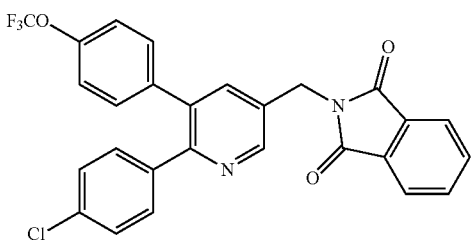 [SMILES: O=C1c2ccccc2C(=O)N1Cc1cnc(-c2ccc(Cl)cc2)c(-c2ccc(OC(F)(F)F)cc2)c1]

The title compound (0.40 g) was obtained in the same way as in Reference Example 15 using 2-((6-chloro-5-(4-(trifluoromethoxy)phenyl)pyridin-3-yl)methyl)isoindoline-1,3-dione (0.34 g) synthesized in Reference Example 13 and 4-chlorophenylboronic acid (0.18 g).

$^1$H-NMR (CDCl$_3$) δ: 4.95 (2H, s), 7.11-7.18 (4H, m), 7.19-7.25 (4H, m), 7.71-7.78 (3H, m), 7.87 (2H, dd, J=5.4, 3.2 Hz), 8.79 (1H, d, J=2.3 Hz).

MS (ESI) [M+H]$^+$: 509.

Reference Example 37 Synthesis of 2-((6-(4-chloro-phenyl)-5-(4-isopropoxyphenyl)pyridin-3-yl)methyl)isoindoline-1,3-dione

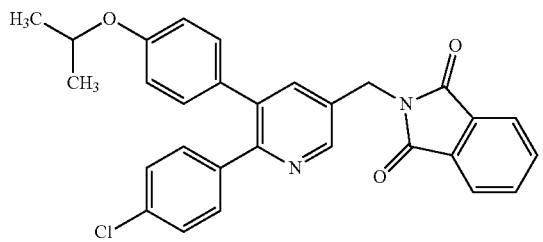 [SMILES: CC(C)Oc1ccc(-c2cc(CN3C(=O)c4ccccc4C3=O)cnc2-c2ccc(Cl)cc2)cc1]

The title compound (0.35 g) was obtained in the same way as in Reference Example 15 using 2-((6-chloro-5-(4-isopropoxyphenyl)pyridin-3-yl)methyl)isoindoline-1,3-dione (0.31 g) synthesized in Reference Example 14 and 4-chlorophenylboronic acid (0.18 g).

$^1$H-NMR (CDCl$_3$) δ: 1.32 (3H, s), 1.34 (3H, s), 4.50-4.56 (1H, m), 4.93 (2H, s), 6.78 (2H, td, J=5.8, 3.5 Hz), 7.00-7.03 (2H, m), 7.20 (2H, dt, J=8.8, 2.2 Hz), 7.26-7.29 (2H, m), 7.71-7.75 (3H, m), 7.84-7.88 (2H, m), 8.73 (1H, d, J=2.3 Hz).

MS (ESI) [M+H]$^+$: 483.

Reference Example 38 Synthesis of 2-((5-(4-methoxyphenyl)-6-(4-methylphenyl)pyridin-3-yl)methyl)isoindoline-1,3-dione

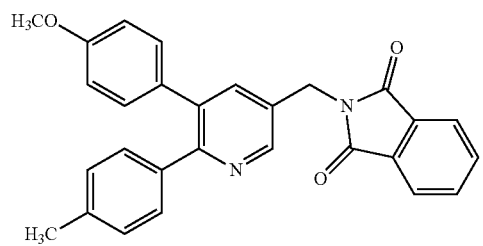 [SMILES: COc1ccc(-c2cc(CN3C(=O)c4ccccc4C3=O)cnc2-c2ccc(C)cc2)cc1]

The title compound (0.052 g) was obtained in the same way as in Reference Example 15 using 2-((6-chloro-5-(4-methoxyphenyl)pyridin-3-yl)methyl)isoindoline-1,3-dione (0.12 g) synthesized in Reference Example 9 and 4-methylphenylboronic acid (0.065 g).

$^1$H-NMR (CDCl$_3$) δ: 2.30 (3H, s), 3.79 (3H, s), 4.93 (2H, s), 6.79 (2H, d, J=8.6 Hz), 7.03 (2H, d, J=8.2 Hz), 7.07 (2H, d, J=8.6 Hz), 7.21 (2H, d, J=8.2 Hz), 7.70-7.74 (3H, m), 7.86 (2H, dd, J=5.7, 2.9 Hz), 8.72 (1H, d, J=2.3 Hz).

MS (ESI) [M+H]$^+$: 435.

Reference Example 39 Synthesis of 2-((6-(4-methylphenyl)-5-(4-(trifluoromethyl)phenyl)pyridin-3-yl)methyl)isoindoline-1,3-dione

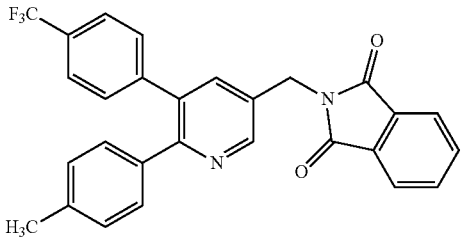

The title compound (0.91 g) was obtained in the same way as in Reference Example 15 using 2-((6-chloro-5-(4-(trifluoromethyl)phenyl)pyridin-3-yl)methyl)isoindoline-1,3-dione (1.0 g) synthesized in Reference Example 12 and 4-methylphenylboronic acid (0.65 g).

$^1$H-NMR (CDCl$_3$) δ: 2.31 (3H, s), 4.95 (2H, s), 7.04 (2H, d, J=8.2 Hz), 7.17 (2H, d, J=8.2 Hz), 7.28 (2H, d, J=8.2 Hz), 7.52 (2H, d, J=8.2 Hz), 7.71-7.76 (3H, m), 7.85-7.89 (2H, m), 8.80 (1H, d, J=2.3 Hz).

MS (ESI) [M+H]$^+$: 473.

Reference Example 40 Synthesis of S-methylisothiourea Hydroiodide

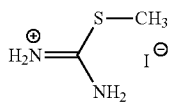

Thioamide (10.0 g) was dissolved in methanol (100 mL). To the solution, methyl iodide (19.0 g) was then added. The mixture was heated to reflux for 1 hour, and then, the reaction mixture was concentrated under reduced pressure to obtain the title compound (27.6 g).

$^1$H-NMR (DMSO-d$_6$) δ: 2.57 (3H, s), 8.89 (4H, s).

Reference Example 41 Synthesis of N-(tert-butoxycarbonyl)-S-methylisothiourea

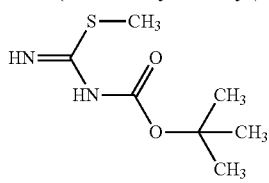

S-Methylisothiourea hydroiodide (28.0 g) synthesized in Reference Example 40 and triethylamine (18 mL) were dissolved in dichloromethane (250 mL). To the solution, di-tert-butyl dicarbonate (28 mL) was then added. The reaction mixture was stirred overnight at room temperature, and then, water was added thereto, followed by extraction with chloroform. The organic layer was washed with saturated saline, dried over anhydrous sodium sulfate, and then concentrated under reduced pressure. The obtained solid was washed with ethyl acetate to obtain the title compound (24.0 g).

$^1$H-NMR (CDCl$_3$) δ:1.51 (9H, s), 2.46 (3H, s).

Reference Example 42 Synthesis of N-(phenylsulfonyl)-N'-(tert-butoxycarbonyl)-S-methylisothiourea

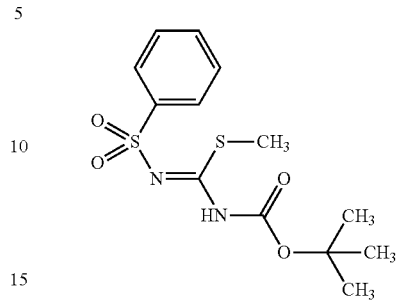

Sodium hydride (55% by weight in mineral oil, 2.5 g) was suspended in DMF (100 mL). To the suspension, N-(tert-butoxycarbonyl)-S-methylisothiourea (10.0 g) synthesized in Reference Example 41 was then added. The mixture was cooled to 4° C., and then, benzenesulfonyl chloride (8.1 mL) was gradually added dropwise thereto. The reaction mixture was warmed to room temperature and then stirred for 3 hours. The reaction mixture was added to ice water/ethyl acetate/n-hexane (100 mL/50 mL/50 mL) to separate an organic layer. The aqueous layer was subjected to extraction with ethyl acetate/n-hexane (1/1, v/v). The organic layers were combined, then washed with water and saturated saline, dried over anhydrous sodium sulfate, and then concentrated under reduced pressure. The obtained crude product was purified by silica gel column chromatography (n-hexane/ethyl acetate) to obtain the title compound (4.8 g).

$^1$H-NMR (CDCl$_3$) δ: 1.52 (9H, s), 2.29 (3H, s), 7.50-7.62 (3H, m), 7.93-7.96 (2H, m), 10.33 (1H, s).

Reference Example 43 Synthesis of N-(2-fluorophenylsulfonyl)-N'-(tert-butoxycarbonyl)-S-methylisothiourea

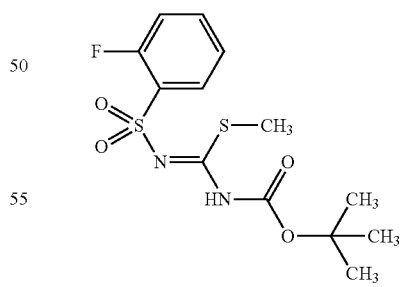

The title compound (0.31 g) was obtained in the same way as in Reference Example 42 using N-(tert-butoxycarbonyl)-S-methylisothiourea (0.50 g) synthesized in Reference Example 41 and 2-fluorobenzenesulfonyl chloride (0.61 g).

$^1$H-NMR (CDCl$_3$) δ: 1.53 (9H, s), 2.30 (3H, s), 7.21 (1H, t, J=9.1 Hz), 7.29 (1H, t, J=7.7 Hz), 7.56-7.62 (1H, m), 7.98 (1H, td, J=7.6, 1.6 Hz), 10.39 (1H, brs).

Reference Example 44 Synthesis of N-(3-fluorophenylsulfonyl)-N'-(tert-butoxycarbonyl)-S-methylisothiourea

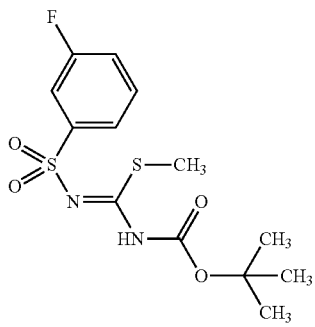 [SMILES: CS/C(=N\S(=O)(=O)c1cccc(F)c1)NC(=O)OC(C)(C)C]

The title compound (0.24 g) was obtained in the same way as in Reference Example 42 using N-(tert-butoxycarbonyl)-S-methylisothiourea (0.5 g) synthesized in Reference Example 41 and 3-fluorobenzenesulfonyl chloride (0.61 g).
$^1$H-NMR (CDCl$_3$) δ: 1.53 (9H, s), 2.30 (3H, s), 7.27-7.32 (1H, m), 7.51 (1H, td, J=8.1, 5.3 Hz), 7.65 (1H, dt, J=8.1, 2.0 Hz), 7.74 (1H, dq, J=7.8, 0.8 Hz), 10.26 (1H, brs).

Reference Example 45 Synthesis of N-(4-fluorophenylsulfonyl)-N'-(tert-butoxycarbonyl)-S-methylisothiourea

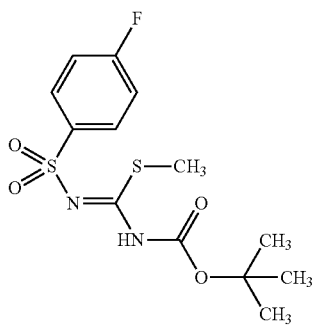 [SMILES: CS/C(=N\S(=O)(=O)c1ccc(F)cc1)NC(=O)OC(C)(C)C]

The title compound (0.25 g) was obtained in the same way as in Reference Example 42 using N-(tert-butoxycarbonyl)-S-methylisothiourea (0.50 g) synthesized in Reference Example 41 and 4-fluorobenzenesulfonyl chloride (0.61 g).
$^1$H-NMR (CDCl$_3$) δ: 1.53 (9H, s), 2.28 (3H, s), 7.17-7.23 (2H, m), 7.93-7.98 (2H, m), 10.27 (1H, brs).

Reference Example 46 Synthesis of N-(2-thiophenesulfonyl)-N'-(tert-butoxycarbonyl)-S-methylisothiourea

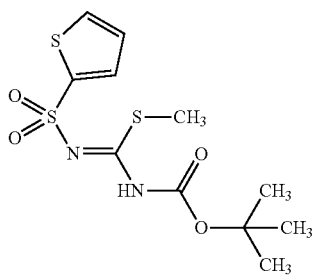

The title compound (0.1 g) was obtained in the same way as in Reference Example 42 using N-(tert-butoxycarbonyl)-S-methylisothiourea (0.20 g) synthesized in Reference Example 41 and 2-thiophenesulfonyl chloride (0.23 g).
$^1$H-NMR (CDCl$_3$) δ:1.52 (9H, s), 2.34 (3H, s), 7.08 (1H, dd, J=5.0, 3.8 Hz), 7.61 (1H, dd, J=5.0, 1.3 Hz), 7.68 (1H, dd, J=3.8, 1.3 Hz), 10.20 (1H, brs).

Reference Example 47 Synthesis of N-(3-thiophenesulfonyl)-N'-(tert-butoxycarbonyl)-S-methylisothiourea

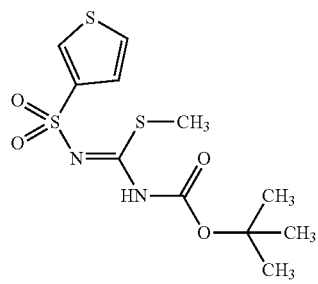 [SMILES: CS/C(=N\S(=O)(=O)c1ccsc1)NC(=O)OC(C)(C)C]

The title compound (0.10 g) was obtained in the same way as in Reference Example 42 using N-(tert-butoxycarbonyl)-S-methylisothiourea (0.20 g) synthesized in Reference Example 41 and 3-thiophenesulfonyl chloride (0.23 g).
$^1$H-NMR (CDCl$_3$) δ: 1.52 (9H, s), 2.32 (3H, s), 7.42 (2H, d, J=2.3 Hz), 8.03 (1H, t, J=2.3 Hz), 10.28 (1H, brs).

Reference Example 48 Synthesis of N-(furan-2-sulfonyl)-N'-(tert-butoxycarbonyl)-S-methylisothiourea

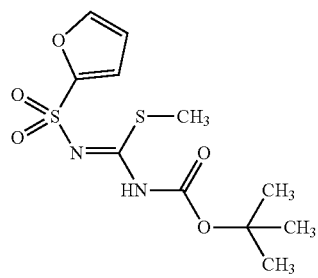 [SMILES: CS/C(=N\S(=O)(=O)c1ccco1)NC(=O)OC(C)(C)C]

The title compound (0.11 g) was obtained in the same way as in Reference Example 42 using N-(tert-butoxycarbonyl)-S-methylisothiourea (0.20 g) synthesized in Reference Example 41 and furan-2-sulfonyl chloride (0.21 g).
$^1$H-NMR (CDCl$_3$) δ: 1.53 (9H, s), 2.34 (3H, s), 6.52 (1H, dd, J=3.6, 1.8 Hz), 7.08 (1H, dd, J=3.6, 0.9 Hz), 7.57 (1H, dd, J=1.8, 0.9 Hz), 10.25 (1H, s).

Reference Example 49 Synthesis of N-(furan-3-sulfonyl)-N'-(tert-butoxycarbonyl)-S-methylisothiourea

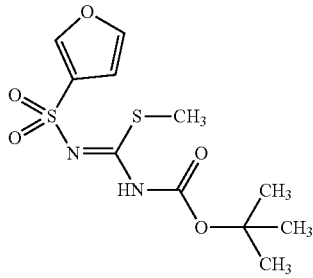 [SMILES: CS/C(=N\S(=O)(=O)c1ccoc1)NC(=O)OC(C)(C)C]

The title compound (0.10 g) was obtained in the same way as in Reference Example 42 using N-(tert-butoxycarbonyl)-S-methylisothiourea (0.20 g) synthesized in Reference Example 41 and furan-3-sulfonyl chloride (0.21 g).

$^1$H-NMR (CDCl$_3$) δ: 1.52 (9H, s), 2.33 (3H, s), 6.71-6.72 (1H, m), 7.48 (1H, dd, J=4.5, 2.7 Hz), 7.98 (1H, dd, J=1.8, 0.9 Hz), 10.20 (1H, brs).

Reference Example 50 Synthesis of N-(benzenecarbonyl)-N'-(tert-butoxycarbonyl)-S-methylisothiourea

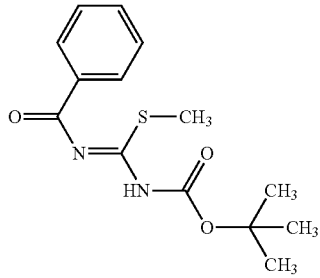 [SMILES: CS/C(=N\C(=O)c1ccccc1)NC(=O)OC(C)(C)C]

N-(tert-Butoxycarbonyl)-S-methylisothiourea (0.20 g) synthesized in Reference Example 41 was dissolved in dichloromethane (3 mL). To the solution, N,N-diisopropylethylamine (0.22 mL) and benzoyl chloride (0.15 mL) were then added. The mixture was stirred overnight at room temperature, and then, water was added thereto, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (0.091 g).

$^1$H-NMR (CDCl$_3$) δ: 1.53 (9H, s), 2.59 (3H, s), 7.43-7.48 (2H, m), 7.50-7.57 (1H, m), 8.27-8.29 (2H, m).

Reference Example 51 Synthesis of N-(2-thiophenecarbonyl)-N'-(tert-butoxycarbonyl)-S-methylisothiourea

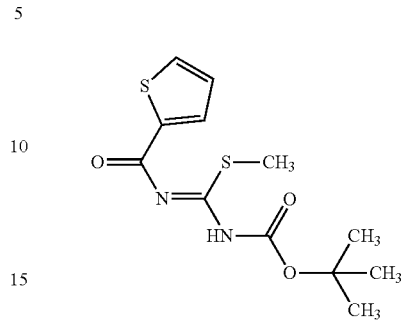

The title compound (0.27 g) was obtained in the same way as in Reference Example 50 using N-(tert-butoxycarbonyl)-S-methylisothiourea (0.20 g) synthesized in Reference Example 41 and thiophene-2-carbonyl chloride (0.19 g).

$^1$H-NMR (CDCl$_3$) δ: 1.52 (9H, s), 2.55 (3H, s), 7.11-7.13 (1H, m), 7.58 (1H, dd, J=4.9, 1.2 Hz), 7.89 (1H, dd, J=3.9, 1.2 Hz), 12.39 (1H, brs).

Reference Example 52 Synthesis of 2-benzenesulfonyl-3-((5,6-bis(4-chlorophenyl)pyridin-3-yl)methyl)-1-(tert-butoxycarbonyl)guanidine

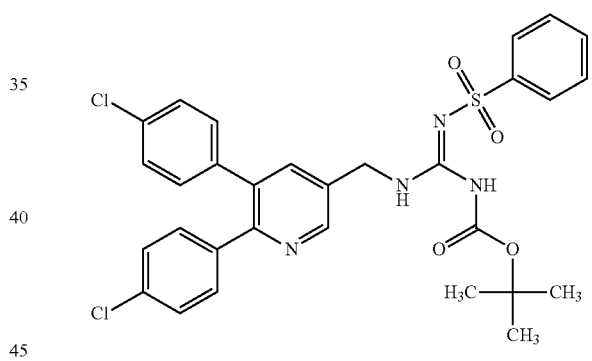

1. Deprotection Reaction 2-((5,6-Bis(4-chlorophenyl)pyridin-3-yl)methyl)isoindoline-1,3-dione (9.5 g) synthesized in Reference Example 15 was suspended in methanol (40 mL). To the suspension, hydrazine monohydrate (6 mL) was then added. The mixture was heated to reflux for 2 hours, and then, the reaction mixture was cooled to room temperature, diluted with ethyl acetate, and filtered. The filtrate was washed with water and saturated saline, dried over anhydrous sodium sulfate, and then concentrated under reduced pressure to obtain (5,6-bis(4-chlorophenyl)pyridin-3-yl)methanamine (5.3 g).

2. Guanidination Reaction

The preliminarily synthesized (5,6-bis(4-chlorophenyl)pyridin-3-yl)methanamine (3.5 g) was dissolved in tetrahydrofuran (30 mL). To the solution, N-(phenylsulfonyl)-N'-(tert-butoxycarbonyl)-S-methylisothiourea (3.9 g) synthesized in Reference Example 42 was then added. The reaction mixture was stirred at 60° C. for 6 hours and then concentrated under reduced pressure. The crude product was purified by silica gel chromatography (n-hexane/ethyl acetate) to obtain the title compound (6.4 g).

¹H-NMR (CDCl₃) δ: 1.51 (9H, s), 4.60 (2H, d, J=5.4 Hz), 6.99-7.00 (2H, m), 7.23-7.27 (6H, m), 7.35-7.39 (2H, m), 7.44-7.49 (1H, m), 7.55 (1H, d, J=1.8 Hz), 7.80-7.83 (2H, m), 8.55 (1H, d, J=1.4 Hz), 8.99 (1H, t, J=5.4 Hz), 10.00 (1H, s).
MS (ESI) [M+H]⁺: 611.

Reference Example 53 Synthesis of 2-benzenesulfonyl-3-((5-(4-chlorophenyl)-6-phenylpyridin-3-yl)methyl)-1-(tert-butoxycarbonyl)guanidine

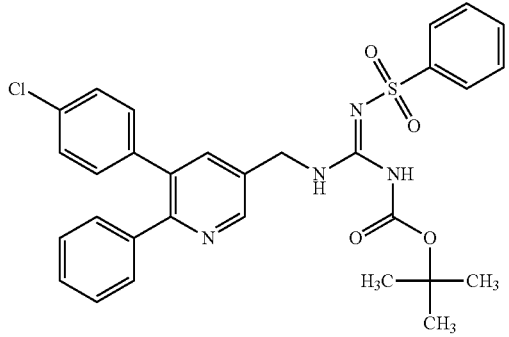 [SMILES: CC(C)(C)OC(=O)N/C(=N\S(=O)(=O)c1ccccc1)NCc1cnc(-c2ccccc2)c(-c2ccc(Cl)cc2)c1]

The title compound (0.042 g) was obtained in the same way as in Reference Example 52 using 2-((5-(4-chlorophenyl)-6-phenylpyridin-3-yl)methyl)isoindoline-1,3-dione (0.058 g) synthesized in Reference Example 16 and N-(phenylsulfonyl)-N'-(tert-butoxycarbonyl)-S-methylisothiourea (0.049 g) synthesized in Reference Example 42.

¹H-NMR (CDCl₃) δ: 1.51 (9H, s), 4.60 (2H, d, J=5.9 Hz), 6.99 (2H, dt, J=8.9, 2.3 Hz), 7.23 (2H, dt, J=8.8, 2.3 Hz), 7.26-7.30 (5H, m), 7.35-7.39 (2H, m), 7.44-7.48 (1H, m), 7.55 (1H, d, J=2.3 Hz), 7.80-7.84 (2H, m), 8.56 (1H, d, J=2.3 Hz), 8.99 (1H, t, J=5.4 Hz), 10.00 (1H, s).
MS (ESI) [M+H]⁺: 577.

Reference Example 54 Synthesis of 2-benzenesulfonyl-3-((6-(3-chlorophenyl)-5-(4-chlorophenyl)pyridin-3-yl)methyl)-1-(tert-butoxycarbonyl)guanidine

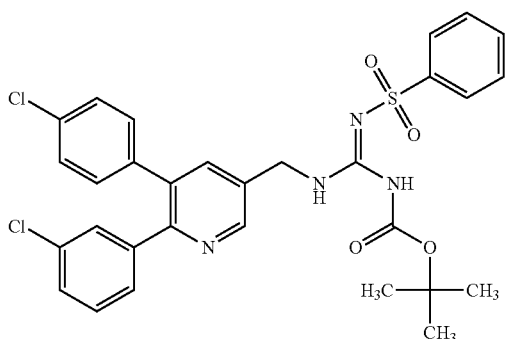

The title compound (0.12 g) was obtained in the same way as in Reference Example 52 using 2-((6-(3-chlorophenyl)-5-(4-chlorophenyl)pyridin-3-yl)methyl)isoindoline-1,3-dione (0.10 g) synthesized in Reference Example 17 and N-(phenylsulfonyl)-N'-(tert-butoxycarbonyl)-S-methylisothiourea (0.081 g) synthesized in Reference Example 42.

¹H-NMR (CDCl₃) δ: 1.51 (9H, s), 4.60 (2H, d, J=5.9 Hz), 6.97-7.04 (3H, m), 7.14 (1H, t, J=7.7 Hz), 7.24-7.27 (3H, m), 7.35-7.40 (2H, m), 7.42 (1H, t, J=1.8 Hz), 7.45-7.49 (1H, m), 7.56 (1H, d, J=1.8 Hz), 7.80-7.83 (2H, m), 8.56 (1H, d, J=2.3 Hz), 9.00 (1H, t, J=5.7 Hz), 10.00 (1H, s).
MS (ESI) [M+H]⁺: 611.

Reference Example 55 Synthesis of 2-benzenesulfonyl-3-((5-(4-chlorophenyl)-6-(4-methylphenyl)pyridin-3-yl)methyl)-1-(tert-butoxycarbonyl)guanidine

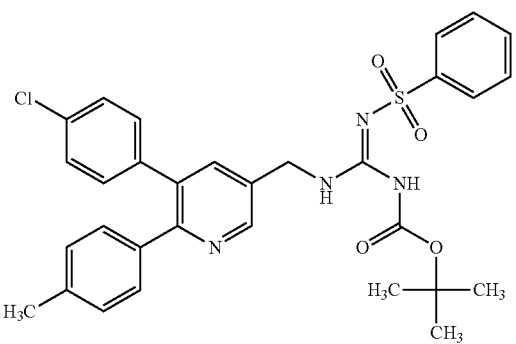

The title compound (0.085 g) was obtained in the same way as in Reference Example 52 using 2-((5-(4-chlorophenyl)-6-(4-methylphenyl)pyridin-3-yl)methyl)isoindoline-1,3-dione (0.092 g) synthesized in Reference Example 18 and N-(phenylsulfonyl)-N'-(tert-butoxycarbonyl)-S-methylisothiourea (0.084 g) synthesized in Reference Example 42.

¹H-NMR (CDCl₃) δ: 1.50 (9H, s), 2.32 (3H, s), 4.59 (2H, d, J=5.9 Hz), 7.00 (2H, dt, J=8.9, 2.3 Hz), 7.06 (2H, d, J=7.7 Hz), 7.16-7.19 (2H, m), 7.21-7.26 (2H, m), 7.34-7.39 (2H, m), 7.43-7.47 (1H, m), 7.52 (1H, d, J=2.3 Hz), 7.80-7.83 (2H, m), 8.54 (1H, d, J=2.3 Hz), 8.98 (1H, t, J=5.4 Hz), 9.99 (1H, s).
MS (ESI) [M+H]⁺: 591.

Reference Example 56 Synthesis of 2-benzenesulfonyl-3-((5-(4-chlorophenyl)-6-(4-methoxyphenyl)pyridin-3-yl)methyl)-1-(tert-butoxycarbonyl)guanidine

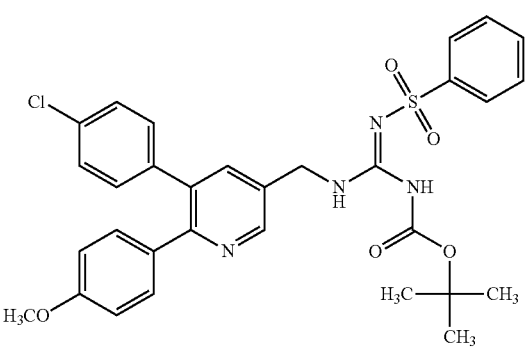 [SMILES: COc1ccc(-c2ncc(CN/C(=N/S(=O)(=O)c3ccccc3)NC(=O)OC(C)(C)C)cc2-c2ccc(Cl)cc2)cc1]

The title compound (0.055 g) was obtained in the same way as in Reference Example 52 using 2-((5-(4-chlorophenyl)-6-(4-methoxyphenyl)pyridin-3-yl)methyl)isoindoline- 1,3-dione (0.045 g) synthesized in Reference Example 19 and N-(phenylsulfonyl)-N'-(tert-butoxycarbonyl)-S-methyl-isothiourea (0.036 g) synthesized in Reference Example 42.

¹H-NMR (CDCl₃) δ: 1.50 (9H, s), 3.80 (3H, s), 4.59 (2H, d, J=5.9 Hz), 6.79 (2H, d, J=8.2 Hz), 7.01 (2H, d, J=7.7 Hz), 7.22-7.27 (4H, m), 7.35-7.39 (2H, m), 7.44-7.48 (1H, m), 7.51 (1H, d, J=1.4 Hz), 7.82 (2H, d, J=8.2 Hz), 8.53 (1H, d, J=1.4 Hz), 8.97 (1H, t, J=5.4 Hz), 9.99 (1H, s).

MS (ESI) [M+H]⁺: 607.

Reference Example 57 Synthesis of 2-benzenesulfonyl-3-((5-(4-chlorophenyl)-6-(4-cyanophenyl)pyridin-3-yl)methyl)-1-(tert-butoxycarbonyl)guanidine

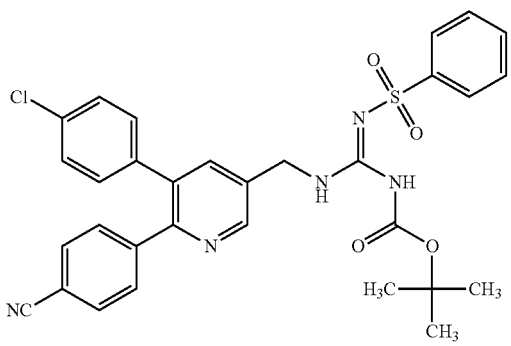 [SMILES: CC(C)(C)OC(=O)N/C(=N\S(=O)(=O)c1ccccc1)NCc1cnc(-c2ccc(C#N)cc2)c(-c2ccc(Cl)cc2)c1]

The title compound (0.098 g) was obtained in the same way as in Reference Example 52 using 2-((5-(4-chlorophenyl)-6-(4-cyanophenyl)pyridin-3-yl)methyl)isoindoline-1,3-dione (0.10 g) synthesized in Reference Example 20 and N-(phenylsulfonyl)-N'-(tert-butoxycarbonyl)-S-methylisothiourea (0.081 g) synthesized in Reference Example 42.

¹H-NMR (CDCl₃) δ: 1.51 (9H, s), 4.61 (2H, d, J=5.9 Hz), 6.98 (2H, d, J=8.2 Hz), 7.25-7.29 (2H, m), 7.38 (2H, t, J=8.2 Hz), 7.41 (2H, d, J=8.6 Hz), 7.47 (1H, tt, J=7.5, 1.6 Hz), 7.56 (2H, d, J=8.6 Hz), 7.60 (1H, d, J=2.3 Hz), 7.81-7.83 (2H, m), 8.59 (1H, d, J=1.8 Hz), 9.01 (1H, t, J=5.4 Hz), 10.00 (1H, s).

MS (ESI) [M+H]⁺: 602.

Reference Example 58 Synthesis of 2-benzenesulfonyl-3-((5-(4-chlorophenyl)-6-(4-fluorophenyl)pyridin-3-yl)methyl)-1-(tert-butoxycarbonyl)guanidine

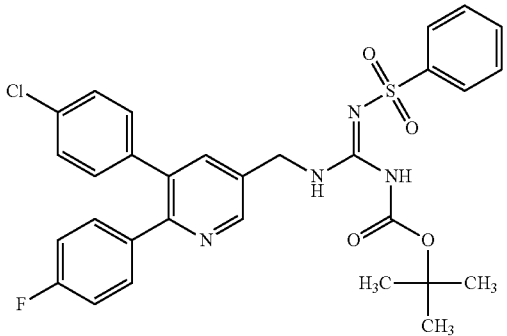

The title compound (0.21 g) was obtained in the same way as in Reference Example 52 using 2-((5-(4-chlorophenyl)-6-(4-fluorophenyl)pyridin-3-yl)methyl)isoindoline-1,3-dione (0.18 g) synthesized in Reference Example 21 and N-(phenylsulfonyl)-N'-(tert-butoxycarbonyl)-S-methylisothiourea (0.15 g) synthesized in Reference Example 42.

¹H-NMR (CDCl₃) δ: 1.51 (9H, s), 4.60 (2H, d, J=5.9 Hz), 6.93-7.00 (4H, m), 7.24-7.29 (4H, m), 7.37 (2H, t, J=7.7 Hz), 7.46 (1H, t, J=7.5 Hz), 7.55 (1H, d, J=2.3 Hz), 7.81-7.83 (2H, m), 8.55 (1H, d, J=2.3 Hz), 8.99 (1H, t, J=5.4 Hz), 10.00 (1H, s).

MS (ESI) [M+H]⁺: 595.

Reference Example 59 Synthesis of 2-benzenesulfonyl-3-((5-(4-chlorophenyl)-6-(3-fluorophenyl)pyridin-3-yl)methyl)-1-(tert-butoxycarbonyl)guanidine

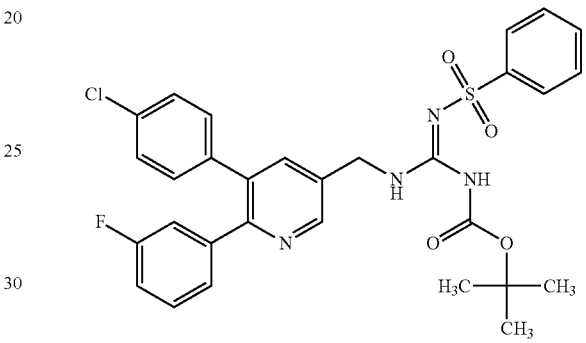

The title compound (0.13 g) was obtained in the same way as in Reference Example 52 using 2-((5-(4-chlorophenyl)-6-(3-fluorophenyl)pyridin-3-yl)methyl)isoindoline-1,3-dione (0.12 g) synthesized in Reference Example 22 and N-(phenylsulfonyl)-N'-(tert-butoxycarbonyl)-S-methylisothiourea (0.098 g) synthesized in Reference Example 42.

¹H-NMR (CDCl₃) δ: 1.51 (9H, s), 4.60 (2H, d, J=5.9 Hz), 6.96-7.01 (4H, m), 7.07 (1H, dq, J=10.0, 1.4 Hz), 7.17-7.23 (1H, m), 7.23-7.26 (2H, m), 7.38 (2H, t, J=7.7 Hz), 7.47 (1H, t, J=7.2 Hz), 7.56 (1H, d, J=2.3 Hz), 7.80-7.83 (2H, m), 8.56 (1H, d, 2.3 Hz), 9.00 (1H, t, J=5.7 Hz), 10.00 (1H, s).

MS (ESI) [M+H]⁺: 595.

Reference Example 60 Synthesis of 2-benzenesulfonyl-3-((5-(4-chlorophenyl)-6-(4-(trifluoromethyl)phenyl)pyridin-3-yl)methyl)-1-(tert-butoxycarbonyl)guanidine

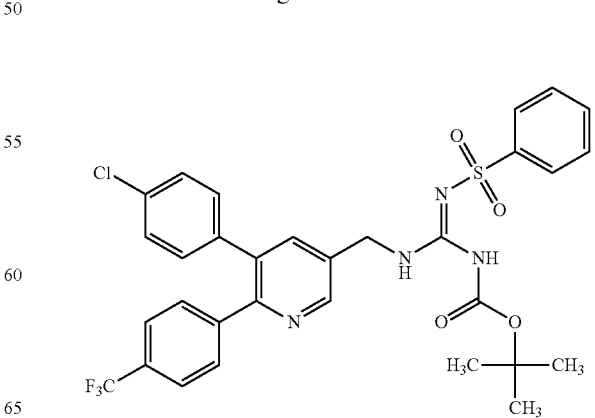

The title compound (0.30 g) was obtained in the same way as in Reference Example 52 using 2-((5-(4-chlorophenyl)-6-(4-(trifluoromethyl)phenyl)pyridin-3-yl)methyl)isoindoline-1,3-dione (0.30 g) synthesized in Reference Example 23 and N-(phenylsulfonyl)-N'-(tert-butoxycarbonyl)-S-methylisothiourea (0.22 g) synthesized in Reference Example 42.

$^1$H-NMR (CDCl$_3$) δ: 1.51 (9H, s), 4.61 (2H, d, J=5.4 Hz), 6.99 (2H, dt, J=8.9, 2.3 Hz), 7.24-7.28 (2H, m), 7.36-7.48 (5H, m), 7.53 (2H, d, J=8.2 Hz), 7.59 (1H, d, J=2.3 Hz), 7.81-7.84 (2H, m), 8.58 (1H, d, J=1.8 Hz), 9.01 (1H, t, J=5.7 Hz), 10.00 (1H, s).

MS (ESI) [M+H]$^+$: 645.

Reference Example 61 Synthesis of 2-benzenesulfonyl-3-((5-(4-chlorophenyl)-6-(4-(trifluoromethoxy)phenyl)pyridin-3-yl)methyl)-1-(tert-butoxycarbonyl)guanidine

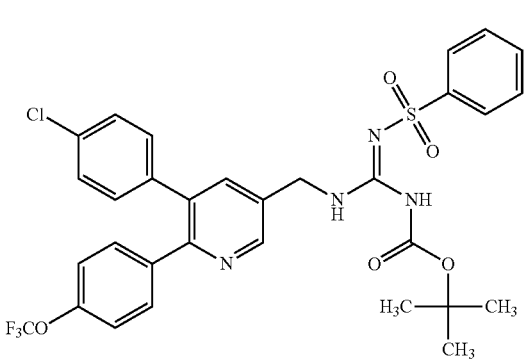 [SMILES: CC(C)(C)OC(=O)N/C(=N\S(=O)(=O)c1ccccc1)NCc1cnc(-c2ccc(OC(F)(F)F)cc2)c(-c2ccc(Cl)cc2)c1]

The title compound (0.35 g) was obtained in the same way as in Reference Example 52 using 2-((5-(4-chlorophenyl)-6-(4-(trifluoromethoxy)phenyl)pyridin-3-yl)methyl)isoindoline-1,3-dione (0.30 g) synthesized in Reference Example 24 and N-(phenylsulfonyl)-N'-(tert-butoxycarbonyl)-S-methylisothiourea (0.21 g) synthesized in Reference Example 42.

$^1$H-NMR (CDCl$_3$) δ: 1.51 (9H, s), 4.60 (2H, d, J=5.4 Hz), 6.99 (2H, d, J=8.6 Hz), 7.11 (2H, d, J=8.6 Hz), 7.24-7.27 (2H, m), 7.32-7.39 (4H, m), 7.47 (1H, t, J=7.5 Hz), 7.57 (1H, d, J=1.8 Hz), 7.82 (2H, d, J=7.7 Hz), 8.56 (1H, d, J=1.8 Hz), 8.99 (1H, brs), 10.00 (1H, s).

Reference Example 62 Synthesis of 2-benzenesulfonyl-3-((5-(4-chlorophenyl)-6-(3-fluoro-4-methylphenyl)pyridin-3-yl)methyl)-1-(tert-butoxycarbonyl)guanidine

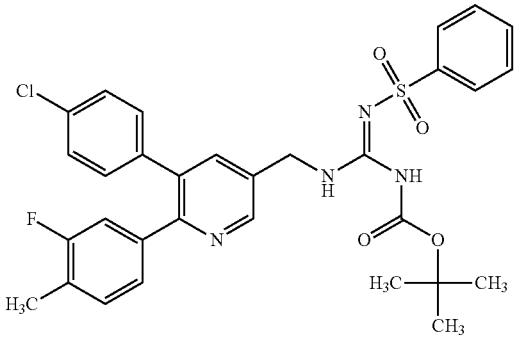

The title compound (0.058 g) was obtained in the same way as in Reference Example 52 using 2-((5-(4-chlorophenyl)-6-(3-fluoro-4-methylphenyl)pyridin-3-yl)methyl)isoindoline-1,3-dione (0.050 g) synthesized in Reference Example 25 and N-(phenylsulfonyl)-N'-(tert-butoxycarbonyl)-S-methylisothiourea (0.040 g) synthesized in Reference Example 42.

$^1$H-NMR (CDCl$_3$) δ: 1.51 (9H, s), 2.25 (3H, d, J=1.4 Hz), 4.59 (2H, d, J=5.9 Hz), 6.89 (1H, dd, J=7.8, 1.8 Hz), 7.02 (4H, tt, J=9.1, 3.1 Hz), 7.25 (2H, dd, J=6.2, 3.9 Hz), 7.37 (2H, td, J=6.9, 1.7 Hz), 7.44-7.49 (1H, m), 7.53 (1H, d, J=2.3 Hz), 7.79-7.83 (2H, m), 8.54 (1H, d, J=2.3 Hz), 8.99 (1H, t, J=5.5 Hz), 10.00 (1H, s).

MS (ESI) [M+H]: 609.

Reference Example 63 Synthesis of 2-benzenesulfonyl-3-((5-(4-chlorophenyl)-6-(2-fluoro-4-methylphenyl)pyridin-3-yl)methyl)-1-(tert-butoxycarbonyl)guanidine

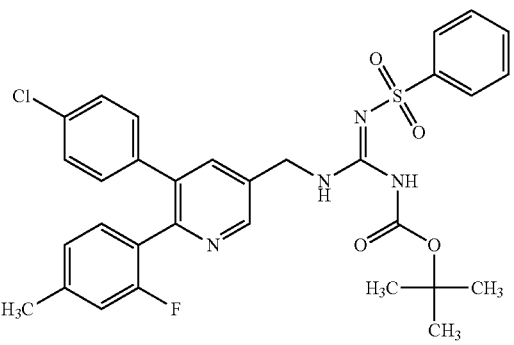

The title compound (0.049 g) was obtained in the same way as in Reference Example 52 using 2-((5-(4-chlorophenyl)-6-(2-fluoro-4-methylphenyl)pyridin-3-yl)methyl)isoindoline-1,3-dione (0.050 g) synthesized in Reference Example 26 and N-(phenylsulfonyl)-N'-(tert-butoxycarbonyl)-S-methylisothiourea (0.040 g) synthesized in Reference Example 42.

$^1$H-NMR (CDCl$_3$) δ: 1.51 (9H, s), 2.34 (3H, s), 4.61 (2H, d, J=5.9 Hz), 6.71 (1H, d, J=11.4 Hz), 6.96-6.99 (3H, m), 7.20 (2H, dd, J=6.6, 2.1 Hz), 7.26 (1H, t, J=7.8 Hz), 7.37 (2H, td, J=6.7, 1.5 Hz), 7.43-7.49 (1H, m), 7.56 (1H, d, J=2.3 Hz), 7.80-7.83 (2H, m), 8.56 (1H, d, J=1.8 Hz), 9.00 (1H, t, J=6.2 Hz), 10.00 (1H, s).

MS (ESI) [M+H]$^+$: 609.

Reference Example 64 Synthesis of 2-benzenesulfonyl-3-((6-(4-chloro-2-methoxyphenyl)-5-(4-chlorophenyl)pyridin-3-yl)methyl)-1-(tert-butoxycarbonyl)guanidine

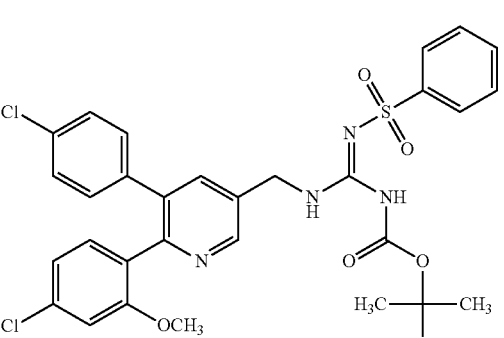

The title compound (0.18 g) was obtained in the same way as in Reference Example 52 using 2-((6-(4-chloro-2-methoxyphenyl)-5-(4-chlorophenyl)pyridin-3-yl)methyl)isoindoline-1,3-dione (0.15 g) synthesized in Reference Example 27 and N-(phenylsulfonyl)-N'-(tert-butoxycarbonyl)-S-methylisothiourea (0.11 g) synthesized in Reference Example 42.

$^1$H-NMR (CDCl$_3$) δ: 1.51 (9H, s), 3.30 (3H, s), 4.61 (2H, d, J=5.9 Hz), 6.68 (1H, d, J=1.8 Hz), 6.97 (2H, dt, J=9.0, 2.3 Hz), 7.01 (1H, dd, J=8.2, 1.8 Hz), 7.20 (2H, dt, J=8.8, 2.3 Hz), 7.31 (1H, d, J=8.2 Hz), 7.37-7.40 (2H, m), 7.45-7.49 (1H, m), 7.56 (1H, d, J=1.8 Hz), 7.84 (2H, td, J=4.8, 2.7 Hz), 8.54 (1H, d, J=1.8 Hz), 8.98 (1H, t, J=5.7 Hz), 10.00 (1H, s).

MS (ESI) [M+H]$^+$: 641.

Reference Example 65 Synthesis of 2-benzenesulfonyl-3-((6-(4-chlorophenyl)-5-phenylpyridin-3-yl)methyl)-1-(tert-butoxycarbonyl)guanidine

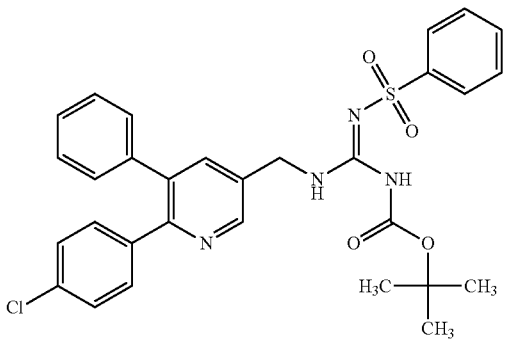

The title compound (0.12 g) was obtained in the same way as in Reference Example 52 using 2-((6-(4-chlorophenyl)-5-phenylpyridin-3-yl)methyl)isoindoline-1,3-dione (0.11 g) synthesized in Reference Example 28 and N-(phenylsulfonyl)-N'-(tert-butoxycarbonyl)-S-methylisothiourea (0.094 g) synthesized in Reference Example 42.

$^1$H-NMR (CDCl$_3$) δ: 1.51 (9H, s), 4.60 (2H, d, J=5.9 Hz), 7.05-7.07 (2H, m), 7.19-7.30 (6H, m), 7.36 (3H, t, J=7.6 Hz), 7.45 (1H, t, J=7.4 Hz), 7.57 (1H, d, J=2.2 Hz), 7.80-7.83 (2H, m), 8.54 (1H, d, J=2.2 Hz), 8.98 (1H, t, J=5.5 Hz), 9.99 (1H, s).

MS (ESI) [M+H]$^+$: 577.

Reference Example 66 Synthesis of 2-benzenesulfonyl-3-((5-(3-chlorophenyl)-6-(4-chlorophenyl)pyridin-3-yl)methyl)-1-(tert-butoxycarbonyl)guanidine

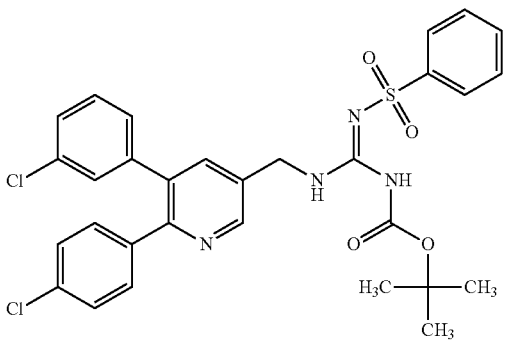 [SMILES: CC(C)(C)OC(=O)N/C(=N\S(=O)(=O)c1ccccc1)NCc1cnc(-c2ccc(Cl)cc2)c(-c2cccc(Cl)c2)c1]

The title compound (0.048 g) was obtained in the same way as in Reference Example 52 using 2-((5-(3-chlorophenyl)-6-(4-chlorophenyl)pyridin-3-yl)methy)isoindoline-1,3-dione (0.048 g) synthesized in Reference Example 29 and N-(phenylsulfonyl)-N'-(tert-butoxycarbonyl)-S-methylisothiourea (0.062 g) synthesized in Reference Example 42.

$^1$H-NMR (CDCl$_3$) δ: 1.51 (9H, s), 4.60 (2H, d, J=5.9 Hz), 6.89 (1H, dt, J=7.7, 1.3 Hz), 7.11 (1H, t, J=1.8 Hz), 7.17-7.22 (2H, m), 7.27-7.30 (2H, m), 7.34-7.53 (5H, m), 7.80-7.82 (2H, m), 8.57 (1H, d, J=2.2 Hz), 8.99 (1H, t, J=6.0 Hz), 9.98 (1H, d, J=7.8 Hz).

MS (ESI) [M+H]$^+$: 611.

Reference Example 67 Synthesis of 2-benzenesulfonyl-3-((5-(2-chlorophenyl)-6-(4-chlorophenyl)pyridin-3-yl)methyl)-1-(tert-butoxycarbonyl)guanidine

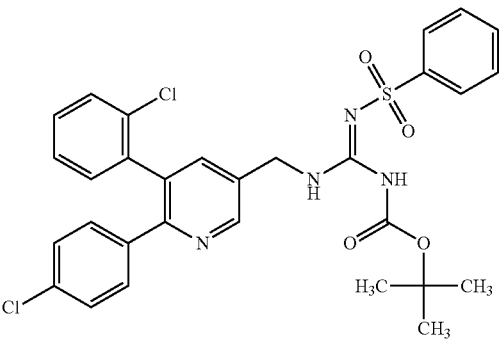 [SMILES: CC(C)(C)OC(=O)N/C(=N\S(=O)(=O)c1ccccc1)NCc1cnc(-c2ccc(Cl)cc2)c(-c2ccccc2Cl)c1]

The title compound (0.047 g) was obtained in the same way as in Reference Example 52 using 2-((5-(2-chlorophenyl)-6-(4-chlorophenyl)pyridin-3-yl)methyl)isoindoline-1,3-dione (0.045 g) synthesized in Reference Example 30 and N-(phenylsulfonyl)-N'-(tert-butoxycarbonyl)-S-methylisothiourea (0.036 g) synthesized in Reference Example 42.

$^1$H-NMR (CDCl$_3$) δ: 1.51 (9H, s), 4.62 (2H, d, J=5.9 Hz), 7.01 (1H, dd, J=7.7, 1.8 Hz), 7.17-7.24 (5H, m), 7.29 (1H, dd, J=7.5, 1.6 Hz), 7.33-7.43 (4H, m), 7.52 (1H, d, J=1.8 Hz), 7.80-7.82 (2H, m), 8.59 (1H, d, J=2.3 Hz), 9.00 (1H, t, J=6.1 Hz), 9.98 (1H, s).

MS (ESI) [M+H]$^+$: 611.

Reference Example 68 Synthesis of 2-benzenesulfonyl-3-((6-(4-chlorophenyl)-5-(4-methylphenyl)pyridin-3-yl)methyl)-1-(tert-butoxycarbonyl)guanidine

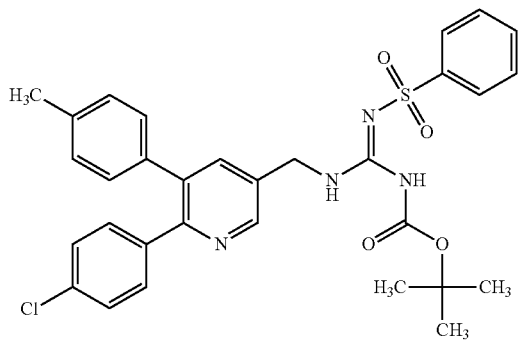

The title compound (0.050 g) was obtained in the same way as in Reference Example 52 using 2-((6-(4-chlorophenyl)-5-(4-methylphenyl)pyridin-3-yl)methyl)isoindoline-1,3-dione (0.050 g) synthesized in Reference Example 31 and N-(phenylsulfonyl)-N'-(tert-butoxycarbonyl)-S-methylisothiourea (0.041 g) synthesized in Reference Example 42.

$^1$H-NMR (CDCl$_3$) δ: 1.50 (9H, s), 2.36 (3H, s), 4.59 (2H, d, J=5.4 Hz), 6.95 (2H, d, J=7.7 Hz), 7.09 (2H, d, J=8.2 Hz), 7.21 (2H, d, J=8.6 Hz), 7.24-7.27 (2H, m), 7.37 (2H, t, J=7.5 Hz), 7.44 (1H, d, J=7.2 Hz), 7.55 (1H, d, J=2.3 Hz), 7.81 (2H, d, J=7.2 Hz), 8.52 (1H, d, J=2.3 Hz), 8.97 (1H, t, J=5.4 Hz), 9.98 (1H, s).

MS (ESI) [M+H]$^+$: 591.

Reference Example 69 Synthesis of 2-benzenesulfonyl-3-((6-(4-chlorophenyl)-5-(4-methoxyphenyl)pyridin-3-yl)methyl)-1-(tert-butoxycarbonyl)guanidine

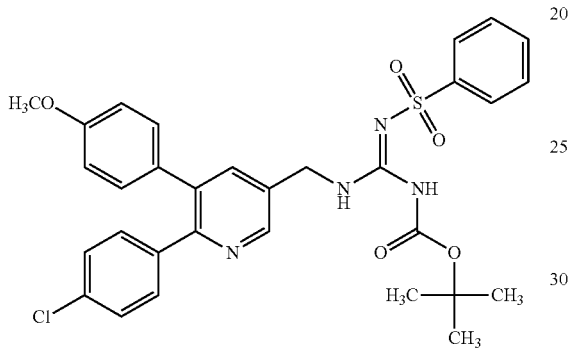

The title compound (0.014 g) was obtained in the same way as in Reference Example 52 using 2-((6-(4-chlorophenyl)-5-(4-methoxyphenyl)pyridin-3-yl)methyl)isoindoline-1,3-dione (0.026 g) synthesized in Reference Example 32 and N-(phenylsulfonyl)-N'-(tert-butoxycarbonyl)-S-methylisothiourea (0.015 g) synthesized in Reference Example 42.

$^1$H-NMR (CDCl$_3$) δ: 1.51 (9H, s), 3.82 (3H, s), 4.59 (2H, d, J=5.9 Hz), 6.81 (2H, d, J=9.2 Hz), 6.98 (2H, d, J=9.1 Hz), 7.22 (2H, d, J=8.6 Hz), 7.26 (2H, d, J=8.8 Hz), 7.36-7.39 (2H, m), 7.44-7.48 (1H, m), 7.56 (1H, d, J=2.2 Hz), 7.81-7.83 (2H, m), 8.51 (1H, d, J=2.2 Hz), 8.97 (1H, t, J=5.6 Hz), 9.99 (1H, s).

MS (ESI) [M+H]$^+$: 607.

Reference Example 70 Synthesis of 2-benzenesulfonyl-3-((6-(4-chlorophenyl)-5-(4-cyanophenyl)pyridin-3-yl)methyl)-1-(tert-butoxycarbonyl)guanidine The title compound (0.12 g) was obtained in the same way as in Reference Example 52 using 2-((6-(4-chlorophenyl)-5-(4-cyanophenyl)pyridin-3-yl)methyl)isoindoline-1,3-dione (0.10 g) synthesized in Reference Example 33 and N-(phenylsulfonyl)-N'-(tert-butoxycarbonyl)-S-methylisothiourea (0.081 g) synthesized in Reference Example 42.

$^1$H-NMR (CDCl$_3$) δ: 1.51 (9H, s), 4.60 (2H, d, J=5.9 Hz), 7.18-7.27 (6H, m), 7.39 (2H, t, J=7.9 Hz), 7.48 (1H, t, J=7.0 Hz), 7.58 (2H, d, J=8.2 Hz), 7.61 (1H, d, J=2.3 Hz), 7.82 (2H, d, J=7.7 Hz), 8.60 (1H, d, J=2.3 Hz), 9.01 (1H, t, J=5.7 Hz), 10.00 (1H, s).

MS (ESI) [M+H]$^+$: 602.

Reference Example 71 Synthesis of 2-benzenesulfonyl-3-((6-(4-chlorophenyl)-5-(4-fluorophenyl)pyridin-3-yl)methyl)-1-(tert-butoxycarbonyl)guanidine

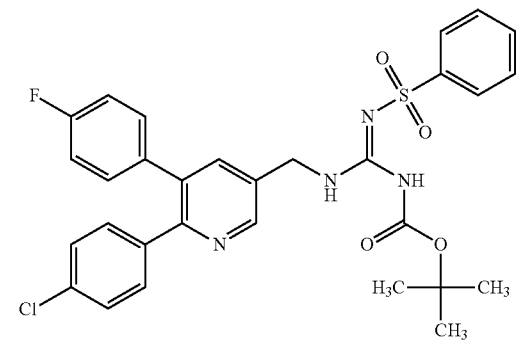 [SMILES: CC(C)(C)OC(=O)N/C(=N\S(=O)(=O)c1ccccc1)NCc1cnc(-c2ccc(Cl)cc2)c(-c2ccc(F)cc2)c1]

The title compound (0.22 g) was obtained in the same way as in Reference Example 52 using 2-((6-(4-chlorophenyl)-5-(4-fluorophenyl)pyridin-3-yl)methyl)isoindoline-1,3-dione (0.19 g) synthesized in Reference Example 34 and N-(phenylsulfonyl)-N'-(tert-butoxycarbonyl)-S-methylisothiourea (0.16 g) synthesized in Reference Example 42.

$^1$H-NMR (CDCl$_3$) δ:1.51 (9H, s), 4.60 (2H, d, J=5.9 Hz), 6.96-7.05 (4H, m), 7.23 (4H, s), 7.35-7.40 (2H, m), 7.45-7.48 (1H, m), 7.56-7.57 (1H, m), 7.81-7.84 (2H, m), 8.55 (1H, d, J=2.3 Hz), 8.99 (1H, t, J=5.7 Hz), 9.99 (1H, s).

MS (ESI) [M+H]$^+$: 595.

Reference Example 72 Synthesis of 2-benzenesulfonyl-3-((6-(4-chlorophenyl)-5-(4-(trifluoromethyl)phenyl)pyridin-3-yl)methyl)-1-(tert-butoxycarbonyl)guanidine

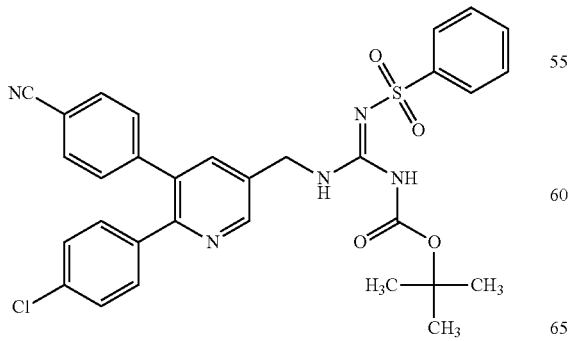

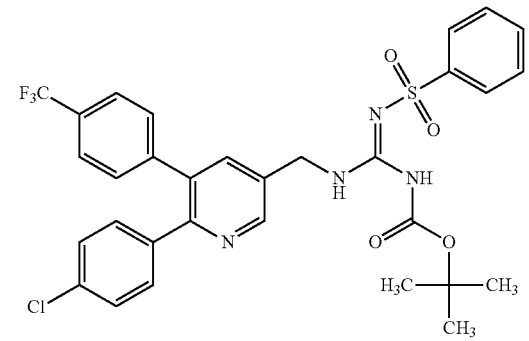 [SMILES: CC(C)(C)OC(=O)N/C(=N\S(=O)(=O)c1ccccc1)NCc1cnc(-c2ccc(Cl)cc2)c(-c2ccc(C(F)(F)F)cc2)c1]

The title compound (0.21 g) was obtained in the same way as in Reference Example 52 using 2-((6-(4-chlorophenyl)-5-(4-(trifluoromethyl)phenyl)pyridin-3-yl)methyl)isoindoline-1,3-dione (0.20 g) synthesized in Reference Example 35 and N-(phenylsulfonyl)-N'-(tert-butoxycarbonyl)-S-methylisothiourea (0.13 g) synthesized in Reference Example 42.

$^1$H-NMR (CDCl$_3$) δ:1.51 (9H, s), 4.61 (2H, d, J=5.9 Hz), 7.19 (2H, d, J=7.7 Hz), 7.23-7.27 (4H, m), 7.36 (2H, t, J=7.7 Hz), 7.44 (1H, t, J=7.5 Hz), 7.55 (2H, d, J=8.2 Hz), 7.58 (1H, d, J=1.8 Hz), 7.82 (2H, d, J=7.7 Hz), 8.59 (1H, d, J=2.3 Hz), 9.01 (1H, t, J=5.4 Hz), 10.00 (1H, s).

MS (ESI) [M+H]$^+$: 645.

Reference Example 73 Synthesis of 2-benzenesulfonyl-3-((6-(4-chlorophenyl)-5-(4-(trifluoromethoxy)phenyl)pyridin-3-yl)methyl)-1-(tert-butoxycarbonyl)guanidine

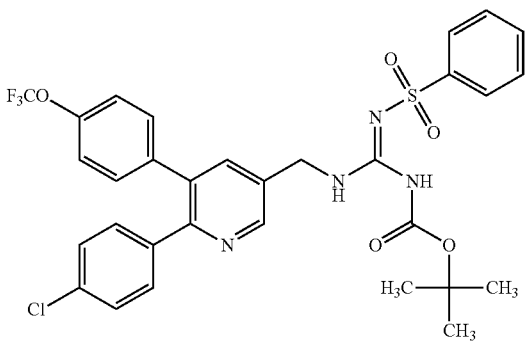 [SMILES: CC(C)(C)OC(=O)N/C(=N\S(=O)(=O)c1ccccc1)NCc1cnc(-c2ccc(Cl)cc2)c(-c2ccc(OC(F)(F)F)cc2)c1]

The title compound (0.19 g) was obtained in the same way as in Reference Example 52 using 2-((6-(4-chlorophenyl)-5-(4-(trifluoromethoxy)phenyl)pyridin-3-yl)methyl)isoindoline-1,3-dione (0.20 g) synthesized in Reference Example 36 and N-(phenylsulfonyl)-N'-(tert-butoxycarbonyl)-S-methylisothiourea (0.14 g) synthesized in Reference Example 42.

$^1$H-NMR (CDCl$_3$) δ: 1.51 (9H, s), 4.60 (2H, d, J=5.9 Hz), 7.08 (2H, d, J=8.6 Hz), 7.14 (2H, d, J=8.6 Hz), 7.22-7.25 (4H, m), 7.34-7.39 (2H, m), 7.42-7.48 (1H, m), 7.57 (1H, d, J=1.8 Hz), 7.82 (2H, d, J=8.2 Hz), 8.56 (1H, d, J=1.8 Hz), 8.99 (1H, t, J=5.4 Hz), 9.99 (1H, brs).

MS (ESI) [M+H]$^+$: 661.

Reference Example 74 Synthesis of 2-benzenesulfonyl-3-((6-(4-chlorophenyl)-5-(4-isopropoxyphenyl)pyridin-3-yl)methyl)-1-(tert-butoxycarbonyl)guanidine

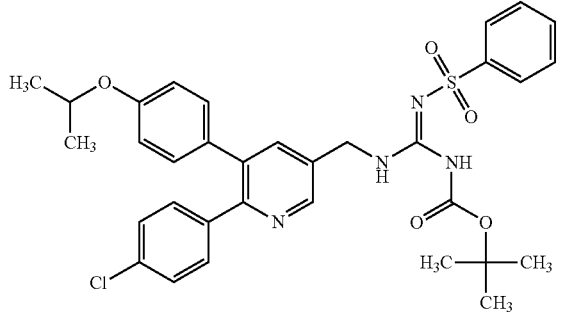 [SMILES: CC(C)Oc1ccc(-c2cc(CN/C(=N/S(=O)(=O)c3ccccc3)NC(=O)OC(C)(C)C)cnc2-c2ccc(Cl)cc2)cc1]

The title compound (0.21 g) was obtained in the same way as in Reference Example 52 using 2-(((6-(4-chlorophenyl)-5-(4-isopropoxyphenyl)pyridin-3-yl)methyl)isoindoline-1,3-dione (0.19 g) synthesized in Reference Example 37 and N-(phenylsulfonyl)-N'-(tert-butoxycarbonyl)-S-methylisothiourea (0.14 g) synthesized in Reference Example 42.

$^1$H-NMR (CDCl$_3$) δ: 1.34 (3H, s), 1.36 (3H, s), 1.50 (9H, s), 4.51-4.57 (1H, m), 4.59 (2H, d, J=5.4 Hz), 6.79 (2H, dt, J=9.4, 2.5 Hz), 6.93-6.98 (2H, m), 7.20-7.23 (2H, m), 7.25-7.28 (2H, m), 7.35-7.40 (2H, m), 7.46 (1H, tt, J=7.5, 1.6 Hz), 7.55 (1H, d, J=2.3 Hz), 7.81-7.84 (2H, m), 8.50 (1H, d, J=2.3 Hz), 8.97 (1H, t, J=5.7 Hz), 9.98 (1H, s).

MS (ESI) [M+H]$^+$: 635.

Reference Example 75 Synthesis of 2-benzenesulfonyl-3-((5-(4-methoxyphenyl)-6-(4-methylphenyl)pyridin-3-yl)methyl)-1-(tert-butoxycarbonyl)guanidine

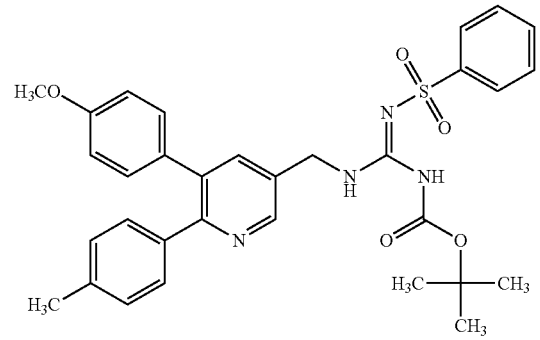

The title compound (0.032 g) was obtained in the same way as in Reference Example 52 using 2-((5-(4-methoxyphenyl)-6-(4-methylphenyl)pyridin-3-yl)methyl)isoindoline-1,3-dione (0.030 g) synthesized in Reference Example 38 and N-(phenylsulfonyl)-N'-(tert-butoxycarbonyl)-S-methylisothiourea (0.025 g) synthesized in Reference Example 42.

$^1$H-NMR (CDCl$_3$) δ: 1.48 (9H, s), 2.30 (3H, s), 3.79 (3H, s), 4.56 (2H, d, J=5.9 Hz), 6.77 (2H, d, J=8.6 Hz), 6.98 (2H, d, J=8.6 Hz), 7.03 (2H, d, J=7.7 Hz), 7.19 (2H, d, J=8.2 Hz), 7.35 (2H, tt, J=7.5, 1.6 Hz), 7.43 (1H, tt, J=7.2, 1.6 Hz), 7.51 (1H, d, J=2.3 Hz), 7.78-7.81 (2H, m), 8.48 (1H, d, J=2.3 Hz), 8.93 (1H, t, J=5.7 Hz), 9.96 (1H, s).

MS (ESI) [M+H]$^+$: 587.

Reference Example 76 Synthesis of 2-benzenesulfonyl-3-((6-(4-methylphenyl)-5-(4-(trifluoromethyl)phenyl)pyridin-3-yl)methyl)-1-(tert-butoxycarbonyl)guanidine

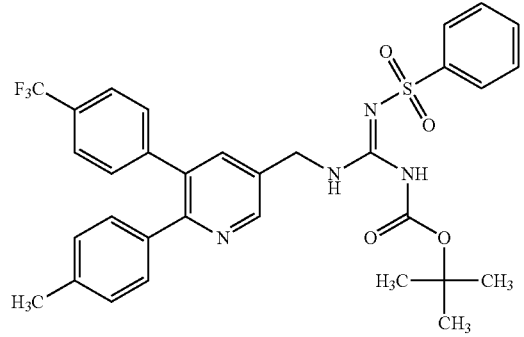

The title compound (0.074 g) was obtained in the same way as in Reference Example 52 using 2-((6-(4-methylphenyl)-5-(4-(trifluoromethyl)phenyl)pyridin-3-yl)methyl)isoindoline-1,3-dione (0.060 g) synthesized in Reference Example 39 and N-(phenylsulfonyl)-N'-(tert-butoxycarbonyl)-S-methylisothiourea (0.046 g) synthesized in Reference Example 42.

$^1$H-NMR (CDCl$_3$) δ: 1.51 (9H, s), 2.33 (3H, s), 4.60 (2H, d, J=5.9 Hz), 7.06 (2H, d, J=8.2 Hz), 7.18 (4H, dd, J=11.8, 8.2 Hz), 7.36 (2H, t, J=7.7 Hz), 7.44 (1H, t, J=7.5 Hz), 7.52 (2H, d, J=8.2 Hz), 7.55 (1H, d, J=1.8 Hz), 7.81 (2H, d, J=8.2 Hz), 8.58 (1H, d, J=2.3 Hz), 8.99 (1H, t, J=5.7 Hz), 10.00 (1H, brs).

MS (ESI) [M+H]$^+$: 625.

Reference Example 77 Synthesis of 3-((5,6-bis(4-chlorophenyl)pyridin-3-yl)methyl)-2-(2-fluorobenzenesulfonyl)-1-(tert-butoxycarbonyl)guanidine

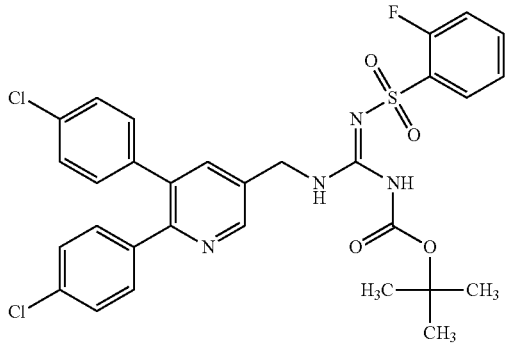 [SMILES: CC(C)(C)OC(=O)N/C(=N\S(=O)(=O)c1ccccc1F)NCc1cnc(-c2ccc(Cl)cc2)c(-c2ccc(Cl)cc2)c1]

The title compound (0.031 g) was obtained in the same way as in the guanidination reaction of Reference Example 52 using (5,6-bis(4-chlorophenyl)pyridin-3-yl)methanamine (0.020 g) synthesized in Reference Example 52 and N-(2-fluorophenylsulfonyl)-N'-(tert-butoxycarbonyl)-S-methylisothiourea (0.028 g) synthesized in Reference Example 43.

$^1$H-NMR (CDCl$_3$) δ: 1.52 (9H, s), 4.59 (2H, d, J=5.9 Hz), 6.92-6.97 (1H, m), 7.00 (2H, dt, J=8.9, 2.3 Hz), 7.17-7.29 (7H, m), 7.39-7.45 (1H, m), 7.57 (1H, d, J=2.2 Hz), 7.93 (1H, td, J=7.6, 1.7 Hz), 8.54 (1H, d, J=2.2 Hz), 9.09 (1H, t, J=5.9 Hz), 10.04 (1H, s).

MS (ESI) [M+H]$^+$: 629.

Reference Example 78 Synthesis of 3-((5,6-bis(4-chlorophenyl)pyridin-3-yl)methyl)-2-(3-fluorobenzenesulfonyl)-1-(tert-butoxycarbonyl)guanidine

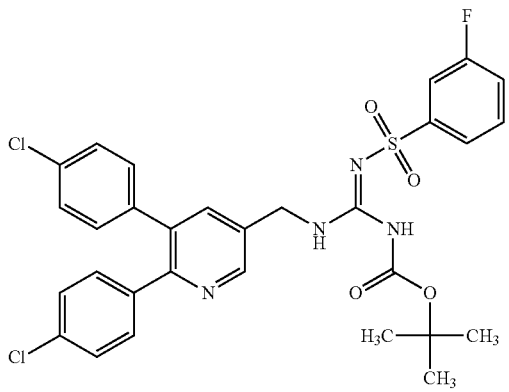 [SMILES: CC(C)(C)OC(=O)N/C(=N\S(=O)(=O)c1cccc(F)c1)NCc1cnc(-c2ccc(Cl)cc2)c(-c2ccc(Cl)cc2)c1]

The title compound (0.034 g) was obtained in the same way as in the guanidination reaction of Reference Example 52 using (5,6-bis(4-chlorophenyl)pyridin-3-yl)methanamine (0.020 g) synthesized in Reference Example 52 and N-(3-fluorophenylsulfonyl)-N'-(tert-butoxycarbonyl)-S-methylisothiourea (0.021 g) synthesized in Reference Example 44.

$^1$H-NMR (CDCl$_3$) δ:1.51 (9H, s), 4.60 (2H, d, J=5.9 Hz), 7.00-7.04 (2H, m), 7.15 (1H, tdd, J=8.3, 2.6, 0.8 Hz), 7.24-7.28 (6H, m), 7.34 (1H, td, J=8.0, 5.4 Hz), 7.49 (1H, dt, J=8.0, 2.1 Hz), 7.55 (1H, d, J=2.2 Hz), 7.61 (1H, dq, J=7.8, 0.8 Hz), 8.55 (1H, d, J=2.2 Hz), 9.05 (1H, t, J=5.6 Hz), 9.92 (1H, s).

MS (ESI) [M+H]$^+$: 629.

Reference Example 79 Synthesis of 3-((5,6-bis(4-chlorophenyl)pyridin-3-yl)methyl)-2-(4-fluorobenzenesulfonyl)-1-(tert-butoxycarbonyl)guanidine

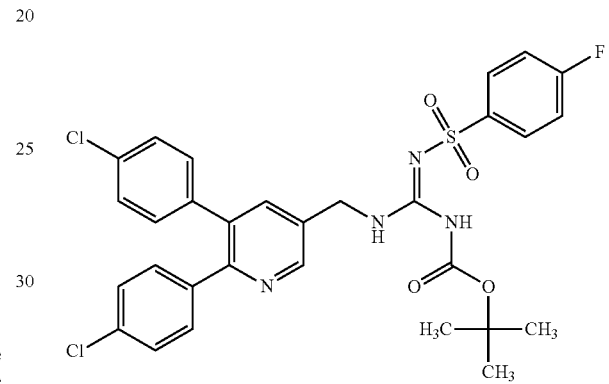

The title compound (0.034 g) was obtained in the same way as in the guanidination reaction of Reference Example 52 using (5,6-bis(4-chlorophenyl)pyridin-3-yl)methanamine (0.020 g) synthesized in Reference Example 52 and N-(4-fluorophenylsulfonyl)-N'-(tert-butoxycarbonyl)-S-methylisothiourea (0.028 g) synthesized in Reference Example 45.

$^1$H-NMR (CDCl$_3$) δ: 1.51 (9H, s), 4.58 (2H, d, J=5.9 Hz), 6.98-7.06 (4H, m), 7.24-7.29 (6H, m), 7.54 (1H, d, J=1.8 Hz), 7.79-7.84 (2H, m), 8.55 (1H, d, J=1.8 Hz), 9.01 (1H, t, J=5.9 Hz), 9.94 (1H, s).

MS (ESI) [M+H]$^+$: 629.

Reference Example 80 Synthesis of 3-((5,6-bis(4-chlorophenyl)pyridin-3-yl)methyl)-2-(thiophene-2-sulfonyl)-1-(tert-butoxycarbonyl)guanidine

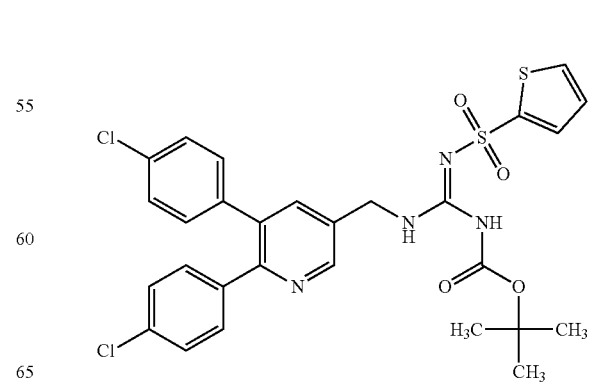

The title compound (0.035 g) was obtained in the same way as in the guanidination reaction of Reference Example 52 using (5,6-bis(4-chlorophenyl)pyridin-3-yl)methanamine (0.020 g) synthesized in Reference Example 52 and N-(2-thiophenesulfonyl)-N'-(tert-butoxycarbonyl)-S-methylisothiourea (0.022 g) synthesized in Reference Example 46.

$^1$H-NMR (CDCl$_3$) δ: 1.50 (9H, s), 4.63 (2H, d, J=5.4 Hz), 6.94 (1H, dd, J=5.0, 3.6 Hz), 7.05 (2H, dt, J=8.9, 2.3 Hz), 7.24-7.28 (6H, m), 7.39 (1H, dd, J=5.0, 1.4 Hz), 7.53 (1H, dd, J=3.6, 1.4 Hz), 7.63 (1H, d, J=1.8 Hz), 8.58 (1H, d, J=2.3 Hz), 9.04 (1H, t, J=5.9 Hz), 9.86 (1H, s).

MS (ESI) [M+H]$^+$: 617.

Reference Example 81 Synthesis of 3-((5,6-bis(4-chlorophenyl)pyridin-3-yl)methyl)-2-(thiophene-3-sulfonyl)-1-(tert-butoxycarbonyl)guanidine

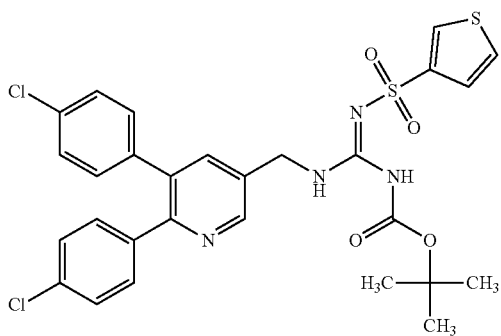 [SMILES: CC(C)(C)OC(=O)N/C(=N\S(=O)(=O)c1ccsc1)NCc1cnc(-c2ccc(Cl)cc2)c(-c2ccc(Cl)cc2)c1]

The title compound (0.032 g) was obtained in the same way as in the guanidination reaction of Reference Example 52 using (5,6-bis(4-chlorophenyl)pyridin-3-yl)methanamine (0.020 g) synthesized in Reference Example 52 and N-(3-thiophenesulfonyl)-N'-(tert-butoxycarbonyl)-S-methylisothiourea (0.022 g) synthesized in Reference Example 47.

$^1$H-NMR (CDCl$_3$) δ: 1.50 (9H, s), 4.61 (2H, d, J=5.9 Hz), 7.04 (2H, dt, J=8.9, 2.3 Hz), 7.22-7.30 (8H, m), 7.59 (1H, d, J=1.8 Hz), 7.83 (1H, dd, J=3.2, 1.4 Hz), 8.58 (1H, d, J=1.8 Hz), 9.01 (1H, t, J=5.7 Hz), 9.94 (1H, s).

MS (ESI) [M+H]$^+$: 617.

Reference Example 82 Synthesis of 3-((5,6-bis(4-chlorophenyl)pyridin-3-yl)methyl)-2-(furan-2-sulfonyl)-1-(tert-butoxycarbonyl)guanidine

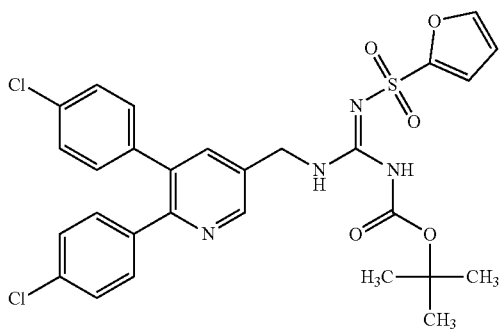

The title compound (0.034 g) was obtained in the same way as in the guanidination reaction of Reference Example 52 using (5,6-bis(4-chlorophenyl)pyridin-3-yl)methanamine (0.020 g) synthesized in Reference Example 52 and N-(furan-2-sulfonyl)-N'-(tert-butoxycarbonyl)-S-methylisothiourea (0.021 g) synthesized in Reference Example 48.

$^1$H-NMR (CDCl$_3$) δ: 1.51 (9H, s), 4.63 (2H, d, J=5.6 Hz), 6.37 (1H, dd, J=3.5, 1.8 Hz), 6.92 (1H, dd, J=3.4, 1.0 Hz), 7.07 (2H, dt, J=8.9, 2.3 Hz), 7.22-7.30 (7H, m), 7.64 (1H, d, J=2.2 Hz), 8.57 (1H, d, J=2.2 Hz), 9.11 (1H, t, J=5.4 Hz), 9.88 (1H, s).

MS (ESI) [M+H]$^+$: 601.

Reference Example 83 Synthesis of 3-((5,6-bis(4-chlorophenyl)pyridin-3-yl)methyl)-2-(furan-3-sulfonyl)-1-(tert-butoxycarbonyl)guanidine

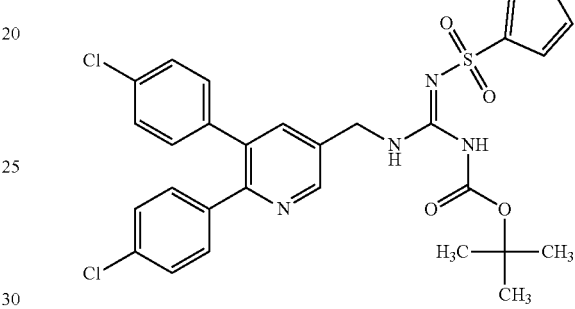

The title compound (0.031 g) was obtained in the same way as in the guanidination reaction of Reference Example 52 using (5,6-bis(4-chlorophenyl)pyridin-3-yl)methanamine (0.020 g) synthesized in Reference Example 52 and N-(furan-3-sulfonyl)-N'-(tert-butoxycarbonyl)-S-methylisothiourea (0.021 g) synthesized in Reference Example 49.

$^1$H-NMR (CDCl$_3$) δ: 1.50 (9H, s), 4.61 (2H, d, J=5.6 Hz), 6.54 (1H, dd, J=2.0, 1.0 Hz), 7.05 (2H, d, J=8.3 Hz), 7.22-7.31 (7H, m), 7.62 (1H, d, J=2.0 Hz), 7.80 (1H, t, J=0.7 Hz), 8.59 (1H, d, J=2.0 Hz), 9.02 (1H, t, J=5.5 Hz), 9.87 (1H, s).

MS (ESI) [M+H]$^+$: 601.

Reference Example 84 Synthesis of 3-((6-(4-methylphenyl)-5-(4-(trifluoromethyl)phenyl)pyridin-3-yl)methyl)-2-(thiophene-2-sulfonyl)-1-(tert-butoxycarbonyl)guanidine

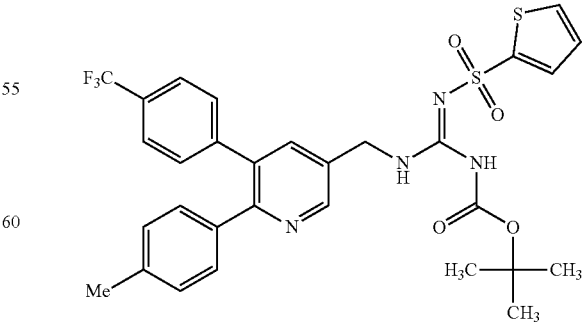

The title compound (0.061 g) was obtained in the same way as in Reference Example 52 using 2-((6-(4-methylphenyl)-5-(4-(trifluoromethyl)phenyl)pyridin-3-yl)methyl) isoindoline-1,3-dione (0.060 g) synthesized in Reference Example 39 and N-(2-thiophenesulfonyl)-N'-(tert-butoxycarbonyl)-S-methylisothiourea (0.047 g) synthesized in Reference Example 46.

$^1$H-NMR (CDCl$_3$) δ: 1.50 (9H, s), 2.33 (3H, s), 4.64 (2H, d, J=5.9 Hz), 6.92 (1H, dd, J=5.0, 3.6 Hz), 7.06 (2H, d, J=8.2 Hz), 7.18 (2H, d, J=8.2 Hz), 7.23-7.26 (2H, m), 7.36 (1H, dd, J=4.8, 1.1 Hz), 7.51-7.55 (3H, m), 7.63 (1H, d, J=2.3 Hz), 8.61 (1H, d, J=2.3 Hz), 9.04 (1H, t, J=5.4 Hz), 9.86 (1H, brs).

MS (ESI) [M+H]$^+$: 631.

Reference Example 85 Synthesis of 2-(benzenecarbonyl)-3-((5,6-bis(4-chlorophenyl)pyridin-3-yl)methyl)-1-(tert-butoxycarbonyl)guanidine

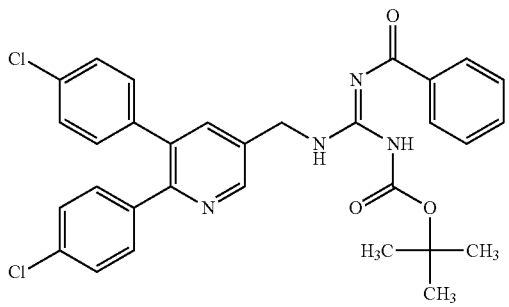

The title compound (0.033 g) was obtained in the same way as in the guanidination reaction of Reference Example 52 using (5,6-bis(4-chlorophenyl)pyridin-3-yl)methanamine (0.020 g) synthesized in Reference Example 52 and N-(benzenecarbonyl)-N'-(tert-butoxycarbonyl)-S-methylisothiourea (0.020 g) synthesized in Reference Example 50.

$^1$H-NMR (CDCl$_3$) δ: 1.51 (9H, s), 4.88 (2H, d, J=5.9 Hz), 7.04 (2H, dt, J=8.9, 2.2 Hz), 7.21-7.29 (6H, m), 7.38-7.41 (2H, m), 7.48-7.49 (1H, m), 7.76 (1H, d, J=2.0 Hz), 8.19-8.21 (2H, m), 8.74 (1H, d, J=2.2 Hz), 9.02 (1H, t, J=5.5 Hz), 12.51 (1H, s).

(The spectral data represents the value of a main isomer among isomers attributed to an amide bond.)

MS(ESI)[M+H]$^+$:575.

Reference Example 86 Synthesis of 3-((5,6-bis(4-chlorophenyl)pyridin-3-yl)methyl)-2-(thiophene-2-carbonyl)-1-(tert-butoxycarbonyl)guanidine

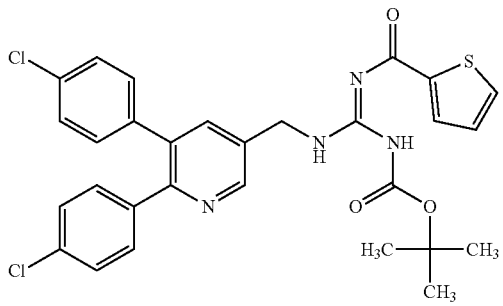 [SMILES: CC(C)(C)OC(=O)N/C(=N\C(=O)c1cccs1)NCc1cnc(-c2ccc(Cl)cc2)c(-c2ccc(Cl)cc2)c1]

The title compound (0.51 g) was obtained in the same way as in the guanidination reaction of Reference Example 52 using (5,6-bis(4-chlorophenyl)pyridin-3-yl)methanamine (0.030 g) synthesized in Reference Example 52 and N-(2-thiophenecarbonyl)-N'-(tert-butoxycarbonyl)-S-methylisothiourea (0.030 g) synthesized in Reference Example 51.

$^1$H-NMR (CDCl$_3$) δ:1.50 (9H, s), 4.81 (2H, d, J=6.1 Hz), 7.05-7.10 (3H, m), 7.21-7.28 (6H, m), 7.46 (1H, dd, J=4.9, 1.2 Hz), 7.79 (2H, dd, J=4.9, 1.7 Hz), 8.75 (1H, d, J=2.2 Hz), 8.99 (1H, t, J=5.9 Hz), 12.23 (1H, s).

MS (ESI) [M+H]$^+$: 581.

Example 1 Synthesis of N-(amino(((5,6-bis(4-chlorophenyl)pyridin-3-yl)methyl)amino)methylene)benzenesulfonamide

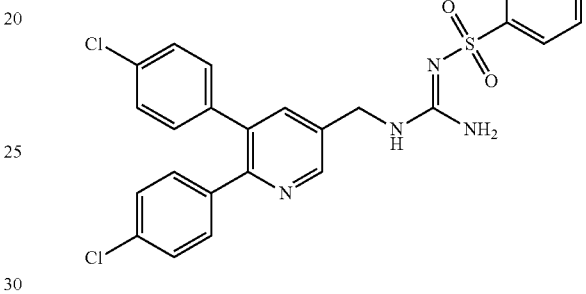

2-Benzenesulfonyl-3-((5,6-bis(4-chlorophenyl)pyridin-3-yl)methyl)-1-(tert-butoxycarbonyl)guanidine (6.4 g) synthesized in Reference Example 52 was dissolved in dichloromethane (50 mL). To the solution, trifluoroacetic acid (40 mL) was then added. The reaction mixture was stirred at room temperature for 2 hours, and then, a saturated aqueous solution of sodium bicarbonate was added thereto, followed by extraction with ethyl acetate. The organic layer was washed with saturated saline, dried over anhydrous sodium sulfate, and then concentrated under reduced pressure to obtain the title compound (hereinafter, referred to as the compound of Example 1) (5.3 g).

$^1$H-NMR (CDCl$_3$) δ: 4.44 (2H, d, J=5.4 Hz), 6.46 (2H, brs), 6.66 (1H, brs), 6.95 (2H, d, J=7.7 Hz), 7.18-7.23 (6H, m), 7.30 (2H, t, J=7.7 Hz), 7.42 (1H, t, J=7.0 Hz), 7.49 (1H, s), 7.72 (2H, d, J=8.6 Hz), 8.49 (1H, s).

MS (ESI) [M+H]$^+$: 511.

Example 2 Synthesis of N-(amino(((5,6-bis(4-chlorophenyl)pyridin-3-yl)methyl)amino)methylene)benzenesulfonamide Hydrochloride

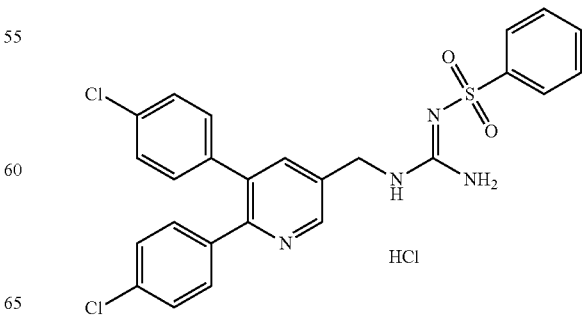

To a solution of the compound of Example 1 (5.3 g) in ethyl acetate (20 mL), a 4 mol/L solution of hydrogen chloride in ethyl acetate (2.4 mL) was added, and then, the mixture was concentrated under reduced pressure. The obtained crude product was recrystallized (n-hexane/ethyl acetate, v/v) to obtain the title compound (hereinafter, referred to as the compound of Example 2) (5.1 g) as a white solid.

$^1$H-NMR (CD$_3$OD) δ: 4.63 (2H, s), 7.18 (2H, d, J=8.8 Hz), 7.37-7.42 (6H, m), 7.47-7.53 (3H, m), 7.77 (2H, m), 8.47 (1H, brs), 8.77 (1H, brs).

MS (ESI) [M+H]$^+$: 511.

Example 3 Synthesis of N-(amino(((5-(4-chlorophenyl)-6-phenylpyridin-3-yl)methyl)amino)methylene)benzenesulfonamide

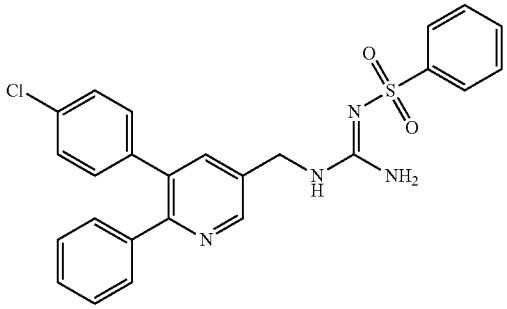 [SMILES: N/C(=N\S(=O)(=O)c1ccccc1)NCc1cnc(-c2ccccc2)c(-c2ccc(Cl)cc2)c1]

The title compound (hereinafter, referred to as the compound of Example 3) (0.035 g) was obtained in the same way as in Example 1 using 2-benzenesulfonyl-3-((5-(4-chlorophenyl)-6-phenylpyridin-3-yl)methyl)-1-(tert-butoxycarbonyl)guanidine (0.046 g) synthesized in Reference Example 53.

$^1$H-NMR (CDCl$_3$) δ: 4.42 (2H, d, J=5.4 Hz), 6.43 (2H, brs), 6.95 (2H, dd, J=8.4, 1.6 Hz), 7.18 (2H, dd, J=8.2, 1.4 Hz), 7.22-7.25 (5H, m), 7.27-7.32 (3H, m), 7.38-7.43 (1H, m), 7.49 (1H, d, J=2.0 Hz), 7.72-7.75 (2H, m), 8.47 (1H, d, J=2.0 Hz).

MS (ESI) [M+H]$^+$: 477.

Example 4 Synthesis of N-(amino(((6-(3-chlorophenyl)-5-(4-chlorophenyl)pyridin-3-yl)methyl)amino)methylene)benzenesulfonamide

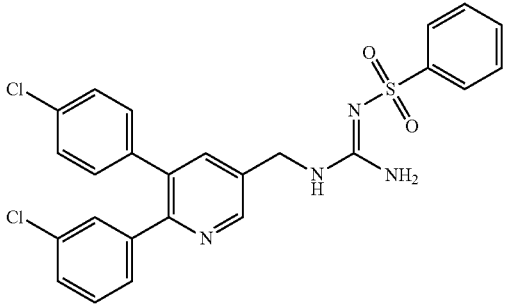 [SMILES: N/C(=N\S(=O)(=O)c1ccccc1)NCc1cnc(-c2cccc(Cl)c2)c(-c2ccc(Cl)cc2)c1]

The title compound (hereinafter, referred to as the compound of Example 4) (0.10 g) was obtained in the same way as in Example 1 using 2-benzenesulfonyl-3-((6-(3-chlorophenyl)-5-(4-chlorophenyl)pyridin-3-yl)methyl)-1-(tert-butoxycarbonyl)guanidine (0.12 g) synthesized in Reference Example 54.

$^1$H-NMR (CDCl$_3$) δ: 4.46 (2H, d, J=5.9 Hz), 6.37-6.63 (3H, m), 6.94-7.00 (3H, m), 7.10 (1H, t, J=7.7 Hz), 7.20-7.25 (3H, m), 7.31 (2H, t, J=7.7 Hz), 7.38-7.45 (2H, m), 7.51 (1H, d, J=2.3 Hz), 7.73-7.76 (2H, m), 8.50 (1H, d, J=2.3 Hz).

MS (ESI) [M+H]$^+$: 511.

Example 5 Synthesis of N-(amino(((5-(4-chlorophenyl)-6-(4-methylphenyl)pyridin-3-yl)methyl)amino)methylene)benzenesulfonamide

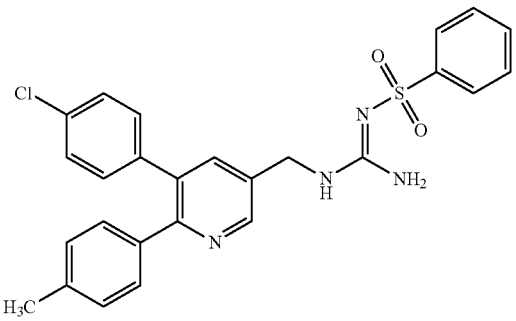

The title compound (hereinafter, referred to as the compound of Example 5) (0.067 g) was obtained in the same way as in Example 1 using 2-benzenesulfonyl-3-((5-(4-chlorophenyl)-6-(4-methylphenyl)pyridin-3-yl)methyl)-1-(tert-butoxycarbonyl)guanidine (0.081 g) synthesized in Reference Example 55.

$^1$H-NMR (CDCl$_3$) δ: 2.30 (3H, s), 4.40 (2H, d, J=5.4 Hz), 6.38 (2H, brs), 6.94-6.98 (2H, m), 7.03 (2H, d, J=8.2 Hz), 7.11-7.15 (2H, m), 7.20 (2H, dd, J=8.6, 2.7 Hz), 7.24-7.33 (3H, m), 7.38-7.43 (1H, m), 7.48 (1H, d, J=2.1 Hz), 7.73-7.76 (2H, m), 8.45 (1H, d, J=2.1 Hz).

MS (ESI) [M+H]$^+$: 491.

Example 6 Synthesis of N-(amino(((5-(4-chlorophenyl)-6-(4-methoxyphenyl)pyridin-3-yl)methyl)amino)methylene)benzenesulfonamide

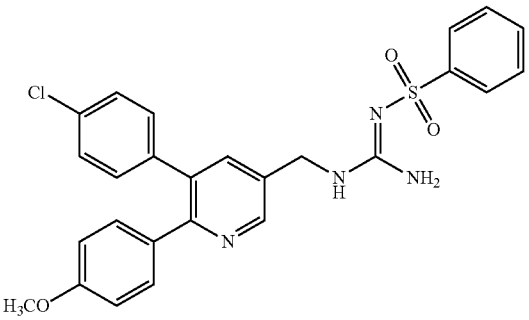 [SMILES: COc1ccc(-c2ncc(CN/C(N)=N/S(=O)(=O)c3ccccc3)cc2-c2ccc(Cl)cc2)cc1]

The title compound (hereinafter, referred to as the compound of Example 6) (0.029 g) was obtained in the same way as in Example 1 using 2-benzenesulfonyl-3-((5-(4-chlorophenyl)-6-(4-methoxyphenyl)pyridin-3-yl)methyl)-1-(tert-butoxycarbonyl)guanidine (0.055 g) synthesized in Reference Example 56.

¹H-NMR (CDCl₃) δ: 3.76 (3H, s), 4.40 (2H, d, J=4.1 Hz), 6.43 (2H, brs), 6.74 (2H, d, J=8.6 Hz), 6.96 (2H, d, J=8.2 Hz), 7.16-7.21 (4H, m), 7.26-7.31 (3H, m), 7.40 (1H, t, J=7.5 Hz), 7.46 (1H, d, J=1.6 Hz), 7.73 (2H, d, J=8.2 Hz), 8.43 (1H, d, J=1.6 Hz).

MS (ESI) [M+H]⁺: 507.

Example 7 Synthesis of N-(amino(((5-(4-chlorophenyl)-6-(4-cyanophenyl)pyridin-3-yl)methyl)amino)methylene)benzenesulfonamide

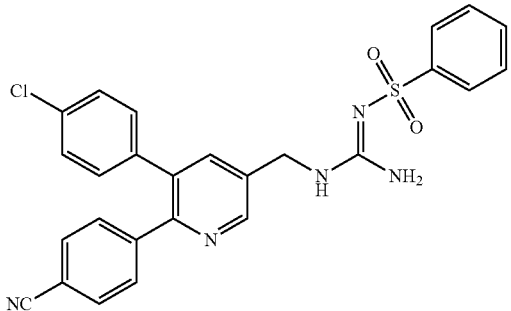 [SMILES: N#Cc1ccc(-c2ncc(CN/C(N)=N/S(=O)(=O)c3ccccc3)cc2-c2ccc(Cl)cc2)cc1]

The title compound (hereinafter, referred to as the compound of Example 7) (0.078 g) was obtained in the same way as in Example 1 using 2-benzenesulfonyl-3-((5-(4-chlorophenyl)-6-(4-cyanophenyl)pyridin-3-yl)methyl)-1-(tert-butoxycarbonyl)guanidine (0.095 g) synthesized in Reference Example 57.

¹H-NMR (DMSO-d₆) δ: 4.44 (2H, d, J=5.4 Hz), 6.91 (1H, brs), 7.11 (2H, d, J=8.6 Hz), 7.35-7.48 (7H, m), 7.64 (1H, d, J=2.0 Hz), 7.66 (2H, brs), 7.78 (2H, d, J=8.6 Hz), 8.57 (1H, d, J=2.0 Hz).

MS (ESI) [M+H]⁺: 502.

Example 8 Synthesis of N-(amino(((5-(4-chlorophenyl)-6-(4-fluorophenyl)pyridin-3-yl)methyl)amino)methylene)benzenesulfonamide

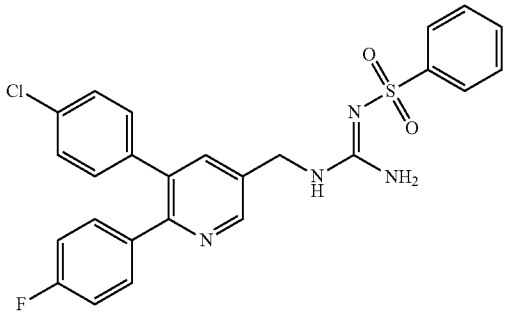 [SMILES: N/C(=N\S(=O)(=O)c1ccccc1)NCc1cnc(-c2ccc(F)cc2)c(-c2ccc(Cl)cc2)c1]

The title compound (hereinafter, referred to as the compound of Example 8) (0.17 g) was obtained in the same way as in Example 1 using 2-benzenesulfonyl-3-((5-(4-chlorophenyl)-6-(4-fluorophenyl)pyridin-3-yl)methyl)-1-(tert-butoxycarbonyl)guanidine (0.21 g) synthesized in Reference Example 58.

¹H-NMR (CDCl₃) δ: 4.45 (2H, d, J=5.4 Hz), 6.33-6.64 (3H, m), 6.89-6.97 (4H, m), 7.20-7.25 (4H, m), 7.31 (2H, t, J=7.5 Hz), 7.42 (1H, t, J=7.5 Hz), 7.50 (1H, d, J=2.3 Hz), 7.73-7.76 (2H, m), 8.49 (1H, d, J=2.3 Hz).

MS (ESI) [M+H]⁺: 495.

Example 9 Synthesis of N-(amino(((5-(4-chlorophenyl)-6-(3-fluorophenyl)pyridin-3-yl)methyl)amino)methylene)benzenesulfonamide

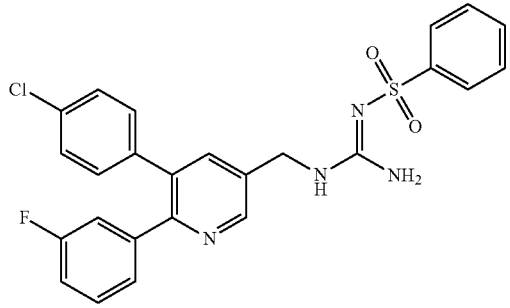 [SMILES: N/C(=N\S(=O)(=O)c1ccccc1)NCc1cnc(-c2cccc(F)c2)c(-c2ccc(Cl)cc2)c1]

The title compound (hereinafter, referred to as the compound of Example 9) (0.10 g) was obtained in the same way as in Example 1 using 2-benzenesulfonyl-3-((5-(4-chlorophenyl)-6-(3-fluorophenyl)pyridin-3-yl)methyl)-1-(tert-butoxycarbonyl)guanidine (0.13 g) synthesized in Reference Example 59.

¹H-NMR (CDCl₃) δ: 4.49 (2H, d, J=5.9 Hz), 6.25 (3H, brs), 6.95-7.00 (4H, m), 7.05 (1H, dt, J=9.7, 2.2 Hz), 7.16-7.26 (3H, m), 7.34 (2H, t, J=7.7 Hz), 7.44 (1H, t, J=7.5 Hz), 7.54 (1H, d, J=2.3 Hz), 7.78-7.80 (2H, m), 8.52 (1H, d, J=2.3 Hz).

MS (ESI) [M+H]⁺: 545.

Example 10 Synthesis of N-(amino(((5-(4-chlorophenyl)-6-(4-(trifluoromethoxy)phenyl)pyridin-3-yl)methyl)amino)methylene)benzenesulfonamide

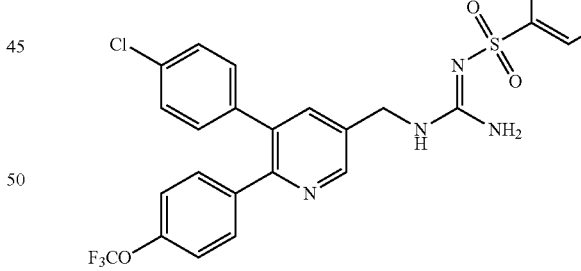

The title compound (hereinafter, referred to as the compound of Example 10) (0.24 g) was obtained in the same way as in Example 1 using 2-benzenesulfonyl-3-((5-(4-chlorophenyl)-6-(4-(trifluoromethoxy)phenyl)pyridin-3-yl)methyl)-1-(tert-butoxycarbonyl)guanidine (0.35 g) synthesized in Reference Example 61.

¹H-NMR (CDCl₃) δ: 4.51 (2H, d, J=5.9 Hz), 6.11 (3H, brs), 6.98-7.01 (2H, m), 7.10 (2H, d, J=8.6 Hz), 7.25-7.38 (6H, m), 7.45 (1H, t, J=7.5 Hz), 7.56 (1H, d, J=2.0 Hz), 7.80-7.83 (2H, m), 8.55 (1H, d, J=2.0 Hz).

MS (ESI) [M+H]⁺: 561.

Example 11 Synthesis of N-(amino(((5-(4-chlorophenyl)-6-(4-(trifluoromethyl)phenyl)pyridin-3-yl)methyl)amino)methylene)benzenesulfonamide

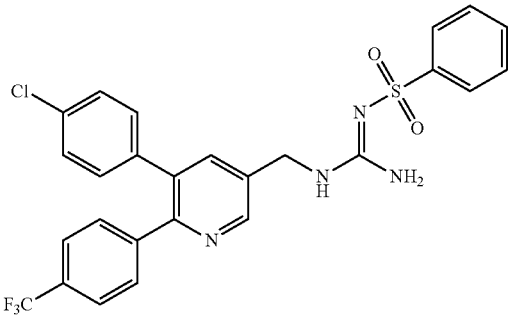 [SMILES: N/C(=N\S(=O)(=O)c1ccccc1)NCc1cnc(-c2ccc(C(F)(F)F)cc2)c(-c2ccc(Cl)cc2)c1]

The title compound (hereinafter, referred to as the compound of Example 11) (0.24 g) was obtained in the same way as in Example 1 using 2-benzenesulfonyl-3-((5-(4-chlorophenyl)-6-(4-(trifluoromethyl)phenyl)pyridin-3-yl)methyl)-1-(tert-butoxycarbonyl)guanidine (0.30 g) synthesized in Reference Example 60.

$^1$H-NMR (CDCl$_3$) δ: 4.49 (2H, d, J=5.4 Hz), 6.38 (3H, brs), 6.96 (2H, d, J=8.6 Hz), 7.23 (2H, d, J=8.6 Hz), 7.29-7.55 (8H, m), 7.75 (2H, d, J=8.2 Hz), 8.54 (1H, s). MS (ESI) [M+H]$^+$: 545.

Example 12 Synthesis of N-(amino(((5-(4-chlorophenyl)-6-(3-fluoro-4-methylphenyl)pyridin-3-yl)methyl)amino)methylene)benzenesulfonamide

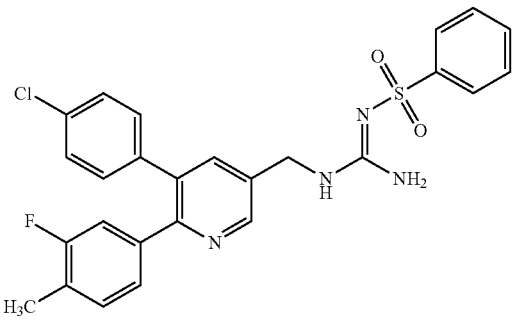

The title compound (hereinafter, referred to as the compound of Example 12) (0.044 g) was obtained in the same way as in Example 1 using 2-benzenesulfonyl-3-((5-(4-chlorophenyl)-6-(3-fluoro-4-methylphenyl)pyridin-3-yl)methyl)-1-(tert-butoxycarbonyl)guanidine (0.058 g) synthesized in Reference Example 62.

$^1$H-NMR (CDCl$_3$, 55° C.) δ: 2.23 (3H, d, J=1.8 Hz), 4.47 (2H, d, J=5.5 Hz), 6.02-6.10 (3H, brm), 6.88 (1H, dd, J=7.8, 1.8 Hz), 6.99-7.02 (4H, m), 7.23 (2H, m), 7.33 (2H, m), 7.40-7.45 (1H, m), 7.51 (1H, d, J=2.3 Hz), 7.70 (2H, m), 8.51 (1H, d, J=2.3 Hz).

MS (ESI) [M+H]$^+$: 509.

Example 13 Synthesis of N-(amino(((5-(4-chlorophenyl)-6-(2-fluoro-4-methylphenyl)pyridin-3-yl)methyl)amino)methylene)benzenesulfonamide

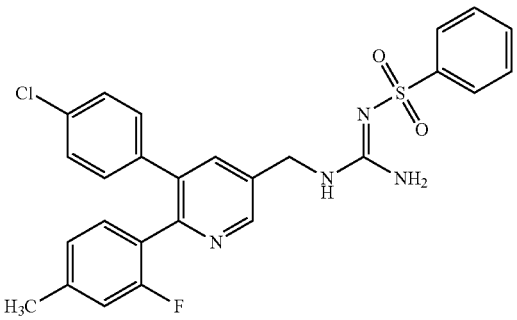

The title compound (hereinafter, referred to as the compound of Example 13) (0.029 g) was obtained in the same way as in Example 1 using 2-benzenesulfonyl-3-((5-(4-chlorophenyl)-6-(2-fluoro-4-methylphenyl)pyridin-3-yl)methyl)-1-(tert-butoxycarbonyl)guanidine (0.049 g) synthesized in Reference Example 63.

$^1$H-NMR (CDCl$_3$, 55° C.) δ: 2.31 (3H, s), 4.47 (2H, d, J=5.9 Hz), 6.13 (3H, brs), 6.69 (1H, d, J=11.0 Hz), 6.92 (1H, d, J=8.2 Hz), 6.98 (2H, m), 7.16-7.21 (3H, m), 7.33 (2H, m), 7.42 (1H, m), 7.54 (1H, d, J=2.3 Hz), 7.80 (2H, m), 8.50 (1H, d, J=2.3 Hz).

MS (ESI) [M+H]$^+$: 509.

Reference Example 87 Synthesis of N-(amino(((6-(4-chloro-2-methoxyphenyl)-5-(4-chlorophenyl)pyridin-3-yl)methyl)amino)methylene)benzenesulfonamide

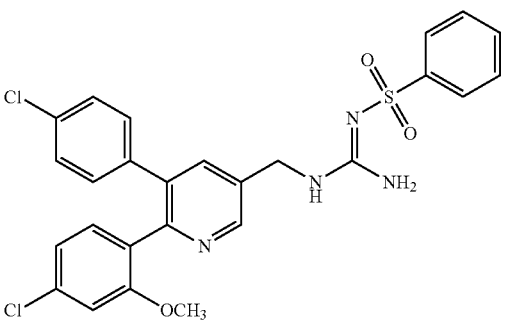 [SMILES: COc1cc(Cl)ccc1-c1ncc(CN/C(N)=N/S(=O)(=O)c2ccccc2)cc1-c1ccc(Cl)cc1]

The title compound (0.14 g) was obtained in the same way as in Example 1 using 2-benzenesulfonyl-3-((6-(4-chloro-2-methoxyphenyl)-5-(4-chlorophenyl)pyridin-3-yl)methyl)-1-(tert-butoxycarbonyl)guanidine (0.18 g) synthesized in Reference Example 64.

$^1$H-NMR (CDCl$_3$) δ: 3.27 (3H, s), 4.47 (2H, d, J=5.5 Hz), 6.21 (3H, brm), 6.67 (1H, d, J=1.8 Hz), 6.95-7.00 (3H, m), 7.19 (2H, d, J=8.2 Hz), 7.27 (1H, d, J=6.4 Hz), 7.34 (2H, t, J=7.5 Hz), 7.44 (1H, t, J=7.5 Hz), 7.54 (1H, d, J=1.6 Hz), 7.80 (2H, d, J=7.3 Hz), 8.49 (1H, d, J=1.6 Hz).

MS (ESI) [M+H]$^+$: 541.

Example 14 Synthesis of N-(amino(((6-(4-chlorophenyl)-5-phenylpyridin-3-yl)methyl)amino)methylene)benzenesulfonamide

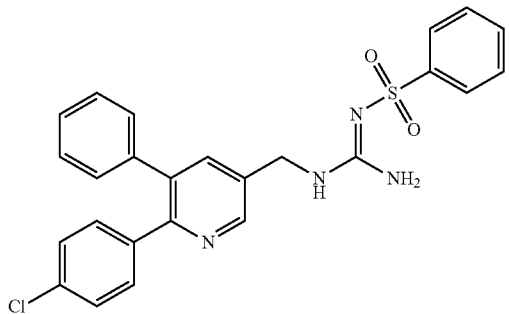 [SMILES: N/C(=N\S(=O)(=O)c1ccccc1)NCc1cnc(-c2ccc(Cl)cc2)c(-c2ccccc2)c1]

The title compound (hereinafter, referred to as the compound of Example 14) (0.073 g) was obtained in the same way as in Example 1 using 2-benzenesulfonyl-3-((6-(4-chlorophenyl)-5-phenylpyridin-3-yl)methyl)-1-(tert-butoxycarbonyl)guanidine (0.12 g) synthesized in Reference Example 65.

$^1$H-NMR (CDCl$_3$) δ: 4.46 (2H, d, J=5.6 Hz), 6.27 (2H, brs), 7.04 (2H, dd, J=7.8, 1.7 Hz), 7.17 (2H, d, J=8.8 Hz), 7.22 (2H, d, J=8.8 Hz), 7.25-7.33 (6H, m), 7.41 (1H, t, J=7.3 Hz), 7.54 (1H, d, J=2.2 Hz), 7.77 (2H, d, J=7.3 Hz), 8.50 (1H, d, J=2.2 Hz).

MS (ESI) [M+H]$^+$: 477.

Example 15 Synthesis of N-(amino(((5-(3-chlorophenyl)-6-(4-chlorophenyl)pyridin-3-yl)methyl)amino)methylene)benzenesulfonamide

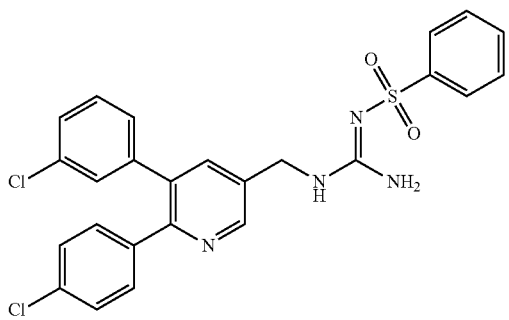 [SMILES: N/C(=N\S(=O)(=O)c1ccccc1)NCc1cnc(-c2ccc(Cl)cc2)c(-c2cccc(Cl)c2)c1]

The title compound (hereinafter, referred to as the compound of Example 15) (0.023 g) was obtained in the same way as in Example 1 using 2-benzenesulfonyl-3-((5-(3-chlorophenyl)-6-(4-chlorophenyl)pyridin-3-yl)methyl)-1-(tert-butoxycarbonyl)guanidine (0.048 g) synthesized in Reference Example 66.

$^1$H-NMR (CDCl$_3$) δ: 4.50 (2H, d, J=5.9 Hz), 6.15 (2H, brs), 6.89 (1H, dt, J=7.9, 1.6 Hz), 7.12 (1H, t, J=1.6 Hz), 7.19 (1H, t, J=7.9 Hz), 7.23 (4H, s), 7.25-7.30 (2H, m), 7.34 (2H, m), 7.43 (1H, tt, J=7.5, 1.6 Hz), 7.53 (1H, d, J=2.3 Hz), 7.81 (2H, m), 8.55 (1H, d, J=2.3 Hz).

MS (ESI) [M+H]$^+$: 511.

Example 16 Synthesis of N-(amino(((5-(2-chlorophenyl)-6-(4-chlorophenyl)pyridin-3-yl)methyl)amino)methylene)benzenesulfonamide

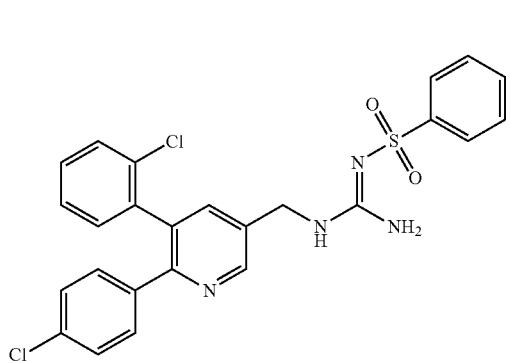 [SMILES: N/C(=N\S(=O)(=O)c1ccccc1)NCc1cnc(-c2ccc(Cl)cc2)c(-c2ccccc2Cl)c1]

The title compound (hereinafter, referred to as the compound of Example 16) (0.022 g) was obtained in the same way as in Example 1 using 2-benzenesulfonyl-3-((5-(2-chlorophenyl)-6-(4-chlorophenyl)pyridin-3-yl)methyl)-1-(tert-butoxycarbonyl)guanidine (0.047 g) synthesized in Reference Example 67.

$^1$H-NMR (CDCl$_3$) δ: 4.51 (2H, d, J=5.4 Hz), 6.16 (2H, brs), 7.03 (1H, dd, J=7.5, 1.6 Hz), 7.15-7.19 (2H, m), 7.20-7.23 (3H, m), 7.25-7.32 (2H, m), 7.33-7.43 (4H, m), 7.50 (1H, d, J=2.3 Hz), 7.79-7.82 (2H, m), 8.57 (1H, d, J=1.8 Hz).

MS (ESI) [M+H]$^+$: 511.

Example 17 Synthesis of N-(amino(((6-(4-chlorophenyl)-5-(4-methylphenyl)pyridin-3-yl)methyl)amino)methylene)benzenesulfonamide

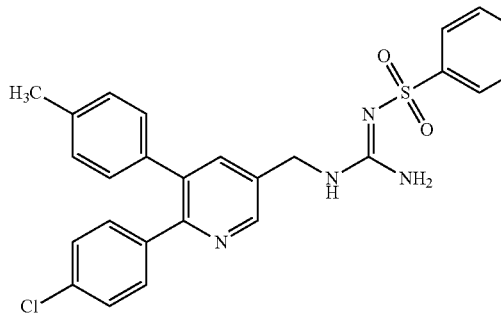

The title compound (hereinafter, referred to as the compound of Example 17) (0.033 g) was obtained in the same way as in Example 1 using 2-benzenesulfonyl-3-((6-(4-chlorophenyl)-5-(4-methylphenyl)pyridin-3-yl)methyl)-1-(tert-butoxycarbonyl)guanidine (0.050 g) synthesized in Reference Example 68.

$^1$H-NMR (CDCl$_3$) δ: 2.36 (3H, s), 4.48 (2H, d, J=5.4 Hz), 6.13 (3H, brs), 6.95 (2H, d, J=8.2 Hz), 7.08 (2H, d, J=7.7 Hz), 7.21 (2H, m), 7.23-7.26 (2H, m), 7.34 (2H, t, J=7.5 Hz), 7.43 (1H, t, J=7.5 Hz), 7.55 (1H, d, J=2.3 Hz), 7.81 (2H, m), 8.49 (1H, d, J=2.3 Hz).

MS (ESI) [M+H]: 491.

Example 18 Synthesis of N-(amino(((6-(4-chlorophenyl)-5-(4-methoxyphenyl)pyridin-3-yl)methyl)amino)methylene)benzenesulfonamide

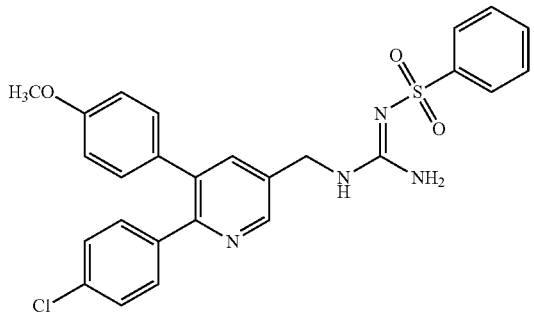

The title compound (hereinafter, referred to as the compound of Example 18) (0.008 g) was obtained in the same way as in Example 1 using 2-benzenesulfonyl-3-((6-(4-chlorophenyl)-5-(4-methoxyphenyl)pyridin-3-yl)methyl)-1-(tert-butoxycarbonyl)guanidine (0.013 g) synthesized in Reference Example 69.

$^1$H-NMR (CDCl$_3$) δ: 3.82 (3H, s), 4.48 (2H, d, J=5.9 Hz), 6.10 (3H, brs), 6.81 (2H, d, J=8.6 Hz), 6.98 (2H, d, J=8.6 Hz), 7.21 (2H, d, J=8.6 Hz), 7.25 (2H, d, J=8.2 Hz), 7.34-7.37 (2H, m), 7.44 (1H, m), 7.55 (1H, d, J=2.3 Hz), 7.81-7.83 (2H, m), 8.48 (1H, d, J=2.3 Hz).

MS (ESI) [M+H]$^+$: 507.

Example 19 Synthesis of N-(amino(((6-(4-chlorophenyl)-5-(4-cyanophenyl)pyridin-3-yl)methyl)amino)methylene)benzenesulfonamide

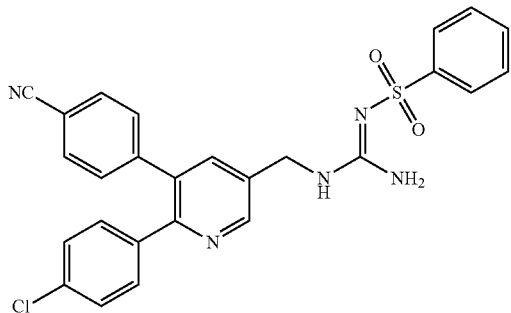

The title compound (hereinafter, referred to as the compound of Example 19) (0.069 g) was obtained in the same way as in Example 1 using 2-benzenesulfonyl-3-((6-(4-chlorophenyl)-5-(4-cyanophenyl)pyridin-3-yl)methyl)-1-(tert-butoxycarbonyl)guanidine (0.12 g) synthesized in Reference Example 70.

$^1$H-NMR (DMSO-d$_6$) δ: 4.44 (2H, d, J=5.4 Hz), 6.86 (1H, brs), 7.25 (2H, d, J=6.8 Hz), 7.30 (2H, d, J=6.8 Hz), 7.35-7.39 (4H, m), 7.46 (1H, t, J=7.0 Hz), 7.64-7.67 (3H, m), 7.83 (2H, d, J=7.2 Hz), 8.57 (1H, s).

MS (ESI) [M+H]$^+$: 502.

Example 20 Synthesis of N-(amino(((6-(4-chlorophenyl)-5-(4-fluorophenyl)pyridin-3-yl)methyl)amino)methylene)benzenesulfonamide

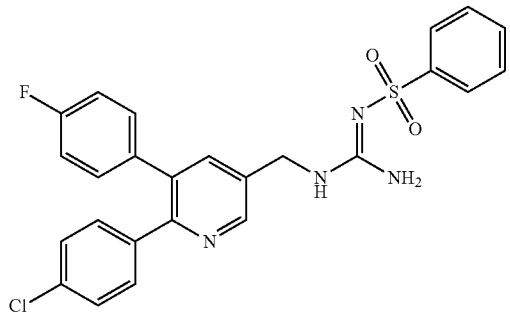

The title compound (hereinafter, referred to as the compound of Example 20) (0.18 g) was obtained in the same way as in Example 1 using 2-benzenesulfonyl-3-((6-(4-chlorophenyl)-5-(4-fluorophenyl)pyridin-3-yl)methyl)-1-(tert-butoxycarbonyl)guanidine (0.22 g) synthesized in Reference Example 71.

$^1$H-NMR (CDCl$_3$) δ: 4.46 (2H, d, J=5.9 Hz), 6.30-6.56 (3H, m), 6.93-7.02 (4H, m), 7.19 (4H, s), 7.32 (2H, t, J=7.7 Hz), 7.42 (1H, m), 7.52 (1H, d, J=2.3 Hz), 7.76 (2H, m), 8.50 (1H, d, J=2.3 Hz).

MS (ESI) [M+H]$^+$: 495.

Example 21 Synthesis of N-(amino(((6-(4-chlorophenyl)-5-(4-(trifluoromethyl)phenyl)pyridin-3-yl)methyl)amino)methylene)benzenesulfonamide

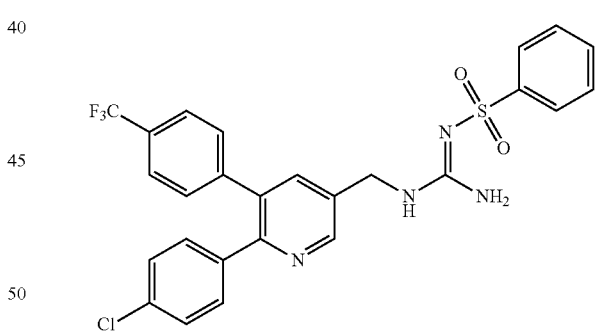

The title compound (hereinafter, referred to as the compound of Example 21) (0.16 g) was obtained in the same way as in Example 1 using 2-benzenesulfonyl-3-((6-(4-chlorophenyl)-5-(4-(trifluoromethyl)phenyl)pyridin-3-yl)methyl)-1-(tert-butoxycarbonyl)guanidine (0.21 g) synthesized in Reference Example 72.

$^1$H-NMR (CDCl$_3$) δ: 4.48 (2H, d, J=5.4 Hz), 6.38-6.57 (3H, m), 7.15 (2H, d, J=8.2 Hz), 7.19-7.22 (4H, m), 7.30 (2H, m), 7.40 (1H, t, J=7.5 Hz), 7.50 (2H, d, J=8.2 Hz), 7.53 (1H, d, J=2.3 Hz), 7.74 (2H, d, J=7.2 Hz), 8.54 (1H, d, J=2.3 Hz).

MS (ESI) [M+H]$^+$: 545.

Example 22 Synthesis of N-(amino(((6-(4-chlorophenyl)-5-(4-(trifluoromethoxy)phenyl)pyridin-3-yl)methyl)amino)methylene)benzenesulfonamide

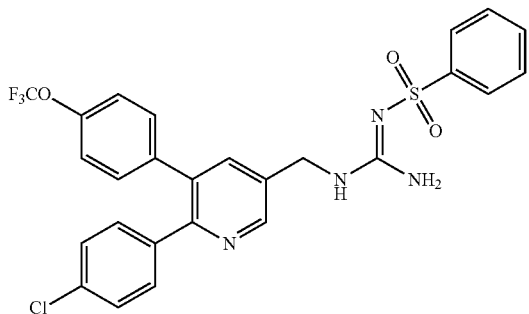 [SMILES: N/C(=N\S(=O)(=O)c1ccccc1)NCc1cnc(-c2ccc(Cl)cc2)c(-c2ccc(OC(F)(F)F)cc2)c1]

The title compound (hereinafter, referred to as the compound of Example 22) (0.16 g) was obtained in the same way as in Example 1 using 2-benzenesulfonyl-3-((6-(4-chlorophenyl)-5-(4-(trifluoromethoxy)phenyl)pyridin-3-yl)methyl)-1-(tert-butoxycarbonyl)guanidine (0.23 g) synthesized in Reference Example 73.

$^1$H-NMR (CDCl$_3$) δ: 4.51 (2H, d, J=5.4 Hz), 6.13 (3H, brs), 7.09 (2H, d, J=8.2 Hz), 7.13 (2H, d, J=8.2 Hz), 7.21-7.24 (4H, m), 7.34 (2H, m), 7.43 (1H, t, J=6.6 Hz), 7.56 (1H, d, J=1.8 Hz), 7.81 (2H, d, J=8.2 Hz), 8.54 (1H, d, J=1.8 Hz).

MS (ESI) [M+H]$^+$: 561.

Example 23 Synthesis of N-(amino(((6-(4-chlorophenyl)-5-(4-isopropoxyphenyl)pyridin-3-yl)methyl)amino)methylene)benzenesulfonamide

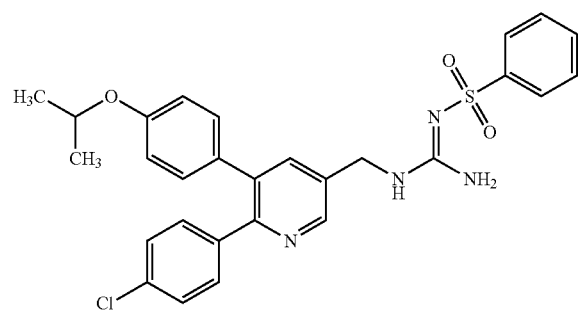 [SMILES: CC(C)Oc1ccc(-c2cc(CN/C(N)=N/S(=O)(=O)c3ccccc3)cnc2-c2ccc(Cl)cc2)cc1]

The title compound (hereinafter, referred to as the compound of Example 23) (0.13 g) was obtained in the same way as in Example 1 using 2-benzenesulfonyl-3-((6-(4-chlorophenyl)-5-(4-isopropoxyphenyl)pyridin-3-yl)methyl)-1-(tert-butoxycarbonyl)guanidine (0.21 g) synthesized in Reference Example 74.

$^1$H-NMR (CDCl$_3$) δ: 1.35 (6H, d, J=5.9 Hz), 4.48 (2H, d, J=5.9 Hz), 4.51-4.58 (1H, m), 6.07 (3H, brs), 6.78 (2H, d, J=8.6 Hz), 6.95 (2H, d, J=8.6 Hz), 7.19-7.22 (2H, m), 7.24-7.28 (2H, m), 7.35 (2H, t, J=7.7 Hz), 7.44 (1H, t, J=7.5 Hz), 7.54 (1H, d, J=2.1 Hz), 7.80-7.83 (2H, m), 8.48 (1H, d, J=2.1 Hz).

MS (ESI) [M+H]$^+$: 535.

Example 24 Synthesis of N-(amino(((5-(4-methoxyphenyl)-6-(4-methylphenyl)pyridin-3-yl)methyl)amino)methylene)benzenesulfoamide

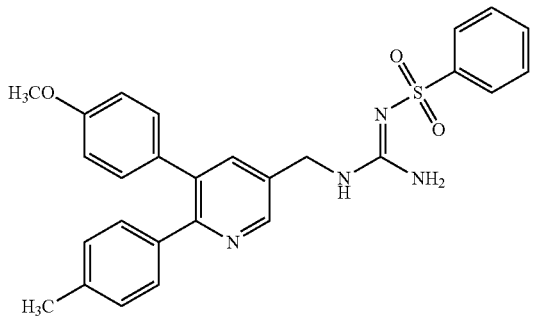 [SMILES: COc1ccc(-c2cc(CN/C(N)=N/S(=O)(=O)c3ccccc3)cnc2-c2ccc(C)cc2)cc1]

The title compound (hereinafter, referred to as the compound of Example 24) (0.027 g) was obtained in the same way as in Example 1 using 2-benzenesulfonyl-3-((5-(4-methoxyphenyl)-6-(4-methylphenyl)pyridin-3-yl)methyl)-1-(tert-butoxycarbonyl)guanidine (0.032 g) synthesized in Reference Example 75.

$^1$H-NMR (CDCl$_3$) δ: 2.31 (3H, s), 3.81 (3H, s), 4.45 (2H, d, J=5.9 Hz), 6.05 (3H, brs), 6.79 (2H, d, J=8.6 Hz), 7.00 (2H, d, J=8.6 Hz), 7.04 (2H, d, J=8.2 Hz), 7.19 (2H, d, J=8.2 Hz), 7.35 (2H, m), 7.43 (1H, m), 7.53 (1H, d, J=2.1 Hz), 7.82 (2H, d, J=7.7 Hz), 8.44 (1H, d, J=2.1 Hz).

MS (ESI) [M+H]$^+$: 487.

Example 25 Synthesis of N-(amino(((6-(4-methylphenyl)-5-(4-(trifluoromethyl)phenyl)pyridin-3-yl)methyl)amino)methylene)benzenesulfonamide hydrochloride

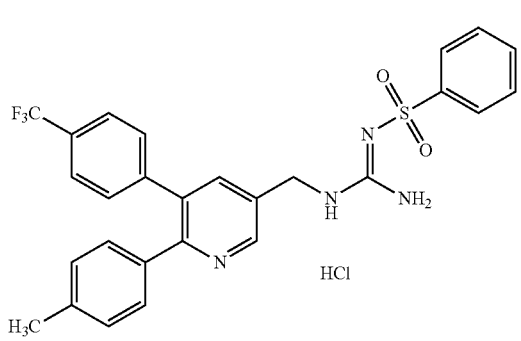

The title compound (hereinafter, referred to as the compound of Example 25) (0.058 g) was obtained in the same way as in Example 1 and Example 2 using 2-benzenesulfonyl-3-((6-(4-methylphenyl)-5-(4-(trifluoromethyl)phenyl)pyridin-3-yl)methyl)-1-(tert-butoxycarbonyl)guanidine (0.075 g) synthesized in Reference Example 76.

$^1$H-NMR (CDCl$_3$) δ: 2.31 (3H, s), 4.54 (2H, s), 6.79 (2H, brs), 7.03-7.07 (4H, m), 7.22 (2H, d, J=8.2 Hz), 7.32 (2H, t, J=7.5 Hz), 7.40 (1H, t, J=7.2 Hz), 7.53 (2H, d, J=7.7 Hz), 7.64 (1H, brs), 7.77 (2H, d, J=7.7 Hz), 7.97 (1H, brs), 8.71 (1H, brs).

MS (ESI) [M+H]$^+$: 525.

Example 26 Synthesis of N-(amino(((5,6-bis(4-chlorophenyl)pyridin-3-yl)methyl)amino)methylene)-2-fluorobenzenesulfonamide

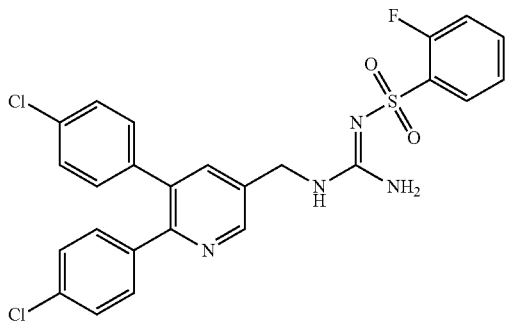 [SMILES: N/C(=N\S(=O)(=O)c1ccccc1F)NCc1cnc(-c2ccc(Cl)cc2)c(-c2ccc(Cl)cc2)c1]

The title compound (hereinafter, referred to as the compound of Example 26) (0.023 g) was obtained in the same way as in Example 1 using 3-((5,6-bis(4-chlorophenyl)pyridin-3-yl)methyl)-2-(2-fluorobenzenesulfonyl)-1-(tert-butoxycarbonyl)guanidine (0.030 g) synthesized in Reference Example 77.

$^1$H-NMR (CDCl$_3$) δ: 4.47 (2H, d, J=5.9 Hz), 6.34 (3H, brs), 6.92-7.00 (3H, m), 7.13 (1H, t, J=7.7 Hz), 7.19-7.27 (6H, m), 7.40 (1H, dd, J=12.4, 6.6 Hz), 7.55 (1H, d, J=2.0 Hz), 7.83 (1H, t, J=6.8 Hz), 8.52 (1H, d, J=2.0 Hz).

MS (ESI) [M+H]$^+$: 529.

Example 27 Synthesis of N-(amino(((5,6-bis(4-chlorophenyl)pyridin-3-yl)methyl)amino)methylene)-3-fluorobenzenesulfonamide

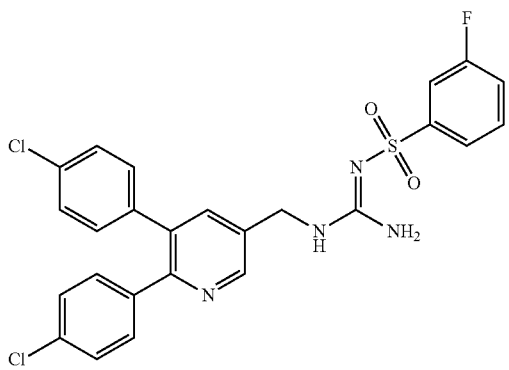 [SMILES: N/C(=N\S(=O)(=O)c1cccc(F)c1)NCc1cnc(-c2ccc(Cl)cc2)c(-c2ccc(Cl)cc2)c1]

The title compound (hereinafter, referred to as the compound of Example 27) (0.028 g) was obtained in the same way as in Example 1 using 3-((5,6-bis(4-chlorophenyl)pyridin-3-yl)methyl)-2-(3-fluorobenzenesulfonyl)-1-(tert-butoxycarbonyl)guanidine (0.033 g) synthesized in Reference Example 78.

$^1$H-NMR (CDCl$_3$) δ: 4.48 (2H, d, J=5.6 Hz), 6.27 (3H, brs), 6.99 (2H, d, J=8.5 Hz), 7.11-7.15 (1H, m), 7.20-7.25 (6H, m), 7.29-7.34 (1H, m), 7.45-7.58 (3H, m), 8.52 (1H, s).

MS (ESI) [M+H]$^+$: 529.

Example 28 Synthesis of N-(amino(((5,6-bis(4-chlorophenyl)pyridin-3-yl)methyl)amino)methylene)-4-fluorobenzenesulfonamide

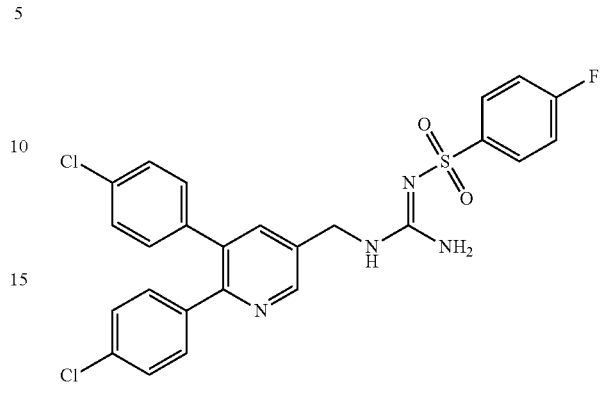

The title compound (hereinafter, referred to as the compound of Example 28) (0.027 g) was obtained in the same way as in Example 1 using 3-((5,6-bis(4-chlorophenyl)pyridin-3-yl)methyl)-2-(4-fluorobenzenesulfonyl)-1-(tert-butoxycarbonyl)guanidine (0.033 g) synthesized in Reference Example 79.

$^1$H-NMR (CDCl$_3$) δ: 4.46 (2H, d, J=5.6 Hz), 6.26 (3H, brs), 6.98-7.02 (4H, m), 7.21-7.33 (6H, m), 7.52 (1H, s), 7.76-7.79 (2H, m), 8.52 (1H, d, J=2.0 Hz).

MS (ESI) [M+H]$^+$: 529.

Example 29 Synthesis of N-(amino(((5,6-bis(4-chlorophenyl)pyridin-3-yl)methyl)amino)methylene)thiophene-2-sulfonamide

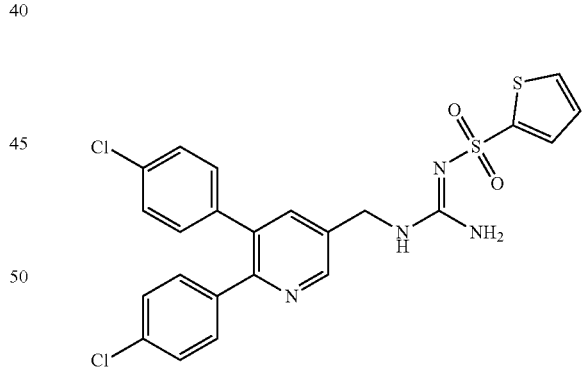

The title compound (hereinafter, referred to as the compound of Example 29) (0.026 g) was obtained in the same way as in Example 1 using 3-((5,6-bis(4-chlorophenyl)pyridin-3-yl)methyl)-2-(thiophene-2-sulfonyl)-1-(tert-butoxycarbonyl)guanidine (0.034 g) synthesized in Reference Example 80.

$^1$H-NMR (CDCl$_3$) δ: 4.45 (2H, d, J=5.0 Hz), 6.41 (3H, brs), 6.87 (1H, s), 7.00 (2H, d, J=8.6 Hz), 7.15-7.24 (6H, m), 7.31 (1H, d, J=5.0 Hz), 7.40 (1H, s), 7.53 (1H, s), 8.51 (1H, s).

MS (ESI) [M+H]$^+$: 517.

Example 30 Synthesis of N-(amino(((5,6-bis(4-chlorophenyl)pyridin-3-yl)methyl)amino)methylene)thiophene-3-sulfonamide

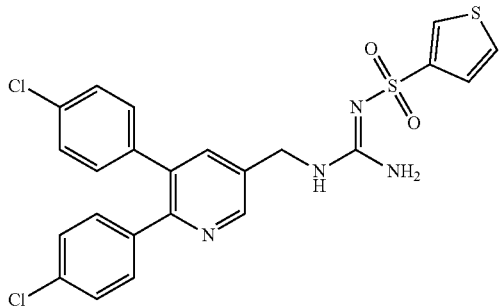

The title compound (hereinafter, referred to as the compound of Example 30) (0.027 g) was obtained in the same way as in Example 1 using 3-((5,6-bis(4-chlorophenyl)pyridin-3-yl)methyl)-2-(thiophene-3-sulfonyl)-1-(tert-butoxycarbonyl)guanidine (0.032 g) synthesized in Reference Example 81.

$^1$H-NMR (CDCl$_3$) δ: 4.43 (2H, d, J=5.4 Hz), 6.46 (3H, brs), 6.99 (2H, dt, J=8.9, 2.3 Hz), 7.14-7.25 (8H, m), 7.51 (1H, d, J=2.3 Hz), 7.70 (1H, dd, J=2.7, 1.4 Hz), 8.50 (1H, d, J=2.3 Hz).

MS (ESI) [M+H]$^+$: 517.

Example 31 Synthesis of N-(amino(((5,6-bis(4-chlorophenyl)pyridin-3-yl)methyl)amino)methylene)furan-2-sulfonamide

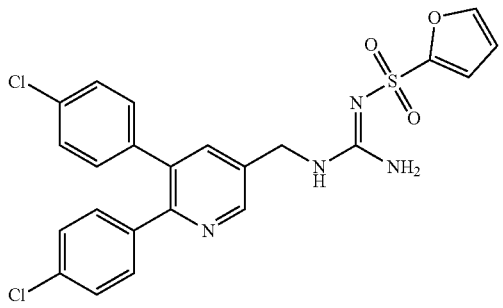

The title compound (hereinafter, referred to as the compound of Example 31) (0.024 g) was obtained in the same way as in Example 1 using 3-((5,6-bis(4-chlorophenyl)pyridin-3-yl)methyl)-2-(furan-2-sulfonyl)-1-(tert-butoxycarbonyl)guanidine (0.033 g) synthesized in Reference Example 82.

$^1$H-NMR (CDCl$_3$) δ: 4.48 (2H, d, J=5.9 Hz), 6.24-6.40 (3H, brs), 6.34 (1H, dd, J=3.6, 1.8 Hz), 6.81 (1H, dd, J=3.6, 0.9 Hz), 7.04 (2H, dt, J=8.9, 2.3 Hz), 7.21 (4H, s), 7.24-7.28 (3H, m), 7.60 (1H, d, J=2.1 Hz), 8.54 (1H, d, J=2.1 Hz).

MS (ESI) [M+H]$^+$: 501.

Example 32 Synthesis of N-(amino(((5,6-bis(4-chlorophenyl)pyridin-3-yl)methyl)amino)methylene)furan-3-sulfonamide

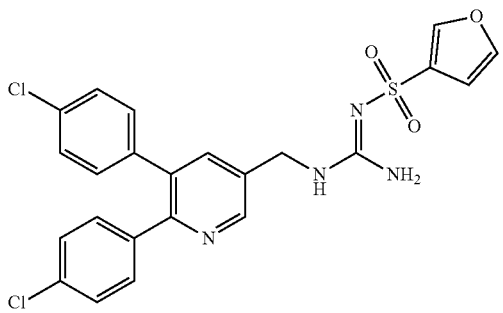 [SMILES: N/C(=N\S(=O)(=O)c1ccsc1)NCc1cnc(-c2ccc(Cl)cc2)c(-c2ccc(Cl)cc2)c1]

The title compound (hereinafter, referred to as the compound of Example 32) (0.023 g) was obtained in the same way as in Example 1 using 3-((5,6-bis(4-chlorophenyl)pyridin-3-yl)methyl)-2-(furan-3-sulfonyl)-1-(tert-butoxycarbonyl)guanidine (0.030 g) synthesized in Reference Example 83.

$^1$H-NMR (CDCl$_3$) δ: 4.46 (2H, d, J=5.9 Hz), 6.31 (3H, brs), 6.49 (1H, s), 7.02 (2H, dt, J=8.8, 2.3 Hz), 7.21 (4H, s), 7.24-7.28 (3H, m), 7.56 (1H, d, J=2.3 Hz), 7.73 (1H, s), 8.53 (1H, d, J=2.3 Hz).

MS (ESI) [M+H]$^+$: 501.

Example 33 Synthesis of N-(amino(((6-(4-methylphenyl)-5-(4-(trifluoromethyl)phenyl)pyridin-3-yl)methyl)amino)methylene)thiophene-2-sulfonamide Hydrochloride

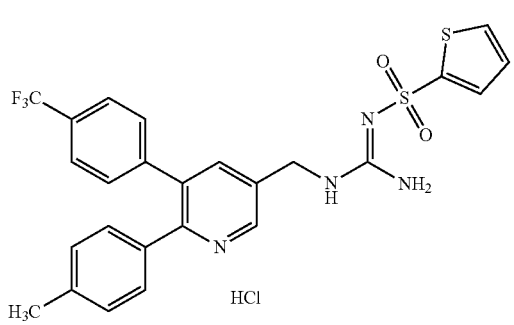 [SMILES: Cc1ccc(-c2ncc(CN/C(N)=N/S(=O)(=O)c3cccs3)cc2-c2ccc(C(F)(F)F)cc2)cc1 ; Cl]

The title compound (hereinafter, referred to as the compound of Example 33) (0.052 g) was obtained in the same way as in Example 1 and Example 2 using 3-((6-(4-methylphenyl)-5-(4-(trifluoromethyl)phenyl)pyridin-3-yl)methyl)-2-(thiophene-2-sulfonyl)-1-(tert-butoxycarbonyl)guanidine (0.061 g) synthesized in Reference Example 84.

$^1$H-NMR (CDCl$_3$) δ: 2.35 (3H, s), 4.61 (2H, d, J=5.4 Hz), 6.85 (2H, brs), 6.90 (1H, q, J=4.2 Hz), 7.12 (4H, t, J=9.1 Hz), 7.29-7.33 (3H, m), 7.47 (1H, td, J=3.4, 1.2 Hz), 7.58 (2H, d, J=6.8 Hz), 7.99 (1H, brs), 8.24 (1H, brs), 8.83 (1H, brs).

MS (ESI) [M+H]$^+$: 531.

Example 34 Synthesis of N-(amino(((5,6-bis(4-chlorophenyl)pyridin-3-yl)methyl)amino)methylene)benzamide

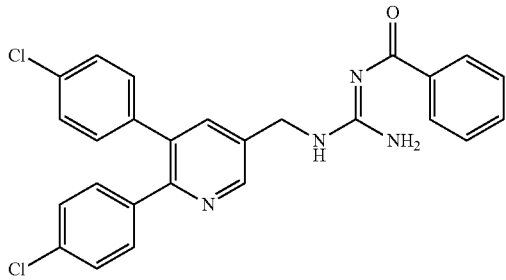 [SMILES: N/C(=N\C(=O)c1ccccc1)NCc1cnc(-c2ccc(Cl)cc2)c(-c2ccc(Cl)cc2)c1]

The title compound (hereinafter, referred to as the compound of Example 34) (0.026 g) was obtained in the same way as in Example 1 using 2-(benzenecarbonyl)-3-((5,6-bis(4-chlorophenyl)pyridin-3-yl)methyl)-1-(tert-butoxycarbonyl)guanidine (0.032 g) synthesized in Reference Example 85.

$^1$H-NMR (CDCl$_3$) δ: 4.60 (2H, brs), 7.03 (2H, d, J=8.2 Hz), 7.21-7.26 (7H, m), 7.35-7.39 (2H, m), 7.43-7.47 (1H, m), 7.68 (1H, s), 8.15 (2H, d, J=7.7 Hz), 8.63 (1H, d, J=1.8 Hz).

MS (ESI) [M+H]$^+$: 475.

Example 35 Synthesis of N-(amino(((5,6-bis(4-chlorophenyl)pyridin-3-yl)methyl)amino)methylene)thiophene-2-carboxamide Hydrochloride

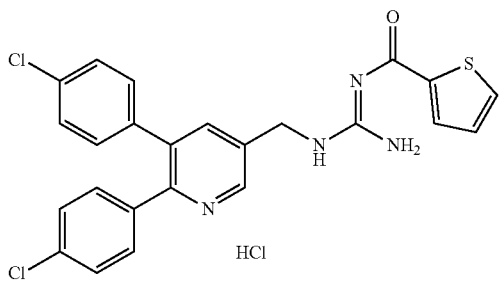 [SMILES: N/C(=N\C(=O)c1cccs1)NCc1cnc(-c2ccc(Cl)cc2)c(-c2ccc(Cl)cc2)c1 ; Cl]

The title compound (hereinafter, referred to as the compound of Example 35) (0.035 g) was obtained in the same way as in Example 1 and Example 2 using 3-((5,6-bis(4-chlorophenyl)pyridin-3-yl)methyl)-2-(thiophene-2-carbonyl)-1-(tert-butoxycarbonyl)guanidine (0.050 g) synthesized in Reference Example 86.

$^1$H-NMR (CD$_3$OD) δ: 4.94 (2H, s), 7.25-7.29 (3H, m), 7.39-7.48 (7H, m), 7.99 (1H, dd, J=5.0, 0.9 Hz), 8.13 (1H, m), 8.51 (1H, s), 8.91 (1H, s).

MS (ESI) [M+H]$^+$: 481.

Reference Example 88 Synthesis of (5-bromo-6-chloropyridin-3-yl)methanamine

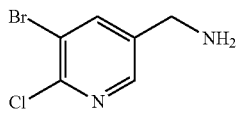

2-((5-Bromo-6-chloro-pyridin-3-yl)methyl)isoindoline-1,3-dione (0.60 g) synthesized in Reference Example 3 was suspended in methanol (16 mL). To the suspension, hydrazine monohydrate (0.25 mL) was then added, and the mixture was heated to reflux for 4.5 hours. The reaction mixture was cooled to room temperature, diluted with ethyl acetate, and then filtered. The filtrate was washed with water and saturated saline, dried over anhydrous sodium sulfate, and then concentrated under reduced pressure to obtain the title compound (0.19 g).

$^1$H-NMR (CDCl$_3$) δ: 3.91 (2H, s), 7.99 (1H, d, J=1.4 Hz), 8.29 (1H, d, J=1.8 Hz).

MS (ESI) [M+H]$^+$: 221.

Reference Example 89 Synthesis of 2-benzenesulfonyl-3-((5-bromo-6-chloropyridin-3-yl)methyl)-1-(tert-butoxycarbonyl)guanidine

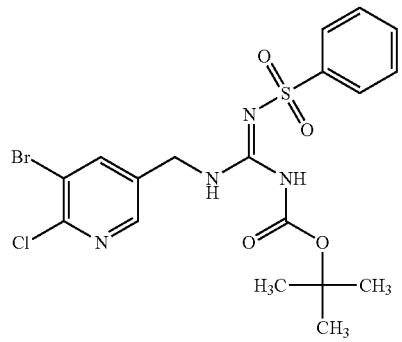 [SMILES: CC(C)(C)OC(=O)N/C(=N\S(=O)(=O)c1ccccc1)NCc1cnc(Cl)c(Br)c1]

(5-Bromo-6-chloropyridin-3-yl)methanamine (0.19 g) synthesized in Reference Example 88 was dissolved in tetrahydrofuran (17 mL). To the solution, N-(phenylsulfonyl)-N'-(tert-butoxycarbonyl)-S-methylisothiourea (0.62 g) synthesized in Reference Example 42 was then added. The reaction mixture was stirred at 60° C. for 16 hours and then concentrated under reduced pressure. The obtained crude product was purified by silica gel chromatography (n-hexane/ethyl acetate) to obtain the title compound (0.35 g).

$^1$H-NMR (CDCl$_3$) δ: 1.52 (9H, s), 4.45 (2H, d, J=5.9 Hz), 7.43-7.47 (2H, m), 7.52-7.56 (1H, m), 7.74-7.77 (3H, m), 8.18 (1H, d, J=1.8 Hz), 8.98 (1H, t, J=5.2 Hz), 9.97 (1H, s).

Reference Example 90 Synthesis of 2-benzenesulfonyl-3-((6-chloro-5-(chlorophenyl)pyridin-3-yl)methyl)-1-(tert-butoxycarbonyl)guanidine

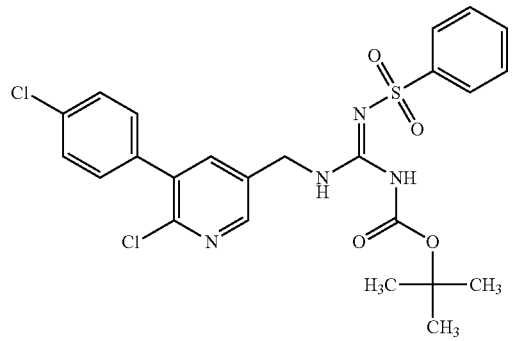 [SMILES: CC(C)(C)OC(=O)N/C(=N\S(=O)(=O)c1ccccc1)NCc1cnc(Cl)c(-c2ccc(Cl)cc2)c1]

2-Benzenesulfonyl-3-((5-bromo-6-chloropyridin-3-yl)methyl)-1-(tert-butoxycarbonyl)guanidine (0.068 g) synthesized in Reference Example 89, 4-chlorophenylboronic acid (0.023 g), potassium carbonate (0.11 g) and [1,1'-bis(diphenylphosphino)ferrocene]palladium(I) dichloride dichloromethane adduct (0.006 g) were suspended in 1,4-dioxane (0.6 mL), and then, the suspension was stirred at 80° C. for 16 hours. The reaction mixture was filtered through celite, and the filtrate was concentrated under reduced pressure. The obtained crude product was purified by silica gel column chromatography (n-hexane/ethyl acetate) to obtain the title compound (0.046 g).

$^1$H-NMR (CDCl$_3$) δ: 1.51 (9H, s), 4.53 (2H, d, J=5.9 Hz), 7.25-7.27 (2H, m), 7.36-7.50 (6H, m), 7.75-7.77 (2H, m), 8.26 (1H, d, J=2.3 Hz), 8.99 (1H, t, J=5.4 Hz), 9.98 (1H, s).

MS (ESI) [M+H]$^+$: 535.

Reference Example 91 Synthesis of N-(amino(((6-chloro-5-(3-fluoro-4-methoxyphenyl)pyridin-3-yl)methyl)amino)methylene)benzenesulfonamide

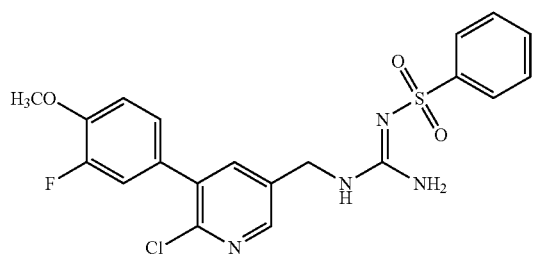 [SMILES: COc1ccc(-c2cc(CN/C(N)=N/S(=O)(=O)c3ccccc3)cnc2Cl)cc1F]

2-Benzenesulfonyl-3-((5-bromo-6-chloropyridin-3-yl)methyl)-1-(tert-butoxycarbonyl)guanidine (0.10 g) synthesized in Reference Example 89, 3-fluoro-4-methoxyphenylboronic acid (0.037 g) and [1,1'-bis(diphenylphosphino)ferrocene]palladium(II) dichloride dichloromethane adduct (0.008 g) were dissolved in 1,4-dioxane (5 mL). To the solution, a 2 mol/L aqueous sodium carbonate solution (1.2 mL) was then added, and the mixture was stirred at 80° C. for 16 hours. The reaction mixture was cooled to room temperature, and then, water was added thereto, followed by extraction with ethyl acetate. The organic layer was dried over anhydrous sodium sulfate and then concentrated under reduced pressure. The obtained crude product was purified by silica gel column chromatography (n-hexane/ethyl acetate) to obtain the title compound (0.032 g).

$^1$H-NMR (CDCl$_3$) δ: 1.51 (9H, s), 3.96 (3H, s), 4.52 (2H, d, J=5.9 Hz), 7.00-7.10 (3H, m), 7.36-7.41 (2H, m), 7.46-7.50 (2H, m), 7.74-7.78 (2H, m), 8.24 (1H, d, J=2.3 Hz), 8.98 (1H, t, J=5.7 Hz), 9.97 (1H, brs).

MS (ESI) [M+H]$^+$: 549.

Example 36 Synthesis of N-(amino(((6-(4-chloro-2-fluorophenyl)-5-(4-chlorophenyl)pyridin-3-yl)methyl)amino)methylene)benzenesulfonamide

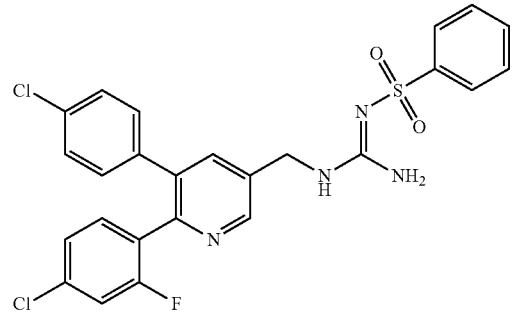 [SMILES: N/C(=N\S(=O)(=O)c1ccccc1)NCc1cnc(-c2ccc(Cl)cc2F)c(-c2ccc(Cl)cc2)c1]

2-Benzenesulfonyl-3-((6-chloro-5-(chlorophenyl)pyridin-3-yl)methyl)-1-(tert-butoxycarbonyl)guanidine (0.050 g) synthesized in Reference Example 90, 4-chloro-2-fluorophenylboronic acid (0.024 g), potassium carbonate (0.039 g) and [1,1'-bis(diphenylphosphino)ferrocene]palladium(II) dichloride dichloromethane adduct (0.008 g) were dissolved in acetonitrile (3 mL) and water (1.2 mL), and then, the solution was stirred at 90° C. for 17 hours. The reaction mixture was cooled to room temperature, and water was added thereto, followed by extraction with ethyl acetate. The organic layer was washed with saturated saline, dried over anhydrous sodium sulfate, and then concentrated under reduced pressure. The obtained crude product was purified by silica gel chromatography (chloroform/methanol) to obtain the title compound (hereinafter, referred to as the compound of Example 36) (0.042 g).

$^1$H-NMR (CDCl$_3$) δ: 4.48 (2H, d, J=5.9 Hz), 6.44 (2H, brs), 6.61 (1H, brs), 6.95-6.89 (3H, m), 7.13 (1H, dd, J=8.4, 1.6 Hz), 7.19 (2H, d, J=8.2 Hz), 7.31 (3H, m), 7.42 (1H, t, J=7.5 Hz), 7.54 (1H, d, J=1.8 Hz), 7.73 (2H, d, J=7.2 Hz), 8.51 (1H, d, J=1.8 Hz).

MS (ESI) [M+H]$^+$: 529.

Example 37 Synthesis of N-(amino(((6-(4-chlorophenyl)-5-(3-fluoro-4-methoxyphenyl)pyridin-3-yl)methyl)amino)methylene)benzenesulfonamide

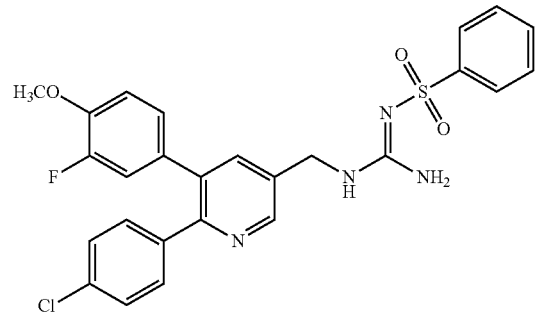 [SMILES: COc1ccc(-c2cc(CN/C(N)=N/S(=O)(=O)c3ccccc3)cnc2-c2ccc(Cl)cc2)cc1F]

N-(Amino(((6-chloro-5-(3-fluoro-4-methoxyphenyl)pyridin-3-yl)methyl)amino)methylene)benzenesulfonamide (0.061 g) synthesized in Reference Example 91, 4-chlorophenylboronic acid (0.032 g) and tetrakistriphenylphosphinepalladium(0) (0.008 g) were dissolved in 1,4-dioxane (5 mL). To the solution, a 2 mol/L aqueous sodium carbonate solution (1.4 mL) was then added, and the mixture was stirred at 90° C. for 15 hours. The reaction mixture was cooled to room temperature, and water was added thereto, followed by extraction with ethyl acetate. The organic layer was washed with saturated saline, dried over anhydrous sodium sulfate, and then concentrated under reduced pressure. The obtained crude product was purified by silica gel chromatography (methanol/chloroform), and then, the obtained solid was recrystallized (ethyl acetate) to obtain the title compound (hereinafter, referred to as the compound of Example 37) (0.019 g).

¹H-NMR (CDCl₃) δ: 3.89 (3H, s), 4.45 (2H, d, J=5.4 Hz), 6.34 (3H, brs), 6.72-6.86 (3H, m), 7.19-7.24 (4H, m), 7.33 (2H, t, J=7.7 Hz), 7.43 (1H, t, J=7.2 Hz), 7.50 (1H, d, J=1.8 Hz), 7.76 (2H, d, J=7.7 Hz), 8.48 (1H, d, J=2.3 Hz).

MS (ESI) [M+H]⁺: 525.

Reference Example 92 Synthesis of methyl 4,5-dichloropicolinate

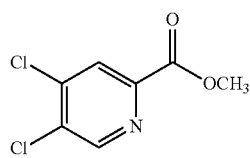 [SMILES: COC(=O)c1cc(Cl)c(Cl)cn1]

4,5-Dichloro-pyridine-2-carboxylic acid (0.50 g) was suspended in dichloromethane (10 mL). To the suspension, DMF (0.020 mL) and oxalyl chloride (1 mL) were then added under ice cooling, and the mixture was stirred at room temperature for 5.5 hours. The reaction mixture was cooled in ice. Methanol (4.1 mL) was added thereto, and the mixture was further stirred at room temperature for 1.5 hours. The reaction mixture was concentrated under reduced pressure, and water was added thereto, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (0.24 g).

¹H-NMR (CDCl₃) δ: 4.03 (3H, s), 8.23 (1H, s), 8.73 (1H, s).

MS (ESI) [M+H]⁺: 206.

Reference Example 93 Synthesis of methyl 5,6-dichloropicolinate

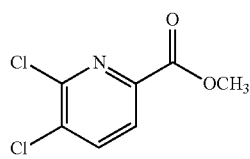 [SMILES: COC(=O)c1ccc(Cl)c(Cl)n1]

The title compound (1.0 g) was obtained in the same way as in Reference Example 92 using 5,6-dichloro-pyridine-2-carboxylic acid (1.0 g).

¹H-NMR (CDCl₃) &: 4.01 (3H, s), 7.93 (1H, d, J=7.7 Hz), 8.03 (1H, d, J=8.2 Hz).

MS (ESI) [M+H]⁺: 206.

Reference Example 94 Synthesis of methyl 5,6-bis(4-chlorophenyl)nicotinate

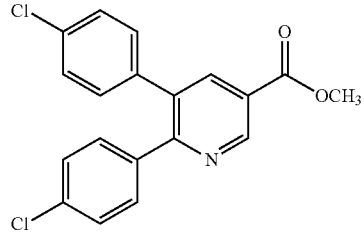 [SMILES: COC(=O)c1cnc(-c2ccc(Cl)cc2)c(-c2ccc(Cl)cc2)c1]

Methyl 5-bromo-6-chloronicotinate (10.0 g), 4-chlorophenylboronic acid (18.7 g), potassium carbonate (16.6 g) and tetrakistriphenylphosphinepalladium(0) (4.6 g) were suspended in 1,4-dioxane (200 mL), and then, the suspension was stirred at 100° C. for 21 hours. The reaction mixture was filtered, and the filtrate was concentrated under reduced pressure. The obtained crude product was purified by silica gel column chromatography (n-hexane/ethyl acetate) to obtain the title compound (9.5 g).

¹H-NMR (CDCl₃) δ: 3.99 (3H, s), 7.13 (2H, dt, J=8.8, 2.3 Hz), 7.25-7.28 (2H, m), 7.29-7.35 (4H, m), 8.29 (1H, d, J=2.3 Hz), 9.25 (1H, d, J=1.8 Hz).

MS (ESI) [M+H]⁺: 358.

Reference Example 95 Synthesis of methyl 4,5-bis(4-chlorophenyl)picolinate

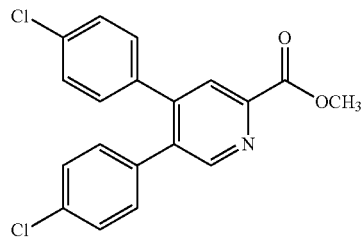 [SMILES: COC(=O)c1cc(-c2ccc(Cl)cc2)c(-c2ccc(Cl)cc2)cn1]

Cl

Methyl 4,5-dichloropicolinate (0.15 g) synthesized in Reference Example 92, 4-chlorophenylboronic acid (0.27 g), potassium carbonate (0.60 g) and [1,1'-bis(diphenylphosphino)ferrocene]palladium(II) dichloride dichloromethane adduct (0.12 g) were suspended in 1,4-dioxane (3 mL), and then, the suspension was stirred overnight at 90° C. The reaction mixture was filtered, and the filtrate was concentrated under reduced pressure. The obtained crude product was purified by silica gel column chromatography (n-hexane/ethyl acetate) to obtain the title compound (0.057 g).

¹H-NMR (CDCl₃) δ: 4.05 (3H, s), 7.09-7.14 (4H, m), 7.29-7.33 (4H, m), 8.17 (1H, d, J=0.5 Hz), 8.72 (1H, d, J=0.5 Hz).

MS (ESI) [M+H]⁺: 358.

Reference Example 96 Synthesis of methyl 5,6-bis(4-chlorophenyl)picolinate

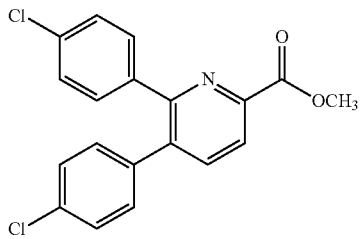 [SMILES: COC(=O)c1ccc(-c2ccc(Cl)cc2)c(-c2ccc(Cl)cc2)n1]

The title compound (0.55 g) was obtained in the same way as in Reference Example 96 using methyl 5,6-dichloropicolinate (0.82 g) synthesized in Reference Example 93.

$^1$H-NMR (CDCl$_3$) δ: 4.03 (3H, s), 7.10-7.13 (2H, m), 7.23-7.34 (6H, m), 7.84 (1H, d, J=7.7 Hz), 8.16 (1H, d, J=7.7 Hz).

MS (ESI) [M+H]$^+$: 358.

Reference Example 97 Synthesis of (5,6-bis(4-chlorophenyl)pyridin-3-yl)methanol

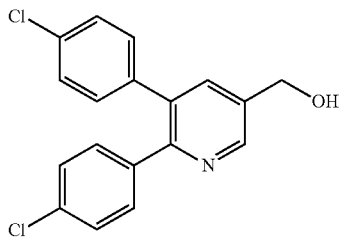 [SMILES: OCc1cnc(-c2ccc(Cl)cc2)c(-c2ccc(Cl)cc2)c1]

Methyl 5,6-bis(4-chlorophenyl)nicotinate (7.0 g) synthesized in Reference Example 94 was dissolved in tetrahydrofuran (50 mL). To the solution, a 1 mol/L solution of diisobutyl aluminum hydride in toluene (49 mL) was then gradually added at −78° C. The reaction mixture was warmed to 0° C. and stirred for 1 hour. Under ice cooling, an aqueous potassium sodium tartrate solution (100 mL) was gradually added to the reaction mixture, and the mixture was stirred at room temperature for 2 hours. The reaction mixture was concentrated under reduced pressure, and then, the aqueous layer was subjected to extraction with ethyl acetate. The organic layer was washed with saturated saline, dried over anhydrous sodium sulfate, and then concentrated under reduced pressure to obtain the title compound (6.5 g) as a white solid.

$^1$H-NMR (CDCl$_3$) δ: 2.03 (1H, t, J=5.7 Hz), 4.83 (2H, d, J=5.5 Hz), 7.11 (2H, dt, J=8.8, 2.2 Hz), 7.23 (2H, dt, J=8.4, 2.1 Hz), 7.26-7.30 (4H, m), 7.73 (1H, d, J=2.3 Hz), 8.66 (1H, d, J=2.3 Hz).

MS (ESI) [M+H]$^+$: 330.

Reference Example 98 Synthesis of (4,5-bis(4-chlorophenyl)pyridin-2-yl)methanol

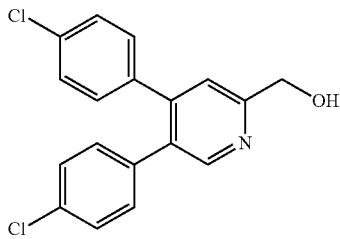 [SMILES: OCc1cc(-c2ccc(Cl)cc2)c(-c2ccc(Cl)cc2)cn1]

The title compound (0.064 g) was obtained in the same way as in Reference Example 98 using methyl 4,5-bis(4-chlorophenyl)picolinate (0.11 g) synthesized in Reference Example 95.

$^1$H-NMR (CDCl$_3$) δ: 3.54 (1H, s), 4.86 (2H, s), 7.05-7.09 (4H, m), 7.26-7.29 (5H, m), 8.56 (1H, s).

MS (ESI) [M+H]$^+$: 330.

Reference Example 99 Synthesis of (5,6-bis(4-chlorophenyl)pyridin-2-yl)methanol

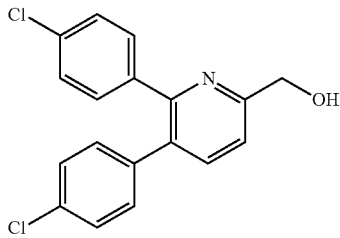 [SMILES: OCc1ccc(-c2ccc(Cl)cc2)c(-c2ccc(Cl)cc2)n1]

The title compound (0.70 g) was obtained in the same way as in Reference Example 98 using methyl 5,6-bis(4-chlorophenyl)picolinate (0.75 g) synthesized in Reference Example 96.

$^1$H-NMR (CDCl$_3$) δ: 3.82-3.85 (1H, m), 4.85 (2H, d, J=5.0 Hz), 7.08-7.11 (2H, m), 7.23-7.32 (7H, m), 7.70 (1H, d, J=8.2 Hz).

MS (ESI) [M+H]$^+$: 330.

Reference Example 100 Synthesis of 5-(chloromethyl)-2,3-bis(4-chlorophenyl)pyridine

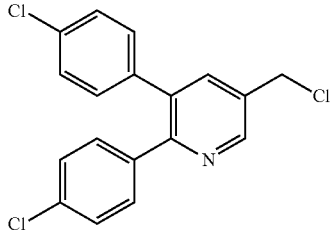 [SMILES: ClCc1cnc(-c2ccc(Cl)cc2)c(-c2ccc(Cl)cc2)c1]

(5,6-Bis(4-chlorophenyl)pyridin-3-yl)methanol (6.5 g) synthesized in Reference Example 97 was dissolved in dichloromethane (40 mL). To the solution, thionyl chloride (4.3 mL) was then added under ice cooling. The mixture was stirred at room temperature for 3 hours, and then, the reaction mixture was concentrated under reduced pressure. Toluene was added to the obtained crude product, and the mixture was concentrated again under reduced pressure to obtain the title compound (6.8 g) as a white solid.

$^1$H-NMR (CDCl$_3$) δ: 4.80 (2H, s), 7.14 (2H, d, J=8.2 Hz), 7.39 (4H, dd, J=8.7, 2.7 Hz), 7.45 (2H, d, J=8.7 Hz), 8.30 (1H, s), 9.02 (1H, s).

MS (ESI) [M+H]$^+$: 348.

Reference Example 101 Synthesis of 2-(chloromethyl)-4,5-bis(4-chlorophenyl)pyridine

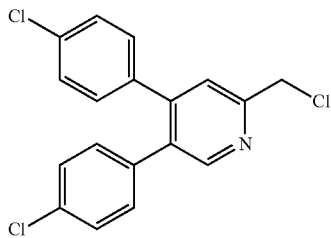 [SMILES: ClCc1cc(-c2ccc(Cl)cc2)c(-c2ccc(Cl)cc2)cn1]

The title compound (0.081 g) was obtained in the same way as in Reference Example 100 using (4,5-bis(4-chlorophenyl)pyridin-2-yl)methanol (0.078 g) synthesized in Reference Example 98.

$^1$H-NMR (CDCl$_3$) δ: 4.75 (2H, s), 7.05-7.11 (4H, m), 7.26-7.30 (4H, m), 7.49 (1H, s), 8.57 (1H, s).

Reference Example 102 Synthesis of 6-(chloromethyl)-2,3-bis(4-chlorophenyl)pyridine

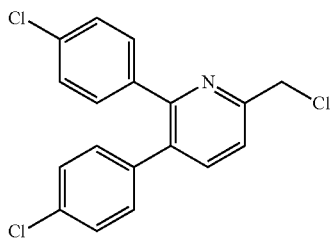 [SMILES: ClCc1ccc(-c2ccc(Cl)cc2)c(-c2ccc(Cl)cc2)n1]

The title compound (0.68 g) was obtained in the same way as in Reference Example 100 using (4,5-bis(4-chlorophenyl)pyridin-2-yl)methanol (0.69 g) synthesized in Reference Example 99.

Reference Example 103 Synthesis of 2-((5,6-bis(4-chlorophenyl)pyridin-3-yl)methyl)isoindoline-1,3-dione

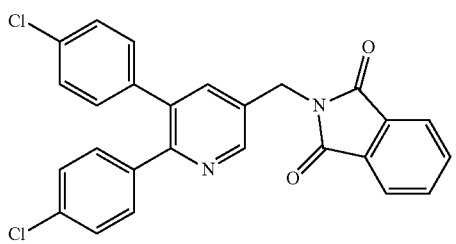

(5-(Chloromethyl)-2,3-bis(4-chlorophenyl)pyridine (0.45 g) synthesized in Reference Example 100 and potassium phthalimide (0.26 g) were dissolved in DMF (5 mL), and then, the solution was stirred at 80° C. for 1.5 hours. The reaction mixture was cooled to room temperature, and then, water was added thereto, followed by extraction with toluene. The organic layer was washed with a 1 mol/L aqueous sodium hydroxide solution and saturated saline, dried over anhydrous sodium sulfate, and then concentrated under reduced pressure. The obtained crude product was purified by silica gel column chromatography (n-hexane/ethyl acetate) to obtain the title compound (0.56 g).

Reference Example 104 Synthesis of 2-((4,5-bis(4-chlorophenyl)pyridin-2-yl)methyl)isoindoline-1,3-dione

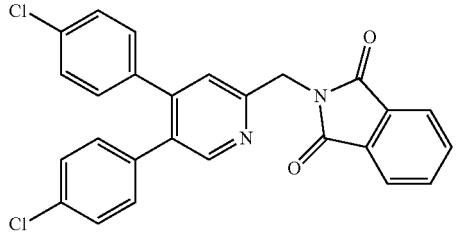 [SMILES: O=C1c2ccccc2C(=O)N1Cc1cc(-c2ccc(Cl)cc2)c(-c2ccc(Cl)cc2)cn1]

The title compound (0.090 g) was obtained in the same way as in Reference Example 103 using 2-(chloromethyl)-4,5-bis(4-chlorophenyl)pyridine (0.080 g) synthesized in Reference Example 101.

$^1$H-NMR (CDCl$_3$) δ: 5.10 (2H, s), 7.00-7.06 (4H, m), 7.24-7.30 (5H, m), 7.75 (2H, ddd, J=11.6, 6.1, 2.0 Hz), 7.91 (2H, ddd, J=11.6, 6.1, 2.0 Hz), 8.50 (1H, s).

MS (ESI) [M+H]$^+$: 459.

Reference Example 105 Synthesis of 2-((5,6-bis(4-chlorophenyl)pyridin-2-yl)methyl)isoindoline-1,3-dione

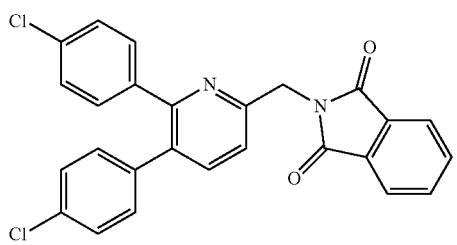 [SMILES: O=C1c2ccccc2C(=O)N1Cc1ccc(-c2ccc(Cl)cc2)c(-c2ccc(Cl)cc2)n1]

The title compound (0.74 g) was obtained in the same way as in Reference Example 103 using 6-(chloromethyl)-2,3-bis(4-chlorophenyl)pyridine (0.68 g) synthesized in Reference Example 102.

$^1$H-NMR (CDCl$_3$) δ: 5.12 (2H, s), 7.04-7.07 (2H, m), 7.12-7.15 (2H, m), 7.18-7.21 (2H, m), 7.25-7.27 (3H, m), 7.62 (1H, d, J=7.7 Hz), 7.76 (2H, ddd, J=11.4, 6.0, 2.2 Hz), 7.91 (2H, ddd, J=11.3, 5.9, 2.3 Hz).

MS (ESI) [M+H]$^+$: 459.

Reference Example 106 Synthesis of 5,6-bis(4-chlorophenyl)pyridin-3-yl)methanamine

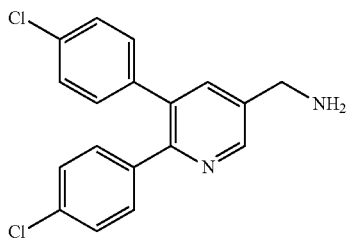 [SMILES: NCc1cnc(-c2ccc(Cl)cc2)c(-c2ccc(Cl)cc2)c1]

2-((5,6-Bis(4-chlorophenyl)pyridin-3-yl)methyl)isoindoline-1,3-dione (9.5 g) synthesized in Reference Example 103 was suspended in methanol (40 mL). To the suspension, hydrazine monohydrate (6 mL) was then added, and the mixture was heated to reflux for 2 hours. The reaction mixture was cooled to room temperature, then diluted with ethyl acetate, and filtered. The filtrate was washed with water and saturated saline, dried over anhydrous sodium sulfate, and then concentrated under reduced pressure to obtain the title compound (5.3 g).

$^1$H-NMR (CDCl$_3$) δ: 4.01 (2H, s), 7.11 (2H, d, J=8.2 Hz), 7.24-7.27 (6H, m), 7.69 (1H, d, J=1.4 Hz), 8.63 (1H, d, J=1.8 Hz).
MS (ESI) [M+H]$^+$: 329.

Reference Example 107 Synthesis of (4,5-bis(4-chlorophenyl)pyridin-2-yl)methanamine

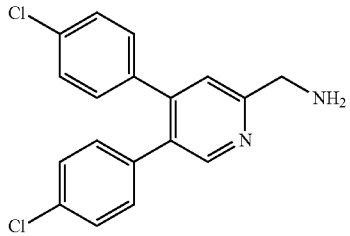 [SMILES: NCc1cc(-c2ccc(Cl)cc2)c(-c2ccc(Cl)cc2)cn1]

The title compound (0.064 g) was obtained in the same way as in Reference Example 106 using 2-((4,5-bis(4-chlorophenyl)pyridin-2-yl)methyl)isoindoline-1,3-dione (0.090 g) synthesized in Reference Example 104.

$^1$H-NMR (CDCl$_3$) δ: 4.07 (2H, s), 7.04-7.10 (4H, m), 7.23-7.32 (5H, m), 8.55 (1H, s).
MS (ESI) [M+H]$^+$: 329.

Reference Example 108 Synthesis of (5,6-bis(4-chlorophenyl)pyridin-2-yl)methanamine

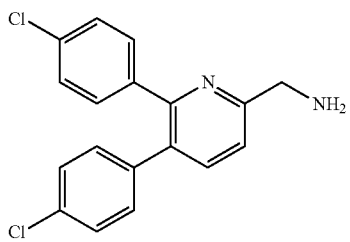 [SMILES: NCc1ccc(-c2ccc(Cl)cc2)c(-c2ccc(Cl)cc2)n1]

The title compound (0.39 g) was obtained in the same way as in Reference Example 106 using 2-((5,6-bis(4-chlorophenyl)pyridin-2-yl)methyl)isoindoline-1,3-dione (0.74 g) synthesized in Reference Example 105.

$^1$H-NMR (CDCl$_3$) δ: 4.07 (2H, s), 7.09 (2H, dt, J=8.9, 2.3 Hz), 7.24 (2H, dd, J=6.6, 2.0 Hz), 7.27-7.35 (5H, m), 7.66 (1H, d, J=7.7 Hz).

Reference Example 109 Synthesis of 1-(5,6-bis(4-chlorophenyl)pyridin-3-yl)ethanone

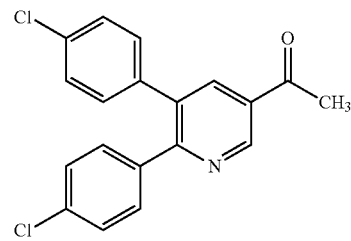 [SMILES: CC(=O)c1cnc(-c2ccc(Cl)cc2)c(-c2ccc(Cl)cc2)c1]

Methyl 5,6-bis(4-chlorophenyl)nicotinate (0.30 g) synthesized in Reference Example 94 and N,O-dimethylhydroxylamine hydrochloride (0.11 g) were dissolved in tetrahydrofuran (5 mL). To the solution, a 3 mol/L solution of methyl magnesium bromide in diethyl ether (1.4 mL) was then gradually added at 0° C. The reaction mixture was warmed to room temperature and stirred for 2 hours. Under ice cooling, a saturated aqueous solution of ammonium chloride was added to the reaction mixture, followed by extraction with diethyl ether. The organic layer was washed with water and saturated saline, dried over anhydrous sodium sulfate, and then concentrated under reduced pressure. The obtained crude product was purified by silica gel chromatography (n-hexane/ethyl acetate) to obtain the title compound (0.20 g) as a white solid.

$^1$H-NMR (CDCl$_3$) δ: 1.60 (3H, s), 7.11-7.15 (2H, m), 7.25-7.34 (6H, m), 8.06 (1H, d, J=1.8 Hz), 9.03 (1H, d, J=1.8 Hz).

Reference Example 110 Synthesis of 1-(5,6-bis(4-chlorophenyl)pyridin-3-yl)ethanol

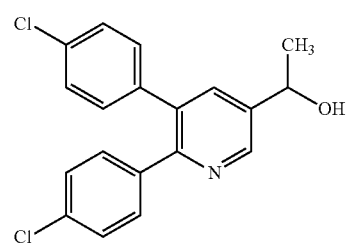 [SMILES: CC(O)c1cnc(-c2ccc(Cl)cc2)c(-c2ccc(Cl)cc2)c1]

1-(5,6-Bis(4-chlorophenyl)pyridin-3-yl)ethanone (0.14 g) synthesized in Reference Example 109 was dissolved in methanol (2.0 mL). To the solution, sodium borohydride (0.022 g) was then added at 0° C. The reaction mixture was warmed to room temperature and stirred for 1 hour. Under ice cooling, an aqueous potassium sodium tartrate solution and ethyl acetate were added to the reaction mixture, and the mixture was stirred at room temperature for 2 hours and then separated into aqueous and organic layers. The aqueous layer was subjected to extraction with ethyl acetate. The organic layer was washed with saturated saline, dried over anhydrous sodium sulfate, and then concentrated under reduced pressure. The obtained crude product was purified by silica gel chromatography (n-hexane/ethyl acetate) to obtain the title compound (0.077 g) as a white solid.

MS(ESI)[M+H]+:344.

Reference Example 111 Synthesis of 5-(1-azidoethyl)-2,3-bis(4-chlorophenyl)pyridine

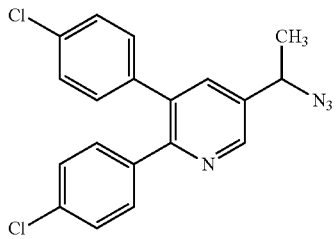 [SMILES: CC(N=[N+]=[N-])c1cnc(-c2ccc(Cl)cc2)c(-c2ccc(Cl)cc2)c1]

1-(5,6-Bis(4-chlorophenyl)pyridin-3-yl)ethanol (0.077 g) synthesized in Reference Example 110 was dissolved in toluene (2.0 mL). To the solution, diphenylphosphoryl azide (0.067 mL) and diazabicycloundecene (0.047 mL) were then added, and the mixture was stirred for 18 hours. The reaction mixture was washed with saturated saline, dried over anhydrous sodium sulfate, and then concentrated under reduced pressure. The obtained crude product was purified by silica gel chromatography (n-hexane/ethyl acetate) to obtain the title compound (0.042 g) as a white solid.

$^1$H-NMR (CDCl$_3$) δ: 1.64 (3H, d, J=6.8 Hz), 4.78 (1H, q, J=6.8 Hz), 7.11-7.13 (2H, m), 7.23-7.32 (6H, m), 7.65 (1H, d, J=2.3 Hz), 8.64 (1H, d, J=2.3 Hz).

MS (ESI) [M+H]+: 369.

Reference Example 112 Synthesis of 1-(5,6-bis(4-chlorophenyl)pyridin-3-yl)ethanamine

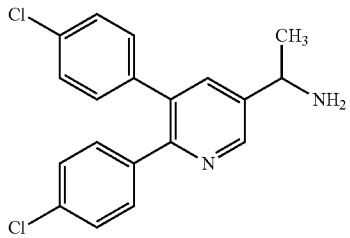 [SMILES: CC(N)c1cnc(-c2ccc(Cl)cc2)c(-c2ccc(Cl)cc2)c1]

5-(1-Azidoethyl)-2,3-bis(4-chlorophenyl)pyridine (0.042 g) synthesized in Reference Example 111 was dissolved in tetrahydrofuran (1.0 mL). To the solution, triphenylphosphine (0.060 g) and water (0.020 g) were then added, and the mixture was stirred at 50° C. for 4 hours. The reaction mixture was cooled to room temperature, and then, water was added thereto, followed by extraction with chloroform. The organic layer was washed with saturated saline, dried over anhydrous sodium sulfate, and then concentrated under reduced pressure. The obtained crude product was purified by silica gel chromatography (aminesilica, methanol/ethyl acetate) to obtain the title compound (0.036 g) as a colorless oil.

$^1$H-NMR (CDCl$_3$) δ: 1.48 (3H, d, J=6.8 Hz), 4.29 (1H, m), 7.11 (2H, q, J=8.2 Hz), 7.24-7.27 (6H, m), 7.71 (1H, d, J=2.3 Hz), 8.65 (1H, d, J=2.3 Hz).

MS (ESI) [M+H]+: 345.

Reference Example 113 Synthesis of diphenyl phenylsulfonylcarbonimidate

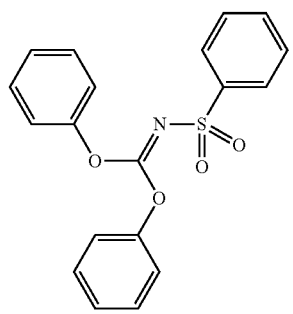 [SMILES: O=S(=O)(N=C(Oc1ccccc1)Oc1ccccc1)c1ccccc1]

Dichlorodiphenoxymethane (5.7 g) and benzenesulfonamide (7.3 g) were suspended in ethyl acetate (25 mL), and then, the reaction mixture was heated to reflux for 25 hours. The reaction mixture was cooled to room temperature, then washed with a saturated aqueous solution of sodium bicarbonate and water, dried over anhydrous sodium sulfate, and then concentrated under reduced pressure. The residue was suspended in dichloromethane, and insoluble matter was filtered off. The filtrate was concentrated under reduced pressure, and the obtained crude product was purified by silica gel chromatography (n-hexane/ethyl acetate). Then, the obtained solid was recrystallized (n-hexane/ethyl acetate) to obtain the title compound (2.4 g).

$^1$HNMR (CDCl$_3$) 7.07-7.09 (m, 4H), 7.27-7.29 (m, 2H) 7.35-7.39 (m, 4H), 7.46-7.50 (m, 2H), 7.55-7.59 (1H, m), 7.94-7.96 (m, 2H).

MS (ESI): 354 (M+H).

Reference Example 114 Synthesis of phenyl N-((5,6-bis(4-chlorophenyl)pyridin-3-yl)methyl)-N'-(phenylsulfonyl)carbamimidate

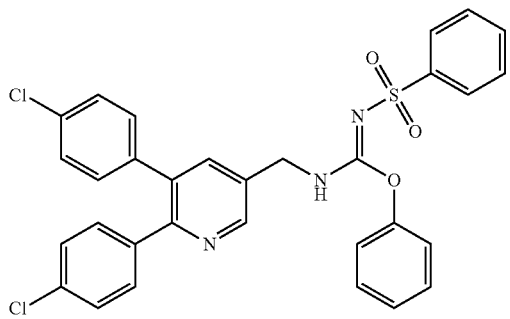 [SMILES: O=S(=O)(/N=C(/NCc1cnc(-c2ccc(Cl)cc2)c(-c2ccc(Cl)cc2)c1)Oc1ccccc1)c1ccccc1]

(5,6-Bis(4-chlorophenyl)pyridin-3-yl)methanamine (0.065 g) synthesized in Reference Example 106 was dissolved in tetrahydrofuran (1 mL). To the solution, diphenyl phenylsulfonylcarbonimidate (0.073 g) synthesized in Reference Example 113 was then added. The reaction mixture was stirred overnight at room temperature and then concentrated under reduced pressure. The obtained crude product was purified by silica gel chromatography (n-hexane/ethyl acetate) to obtain the title compound (0.12 g).

$^1$H-NMR (CDCl$_3$) δ: 4.72 (2H, d, J=5.9 Hz), 6.92-6.96 (2H, m), 7.08 (2H, dt, J=8.9, 2.3 Hz), 7.24-7.41 (11H, m), 7.49 (1H, ddd, J=10.0, 5.0, 2.3 Hz), 7.64 (1H, d, J=2.3 Hz), 7.73-7.75 (2H, m), 8.09 (1H, t, J=5.7 Hz), 8.67 (1H, d, J=2.3 Hz).

MS (ESI) [M+H]$^+$: 588.

Example 38 Synthesis of N-((5,6-bis(4-chlorophenyl)pyridin-3-yl)methyl)-N'-(phenylsulfonyl)hydrazinecarboximidate

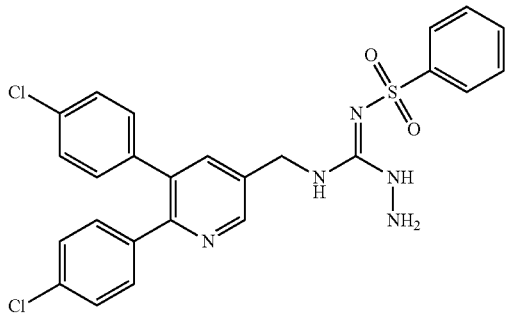

Phenyl N-((5,6-bis(4-chlorophenyl)pyridin-3-yl)methyl)-N'-(phenylsulfonyl)carbamimidate (0.030 g) synthesized in Reference Example 114 was dissolved in acetonitrile (1 mL). To the solution, hydrazine monohydrate (0.012 mL) was then added, and the mixture was heated and stirred at 80° C. for 1.5 hours. The reaction mixture was cooled to room temperature, and then, water was added thereto, followed by extraction with ethyl acetate. The organic layer was washed with saturated saline, dried over anhydrous sodium sulfate, and then concentrated under reduced pressure. The obtained crude product was slurry-washed with diisopropyl ether to obtain the title compound (hereinafter, referred to as the compound of Example 38) (0.015 g).

$^1$H-NMR (DMSO-d$_6$) δ: 4.43 (2H, s), 4.61 (2H, s), 7.11 (2H, d, J=8.3 Hz), 7.27 (2H, d, J=8.5 Hz), 7.32-7.46 (7H, m), 7.62 (3H, d, J=7.3 Hz), 8.14 (2H, brs), 8.56 (1H, d, J=1.5 Hz).

MS (ESI) [M+H]$^+$: 526.

Example 39 Synthesis of N-((((5,6-bis(4-chlorophenyl)pyridin-3-yl)methyl)amino)(hydroxyamino)methylene)benzenesulfonamide

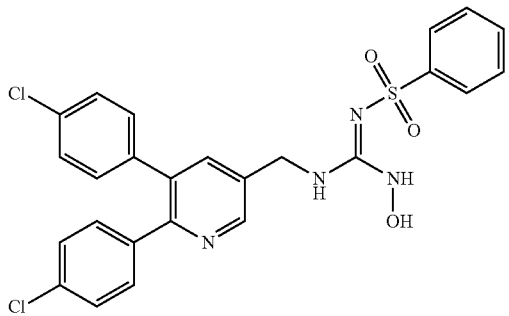

Phenyl N-((5,6-bis(4-chlorophenyl)pyridin-3-yl)methyl)-N'-(phenylsulfonyl)carbamimidate (0.060 g) synthesized in Reference Example 114 and triethylamine (0.28 mL) were dissolved in acetonitrile (1 mL). To the solution, hydroxyamine hydrochloride (0.14 g) was then added, and the mixture was heated and stirred at 80° C. for 4 hours. The reaction mixture was cooled to room temperature, and then, water was added thereto, followed by extraction with ethyl acetate. The organic layer was washed with saturated saline, dried over anhydrous sodium sulfate, and then concentrated under reduced pressure. The obtained crude product was purified by silica gel chromatography (chloroform/methanol) to obtain the title compound (hereinafter, referred to as the compound of Example 39) (0.027 g).

$^1$H-NMR (CD$_3$OD) δ: 4.55 (2H, s), 7.07 (2H, dt, J=8.9, 2.3 Hz), 7.24-7.27 (2H, m), 7.29-7.32 (6H, m), 7.42 (1H, tt, J=7.4, 1.4 Hz), 7.67-7.69 (2H, m), 7.72 (1H, d, J=2.2 Hz), 8.52 (1H, d, J=2.2 Hz).

MS (ESI) [M+H]$^+$: 527.

Example 40 Synthesis of N-(((((5,6-bis(4-chlorophenyl)pyridin-3-yl)methyl)amino)methylamino)methylene)benzenesulfonamide

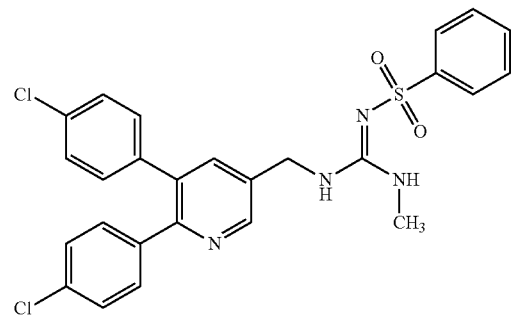

Phenyl N-((5,6-bis(4-chlorophenyl)pyridin-3-yl)methyl)-N'-(phenylsulfonyl)carbamimidate (0.030 g) synthesized in Reference Example 114 was dissolved in acetonitrile (1 mL). To the solution, a 2 mol/L solution of methylamine in tetrahydrofuran (0.052 mL) was then added, and the mixture was heated and stirred at 80° C. for 2 hours. The reaction mixture was cooled to room temperature and then concentrated under reduced pressure. The obtained crude product was purified by silica gel chromatography (chloroform/methanol) to obtain the title compound (hereinafter, referred to as the compound of Example 40) (0.015 g).

$^1$H-NMR (DMSO-ds) δ: 2.74 (3H, s), 3.17 (1H, d, J=5.2 Hz), 4.04 (1H, s), 4.45 (2H, s), 7.10-7.12 (2H, m), 7.24-7.45 (8H, m), 7.59-7.70 (4H, m), 8.53 (1H, s).

MS (ESI) [M+H]$^+$: 525.

Reference Example 115 Synthesis of phenyl N-((5,6-bis(4-chlorophenyl)pyridin-3-yl)-N'-cyanocarbamimidate

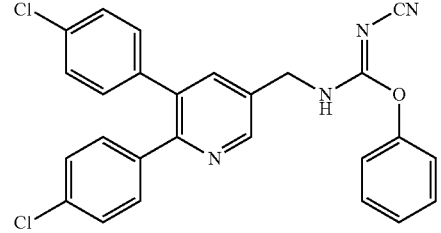 [SMILES: N#C/N=C(/NCc1cnc(-c2ccc(Cl)cc2)c(-c2ccc(Cl)cc2)c1)Oc1ccccc1]

(5,6-Bis(4-chlorophenyl)pyridin-3-yl)methanamine (0.20 g) synthesized in Reference Example 106 was dissolved in dichloromethane (3 mL). To the solution, diphenyl cyanocarbonimidate (0.15 g) was then added. The reaction mixture was stirred for 2 hours and then concentrated under reduced pressure. The obtained crude product was purified by silica gel chromatography (n-hexane/ethyl acetate) to obtain the title compound (0.24 g).

¹H-NMR (CDCl₃) δ: 4.65 (2H, d, J=5.9 Hz), 7.05 (2H, d, J=7.2 Hz), 7.10 (2H, dt, J=8.8, 2.3 Hz), 7.24-7.33 (7H, m), 7.41 (2H, t, J=7.0 Hz), 7.73 (1H, s), 7.83 (1H, brs), 8.71 (1H, s).

MS (ESI) [M+H]⁺: 473.

Reference Example 116 Synthesis of 1-((5,6-bis(4-chlorophenyl)pyridin-3-yl)methyl)-2-cyanoguanidine

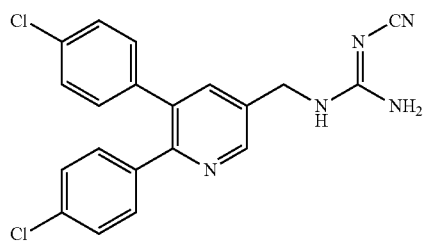 [SMILES: N#C/N=C(\N)NCc1cnc(-c2ccc(Cl)cc2)c(-c2ccc(Cl)cc2)c1]

Phenyl. N-((5,6-bis(4-chlorophenyl)pyridin-3-yl)-N'-cyanocarbamimidate (0.15 g) synthesized in Reference Example 115 was dissolved in acetonitrile (3 mL). To the solution, 28% by weight of ammonia water (0.007 mL) was then added, and the mixture was stirred overnight at 80° C. Water was added to the reaction mixture, followed by extraction with ethyl acetate. The organic layer was washed with water and saturated saline, dried over anhydrous sodium sulfate, and then concentrated under reduced pressure. The obtained crude product was purified by silica gel chromatography (chloroform/methanol) to obtain the title compound (0.075 g).

¹H-NMR (CDCl₃) δ: 4.41 (2H, d, J=5.9 Hz), 5.89 (2H, s), 6.49 (1H, brs), 7.05 (2H, d, J=8.6 Hz), 7.17-7.26 (6H, m), 7.57 (1H, d, J=1.8 Hz), 8.54 (1H, d, J=1.8 Hz).

MS (ESI) [M+H]⁺: 396.

Example 41 Synthesis of 1-(amino(((5,6-bis(4-chlorophenyl)pyridin-3-yl)methyl)amino)methylene)urea Hydrochloride

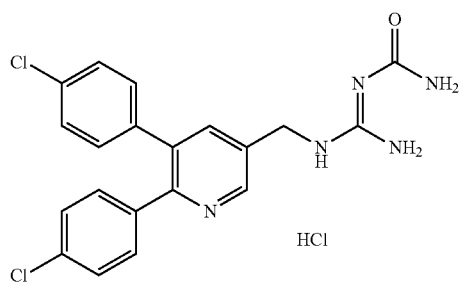 [SMILES: NC(=O)/N=C(\N)NCc1cnc(-c2ccc(Cl)cc2)c(-c2ccc(Cl)cc2)c1 ; Cl]

1-((5,6-Bis(4-chlorophenyl)pyridin-3-yl)methyl)-2-cyanoguanidine (0.040 g) synthesized in Reference Example 116 was dissolved in concentrated hydrochloric acid (1 mL), and then, the solution was stirred at 50° C. for 1.5 hours. The reaction mixture was cooled to room temperature and then concentrated under reduced pressure. The residue was slurry-washed with acetonitrile to obtain the title compound (hereinafter, referred to as the compound of Example 41) (0.034 g).

¹H-NMR (DMSO-d₆) δ: 4.69 (2H, brs), 7.22 (2H, d, J=8.2 Hz), 7.29-7.33 (3H, m), 7.39 (2H, dd, J=8.6, 1.4 Hz), 7.44 (2H, dt, J=8.9, 2.3 Hz), 7.92 (1H, brs), 8.72 (3H, s), 9.53 (1H, brs), 10.23 (1H, brs).

MS (ESI) [M+H]⁺: 414.

Reference Example 117 Synthesis of 2-benzenesulfonyl-3-((4,5-bis(4-chlorophenyl)pyridin-2-yl)methyl)-1-(tert-butoxycarbonyl)guanidine

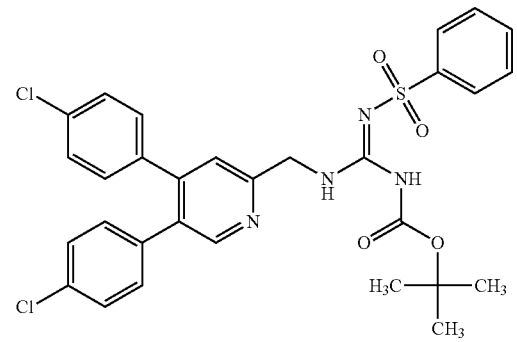 [SMILES: CC(C)(C)OC(=O)N/C(=N\S(=O)(=O)c1ccccc1)NCc1cc(-c2ccc(Cl)cc2)c(-c2ccc(Cl)cc2)cn1]

The title compound (0.027 g) was obtained in the same way as in the guanidination reaction of Reference Example 52 using (4,5-bis(4-chlorophenyl)pyridin-2-yl)methanamine (0.020 g) synthesized in Reference Example 107 and N-(phenylsulfonyl)-N'-(tert-butoxycarbonyl)-S-methylisothiourea (0.022 g) synthesized in Reference Example 42.

¹H-NMR (CDCl₃) δ: 1.53 (9H, s), 4.71 (2H, d, J=4.9 Hz), 6.97-7.07 (4H, m), 7.20 (1H, s), 7.24-7.29 (4H, m), 7.38-7.42 (2H, m), 7.45-7.52 (1H, m), 7.86-7.88 (2H, m), 8.55 (1H, s), 9.48 (1H, t, J=4.6 Hz), 10.00 (1H, s).

MS (ESI) [M+H]⁺: 611.

Reference Example 118 Synthesis of 3-((4,5-bis(4-chlorophenyl)pyridin-2-yl)methyl)-2-(thiophene-2-sulfonyl)-1-(tert-butoxycarbonyl)guanidine

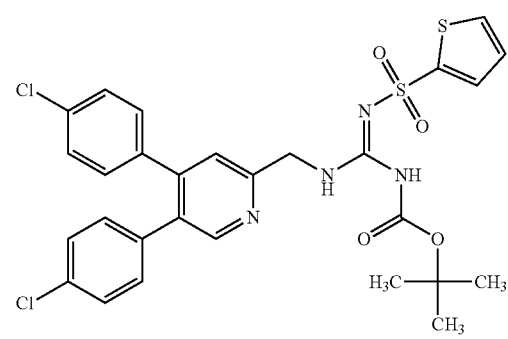 [SMILES: CC(C)(C)OC(=O)N/C(=N\S(=O)(=O)c1cccs1)NCc1cc(-c2ccc(Cl)cc2)c(-c2ccc(Cl)cc2)cn1]

The title compound (0.024 g) was obtained in the same way as in the guanidination reaction of Reference Example 52 using (4,5-bis(4-chlorophenyl)pyridin-2-yl)methanamine (0.022 g) synthesized in Reference Example 107 and N-(2- thiophenesulfonyl)-N'-(tert-butoxycarbonyl)-S-methylisothiourea (0.025 g) synthesized in Reference Example 46.

¹H-NMR (CDCl₃) δ: 1.53 (9H, s), 4.74 (2H, d, J=5.0 Hz), 6.96-6.98 (1H, m), 7.02-7.05 (4H, m), 7.24-7.29 (7H, m), 7.42 (1H, dd, J=5.0, 1.4 Hz), 7.56 (1H, dd, J=3.2, 1.4 Hz), 8.57 (1H, s), 9.56 (1H, t, J=4.5 Hz), 9.85 (1H, s).
MS (ESI) [M+H]⁺: 617.

Reference Example 119 Synthesis of 2-benzenecarbonyl-3-((4,5-bis(4-chlorophenyl)pyridin-2-yl)methyl)-1-(tert-butoxycarbonyl)guanidine

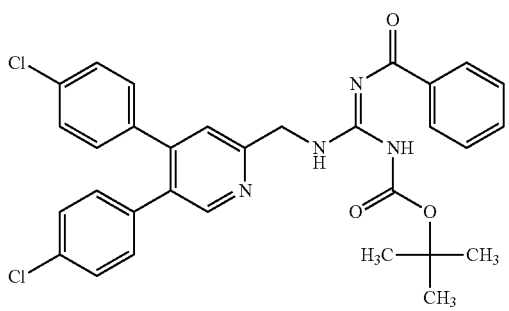 [SMILES: CC(C)(C)OC(=O)N/C(=N\C(=O)c1ccccc1)NCc1cc(-c2ccc(Cl)cc2)c(-c2ccc(Cl)cc2)cn1]

The title compound (0.032 g) was obtained in the same way as in Reference Example 52 using (4,5-bis(4-chlorophenyl)pyridin-2-yl)methanamine (0.022 g) synthesized in Reference Example 107 and N-(benzenecarbonyl)-N'-(tert-butoxycarbonyl)-S-methylisothiourea (0.024 g) synthesized in Reference Example 50.

¹H-NMR (CDCl₃) δ: 1.53 (9H, s), 4.99 (2H, d, J=5.1 Hz), 7.04-7.07 (4H, m), 7.22-7.28 (4H, m), 7.38-7.41 (3H, m), 7.47-7.51 (1H, m), 8.21-8.23 (2H, m), 8.61 (1H, s), 9.42 (1H, t, J=4.8 Hz), 12.50 (1H, s).

(The spectral data represents the value of a main isomer among isomers attributed to an amide bond.)
MS(ESI)[M+H]⁺:575.

Reference Example 120 Synthesis of 2-benzenesulfonyl-3-((5,6-bis(4-chlorophenyl)pyridin-2-yl)methyl)-1-(tert-butoxycarbonyl)guanidine

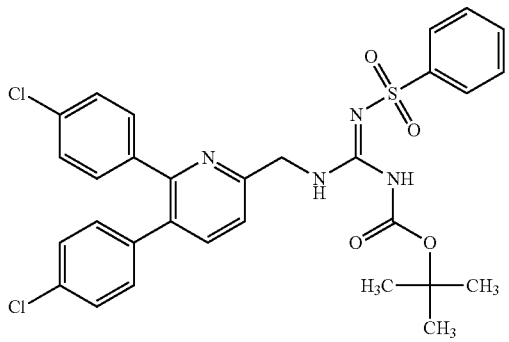 [SMILES: CC(C)(C)OC(=O)N/C(=N\S(=O)(=O)c1ccccc1)NCc1ccc(-c2ccc(Cl)cc2)c(-c2ccc(Cl)cc2)n1]

The title compound (0.054 g) was obtained in the same way as in the guanidination reaction of Reference Example 52 using (5,6-bis(4-chlorophenyl)pyridin-2-yl)methanamine (0.030 g) synthesized in Reference Example 108 and N-(phenylsulfonyl)-N'-(tert-butoxycarbonyl)-S-methylisothiourea (0.033 g) synthesized in Reference Example 42.

¹H-NMR (CDCl₃) δ: 1.56 (9H, s), 4.72 (2H, d, J=4.5 Hz), 7.09-7.12 (2H, m), 7.20-7.24 (3H, m), 7.27-7.32 (2H, m), 7.40-7.53 (5H, m), 7.63 (1H, d, J=8.2 Hz), 7.91-7.93 (2H, m), 9.93 (1H, t, J=4.5 Hz), 10.00 (1H, s).
MS (ESI) [M+H]⁺: 611.

Reference Example 121 Synthesis of 2-benzenesulfonyl-3-(1-(5,6-bis(4-chlorophenyl)pyridin-3-yl)ethyl)-1-(tert-butoxycarbonyl)guanidine

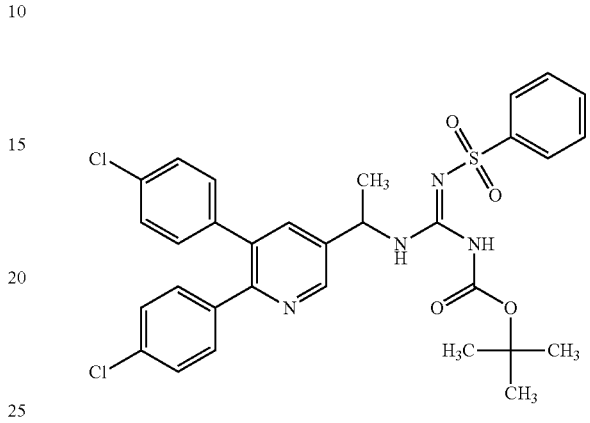

The title compound (0.026 g) was obtained in the same way as in the guanidination reaction of Reference Example 52 using 1-(5,6-bis(4-chlorophenyl)pyridin-3-yl)ethanamine (0.034 g) synthesized in Reference Example 112 and N-(phenylsulfonyl)-N'-(tert-butoxycarbonyl)-S-methylisothiourea (0.033 g) synthesized in Reference Example 42.

¹H-NMR (CDCl₃) δ: 1.56 (3H, d, J=6.9 Hz), 1.61 (9H, s), 5.02-5.05 (1H, m), 7.08-7.11 (2H, m), 7.22-7.29 (6H, m), 7.46-7.60 (4H, m), 7.90-7.93 (2H, m), 8.63 (1H, d, J=2.3 Hz).
MS (ESI) [M+H]⁺: 625.

Example 42 Synthesis of N-(amino(((4,5-bis(4-chlorophenyl)pyridin-2-yl)methyl)amino)methylene)benzenesulfonamide

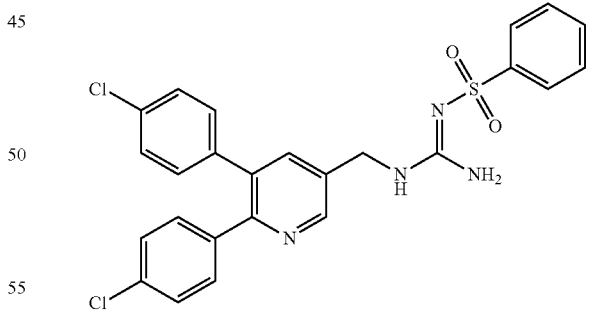

The title compound (hereinafter, referred to as the compound of Example 42) (0.016 g) was obtained in the same way as in Example 1 using 2-benzenesulfonyl-3-((4,5-bis(4-chlorophenyl)pyridin-2-yl)methyl)-1-(tert-butoxycarbonyl)guanidine (0.027 g) synthesized in Reference Example 117.

¹H-NMR (CDCl₃) δ: 4.54 (2H, d, J=5.6 Hz), 6.96-7.04 (4H, m), 7.21-7.23 (2H, m), 7.28-7.44 (6H, m), 7.82 (2H, d, J=7.3 Hz), 8.43 (1H, s).
MS (ESI) [M+H]⁺: 511.

Example 43 Synthesis of N-(amino(((4,5-bis(4-chlorophenyl)pyridin-2-yl)methyl)amino)methylene)thiophene-2-sulfonamide

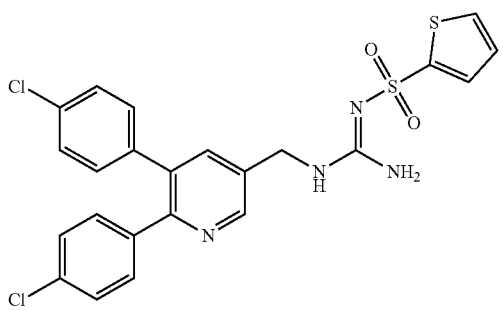

The title compound (hereinafter, referred to as the compound of Example 43) (0.021 g) was obtained in the same way as in Example 1 using 3-((4,5-bis(4-chlorophenyl)pyridin-2-yl)methyl)-2-(thiophene-2-sulfonyl)-1-(tert-butoxycarbonyl)guanidine (0.024 g) synthesized in Reference Example 118.

$^1$H-NMR (CDCl$_3$) δ: 4.56 (2H, d, J=5.6 Hz), 6.90 (1H, dd, J=4.9, 3.3 Hz), 7.00-7.05 (4H, m), 7.23-7.29 (4H, m), 7.33 (1H, dd, J=4.9, 1.3 Hz), 7.44 (1H, s), 7.47 (1H, d, J=3.3 Hz), 8.44 (1H, s).

MS (ESI) [M+H]$^+$: 517.

Example 44 Synthesis of N-(amino(((4,5-bis(4-chlorophenyl)pyridin-2-yl)methyl)amino)methylene)benzamide

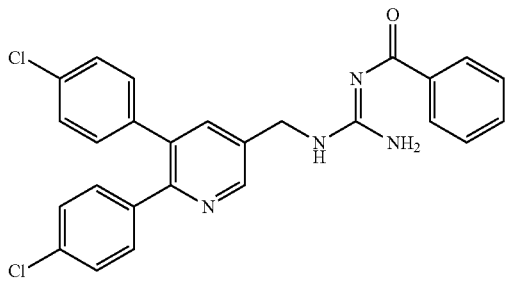

The title compound (hereinafter, referred to as the compound of Example 44) (0.018 g) was obtained in the same way as in Example 1 using 2-benzenecarbonyl-3-((4,5-bis(4-chlorophenyl)pyridin-2-yl)methyl)-1-(tert-butoxycarbonyl)guanidine (0.032 g) synthesized in Reference Example 119.

$^1$H-NMR (CDCl$_3$) δ:4.57 (2H, brs), 7.03-7.07 (4H, m), 7.26-7.30 (5H, m), 7.34-7.39 (3H, m), 8.17 (2H, d, J=6.1 Hz), 8.52 (1H, s).

MS (ESI) [M+H]$^+$: 475.

Example 45 Synthesis of N-(amino(((5,6-bis(4-chlorophenyl)pyridin-2-yl)methyl)amino)methylene)benzenesulfonamide Hydrochloride

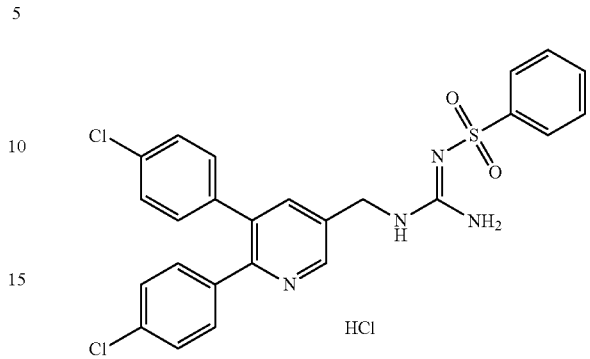

N-(Amino(((5,6-bis(4-chlorophenyl)pyridin-2-yl)methyl)amino)methylene)benzenesulfonamide was obtained in the same way as in Example 1 using 2-benzenesulfonyl-3-((5,6-bis(4-chlorophenyl)pyridin-2-yl)methyl)-1-(tert-butoxycarbonyl)guanidine (0.050 g) synthesized in Reference Example 120. The obtained product was dissolved in ethyl acetate. To the solution, a 4 mol/L solution of hydrogen chloride in ethyl acetate was then added, and the mixture was stirred at room temperature for 2 hours. The precipitated solid was collected by filtration and washed with ethyl acetate/n-heptane (1/5, v/v) to obtain the title compound (hereinafter, referred to as the compound of Example 45) (0.038 g).

$^1$H-NMR (CD$_3$OD) δ:4.74 (2H, s), 7.17-7.20 (2H, m), 7.38-7.45 (6H, m), 7.50-7.52 (3H, m), 7.70 (2H, d, J=7.2 Hz), 7.87 (1H, d, J=8.0 Hz), 8.43 (1H, d, J=8.0 Hz).

MS (ESI) [M+H]$^+$: 511.

Example 46 Synthesis of N-(amino((1-(5,6-bis(4-chlorophenyl)pyridin-3-yl)ethyl)amino)methylene)benzenesulfonamide

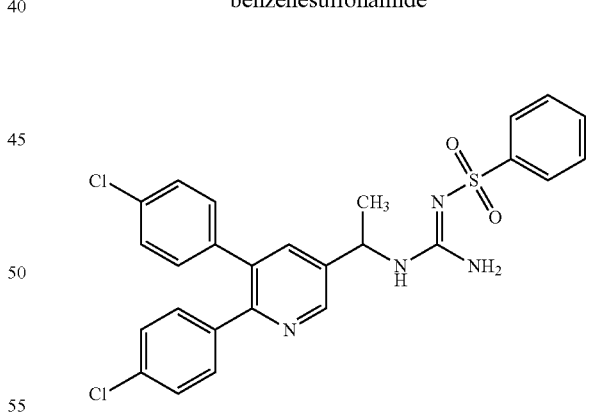

The title compound (hereinafter, referred to as the compound of Example 46) (0.014 g) was obtained in the same way as in Example 1 using 2-benzenesulfonyl-3-(1-(5,6-bis(4-chlorophenyl)pyridin-3-yl)ethyl)-1-(tert-butoxycarbonyl)guanidine (0.020 g) synthesized in Reference Example 121.

$^1$H-NMR (CDCl$_3$) δ: 1.53 (3H, d, J=6.9 Hz), 4.95 (1H, s), 6.12 (2H, s), 6.99-6.97 (2H, m), 7.21-7.42 (11H, m), 7.52 (1H, d, J=2.3 Hz), 7.72 (2H, d, J=7.3 Hz), 8.57 (1H, d, J=2.3 Hz).

MS (ESI) [M+H]$^+$: 525.

Reference Example 122 Synthesis of 1,1-dimethylethyl N-((((5,6-bis(4-chlorophenyl)pyridin-3-yl)methyl)amino)(((1,1-dimethylethoxy)carbonyl)amino)methylene)carbamic acid

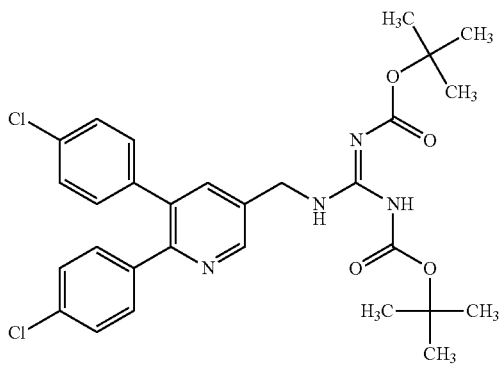 [SMILES: CC(C)(C)OC(=O)/N=C(/NCc1cnc(-c2ccc(Cl)cc2)c(-c2ccc(Cl)cc2)c1)NC(=O)OC(C)(C)C]

(5,6-Bis(4-chlorophenyl)pyridin-3-yl)methanamine (0.90 g) synthesized in Reference Example 106 was dissolved in tetrahydrofuran (14 mL). To the solution, N,N'-bis(tert-butoxycarbonyl)-1H-pyrazole-1-carboxamidine (0.93 g) was then added, and the mixture was stirred for 7 hours. Water was added to the reaction mixture, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (1.54 g).
$^1$H-NMR (CDCl$_3$) δ: 1.49 (9H, s), 1.51 (9H, s), 4.71 (2H, d, J=5.9 Hz), 7.11 (2H, d, J=8.7 Hz), 7.22-7.30 (6H, m), 7.71 (1H, d, J=2.3 Hz), 8.65 (1H, d, J=2.3 Hz), 8.73 (2H, t, J=5.5 Hz), 11.52 (1H, brs).

Reference Example 123 Synthesis of 1-((5,6-bis(4-chlorophenyl)pyridin-3-yl)methyl)guanidine

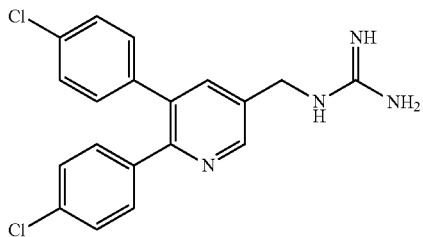 [SMILES: N=C(N)NCc1cnc(-c2ccc(Cl)cc2)c(-c2ccc(Cl)cc2)c1]

1,1-Dimethylethyl N-((((5,6-bis(4-chlorophenyl)pyridin-3-yl)methyl)amino)((1,1-dimethylethoxy)carbonyl)amino)methylene)carbamic acid (1.5 g) synthesized in Reference Example 122 was dissolved in dichloromethane (27 mL), and the solution was cooled to 0° C. Then, trifluoroacetic acid (15.3 mL) was added thereto. The reaction mixture was stirred at room temperature for 12 hours and then concentrated under reduced pressure. Water and a 1 mol/L aqueous sodium hydroxide solution were added to the residue, and the mixture was neutralized, followed by extraction with ethyl acetate. The organic layer was washed with saturated saline, dried over anhydrous sodium sulfate, and then concentrated under reduced pressure to obtain the title compound (1.0 g).
$^1$H-NMR (CDCl$_3$) δ: 4.33 (2H, brs), 6.99 (2H, d, J=8.7 Hz), 7.12 (4H, s), 7.19 (2H, d, J=8.7 Hz), 7.23 (2H, brs), 7.52 (1H, d, J=2.3 Hz), 8.42 (1H, brs), 8.48 (1H, d, J=2.3 Hz).
MS (ESI) [M+H]$^+$: 371.

Example 47 Synthesis of N-(amino(((5,6-bis(4-chlorophenyl)pyridin-3-yl)methyl)amino)methylene)-3-cyanobenzenesulfonamide

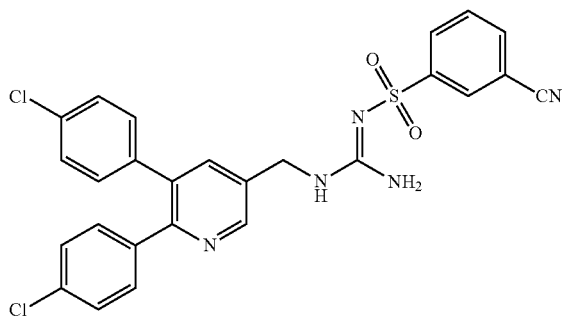

1-((5,6-Bis(4-chlorophenyl)pyridin-3-yl)methyl)guanidine (0.050 g) synthesized in Reference Example 123 was dissolved in tetrahydrofuran (1.4 mL). To the solution, a 1 mol/L aqueous sodium hydroxide solution (0.4 mL) and 3-cyanobenzenesulfonyl chloride (0.030 g) were then added, and the mixture was stirred for 2 hours. Water was added to the reaction mixture, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (hereinafter, referred to as the compound of Example 47) (0.023 g).
$^1$H-NMR (CDCl$_3$) δ: 4.46 (2H, d, J=5.4 Hz), 6.43 (3H, brs), 7.00 (2H, dd, J=8.4, 2.9 Hz), 7.20-7.26 (6H, m), 7.44-7.52 (2H, m), 7.69 (1H, d, J=7.7 Hz), 8.00 (1H, d, J=7.7 Hz), 8.08 (1H, d, J=1.4 Hz), 8.50 (1H, s).
MS (ESI) [M+H]$^+$: 536.

Example 48 Synthesis of N-(amino(((5,6-bis(4-chlorophenyl)pyridin-3-yl)methyl)amino)methylene)-3-chlorobenzenesulfonamide

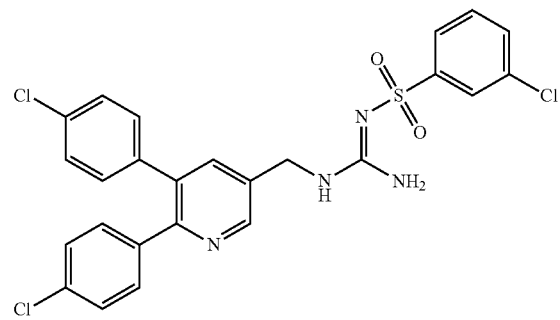 [SMILES: N/C(=N\S(=O)(=O)c1cccc(Cl)c1)NCc1cnc(-c2ccc(Cl)cc2)c(-c2ccc(Cl)cc2)c1]

The title compound (hereinafter, referred to as the compound of Example 48) (0.010 g) was obtained in the same way as in Example 47 using 1-((5,6-bis(4-chlorophenyl)pyridin-3-yl)methyl)guanidine (0.050 g) synthesized in Reference Example 123 and 3-chlorobenzenesulfonyl chloride (0.031 g).
$^1$H-NMR (CDCl$_3$) δ: 4.45 (2H, d, J=5.9 Hz), 6.39 (3H, brs), 6.98 (2H, d, J=8.2 Hz), 7.20 (4H, s), 7.22-7.26 (3H, m), 7.37-7.40 (1H, m), 7.50 (1H, s), 7.62-7.65 (1H, m), 7.76 (1H, d, J=1.8 Hz), 8.50 (1H, d, J=1.8 Hz).
MS (ESI) [M+H]$^+$: 545.

Example 49 Synthesis of N-(amino(((5,6-bis(4-chlorophenyl)pyridin-3-yl)methyl)amino)methylene)-2-methoxybenzenesulfonamide

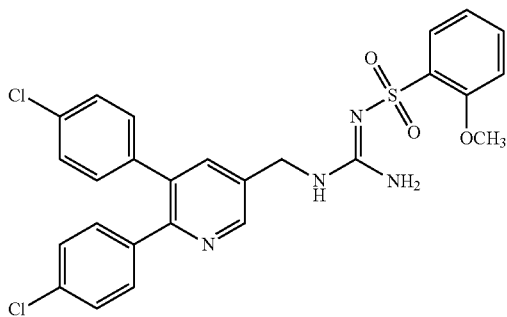

The title compound (hereinafter, referred to as the compound of Example 49) (0.028 g) was obtained in the same way as in Example 47 using 1-((5,6-bis(4-chlorophenyl)pyridin-3-yl)methyl)guanidine (0.050 g) synthesized in Reference Example 123 and 2-methoxybenzenesulfonyl chloride (0.056 g).
$^1$H-NMR (CDCl$_3$) δ: 3.62 (3H, s), 4.41 (2H, d, J=5.5 Hz), 6.65-6.74 (3H, m), 6.86-6.90 (3H, m), 6.94 (1H, brs), 7.14-7.19 (6H, m), 7.35 (1H, t, J=7.8 Hz), 7.46 (1H, s), 7.77 (1H, d, J=7.8 Hz), 8.47 (1H, s).
MS (ESI) [M+H]$^+$: 541.

Example 50 Synthesis of N-(amino(((5,6-bis(4-chlorophenyl)pyridin-3-yl)methyl)amino)methylene)-3-methoxybenzenesulfonamide

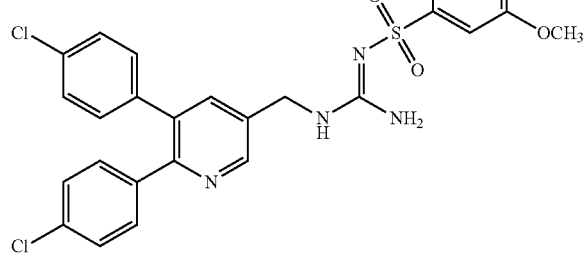

The title compound (hereinafter, referred to as the compound of Example 50) (0.072 g) was obtained in the same way as in Example 47 using 1-((5,6-bis(4-chlorophenyl)pyridin-3-yl)methyl)guanidine (0.15 g) synthesized in Reference Example 123 and 3-methoxybenzenesulfonyl chloride (0.18 g).

$^1$H-NMR (CDCl$_3$) δ: 3.70 (3H, s), 4.42 (2H, d, J=5.4 Hz), 6.53 (2H, brs), 6.79 (1H, brs), 6.91-6.94 (3H, m), 7.15-7.21 (7H, m), 7.24-7.27 (2H, m), 7.46 (1H, s), 8.47 (1H, s).
MS (ESI) [M+H]$^+$: 541.

Example 51 Synthesis of N-(amino(((5,6-bis(4-chlorophenyl)pyridin-3-yl)methyl)amino)methylene)-3-ethoxybenzenesulfonamide

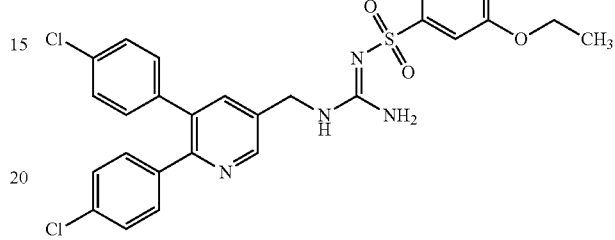

The title compound (hereinafter, referred to as the compound of Example 51) (0.011 g) was obtained in the same way as in Example 47 using 1-((5,6-bis(4-chlorophenyl)pyridin-3-yl)methyl)guanidine (0.040 g) synthesized in Reference Example 123 and 3-ethoxybenzenesulfonyl chloride (0.071 g).
$^1$H-NMR (DMSO-d$_6$) δ: 1.27 (3H, t, J=6.9 Hz), 3.99 (2H, m), 4.44 (2H, d, J=10.0 Hz), 6.90 (2H, brs), 7.01 (1H, d, J=6.9 Hz), 7.11 (2H, d, J=8.7 Hz), 7.19-7.29 (6H, m), 7.37-7.42 (4H, m), 7.67 (1H, s), 8.55 (1H, s).
MS (ESI) [M+H]$^+$: 555.

Example 52 Synthesis of N-(amino(((5,6-bis(4-chlorophenyl)pyridin-3-yl)methyl)amino)methylene)-6-cyanopyridine-3-sulfonamide

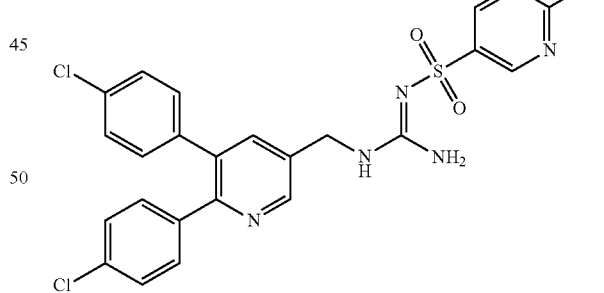

The title compound (hereinafter, referred to as the compound of Example 52) (0.019 g) was obtained in the same way as in Example 47 using 1-((5,6-bis(4-chlorophenyl)pyridin-3-yl)methyl)guanidine (0.058 g) synthesized in Reference Example 123 and 6-cyanopyridine-3-sulfonyl chloride (0.035 g).
$^1$H-NMR (CDCl$_3$) δ: 4.51 (2H, d, J=5.0 Hz), 6.19 (3H, brs), 7.06 (2H, d, J=8.6 Hz), 7.25 (4H, s), 7.30 (2H, d, J=8.2 Hz), 7.58 (1H, d, J=2.3 Hz), 7.70 (1H, d, J=8.2 Hz), 8.25 (1H, dd, J=7.9, 2.0 Hz), 8.52 (1H, s), 9.04 (1H, s).
MS (ESI) [M+H]$^+$: 537.

Example 53 Synthesis of N-(amino(((5,6-bis(4-chlorophenyl)pyridin-3-yl)methyl)amino)methylene)-1-methyl-1H-pyrazole-4-sulfonamide

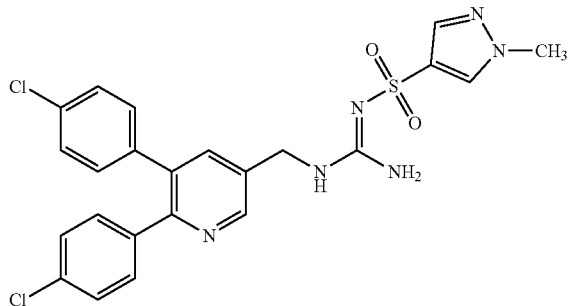 [SMILES: Cn1cc(S(=O)(=O)/N=C(\N)NCc2cnc(-c3ccc(Cl)cc3)c(-c3ccc(Cl)cc3)c2)cn1]

The title compound (hereinafter, referred to as the compound of Example 53) (0.011 g) was obtained in the same way as in Example 47 using 1-((5,6-bis(4-chlorophenyl)pyridin-3-yl)methyl)guanidine (0.050 g) synthesized in Reference Example 123 and 1-methyl-1H-pyrazole-4-sulfonyl chloride (0.027 g).

$^{1}$H-NMR (CDCl$_{3}$) δ: 3.78 (3H, s), 4.43 (2H, d, J=5.4 Hz), 6.41 (2H, brs), 6.63 (1H, brs), 7.02 (2H, dt, J=8.8, 2.3 Hz), 7.18-7.22 (4H, m), 7.23-7.25 (2H, m), 7.55 (1H, d, J=2.3 Hz), 7.59 (1H, s), 7.63 (1H, s), 8.50 (1H, d, J=2.3 Hz).

MS (ESI) [M+H]$^{+}$: 515.

Example 54 Synthesis of N-(amino(((5,6-bis(4-chlorophenyl)pyridin-3-yl)methyl)amino)methylene)-5-chlorothiophene-2-sulfonamide

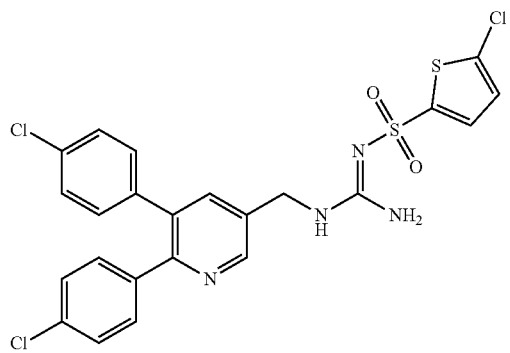 [SMILES: N/C(=N\S(=O)(=O)c1ccc(Cl)s1)NCc1cnc(-c2ccc(Cl)cc2)c(-c2ccc(Cl)cc2)c1]

The title compound (hereinafter, referred to as the compound of Example 54) (0.007 g) was obtained in the same way as in Example 47 using 1-((5,6-bis(4-chlorophenyl)pyridin-3-yl)methyl)guanidine (0.050 g) synthesized in Reference Example 123 and 5-chlorothiophene-2-sulfonyl chloride (0.032 g).

$^{1}$H-NMR (CDCl$_{3}$) δ: 4.45 (2H, s), 6.45 (1H, brs), 6.71 (1H, d, J=4.1 Hz), 7.02 (2H, d, J=8.6 Hz), 7.18-7.26 (7H, m), 7.56 (1H, s), 8.52 (1H, s).

MS (ESI) [M+H]$^{+}$: 551.

Example 55 Synthesis of N-(amino(((5,6-bis(4-chlorophenyl)pyridin-3-yl)methyl)amino)methylene)benzo[b]thiophene-2-sulfonamide

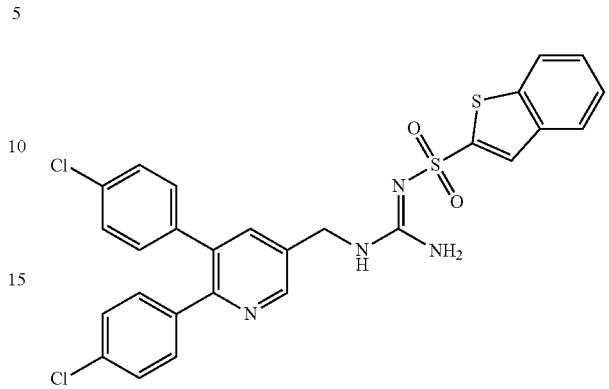

The title compound (hereinafter, referred to as the compound of Example 55) (0.032 g) was obtained in the same way as in Example 47 using 1-((5,6-bis(4-chlorophenyl)pyridin-3-yl)methyl)guanidine (0.050 g) synthesized in Reference Example 123 and 1-benzothiophene-2-sulfonyl chloride (0.063 g).

$^{1}$H-NMR (DMSO-d$_{6}$) δ: 4.47 (2H, d, J=4.1 Hz), 6.99 (2H, brs), 7.05 (2H, d, J=7.8 Hz), 7.22 (2H, d, J=8.7 Hz), 7.32-7.36 (4H, m), 7.42-7.49 (2H, m), 7.60 (1H, brs), 7.65 (1H, s), 7.80 (1H, s), 7.88 (2H, d, J=8.2 Hz), 8.57 (1H, d, J=2.3 Hz).

MS (ESI) [M+H]$^{+}$: 567.

Example 56 Synthesis of N-(amino(((5,6-bis(4-chlorophenyl)pyridin-3-yl)methyl)amino)methylene)cyclohexanesulfonamide

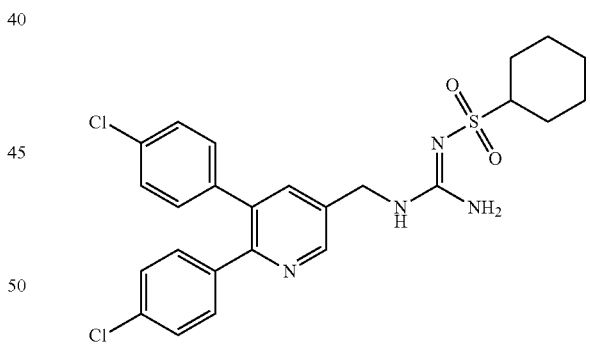

The title compound (hereinafter, referred to as the compound of Example 56) (0.046 g) was obtained in the same way as in Example 47 using 1-((5,6-bis(4-chlorophenyl)pyridin-3-yl)methyl)guanidine (0.050 g) synthesized in Reference Example 123 and cyclohexanesulfonyl chloride (0.049 g).

$^{1}$H-NMR (CDCl$_{3}$) δ: 1.01 (1H, t, J=12.6 Hz), 1.14 (2H, m), 1.31 (3H, m), 1.73 (2H, d, J=13.7 Hz), 2.05 (2H, t, J=6.2 Hz), 2.70-2.77 (1H, m), 4.45 (2H, d, J=5.5 Hz), 6.29 (2H, brs), 6.42 (1H, brs), 7.08 (2H, dt, J=8.8, 2.3 Hz), 7.20-7.23 (4H, m), 7.25-7.28 (2H, m), 7.64 (1H, d, J=1.8 Hz), 8.58 (1H, d, J=2.3 Hz).

MS (ESI) [M+H]$^{+}$: 517.

Example 57 Synthesis of N-(amino(((5,6-bis(4-chlorophenyl)pyridin-3-yl)methyl)amino)methylene)cyclopentanesulfonamide

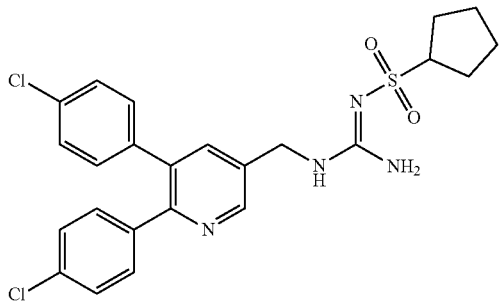 [SMILES: N/C(=N\S(=O)(=O)C1CCCC1)NCc1cnc(-c2ccc(Cl)cc2)c(-c2ccc(Cl)cc2)c1]

The title compound (hereinafter, referred to as the compound of Example 57) (0.041 g) was obtained in the same way as in Example 47 using 1-((5,6-bis(4-chlorophenyl)pyridin-3-yl)methyl)guanidine (0.050 g) synthesized in Reference Example 123 and cyclopentanesulfonyl chloride (0.045 g).

$^1$H-NMR (CDCl$_3$) δ: 1.27 (1H, m), 1.50 (1H, m), 1.64 (2H, m), 1.82-1.92 (4H, m), 3.36 (1H, m), 4.44 (2H, d, J=5.9 Hz), 6.29 (2H, brs), 6.38 (1H, brs), 7.07 (2H, dt, J=8.8, 2.2 Hz), 7.20-7.24 (4H, m), 7.27 (2H, dt, J=8.2, 2.5 Hz), 7.63 (1H, d, J=1.8 Hz), 8.57 (1H, d, J=2.3 Hz).

MS (ESI) [M+H]$^+$: 503.

Example 58 Synthesis of N-(amino(((5,6-bis(4-chlorophenyl)pyridin-3-yl)methyl)amino)methylene)cyclopropanesulfonamide

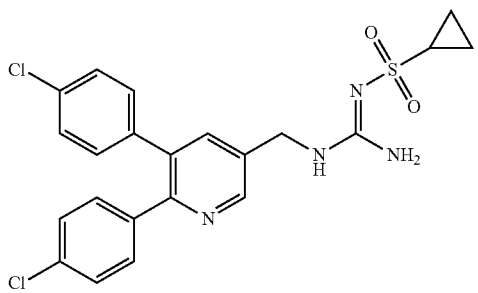 [SMILES: N/C(=N\S(=O)(=O)C1CC1)NCc1cnc(-c2ccc(Cl)cc2)c(-c2ccc(Cl)cc2)c1]

The title compound (hereinafter, referred to as the compound of Example 58) (0.025 g) was obtained in the same way as in Example 47 using 1-((5,6-bis(4-chlorophenyl)pyridin-3-yl)methyl)guanidine (0.050 g) synthesized in Reference Example 123 and cyclopropanesulfonyl chloride (0.038 g).

$^1$H-NMR (CDCl$_3$) δ: 0.82 (2H, m), 1.04 (2H, m), 2.42 (1H, m), 4.47 (2H, d, J=5.5 Hz), 6.19 (2H, brs), 6.27 (1H, brs), 7.08 (2H, dt, J=8.8, 2.2 Hz), 7.21-7.24 (4H, m), 7.24-7.28 (2H, m), 7.65 (1H, d, J=1.8 Hz), 8.58 (1H, d, J=2.3 Hz).

MS (ESI) [M+H]$^+$: 475.

Example 59 Synthesis of N-(amino(((5,6-bis(4-chlorophenyl)pyridin-3-yl)methyl)amino)methylene)-1-phenylmethanesulfonamide

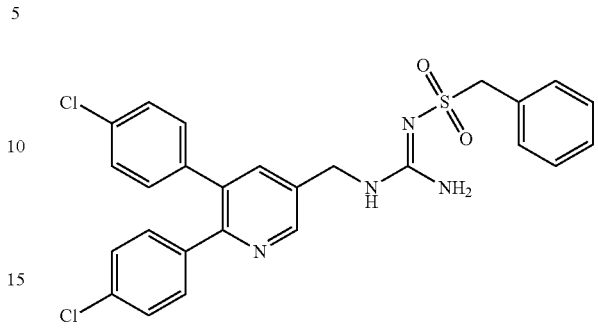

The title compound (hereinafter, referred to as the compound of Example 59) (0.014 g) was obtained in the same way as in Example 47 using 1-((5,6-bis(4-chlorophenyl)pyridin-3-yl)methyl)guanidine (0.050 g) synthesized in Reference Example 123 and benzylsulfonyl chloride (0.051 g).

$^1$H-NMR (CDCl$_3$) δ: 4.13 (2H, s), 4.27 (2H, s), 5.99 (2H, brs), 6.40 (1H, brs), 7.06 (2H, d, J=8.2 Hz), 7.17-7.23 (9H, m), 7.24-7.28 (2H, m), 7.51 (1H, s), 8.48 (1H, s).

MS (ESI) [M+H]$^+$: 525.

Example 60 Synthesis of ((2-amino-2-(((5,6-bis(4-chlorophenyl)pyridin-3-yl)methyl)amino)-1-azavinyl)sulfonyl)dimethylamine

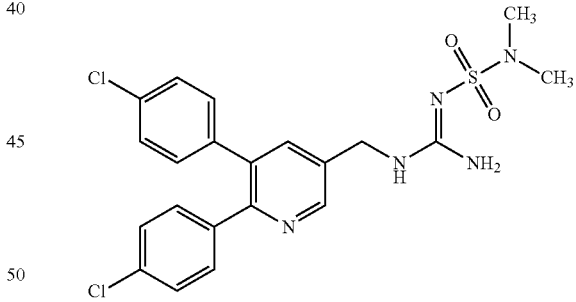

The title compound (hereinafter, referred to as the compound of Example 60) (0.006 g) was obtained in the same way as in Example 47 using 1-((5,6-bis(4-chlorophenyl)pyridin-3-yl)methyl)guanidine (0.050 g) synthesized in Reference Example 123 and dimethylsulfamoyl chloride (0.039 g).

$^1$H-NMR (CDCl$_3$) δ: 2.58 (6H, s), 4.45 (2H, d, J=5.4 Hz), 6.25 (2H, brs), 6.39 (1H, brs), 7.07 (2H, d, J=8.2 Hz), 7.19-7.27 (6H, m), 7.64 (1H, s), 8.58 (1H, s).

MS (ESI) [M+H]$^+$: 478.

Example 61 Synthesis of N-(amino(((5,6-bis(4-chlorophenyl)pyridin-3-yl)methyl)amino)methylene)thiazole-2-carboxamide

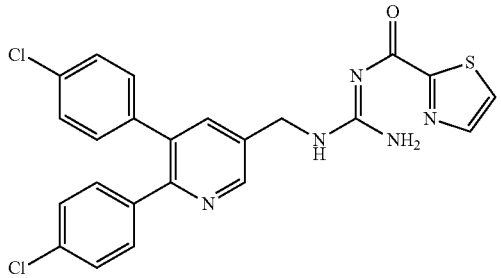 [SMILES: N/C(=N\C(=O)c1nccs1)NCc1cnc(-c2ccc(Cl)cc2)c(-c2ccc(Cl)cc2)c1]

The title compound (hereinafter, referred to as the compound of Example 61) (0.022 g) was obtained in the same way as in Example 47 using 1-((5,6-bis(4-chlorophenyl)pyridin-3-yl)methyl)guanidine (0.050 g) synthesized in Reference Example 123 and 1,3-thiazole-2-carbonyl chloride (0.042 g).

$^1$H-NMR (DMSO-$d_6$) δ: 4.59 (2H, m), 7.18 (2H, s), 7.30-7.40 (6H, m), 7.59 (1H, s), 7.81 (1H, s), 7.90 (1H, s), 8.72 (1H, s).

MS (ESI) [M+H]$^+$: 482.

Example 62 Synthesis of N-(amino(((5,6-bis(4-chlorophenyl)pyridin-3-yl)methyl)amino)methylene)-4-cyanobenzamide

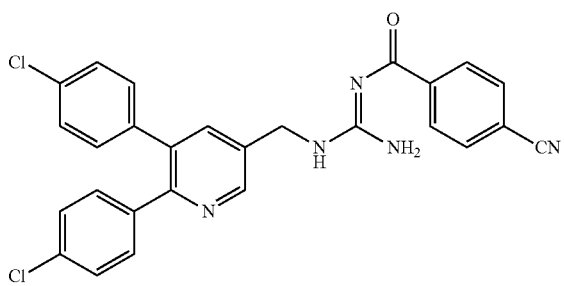 [SMILES: N#Cc1ccc(C(=O)/N=C(\N)NCc2cnc(-c3ccc(Cl)cc3)c(-c3ccc(Cl)cc3)c2)cc1]

The title compound (hereinafter, referred to as the compound of Example 62) (0.035 g) was obtained in the same way as in Example 47 using 1-((5,6-bis(4-chlorophenyl)pyridin-3-yl)methyl)guanidine (0.050 g) synthesized in Reference Example 123 and 4-cyanobenzoyl chloride (0.047 g).

$^1$H-NMR (CDCl$_3$) δ: 4.68 (2H, s), 7.08 (2H, d, J=8.6 Hz), 7.23-7.29 (6H, m), 7.68 (2H, d, J=8.2 Hz), 7.70 (1H, d, J=2.3 Hz), 8.26 (2H, d, J=8.6 Hz), 8.70 (1H, d, J=2.3 Hz).

MS (ESI) [M+H]$^+$: 500.

Example 63 Synthesis of N-(amino(((5,6-bis(4-chlorophenyl)pyridin-3-yl)methyl)amino)methylene)-2-methoxyacetamide

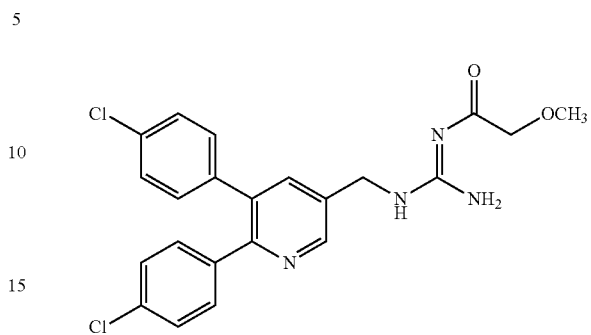

The title compound (hereinafter, referred to as the compound of Example 63) (0.018 g) was obtained in the same way as in Example 47 using 1-((5,6-bis(4-chlorophenyl)pyridin-3-yl)methyl)guanidine (0.050 g) synthesized in Reference Example 123 and methoxyacetyl chloride (0.031 g).

$^1$H-NMR (CDCl$_3$) δ: 3.38 (3H, s), 3.97 (2H, s), 4.52 (2H, s), 7.08 (2H, dt, J=8.9, 2.3 Hz), 7.22-7.28 (6H, m), 7.66 (1H, d, J=1.8 Hz), 8.62 (1H, d, J=1.8 Hz).

MS (ESI) [M+H]$^+$: 443.

Example 64 Synthesis of N-(amino(((5,6-bis(4-chlorophenyl)pyridin-3-yl)methyl)amino)methylene)butylamide

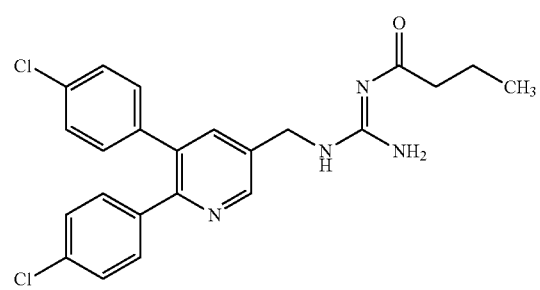

The title compound (hereinafter, referred to as the compound of Example 64) (0.035 g) was obtained in the same way as in Example 47 using 1-((5,6-bis(4-chlorophenyl)pyridin-3-yl)methyl)guanidine (0.050 g) synthesized in Reference Example 123 and butyryl chloride (0.030 g).

$^1$H-NMR (CDCl$_3$) δ: 0.92 (3H, t, J=7.2 Hz), 1.60-1.69 (2H, m), 2.33 (2H, t, J=7.5 Hz), 4.54 (2H, s), 7.08 (2H, d, J=8.2 Hz), 7.22-7.29 (6H, m), 7.67 (1H, s), 8.63 (1H, s).

MS (ESI) [M+H]$^+$: 441.

Example 65 Synthesis of N-(amino(((5,6-bis(4-chlorophenyl)pyridin-3-yl)methyl)amino)methylene)hexanamide

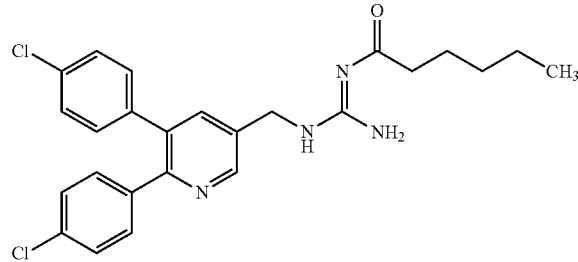 [SMILES: CCCCCC(=O)/N=C(\N)NCc1cnc(-c2ccc(Cl)cc2)c(-c2ccc(Cl)cc2)c1]

The title compound (hereinafter, referred to as the compound of Example 65) (0.038 g) was obtained in the same way as in Example 47 using 1-((5,6-bis(4-chlorophenyl)pyridin-3-yl)methyl)guanidine (0.050 g) synthesized in Reference Example 123 and hexanoyl chloride (0.038 g).

$^1$H-NMR (DMSO-$d_6$) δ: 0.86 (3H, t, J=6.9 Hz), 1.25-1.29 (4H, m), 1.56-1.60 (2H, m), 2.42 (2H, t, J=7.3 Hz), 4.70 (2H, d, J=6.4 Hz), 7.20-7.23 (2H, m), 7.28-7.32 (2H, m), 7.36-7.39 (2H, m), 7.44 (2H, dd, J=6.4, 1.8 Hz), 7.86 (1H, d, J=1.8 Hz), 8.70 (1H, d, J=1.8 Hz), 9.52 (1H, brs), 11.75 (2H, s).

MS (ESI) [M+H]$^+$: 469.

Example 66 Synthesis of N-(amino(((5,6-bis(4-chlorophenyl)pyridin-3-yl)methyl)amino)methylene)-4-fluorobenzamide

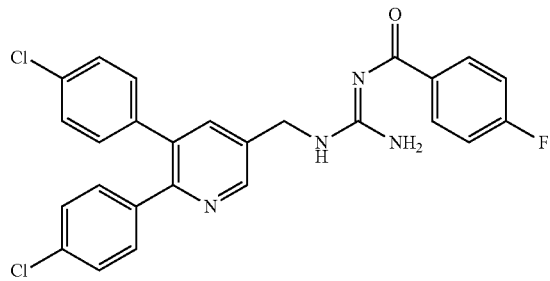 [SMILES: N/C(=N\C(=O)c1ccc(F)cc1)NCc1cnc(-c2ccc(Cl)cc2)c(-c2ccc(Cl)cc2)c1]

The title compound (hereinafter, referred to as the compound of Example 66) (0.025 g) was obtained in the same way as in Example 47 using 1-((5,6-bis(4-chlorophenyl)pyridin-3-yl)methyl)guanidine (0.050 g) synthesized in Reference Example 123 and 4-fluorobenzoyl chloride (19 μL).

$^1$H-NMR (CDCl$_3$) δ: 4.64 (2H, s), 7.01-7.08 (4H, m), 7.23-7.28 (6H, m), 7.71 (1H, d, J=2.3 Hz), 8.16-8.20 (2H, m), 8.67 (1H, d, 2.3 Hz).

MS (ESI) [M+H]$^+$: 493.

Example 67 Synthesis of N-(amino(((5,6-bis(4-chlorophenyl)pyridin-3-yl)methyl)amino)methylene)-2-fluorobenzamide

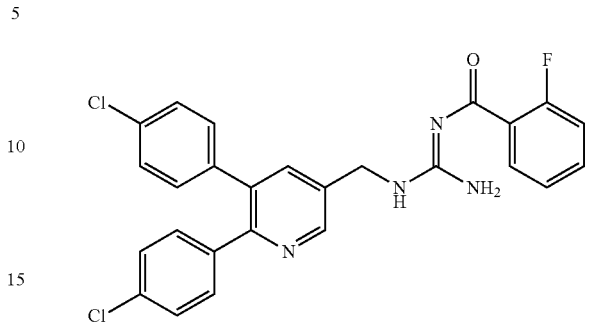

The title compound (hereinafter, referred to as the compound of Example 67) (0.028 g) was obtained in the same way as in Example 47 using 1-((5,6-bis(4-chlorophenyl)pyridin-3-yl)methyl)guanidine (0.050 g) synthesized in Reference Example 123 and 2-fluorobenzoyl chloride (19 μL).

$^1$H-NMR (CDCl$_3$) δ: 4.58 (2H, s), 7.03-7.14 (4H, m), 7.23-7.28 (6H, m), 7.38 (1H, m), 7.70 (1H, d, J=2.3 Hz), 7.92 (1H, td, J=7.7, 1.8 Hz), 8.64 (1H, d, 2.3 Hz).

MS (ESI) [M+H]$^+$: 493.

Example 68 Synthesis of N-(amino(((5,6-bis(4-chlorophenyl)pyridin-3-yl)methyl)amino)methylene)thiophene-3-carboxamide

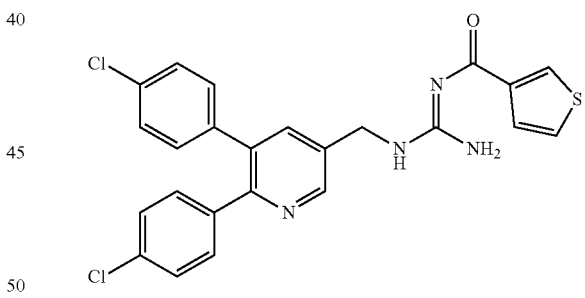

The title compound (hereinafter, referred to as the compound of Example 68) (0.020 g) was obtained in the same way as in Example 47 using 1-((5,6-bis(4-chlorophenyl)pyridin-3-yl)methyl)guanidine (0.050 g) synthesized in Reference Example 123 and thiophene-3-carbonyl chloride (0.043 g).

$^1$H-NMR (CDCl$_3$) δ: 4.61 (2H, s), 7.06 (2H, d, J=8.2 Hz), 7.22-7.28 (7H, m), 7.59 (1H, dd, J=5.0, 1.3 Hz), 7.70 (1H, d, J=2.3 Hz), 8.08 (1H, dd, J=3.0, 1, 3 Hz), 8.65 (1H, d, J=2.3 Hz).

MS (ESI) [M+H]$^+$: 481.

Example 69 Synthesis of N-(amino(((5,6-bis(4-chlorophenyl)pyridin-3-yl)methyl)amino)methylene)-4-methoxybenzamide

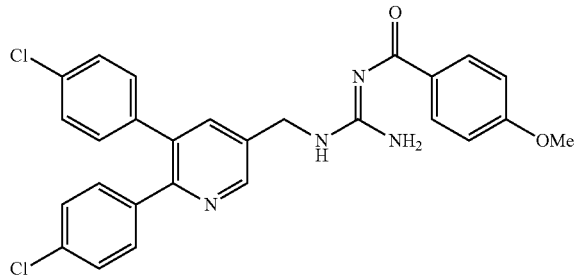 [SMILES: COc1ccc(C(=O)/N=C(\N)NCc2cnc(-c3ccc(Cl)cc3)c(-c3ccc(Cl)cc3)c2)cc1]

The title compound (hereinafter, referred to as the compound of Example 69) (0.014 g) was obtained in the same way as in Example 47 using 1-((5,6-bis(4-chlorophenyl)pyridin-3-yl)methyl)guanidine (0.050 g) synthesized in Reference Example 123 and 4-methoxybenzoyl chloride (0.046 g).

$^1$H-NMR (CDCl$_3$) δ: 3.84 (3H, s), 4.64 (2H, s), 6.88 (2H, d, J=9.1 Hz), 7.06 (2H, d, J=8.6 Hz), 7.23-7.28 (6H, m), 7.73 (1H, d, J=2.3 Hz), 8.14 (2H, d, J=9.1 Hz), 8.67 (1H, d, 2.3 Hz).

MS (ESI) [M+H]$^+$: 505.

Example 70 Synthesis of N-(amino(((5,6-bis(4-chlorophenyl)pyridin-3-yl)methyl)amino)methylene)cyclopentanecarboxamide

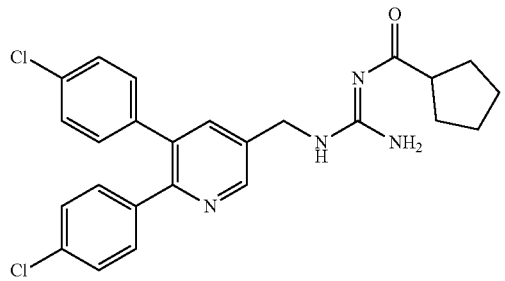 [SMILES: N/C(=N\C(=O)C1CCCC1)NCc1cnc(-c2ccc(Cl)cc2)c(-c2ccc(Cl)cc2)c1]

The title compound (hereinafter, referred to as the compound of Example 70) (0.024 g) was obtained in the same way as in Example 47 using 1-((5,6-bis(4-chlorophenyl)pyridin-3-yl)methyl)guanidine (0.050 g) synthesized in Reference Example 123 and cyclopentanecarbonyl chloride (18 μL).

$^1$H-NMR (CDCl$_3$) δ: 1.53-1.88 (8H, m), 2.68 (1H, m), 4.48 (2H, s), 7.09 (2H, d, J=8.6 Hz), 7.23-7.30 (6H, m), 7.68 (1H, d, J=2.3 Hz), 8.64 (1H, d, 2.3 Hz).

MS (ESI) [M+H]$^+$: 467.

Example 71 Synthesis of N-(amino(((5,6-bis(4-chlorophenyl)pyridin-3-yl)methyl)amino)methylene)cyclopropanecarboxamide

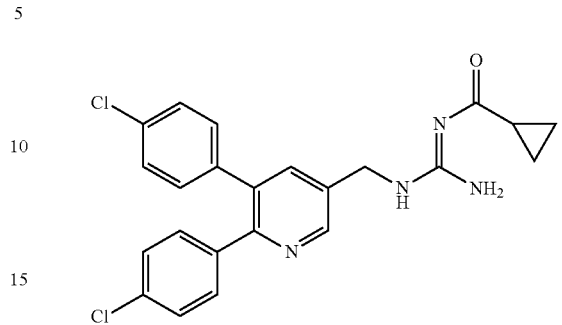

The title compound (hereinafter, referred to as the compound of Example 71) (0.026 g) was obtained in the same way as in Example 47 using 1-((5,6-bis(4-chlorophenyl)pyridin-3-yl)methyl)guanidine (0.050 g) synthesized in Reference Example 123 and cyclopropanecarbonyl chloride (15 μL).

$^1$H-NMR (CDCl$_3$) δ: 0.75 (2H, m), 0.94 (2H, m), 1.63 (1H, m), 4.50 (2H, s), 7.09 (2H, dt, J=8.9, 2.3 Hz), 7.23-7.30 (6H, m), 7.67 (1H, d, J=2.3 Hz), 8.63 (1H, d, 2.3 Hz).

MS (ESI) [M+H]$^+$: 439.

Example 72 Synthesis of N-(amino(((5,6-bis(4-chlorophenyl)pyridin-3-yl)methyl)amino)methylene)cyclohexanecarboxamide

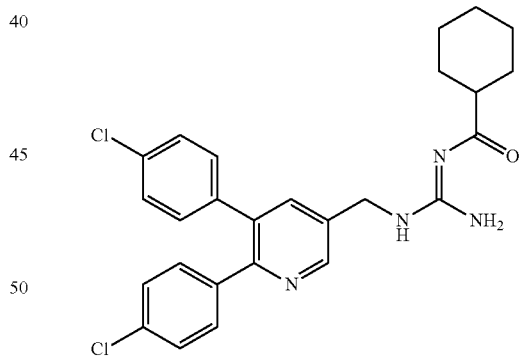

The title compound (hereinafter, referred to as the compound of Example 72) (0.038 g) was obtained in the same way as in Example 47 using 1-((5,6-bis(4-chlorophenyl)pyridin-3-yl)methyl)guanidine (0.050 g) synthesized in Reference Example 123 and cyclohexanecarbonyl chloride (18 μL).

$^1$H-NMR (CDCl$_3$) δ: 1.18-2.36 (11H, m), 4.50 (2H, s), 7.08-7.30 (8H, m), 7.69 (1H, d, J=2.3 Hz), 8.64 (1H, d, J=2.3 Hz).

MS (ESI) [M+H]$^+$: 481.

Example 73 Synthesis of N-(amino(((5,6-bis(4-chlorophenyl)pyridin-3-yl)methyl)amino)methylene)cyclohexanecarboxamide Hydrochloride

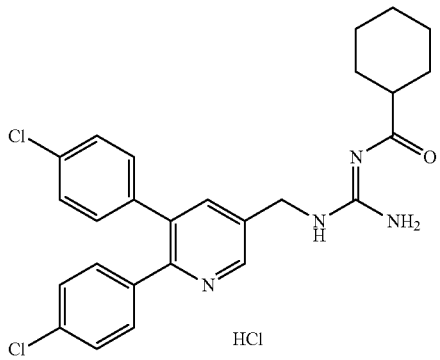 [SMILES: N/C(=N\C(=O)C1CCCCC1)NCc1cnc(-c2ccc(Cl)cc2)c(-c2ccc(Cl)cc2)c1 ; Cl]

To a solution of the compound of Example 72 (0.038 g) in methanol (1 mL), a solution of 10% by weight of hydrogen chloride in methanol (0.3 mL) was added, and then, the mixture was concentrated under reduced pressure. The obtained crude product was recrystallized (ethanol/diethyl ether) to obtain the title compound (hereinafter, referred to as the compound of Example 73) (0.028 g) as a white solid.

$^1$H-NMR (CD$_3$OD) δ: 1.16-1.99 (10H, m), 2.40-2.44 (1H, m), 4.85 (2H, s), 7.23-7.25 (2H, m), 7.36-7.46 (6H, m), 8.36 (1H, d, J=2.3 Hz), 8.83 (1H, d, J=2.3 Hz).

MS (ESI) [M+H]$^+$: 481.

Example 74 Synthesis of N-(amino(((5,6-bis(4-chlorophenyl)pyridin-3-yl)methyl)amino)methylene)-3-phenylpropanamide

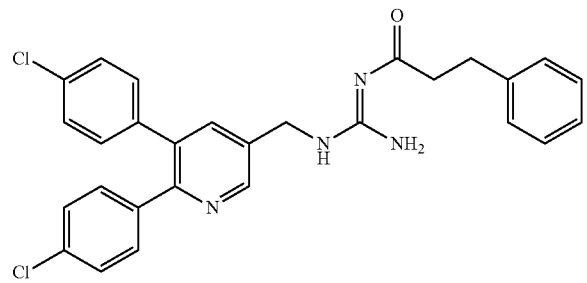 [SMILES: N/C(=N\C(=O)CCc1ccccc1)NCc1cnc(-c2ccc(Cl)cc2)c(-c2ccc(Cl)cc2)c1]

The title compound (hereinafter, referred to as the compound of Example 74) (0.018 g) was obtained in the same way as in Example 47 using 1-((5,6-bis(4-chlorophenyl)pyridin-3-yl)methyl)guanidine (0.050 g) synthesized in Reference Example 123 and 3-phenylpropionyl chloride (36 μL).

$^1$H-NMR (CDCl$_3$) δ: 2.65 (2H, t, J=7.9 Hz), 2.95 (2H, t, J=7.9 Hz), 4.50 (2H, s), 7.08 (2H, d, J=8.6 Hz), 7.15-7.30 (11H, m), 7.66 (1H, d, J=2.3 Hz), 8.63 (1H, d, 2.3 Hz).

MS (ESI) [M+H]$^+$: 503.

Example 75 Synthesis of N-(amino(((5,6-bis(4-chlorophenyl)pyridin-3-yl)methyl)amino)methylene)-2-phenylacetamide

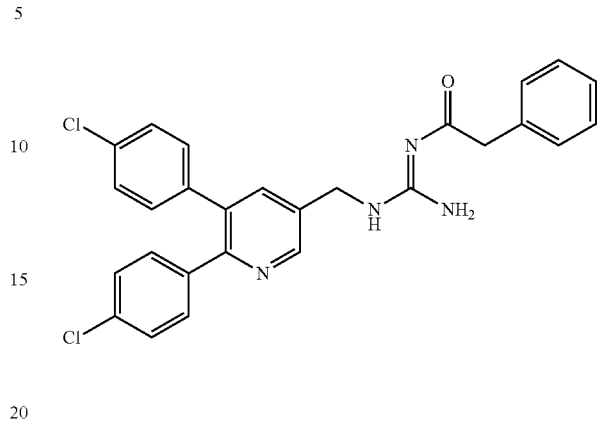

The title compound (hereinafter, referred to as the compound of Example 75) (0.009 g) was obtained in the same way as in Example 47 using 1-((5,6-bis(4-chlorophenyl)pyridin-3-yl)methyl)guanidine (0.050 g) synthesized in Reference Example 123 and phenylacetyl chloride (36 μL).

$^1$H-NMR (CDCl$_3$) δ: 3.64 (2H, s), 4.47 (2H, s), 7.07 (2H, d, J=8.6 Hz), 7.20-7.30 (11H, m), 7.62 (1H, d, J=2.3 Hz), 8.61 (1H, d, 2.3 Hz).

MS (ESI) [M+H]$^+$: 489.

Example 76 Synthesis of N-(amino(((5,6-bis(4-chlorophenyl)pyridin-3-yl)methyl)amino)methylene)-4-chlorobenzamide

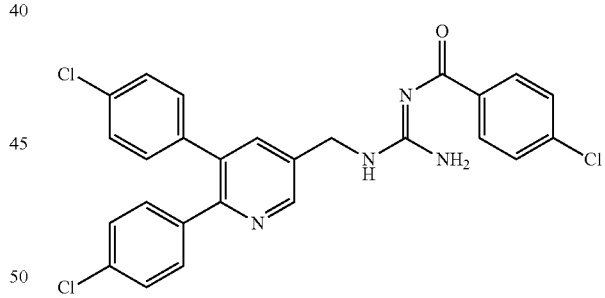

The title compound (hereinafter, referred to as the compound of Example 76) (0.011 g) was obtained in the same way as in Example 47 using 1-((5,6-bis(4-chlorophenyl)pyridin-3-yl)methyl)guanidine (0.050 g) synthesized in Reference Example 123 and 4-chlorobenzoyl chloride (0.049 g).

$^1$H-NMR (CDCl$_3$) δ: 4.61 (2H, s), 7.04 (2H, d, J=8.2 Hz), 7.23-7.25 (6H, m), 7.34 (2H, m), 7.68 (1H, d, J=2.1 Hz), 8.09 (2H, m), 8.64 (1H, d, J=2.1 Hz).

MS (ESI) [M+H]$^+$: 509.

Example 77 Synthesis of N-(amino(((5,6-bis(4-chlorophenyl)pyridin-3-yl)methyl)amino)methylene)-4-trifluoromethylbenzamide

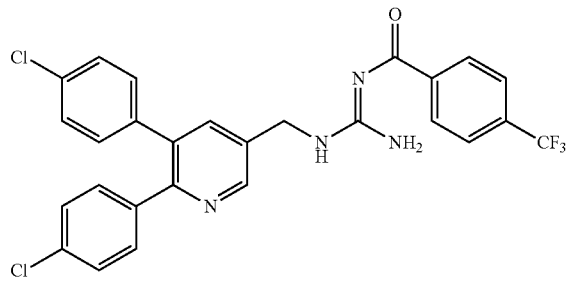 [SMILES: N/C(=N\C(=O)c1ccc(C(F)(F)F)cc1)NCc1cnc(-c2ccc(Cl)cc2)c(-c2ccc(Cl)cc2)c1]

The title compound (hereinafter, referred to as the compound of Example 77) (0.027 g) was obtained in the same way as in Example 47 using 1-((5,6-bis(4-chlorophenyl)pyridin-3-yl)methyl)guanidine (0.050 g) synthesized in Reference Example 123 and 4-trifluoromethylbenzoyl chloride (0.05 g).

$^1$H-NMR (CDCl$_3$) δ: 4.59 (2H, s), 7.02 (2H, d, J=8.7 Hz), 7.22-7.24 (6H, m), 7.61 (2H, d, J=8.2 Hz), 7.67 (1H, s), 8.24 (2H, d, J=7.8 Hz), 8.61 (1H, d, J=2.3 Hz).

MS (ESI) [M+H]$^+$: 543.

Example 78 Synthesis of N-(amino(((5,6-bis(4-chlorophenyl)pyridin-3-yl)methyl)amino)methylene) furan-2-carboxamide

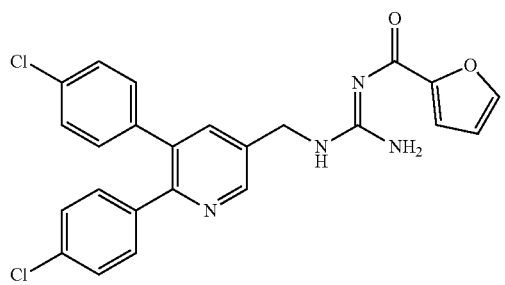 [SMILES: N/C(=N\C(=O)c1ccco1)NCc1cnc(-c2ccc(Cl)cc2)c(-c2ccc(Cl)cc2)c1]

The title compound (hereinafter, referred to as the compound of Example 78) (0.022 g) was obtained in the same way as in Example 47 using 1-((5,6-bis(4-chlorophenyl)pyridin-3-yl)methyl)guanidine (0.050 g) synthesized in Reference Example 123 and 2-furoyl chloride (0.037 g).

$^1$H-NMR (CDCl$_3$) δ: 4.57 (2H, s), 6.41 (1H, dd, J=3.2, 1.8 Hz), 7.03 (2H, d, J=8.7 Hz), 7.08 (1H, m), 7.21-7.24 (6H, m), 7.39 (1H, s), 7.68 (1H, s), 8.61 (1H, d, J=2.3 Hz).

MS (ESI) [M+H]$^+$: 465.

Example 79 Synthesis of 3-(amino(((5,6-bis(4-chlorophenyl)pyridin-3-yl)methyl)amino)methylene)-1,1-dimethylurea

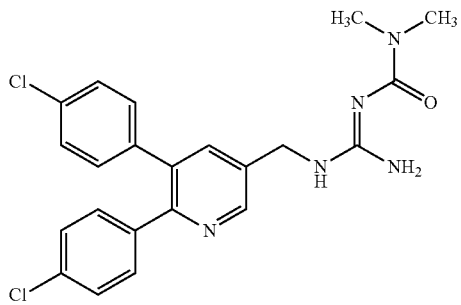 [SMILES: CN(C)C(=O)/N=C(\N)NCc1cnc(-c2ccc(Cl)cc2)c(-c2ccc(Cl)cc2)c1]

1-((5,6-Bis(4-chlorophenyl)pyridin-3-yl)methyl)guanidine (0.050 g) synthesized in Reference Example 123 was dissolved in dichloromethane (1.4 mL). To the solution, triethylamine (0.04 mL) and dimethylcarbamoyl chloride (0.02 g) were then added. The mixture was stirred at room temperature for 6 hours, and then, the reaction solution was concentrated under reduced pressure. The obtained crude product was purified by silica gel column chromatography (chloroform/methanol) to obtain the title compound (hereinafter, referred to as the compound of Example 79) (0.020 g).

$^1$H-NMR (CDCl$_3$) δ: 2.92 (3H, s), 3.04 (3H, s), 4.54 (2H, s), 7.07-7.10 (2H, m), 7.22-7.29 (6H, m), 7.67 (1H, d, J=1.8 Hz), 8.63 (1H, d, J=1.8 Hz).

MS (ESI) [M+H]$^+$: 442.

Example 80 Synthesis of 1-((5,6-bis(4-chlorophenyl)pyridin-3-yl)methyl)-2-(ethoxycarbonyl)guanidine

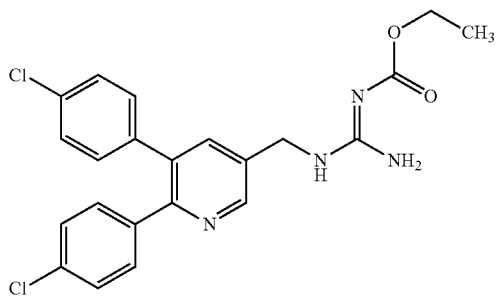 [SMILES: CCOC(=O)/N=C(\N)NCc1cnc(-c2ccc(Cl)cc2)c(-c2ccc(Cl)cc2)c1]

1-((5,6-Bis(4-chlorophenyl)pyridin-3-yl)methyl)guanidine (0.030 g) synthesized in Reference Example 123 was dissolved in dichloromethane (1.0 mL). To the solution, triethylamine (0.020 mL) and ethyl chloroformate (0.010 g) were then added at 0° C. The mixture was stirred at 0° C. for 1 hour, and then, the reaction mixture was concentrated under reduced pressure. The obtained crude product was purified by silica gel column chromatography (chloroform/methanol) to obtain the title compound (hereinafter, referred to as the compound of Example 80) (0.016 g).

$^1$H-NMR (CDCl$_3$) δ: 1.20 (3H, t, J=7.2 Hz), 4.06 (2H, q, J=7.2 Hz), 4.55 (2H, s), 7.07-7.09 (2H, m), 7.23-7.30 (6H, m), 7.67 (1H, d, J=2.3 Hz), 8.64 (1H, d, J=2.3 Hz).

MS (ESI) [M+H]$^+$: 443.

Example 81 Synthesis of 1-((5,6-bis(4-chlorophenyl)pyridin-3-yl)methyl)-2-(ethoxycarbonyl)guanidine Hydrochloride

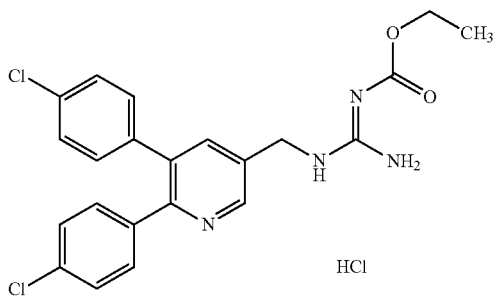 [SMILES: CCOC(=O)/N=C(\N)NCc1cnc(-c2ccc(Cl)cc2)c(-c2ccc(Cl)cc2)c1 ; Cl]

The title compound (hereinafter, referred to as the compound of Example 81) (0.014 g) was obtained as a white solid in the same way as in Example 73 using the compound of Example 80 (0.016 g).

$^1$H-NMR (CD$_3$OD) δ: 1.34 (3H, t, J=7.2 Hz), 4.33 (2H, q, J=7.2 Hz), 4.84 (2H, s), 7.23-7.24 (2H, m), 7.35-7.44 (6H, m), 8.30 (1H, s), 8.79 (1H, s).

MS (ESI) [M+H]$^+$: 443.

Example 82 Synthesis of N-(amino(((5,6-bis(4-chlorophenyl)pyridin-3-yl)methyl)amino)methylene)picolinamide

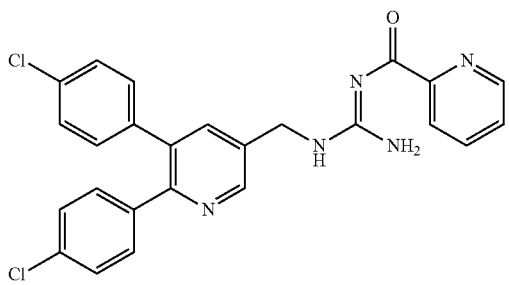 [SMILES: N/C(=N\C(=O)c1ccccn1)NCc1cnc(-c2ccc(Cl)cc2)c(-c2ccc(Cl)cc2)c1]

1-((5,6-Bis(4-chlorophenyl)pyridin-3-yl)methyl)guanidine (0.050 g) synthesized in Reference Example 123, picolinic acid (0.033 g) and COMU (0.12 g) were dissolved in tetrahydrofuran (1.0 mL). To the solution, N,N-diisopropylethylamine (0.07 mL) was then added, and the mixture was stirred for 3 hours. A 1 mol/L aqueous sodium hydroxide solution (0.5 mL) was added to the reaction mixture, and the mixture was stirred for 4 hours. Water was added to the reaction mixture, followed by extraction with ethyl acetate. The organic layer was washed with saturated saline, dried over anhydrous sodium sulfate, and then concentrated under reduced pressure. The obtained crude product was purified by silica gel column chromatography (chloroform/methanol) to obtain the title compound (hereinafter, referred to as the compound of Example 82) (0.023 g).

$^1$H-NMR (CDCl$_3$) δ: 4.57 (2H, s), 7.08 (2H, d, J=8.2 Hz), 7.22-7.28 (6H, m), 7.41 (1H, m), 7.74 (1H, d, J=2.1 Hz), 7.82 (1H, m), 8.21 (1H, d, J=7.8 Hz), 8.63 (1H, d, J=4.1 Hz), 8.69 (1H, d, J=2.1 Hz).

MS (ESI) [M+H]: 476.

Example 83 Synthesis of N-(amino(((5,6-bis(4-chlorophenyl)pyridin-3-yl)methyl)amino)methylene)thiazole-4-carboxamide

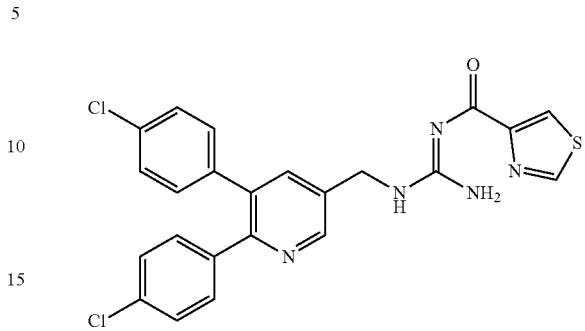

The title compound (hereinafter, referred to as the compound of Example 83) (0.013 g) was obtained in the same way as in Example 82 using 1-((5,6-bis(4-chlorophenyl)pyridin-3-yl)methyl)guanidine (0.050 g) synthesized in Reference Example 123 and thiazole-4-carboxylic acid (0.035 g).

$^1$H-NMR (DMSO-d$_6$) δ: 4.64 (2H, brs), 7.17 (2H, brs), 7.28 (2H, d, J=8.2 Hz), 7.34-7.41 (5H, m), 7.92 (1H, brs), 8.72 (1H, s), 9.01 (1H, d, 1.8 Hz).

MS (ESI) [M+H]$^+$: 482.

Example 84 Synthesis of N-(amino(((5,6-bis(4-chlorophenyl)pyridin-3-yl)methyl)amino)methylene)-3,3,3-trifluoropropanamide

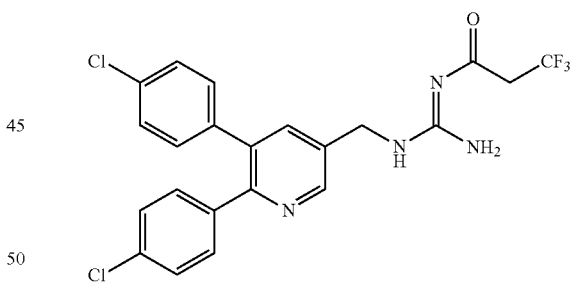

The title compound (hereinafter, referred to as the compound of Example 84) (0.003 g) was obtained in the same way as in Example 82 using 1-((5,6-bis(4-chlorophenyl)pyridin-3-yl)methyl)guanidine (0.050 g) synthesized in Reference Example 123 and 3,3,3-trifluoropropionic acid (24 µL).

$^1$H-NMR (CDCl$_3$) δ: 3.15 (2H, q, J=10.8 Hz), 4.55 (2H, s), 7.08-7.11 (2H, m), 7.24-7.31 (6H, m), 7.66 (1H, d, J=2.3 Hz), 8.64 (1H, d, J=2.3 Hz).

MS (ESI) [M+H]$^+$: 481.

Example 85 Synthesis of N-(amino(((5,6-bis(4-chlorophenyl)pyridin-3-yl)methyl)amino)methylene)-4,4-difluorocyclohexanecarboxamide

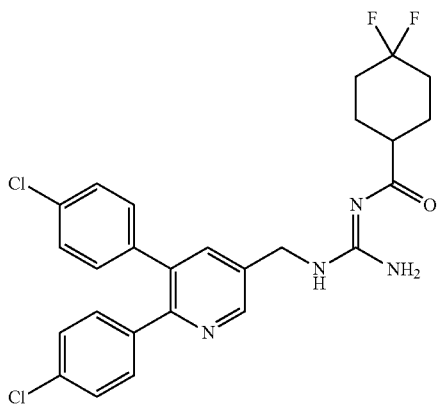 [SMILES: N/C(=N\C(=O)C1CCC(F)(F)CC1)NCc1cnc(-c2ccc(Cl)cc2)c(-c2ccc(Cl)cc2)c1]

The title compound (hereinafter, referred to as the compound of Example 85) (0.023 g) was obtained in the same way as in Example 82 using 1-((5,6-bis(4-chlorophenyl)pyridin-3-yl)methyl)guanidine (0.050 g) synthesized in Reference Example 123 and 4,4-difluorocyclohexanecarbonyl chloride (18 µL).

$^1$H-NMR (CDCl$_3$) δ: 1.61-2.29 (9H, m), 4.54 (2H, s), 7.08-7.10 (2H, m), 7.23-7.30 (6H, m), 7.67 (1H, d, J=2.3 Hz), 8.64 (1H, d, J=2.3 Hz).

MS (ESI) [M+H]$^+$: 517.

Example 86 Synthesis of N-(amino(((5,6-bis(4-chlorophenyl)pyridin-3-yl)methyl)amino)methylene)-2-methyl-2-phenylpropanamide

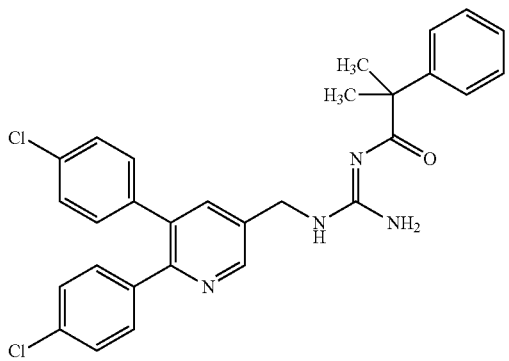 [SMILES: CC(C)(C(=O)/N=C(\N)NCc1cnc(-c2ccc(Cl)cc2)c(-c2ccc(Cl)cc2)c1)c1ccccc1]

The title compound (hereinafter, referred to as the compound of Example 86) (0.016 g) was obtained in the same way as in Example 82 using 1-((5,6-bis(4-chlorophenyl)pyridin-3-yl)methyl)guanidine (0.050 g) synthesized in Reference Example 123 and 2-phenylisobutyric acid (0.022 g).

$^1$H-NMR (CDCl$_3$) δ: 1.55 (6H, s), 4.41 (2H, s), 7.06 (2H, d, J=8.7 Hz), 7.15 (1H, t, J=7.3 Hz), 7.23-7.30 (8H, m), 7.36 (2H, m), 7.58 (1H, d, J=1.8 Hz), 8.57 (1H, d, J=1.8 Hz).

MS (ESI) [M+H]$^+$: 517.

Reference Example 124 Synthesis of 1,2-bis(4-chlorophenyl)ethanone

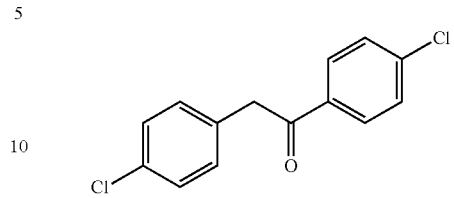

Aluminum chloride (8.0 g) was suspended in chlorobenzene (25 mL). To the suspension, 4-chlorophenylacetic acid chloride (7.0 mL) was then added at 0° C. The mixture was stirred at 50° C. for 5 hours, and then, the reaction mixture was cooled to room temperature and poured to crushed ice. The organic layer was washed with 2 mol/L hydrochloric acid, a saturated aqueous solution of sodium bicarbonate and saturated saline, dried over sodium sulfate, and then concentrated under reduced pressure. The obtained crude product was washed with n-hexane to obtain the title compound (11.4 g).

$^1$H-NMR (DMSO-d$_6$) δ: 4.43 (2H, m), 7.27-7.29 (2H, m), 7.37-7.39 (2H, m), 7.61-7.63 (2H, m), 8.01-8.07 (2H, m).

Reference Example 125 Synthesis of 1,2-bis(4-chlorophenyl)-3-(dimethylamino)prop-2-en-1-one

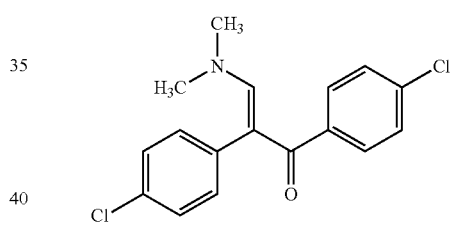

1,2-Bis(4-chlorophenyl)ethanone (1.00 g) synthesized in Reference Example 124 was dissolved in DMF (12 mL). To the solution, N,N-dimethylformamide dimethyl acetal (2.0 mL) was then added, and the mixture was stirred at 100° C. for 12 hours. The reaction mixture was cooled to room temperature and then concentrated under reduced pressure, and the obtained crude product was used directly in the next reaction without being purified.

Reference Example 126 Synthesis of (4,5-bis(4-chlorophenyl)pyrimidin-2-yl)ethanamine

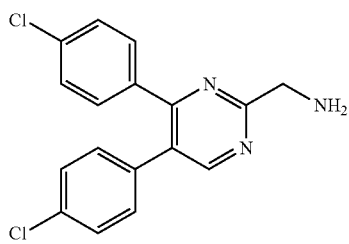 [SMILES: NCc1ncc(-c2ccc(Cl)cc2)c(-c2ccc(Cl)cc2)n1]

1,2-Bis(4-chlorophenyl)-3-(dimethylamino)prop-2-en-1-one (1.3 g) synthesized in Reference Example 125 was dissolved in ethanol (20 mL). To the solution, 2-aminoacetamidine dihydrobromide (1.1 g) and sodium ethoxide (1.4 g) were then added, and the mixture was stirred at 80° C. for 4 hours. The reaction mixture was cooled to room temperature and then filtered, and the filtrate was concentrated. Diethyl ether was added to the residue, followed by extraction with 1 mol/L hydrochloric acid. The aqueous layer was neutralized with a 1 mol/L aqueous sodium hydroxide solution, followed by extraction with ethyl acetate. The organic layer was washed with saturated saline, dried over sodium sulfate, and then concentrated under reduced pressure. The crude product was purified by silica gel column chromatography (aminesilica, n-hexane/ethyl acetate) to obtain the title compound (0.17 g).

$^1$H-NMR (CDCl$_3$) δ: 4.21 (2H, s), 7.12-7.14 (2H, m), 7.28-7.41 (6H, m), 8.67 (18H, s).

MS (ESI) [M+H]$^+$: 330.

Reference Example 127 Synthesis of 2-benzenesulfonyl-3-((4,5-bis(4-chlorophenyl)pyrimidin-2-yl)methyl)-1-(tert-butoxycarbonyl)guanidine

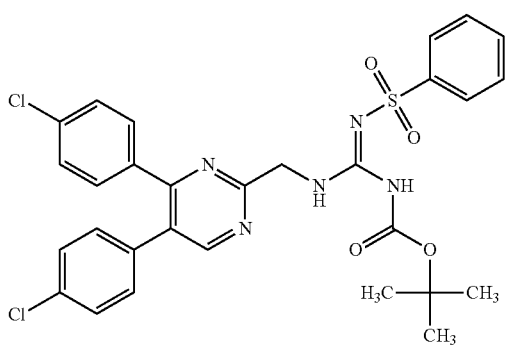

The title compound (0.060 g) was obtained in the same way as in the guanidination reaction of Reference Example 52 using (4,5-bis(4-chlorophenyl)pyrimidin-2-yl)ethanamine (0.040 g) synthesized in Reference Example 126.

$^1$H-NMR (CDCl$_3$) δ: 1.56 (9H, s), 4.85 (2H, d, J=4.5 Hz), 7.13-7.15 (2H, m), 7.26-7.28 (2H, m), 7.36-7.38 (2H, m), 7.43-7.48 (5H, m), 7.91-7.93 (2H, m), 8.66 (1H, s), 9.84 (1H, s), 10.01 (1H, 2).

Example 87 Synthesis of N-(amino(((4,5-bis(4-chlorophenyl)pyrimidin-2-yl)methyl)amino)methylene)benzenesulfonamide

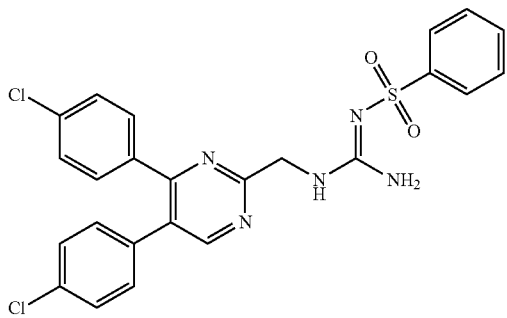

The title compound (hereinafter, referred to as the compound of Example 87) (0.036 g) was obtained in the same way as in Example 1 using 2-benzenesulfonyl-3-((4,5-bis(4-chlorophenyl)pyrimidin-2-yl)methyl)-1-(tert-butoxycarbonyl)guanidine (0.050 g) synthesized in Reference Example 127.

$^1$H-NMR (CDCl$_3$) δ: 4.69 (2H, s), 6.54 (1H, s), 7.10-7.13 (2H, m), 7.33-7.42 (9H, m), 7.90-7.93 (2H, m), 8.64 (1H, s).

MS (ESI) [M+H]$^+$: 512.

Reference Example 128 Synthesis of 5,6-bis(4-chlorophenyl)-2-oxo-1,2-dihydropyridine-3-carbonitrile

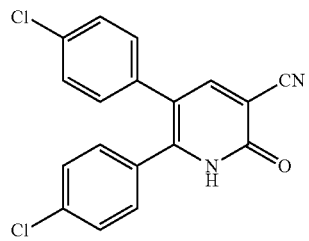 [SMILES: N#Cc1cc(-c2ccc(Cl)cc2)c(-c2ccc(Cl)cc2)[nH]c1=O]

Sodium hydride (55% by weight in mineral oil, 1.7 g) was suspended in DMF (20 mL). To the suspension, a solution of 1,2-bis(4-chlorophenyl)-3-(dimethylamino)prop-2-en-1-one (5.5 g) synthesized in Reference Example 125 and 2-cyanoacetamide (1.6 g) in methanol (1.5 mL)/DMF (40 mL) was then added. The mixture was stirred at 95° C. for 2.5 hours, and then, the reaction mixture was cooled to room temperature. An aqueous solution of 10% by weight of citric acid was added thereto. The precipitated solid was slurry-washed with diethyl ether to obtain the title compound (4.1 g).

$^1$H-NMR (DMSO-d$_6$) δ: 7.08 (2H, d, J=8.2 Hz), 7.28 (2H, dd, J=8.6, 0.9 Hz), 7.33 (2H, dd, J=8.6, 0.9 Hz), 7.43 (2H, d, J=8.6 Hz), 8.27 (1H, s).

MS (ESI) [M+H]$^+$: 341.

Reference Example 129 Synthesis of 5,6-bis(4-chlorophenyl)-2-methoxynicotinonitrile

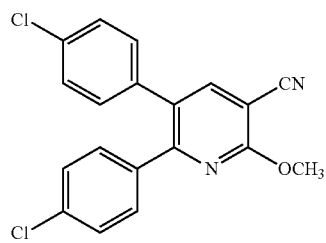 [SMILES: COc1nc(-c2ccc(Cl)cc2)c(-c2ccc(Cl)cc2)cc1C#N]

5,6-Bis(4-chlorophenyl)-2-oxo-1,2-dihydropyridine-3-carbonitrile (0.50 g) synthesized in Reference Example 128 and cesium carbonate (0.62 g) were suspended in DMF (10 mL). To the suspension, methyl iodide (0.12 mL) was then added. The mixture was stirred at 60° C. for 2.5 hours, and then, the reaction mixture was cooled to room temperature, and water was added thereto, followed by extraction with toluene. The organic layer was washed with saturated saline, dried over anhydrous sodium sulfate, and then concentrated

Reference Example 130 Synthesis of 2-chloro-5,6-bis(4-chlorophenyl)nicotinonitrile

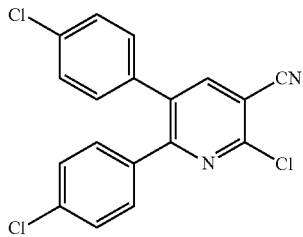 [SMILES: N#Cc1cc(-c2ccc(Cl)cc2)c(-c2ccc(Cl)cc2)nc1Cl]

5,6-Bis(4-chlorophenyl)-2-oxo-1,2-dihydropyridine-3-carbonitrile (0.50 g) synthesized in Reference Example 128 was suspended in phosphorus oxychloride (5.0 mL), and the suspension was stirred at 120° C. for 2 hours. The reaction mixture was cooled to room temperature. Then, excess phosphorus oxychloride was distilled off under reduced pressure, and water was added to the residue, followed by extraction with chloroform. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (0.073 g).

$^1$H-NMR (CDCl$_3$) δ: 7.09-7.11 (2H, m), 7.26-7.36 (6H, m), 7.97 (1H, s).

Reference Example 131 Synthesis of 5,6-bis(4-chlorophenyl)-3-cyanopyridin-2-yl trifluoromethanesulfonate

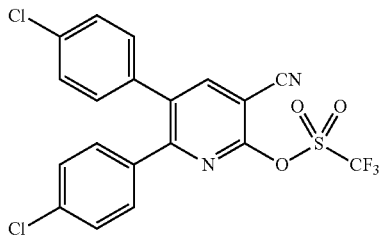 [SMILES: N#Cc1cc(-c2ccc(Cl)cc2)c(-c2ccc(Cl)cc2)nc1OS(=O)(=O)C(F)(F)F]

5,6-Bis(4-chlorophenyl)-2-oxo-1,2-dihydropyridine-3-carbonitrile (0.20 g) synthesized in Reference Example 128 was suspended in dichloromethane (2.0 mL). To the suspension, pyridine (0.24 mL) and trifluoromethanesulfonic anhydride (0.15 mL) were added, and the mixture was stirred for 24 hours. Water was added to the reaction mixture, followed by extraction with ethyl acetate. The organic layer was washed with 1 mol/L hydrochloric acid, a saturated aqueous solution of sodium bicarbonate and saturated saline, dried over anhydrous sodium sulfate, and then concentrated under reduced pressure. The obtained crude product was purified by silica gel column chromatography (n-hexane/ethyl acetate) to obtain the title compound (0.24 g).

$^1$H-NMR (CDCl$_3$) δ: 7.12-7.14 (2H, m), 7.29-7.33 (4H, m), 7.38 (2H, d, J=8.7 Hz), 8.09 (1H, s).

Reference Example 132 Synthesis of 5,6-bis(4-chlorophenyl)-2-fluoronicotinonitrile

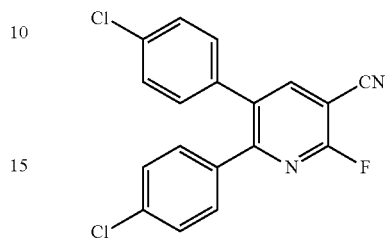

2-Chloro-5,6-bis(4-chlorophenyl)nicotinonitrile (0.050 g) synthesized in Reference Example 130 was suspended in DMSO (1.0 mL). To the suspension, potassium fluoride (0.020 g) was added, and the mixture was stirred at 140° C. for 10 minutes under microwave irradiation. The reaction mixture was cooled to room temperature, and then, water was added thereto, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (0.040 g).

$^1$H-NMR (CDCl$_3$) δ: 7.09-7.11 (2H, m), 7.25-7.36 (6H, m), 8.03 (1H, d, J=8.2 Hz).

Reference Example 133 Synthesis of 5,6-bis(4-chlorophenyl)-2-methylnicotinonitrile

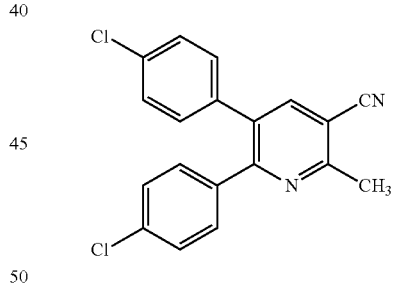

5,6-Bis(4-chlorophenyl)-3-cyanopyridin-2-yl trifluoromethanesulfonate (0.14 g) synthesized in Reference Example 131 was dissolved in 1,4-dioxane (1.5 mL). To the solution, potassium carbonate (0.079 g), tetrakistriphenylphosphinepalladium(0) (0.033 g) and trimethylboroxin (0.040 mL) were added, and the mixture was stirred at 80° C. for 12 hours. The reaction mixture was cooled to room temperature, and then, water was added thereto, followed by extraction with ethyl acetate. The organic layer was washed with saturated saline, dried over anhydrous sodium sulfate, and then concentrated under reduced pressure. The obtained crude product was purified by silica gel column chromatography (n-hexane/ethyl acetate) to obtain the title compound (0.025 g).

$^1$H-NMR (CDCl$_3$) δ: 2.86 (3H, s), 7.07-7.09 (2H, m), 7.25-7.32 (6H, m), 7.88 (1H, s).

---

(preceding text from column 1 top:)

under reduced pressure. The obtained crude product was purified by silica gel column chromatography (n-hexane/ethyl acetate) to obtain the title compound (0.14 g).

$^1$H-NMR (CDCl$_3$) δ: 4.14 (3H, s), 7.05-7.08 (2H, m), 7.25-7.34 (6H, m), 7.87 (1H, s).

Reference Example 134 Synthesis of (5,6-bis(4-chlorophenyl)-2-methoxypyridin-3-yl)methanamine

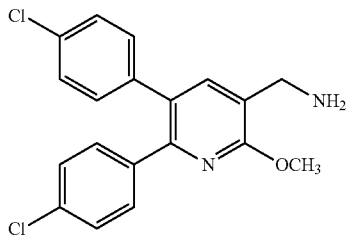 [SMILES: COc1nc(-c2ccc(Cl)cc2)c(-c2ccc(Cl)cc2)cc1CN]

5,6-Bis(4-chlorophenyl)-2-methoxynicotinonitrile (0.14 g) synthesized in Reference Example 129 was suspended in methanol (4 mL). To the suspension, cobalt(II) chloride (0.10 g) and sodium borohydride (0.36 g) were then added. The mixture was stirred at room temperature for 4.5 hours, and then, the reaction mixture was filtered through celite. The filtrate was concentrated under reduced pressure and diluted with ethyl acetate. The organic layer was washed with water and saturated saline, dried over anhydrous sodium sulfate, and then concentrated under reduced pressure to obtain the title compound (0.078 g).

$^1$H-NMR (CDCl$_3$) δ: 3.87 (2H, s), 4.05 (3H, s), 7.05-7.09 (2H, m), 7.20-7.33 (6H, m), 7.51 (1H, s).

Reference Example 135 Synthesis of (5,6-bis(4-chlorophenyl)-2-fluoropyridin-3-yl)methanamine

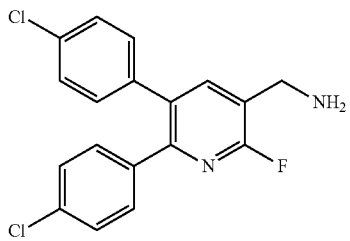 [SMILES: NCc1cc(-c2ccc(Cl)cc2)c(-c2ccc(Cl)cc2)nc1F]

The title compound (0.040 g) was obtained in the same way as in Reference Example 134 using 5,6-bis(4-chlorophenyl)-2-fluoronicotinonitrile (0.040 g) synthesized in Reference Example 132.

Reference Example 136 Synthesis of (5,6-bis(4-chlorophenyl)-2-methylpyridin-3-yl)methanamine

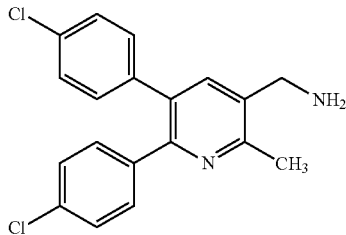 [SMILES: Cc1nc(-c2ccc(Cl)cc2)c(-c2ccc(Cl)cc2)cc1CN]

5,6-Bis(4-chlorophenyl)-2-methylnicotinonitrile (0.047 g) synthesized in Reference Example 133 was dissolved in tetrahydrofuran (1.0 mL). To the solution, a 1 mol/L solution of a borane-tetrahydrofuran complex in tetrahydrofuran (0.69 mL) was then added at 0° C., and the mixture was stirred at room temperature for 20 minutes. 2 mol/L hydrochloric acid was added to the reaction solution, and the mixture was further stirred at 70° C. for 2 hours. The reaction mixture was cooled to room temperature and then neutralized with a 1 mol/L aqueous sodium hydroxide solution, followed by extraction with chloroform. The organic layer was washed with saturated saline, dried over anhydrous sodium sulfate, and then concentrated under reduced pressure to obtain the title compound (0.047 g).

Reference Example 137 Synthesis of 2-benzenesulfonyl-3-((5,6-bis(4-chlorophenyl)-2-methoxypyridin-3-yl)methyl)-1-(tert-butoxycarbonyl)guanidine

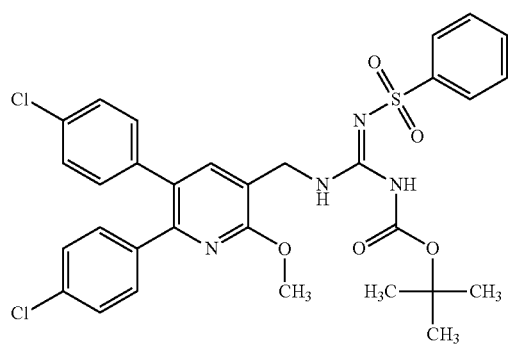 [SMILES: COc1nc(-c2ccc(Cl)cc2)c(-c2ccc(Cl)cc2)cc1CN/C(=N/S(=O)(=O)c1ccccc1)NC(=O)OC(C)(C)C]

The title compound (0.088 g) was obtained in the same way as in the guanidination reaction of Reference Example 52 using (5,6-bis(4-chlorophenyl)-2-methoxypyridin-3-yl)methanamine (0.078 g) synthesized in Reference Example 134 and N-(phenylsulfonyl)-N'-(tert-butoxycarbonyl)-S-methylisothiourea (0.079 g) synthesized in Reference Example 42.

$^1$H-NMR (CDCl$_3$) δ: 1.51 (9H, d, J=5.9 Hz), 4.04 (3H, s), 4.52 (2H, d, J=5.9 Hz), 6.93 (2H, dt, J=8.9, 2.3 Hz), 7.19-7.33 (8H, m), 7.39-7.43 (2H, m), 7.80-7.82 (2H, m), 9.08 (1H, t, J=5.6 Hz), 9.92 (1H, s).

MS (ESI) [M+H]$^+$: 641.

Reference Example 138 Synthesis of 2-benzenesulfonyl-3-((5,6-bis(4-chlorophenyl)-2-fluoropyridin-3-yl)methyl)-1-(tert-butoxycarbonyl)guanidine

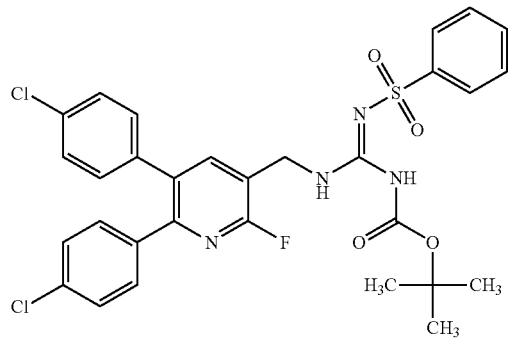 [SMILES: CC(C)(C)OC(=O)N/C(=N\S(=O)(=O)c1ccccc1)NCc1cc(-c2ccc(Cl)cc2)c(-c2ccc(Cl)cc2)nc1F]

The title compound (0.037 g) was obtained in the same way as in the guanidination reaction of Reference Example 52 using (5,6-bis(4-chlorophenyl)-2-fluoropyridin-3-yl)methanamine (0.040 g) synthesized in Reference Example 135 and N-(phenylsulfonyl)-N'-(tert-butoxycarbonyl)-S-methylisothiourea (0.079 g) synthesized in Reference Example 42.

$^1$H-NMR (CDCl$_3$) δ:1.51 (9H, s), 4.57 (2H, d, J=6.4 Hz), 6.93-6.95 (2H, m), 7.22-7.35 (8H, m), 7.42 (1H, m), 7.65 (1H, d, J=9.1 Hz), 7.78-7.80 (2H, m), 9.03 (1H, m), 9.95 (1H, s).

MS (ESI) [M+H]$^+$: 629.

Reference Example 139 Synthesis of 2-benzenesulfonyl-3-((5,6-bis(4-chlorophenyl)-2-methylpyridin-3-yl)methyl)-1-(tert-butoxycarbonyl)guanidine

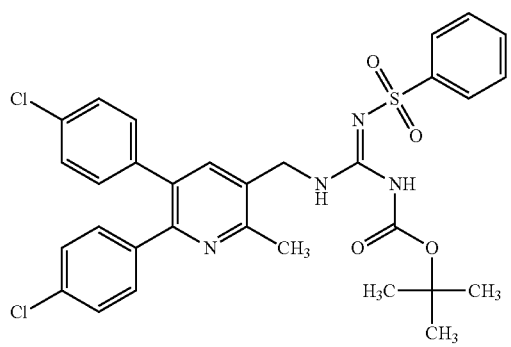 [SMILES: Cc1nc(-c2ccc(Cl)cc2)c(-c2ccc(Cl)cc2)cc1CN/C(=N/S(=O)(=O)c1ccccc1)NC(=O)OC(C)(C)C]

The title compound (0.050 g) was obtained in the same way as in the guanidination reaction of Reference Example 52 using (5,6-bis(4-chlorophenyl)-2-methylpyridin-3-yl)methanamine (0.047 g) synthesized in Reference Example 136 and N-(phenylsulfonyl)-N'-(tert-butoxycarbonyl)-S-methylisothiourea (0.079 g) synthesized in Reference Example 42.

$^1$H-NMR (CDCl$_3$) δ: 2.57 (3H, s), 4.47 (2H, d, J=5.9 Hz), 5.91 (2H, s), 6.96-6.98 (2H, m), 7.27-7.37 (10H, m), 7.82-7.84 (2H, m).

MS (ESI) [M+H]$^+$: 625.

Example 88 Synthesis of N-(amino(((5,6-bis(4-chlorophenyl)-2-methoxypyridin-3-yl)methyl)amino)methylene)benzenesulfonamide

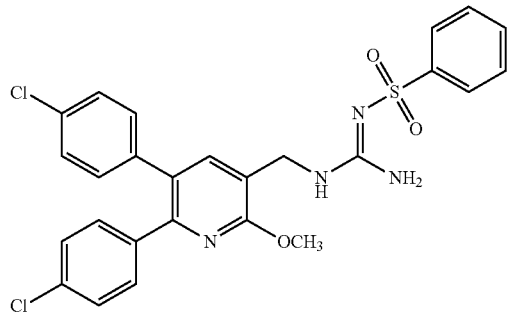

The title compound (hereinafter, referred to as the compound of Example 88) (0.057 g) was obtained in the same way as in Example 1 using 2-benzenesulfonyl-3-((5,6-bis(4-chlorophenyl)-2-methoxypyridin-3-yl)methyl)-1-(tert-butoxycarbonyl)guanidine (0.085 g) synthesized in Reference Example 137.

$^1$H-NMR (CDCl$_3$) δ: 4.01 (3H, s), 4.38 (2H, d, J=6.3 Hz), 6.42 (2H, brs), 6.92 (2H, d, J=8.5 Hz), 7.17-7.28 (9H, m), 7.38 (1H, t, J=7.4 Hz), 7.52 (1H, s), 7.76 (2H, dd, J=8.4, 1.3 Hz).22 MS (ESI) [M+H]$^+$: 541.

Example 89 Synthesis of N-(amino(((5,6-bis(4-chlorophenyl)-2-fluoropyridin-3-yl)methyl)amino)methylene)benzenesulfonamide

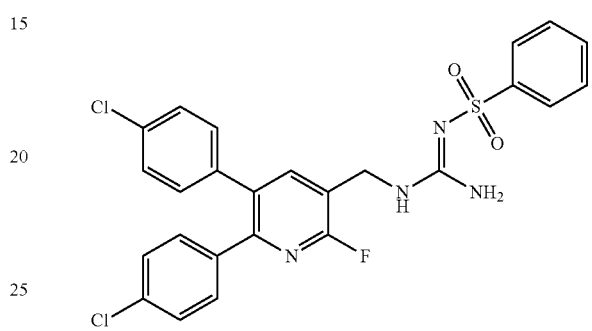

The title compound (hereinafter, referred to as the compound of Example 89) (0.024 g) was obtained in the same way as in Example 1 using 2-benzenesulfonyl-3-((5,6-bis(4-chlorophenyl)-2-fluoropyridin-3-yl)methyl)-1-(tert-butoxycarbonyl)guanidine (0.030 g) synthesized in Reference Example 138.

$^1$H-NMR (CDCl$_3$) δ: 4.47 (2H, d, J=5.9 Hz), 6.93-6.95 (2H, m), 7.24-7.27 (8H, m), 7.39 (1H, m), 7.67 (1H, d, J=9.1 Hz), 7.74-7.75 (2H, m).

MS (ESI) [M+H]$^+$: 529.

Example 90 Synthesis of N-(amino(((5,6-bis(4-chlorophenyl)-2-methylpyridin-3-yl)methyl)amino)methylene)benzenesulfonamide

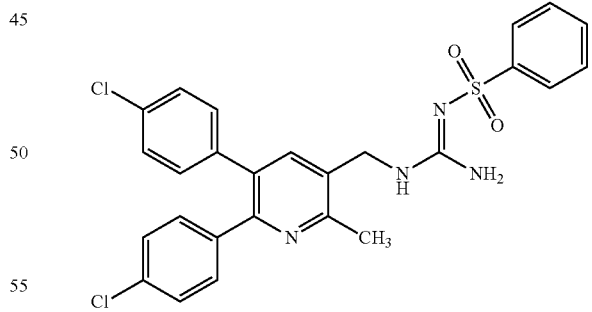

The title compound (hereinafter, referred to as the compound of Example 90) (0.019 g) was obtained in the same way as in Example 1 using 2-benzenesulfonyl-3-((5,6-bis(4-chlorophenyl)-2-methylpyridin-3-yl)methyl)-1-(tert-butoxycarbonyl)guanidine (0.048 g) synthesized in Reference Example 139.

$^1$H-NMR (CDCl$_3$) δ: 2.56 (3H, s), 4.48 (2H, d, J=5.4 Hz), 6.94-6.96 (2H, m), 7.26-7.38 (10H, m), 7.81 (2H, d, J=7.7 Hz).

MS (ESI) [M+H]$^+$: 541.

Example 91 Synthesis of N-(amino(((5,6-bis(4-chlorophenyl)-2-hydroxypyridin-3-yl)methyl)amino)methylene)benzenesulfonamide

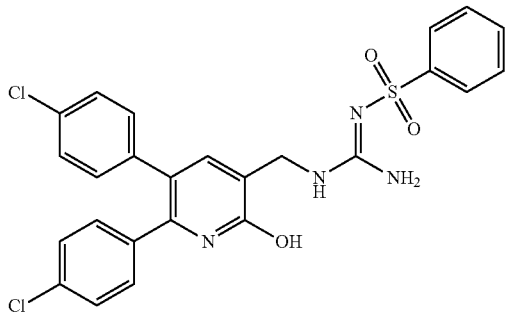

N-(Amino(((5,6-bis(4-chlorophenyl)-2-methoxypyridin-3-yl)methyl)amino)methylene)benzenesulfonamide (0.020 g) synthesized in Example 88 was dissolved in 1,4-dioxane (1 mL). To the solution, a 4 mol/L solution of hydrogen chloride in 1,4-dioxane (0.92 mL) was then added, and the mixture was heated to reflux for 10 hours. The reaction mixture was cooled to room temperature and then neutralized with a saturated aqueous solution of sodium bicarbonate, followed by extraction with ethyl acetate. The organic layer was washed with saturated saline, dried over anhydrous sodium sulfate, and then concentrated under reduced pressure. The obtained crude product was slurry-washed with ethyl acetate to obtain the title compound (hereinafter, referred to as the compound of Example 91) (0.013 g).

$^1$H-NMR (DMSO-$d_6$) δ: 4.16 (2H, d, J=5.9 Hz), 6.78 (1H, brs), 6.94 (2H, d, J=6.8 Hz), 7.21-7.47 (12H, m), 7.70 (2H, brs).

MS (ESI) [M+H]$^+$: 527.

Example 92 Synthesis of N-(amino(((6-phenyl-5-(4-(trifluoromethyl)phenyl)pyridin-3-yl)methyl)amino)methylene)benzenesulfonamide

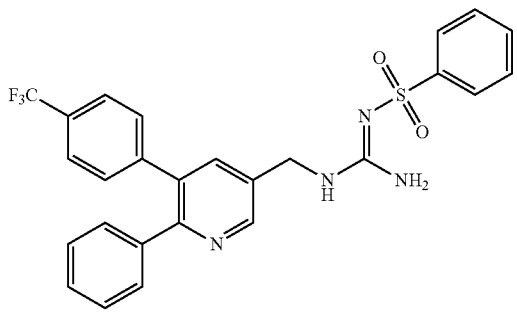 [SMILES: N/C(=N\S(=O)(=O)c1ccccc1)NCc1cnc(-c2ccccc2)c(-c2ccc(C(F)(F)F)cc2)c1]

N-(Amino(((6-(4-chlorophenyl)-5-(4-(trifluoromethyl)phenyl)pyridin-3-yl)methyl)amino)methylene)benzenesulfonamide (0.060 g) synthesized in Example 21 was dissolved in methanol (1 mL) and a 2 mol/L solution of hydrogen chloride in ethyl acetate (0.28 mL). To the solution, 10% by weight of palladium carbon (0.01 g) was then added, and the mixture was stirred overnight in a hydrogen atmosphere. The reaction mixture was filtered through celite, and the filtrate was washed with a saturated aqueous solution of sodium bicarbonate, dried over anhydrous sodium sulfate, and then concentrated under reduced pressure. The obtained crude product was purified by silica gel column chromatography (chloroform/methanol) to obtain the title compound (hereinafter, referred to as the compound of Example 92) (0.041 g).

$^1$H-NMR (CDCl$_3$) δ: 4.47 (2H, d, J=5.9 Hz), 6.33-6.36 (3H, brm), 7.16 (2H, d, J=7.7 Hz), 7.21-7.32 (7H, m), 7.40 (1H, m), 7.47-7.54 (3H, m), 7.76-7.77 (2H, m), 8.54 (1H, d, J=2.3 Hz).

MS (ESI) [M+H]$^+$: 511.

Example 93 Synthesis of N-(amino(((5-phenyl-6-(4-(trifluoromethyl)phenyl)pyridin-3-yl)methyl)amino)methylene)benzenesulfonamide

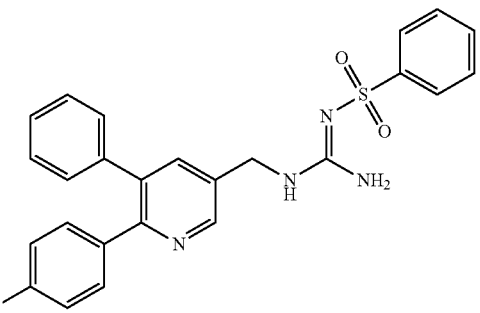

The title compound (hereinafter, referred to as the compound of Example 93) (0.10 g) was obtained in the same way as in Example 92 using N-(amino(((5-(4-chlorophenyl)-6-(4-(trifluoromethyl)phenyl)pyridin-3-yl)methyl)amino)methylene)benzenesulfonamide (0.14 g) synthesized in Example 11.

$^1$H-NMR (CDCl$_3$) δ: 4.53 (2H, d, J=6.0 Hz), 6.14 (3H, brs), 7.06 (2H, d, J=7.6 Hz), 7.25-7.49 (10H, m), 7.61 (1H, d, J=2.4 Hz), 7.82 (2H, d, J=7.6 Hz), 8.56 (1H, d, J=2.0 Hz).

MS (ESI) [M+H]$^+$: 511.

Example 94 Synthesis of N-(amino(((6-(4-chlorophenyl)-5-(4-hydroxyphenyl)pyridin-3-yl)methyl)amino)methylene)benzenesulfonamide Hydrochloride

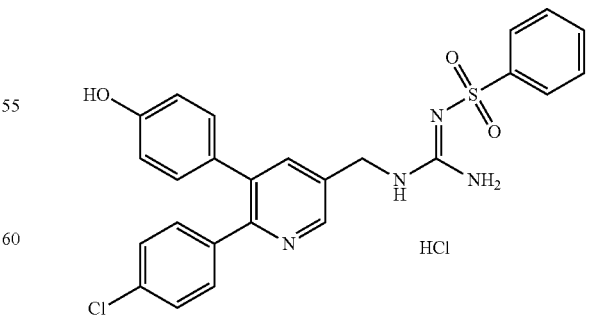

N-(Amino(((6-(4-chlorophenyl)-5-(4-methoxyphenyl)pyridin-3-yl)methyl)amino)methylene)benzenesulfonamide (0.019 g) synthesized in Example 18 was dissolved in dichloromethane (0.4 mL). To the solution, a 1 mol/L solution of boron tribromide in dichloromethane (0.1 mL) was then added at −78° C. The reaction mixture was warmed to 0° C. and stirred for 1 hour, and then, a saturated aqueous solution of sodium bicarbonate was added thereto, followed by extraction with ethyl acetate. The organic layer was washed with saturated saline, dried over anhydrous sodium sulfate, and then concentrated under reduced pressure. The obtained crude product was dissolved in ethyl acetate (0.4 mL). To the solution, a 4 mol/L solution of hydrogen chloride in ethyl acetate (0.02 mL) was then added. The mixture was stirred for 10 minutes, and then, the reaction mixture was concentrated under reduced pressure. The obtained crude product was recrystallized (ethyl acetate/n-hexane) to obtain the title compound (hereinafter, referred to as the compound of Example 94) (0.018 g).

$^1$H-NMR (DMSO-$d_6$) δ: 4.45 (2H, s), 6.72 (2H, d, J=7.3 Hz), 6.90 (2H, d, J=6.9 Hz), 7.32 (2H, d, J=5.0 Hz), 7.37-7.41 (4H, m), 7.48 (1H, m), 7.67 (2H, s), 7.75 (1H, s), 8.53 (1H, s).

MS (ESI) [M+H]$^+$: 493.

Example 95 Synthesis of N-(amino(((5-(4-chlorophenyl)-6-(4-hydroxyphenyl)pyridin-3-yl)methyl)amino)methylene)benzenesulfonamide Hydrochloride

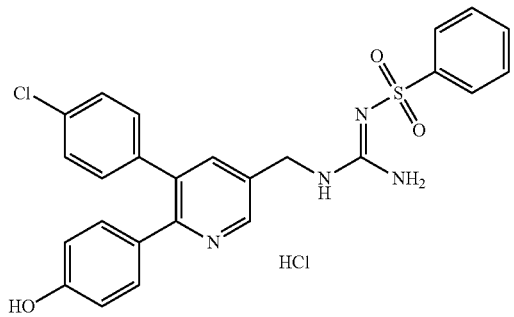

The title compound (hereinafter, referred to as the compound of Example 95) (0.012 g) was obtained in the same way as in Example 94 using N-(amino(((5-(4-chlorophenyl)-6-(4-methoxyphenyl)pyridin-3-yl)methyl)amino)methylene)benzenesulfonamide (0.020 g) synthesized in Example 6.

$^1$H-NMR (DMSO-$d_6$) δ: 4.47 (2H, d, J=5.5 Hz), 6.74 (2H, d, J=8.2 Hz), 6.98 (2H, brs), 7.14 (4H, d, J=8.2 Hz), 7.38 (2H, t, J=7.5 Hz), 7.46 (3H, dd, J=12.8, 7.8 Hz), 7.56 (1H, s), 7.67 (2H, d, J=5.9 Hz), 7.94 (1H, brs), 8.60 (1H, s), 9.94 (1H, brs).21

MS (ESI) [M+H]$^+$: 493.

Example 96 Synthesis of N-(amino(((5,6-bis(4-chlorophenyl)pyridin-3-yl)methyl)amino)methylene)-3-hydroxybenzenesulfonamide Hydrochloride

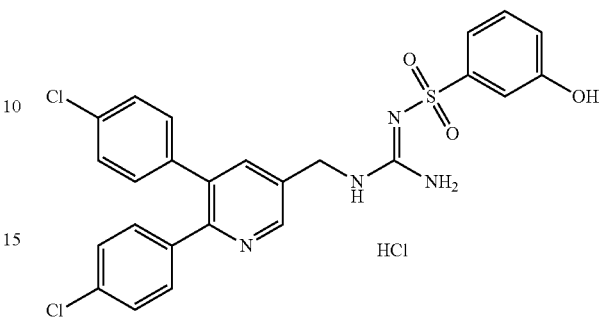

The title compound (hereinafter, referred to as the compound of Example 96) (0.059 g) was obtained in the same way as in Example 94 using N-(amino(((5,6-bis(4-chlorophenyl)pyridin-3-yl)methyl)amino)methylene)-3-methoxybenzenesulfonamide (0.073 g) synthesized in Example 69.

$^1$H-NMR (DMSO-$d_6$) δ:4.44 (2H, d, J=5.9 Hz), 6.83-6.86 (3H, m), 7.08-7.17 (6H, m), 7.28 (2H, t, J=4.3 Hz), 7.39 (4H, dd, J=10.6, 8.4 Hz), 7.71 (1H, s), 8.57 (1H, s).

MS (ESI) [M+H]: 527.

Example 97 Synthesis of N-(amino(((6-(4-chloro-2-hydroxyphenyl)-5-(4-chlorophenyl)pyridin-3-yl)methyl)amino)methylene)benzenesulfonamide

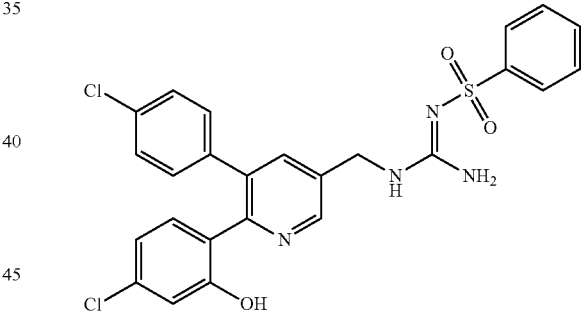

N-(Amino(((6-(4-chloro-2-methoxyphenyl)-5-(4-chlorophenyl)pyridin-3-yl)methyl)amino)methylene)benzenesulfonamide (0.080 g) synthesized in Reference Example 87 was dissolved in dichloromethane (1.5 mL). To the solution, a 1 mol/L solution of boron tribromide in dichloromethane (0.89 mL) was then added at −78° C. The reaction mixture was warmed to 30° C. and stirred for 5 hours. The reaction mixture was cooled to room temperature, and then, a saturated aqueous solution of sodium bicarbonate was added thereto, followed by extraction with ethyl acetate. The organic layer was dried over anhydrous sodium sulfate and then concentrated under reduced pressure. The obtained crude product was purified by column chromatography (chloroform/methanol) and recrystallization (ethyl acetate) to obtain the title compound (hereinafter, referred to as the compound of Example 97) (0.054 g).

$^1$H-NMR (DMSO-$d_6$) δ: 4.43 (2H, d, J=5.5 Hz), 6.73 (1H, s), 6.84 (2H, d, J=8.2 Hz), 7.05-7.15 (4H, m), 7.34-7.48 (6H, m), 7.59 (1H, s), 7.68 (2H, s), 8.48 (1H, s), 10.01 (1H, brs).

MS (ESI) [M+H]$^+$: 527.

Example 98 Evaluation of Inhibition of Protease Activity of MALT1

The guanidine derivative (I) or the pharmacologically acceptable salt thereof was evaluated for its inhibition of the protease activity of MALT1 in an in vitro experimental system in accordance with the method described in the literature (Cancer Cell, 2012, Vol. 22, p. 825-837). Specifically, the evaluation was conducted by measuring the degree of reduction in fluorescence value by the compound relative to elevation in fluorescence value resulting from the cleavage of a fluorescently labeled artificial peptide substrate by recombinant MALT1.

A) Preparation of Recombinant GST Fusion MALT1:

Full-length cDNA of human MALT1 gene (GenBank accession No: AB026118.1) amplified by PCR was inserted in flame to a SalI site located downstream of GST gene in a pGEX6P3 vector (GE Healthcare Japan Corp.) to prepare a vector (hereinafter, referred to as a pGEX6P3-MALT1 vector). Subsequently, E. coli for protein expression (BL21-RIL-codon plus-DE3, Agilent Technologies, Inc.) was transformed with the pGEX6P3-MALT1 vector and then analyzed by ampicillin resistance screening and colony PCR to obtain an E. coli strain expressing recombinant GST fusion MALT1. Protein expression was induced with isopropyl-(3-thiogalactopyranoside. After the expression induction, E. coli precipitates were recovered by centrifugation from the E. coli culture solution, and the E. coli precipitates were homogenized and then centrifuged to obtain a supernatant. The supernatant was purified using GSTrap FF column (GE Healthcare Japan Corp.) to obtain recombinant GST fusion MALT1.

B) Evaluation of Inhibition of Protease Activity of MALT1:

To 89 μL of an enzyme solution (4.8 g/mL GST fusion MALT1, 50 mmol/L MES, 150 mmol/L NaCl, 10% sucrose, 0.1% CHAPS, 10 mmol/L dithiothreitol, and 1 mol/L triammonium citrate) per specimen, 1 μL of a test compound (DMSO-diluted solution) of each concentration was added to prepare a mixed solution. The mixed solution was incubated at room temperature for 30 minutes, followed by the measurement of the fluorescence value of the mixed solution (fluorescence value of the first measurement) (Ex: 380 nm, Em: 460 nm; Envision (Perkin Elmer Inc.)). Next, 10 μL of 200 μmol/L substrate (Ac-LRSR-AMC, SM Biochemicals LLC) was added (final concentration: 20 μmol/L) to the mixed solution, and the mixture was reacted by incubation at 30° C. for 80 minutes, followed by the measurement of the fluorescence value of the reaction solution (fluorescence value of the second measurement) (Ex: 380 nm, Em: 460 nm; Envision (Perkin Elmer Inc.)). A "well nonsupplemented with the test compound (only DMSO was added), nonsupplemented with the enzyme and supplemented with the substrate", and a "well nonsupplemented with the test compound (only DMSO was added), supplemented with the enzyme and supplemented with the substrate" were established.

The fluorescence value of the first measurement was defined as "F1", and the fluorescence value of the second measurement was defined as "F2". F2−F1 of the "well nonsupplemented with the test compound (only DMSO was added), nonsupplemented with the enzyme and supplemented with the substrate" was defined as "Fback", F2−F1 of the "well nonsupplemented with the test compound (only DMSO was added), supplemented with the enzyme and supplemented with the substrate" was defined as "Fpositive", and F2−F1 of the "well supplemented with the test compound, supplemented with the enzyme and supplemented with the substrate" was defined as "Fsample". The rate of inhibition (%) of the protease activity of MALT1 by the test compound was calculated according to the following expression.

Rate of inhibition (%)=100×(1−($F$sample−$F$back)/($F$positive−$F$back))

The $IC_{50}$ value of each test compound is shown in Tables 2-1 to 2-3. As is evident from the results of Tables 2-1 to 2-3, the guanidine derivative (I) or the pharmacologically acceptable salt thereof was found to have the effect of inhibiting the protease activity of MALT1.

TABLE 2-1

| Test compound | $IC_{50}$ (nmol/L) |
|---|---|
| Compound of Example 2 | 270 |
| Compound of Example 3 | 705 |
| Compound of Example 4 | 1400 |
| Compound of Example 5 | 66 |
| Compound of Example 6 | 505 |
| Compound of Example 7 | 192 |
| Compound of Example 8 | 1287 |
| Compound of Example 9 | 1708 |
| Compound of Example 10 | 297 |
| Compound of Example 11 | 348 |
| Compound of Example 12 | 338 |
| Compound of Example 13 | 237 |
| Compound of Example 14 | 692 |
| Compound of Example 15 | 308 |
| Compound of Example 16 | 2406 |
| Compound of Example 17 | 606 |
| Compound of Example 18 | 24 |
| Compound of Example 19 | 1515 |
| Compound of Example 20 | 1114 |
| Compound of Example 21 | 1035 |
| Compound of Example 22 | 745 |
| Compound of Example 23 | 1725 |
| Compound of Example 24 | 140 |
| Compound of Example 25 | 1840 |
| Compound of Example 26 | 315 |
| Compound of Example 27 | 532 |
| Compound of Example 28 | 356 |
| Compound of Example 29 | 100 |
| Compound of Example 30 | 115 |
| Compound of Example 31 | 102 |
| Compound of Example 32 | 156 |
| Compound of Example 33 | 2066 |
| Compound of Example 34 | 817 |
| Compound of Example 35 | 314 |
| Compound of Example 36 | 237 |
| Compound of Example 37 | 1274 |
| Compound of Example 38 | 90 |
| Compound of Example 39 | 106 |
| Compound of Example 40 | 37 |
| Compound of Example 41 | 679 |
| Compound of Example 42 | 192 |
| Compound of Example 43 | 23 |
| Compound of Example 44 | 175 |
| Compound of Example 45 | 221 |

TABLE 2-2

| Test compound | $IC_{50}$ (nmol/L) |
|---|---|
| Compound of Example 46 | 539 |
| Compound of Example 47 | 320 |
| Compound of Example 48 | 333 |
| Compound of Example 49 | 326 |
| Compound of Example 50 | 114 |
| Compound of Example 51 | 185 |
| Compound of Example 52 | 390 |
| Compound of Example 53 | 2007 |
| Compound of Example 54 | 169 |

TABLE 2-2-continued

| Test compound | IC$_{50}$ (nmol/L) |
|---|---|
| Compound of Example 55 | 183 |
| Compound of Example 56 | 429 |
| Compound of Example 57 | 517 |
| Compound of Example 58 | 743 |
| Compound of Example 59 | 746 |
| Compound of Example 60 | 1325 |
| Compound of Example 61 | 408 |
| Compound of Example 62 | 471 |
| Compound of Example 63 | 640 |
| Compound of Example 64 | 572 |
| Compound of Example 65 | 462 |
| Compound of Example 66 | 1134 |
| Compound of Example 67 | 644 |
| Compound of Example 68 | 570 |
| Compound of Example 69 | 778 |
| Compound of Example 70 | 341 |
| Compound of Example 71 | 565 |
| Compound of Example 73 | 300 |
| Compound of Example 74 | 296 |
| Compound of Example 75 | 353 |
| Compound of Example 76 | 1507 |
| Compound of Example 77 | 817 |
| Compound of Example 78 | 754 |
| Compound of Example 79 | 1879 |
| Compound of Example 81 | 534 |
| Compound of Example 82 | 744 |
| Compound of Example 83 | 942 |
| Compound of Example 84 | 1376 |
| Compound of Example 85 | 373 |
| Compound of Example 86 | 880 |
| Compound of Example 87 | 72 |
| Compound of Example 88 | 104 |
| Compound of Example 89 | 368 |
| Compound of Example 90 | 234 |

TABLE 2-3

| Test compound | IC$_{50}$ (nmol/L) |
|---|---|
| Compound of Example 91 | 112 |
| Compound of Example 92 | 1036 |
| Compound of Example 93 | 1068 |
| Compound of Example 94 | 1614 |
| Compound of Example 95 | 1027 |
| Compound of Example 96 | 2135 |
| Compound of Example 97 | 922 |

Example 99 Suppressive Effect on Auricular Hypertrophy in Imiquimod-Induced Psoriasis Mouse Model The guanidine derivative (I) or the pharmacologically acceptable salt thereof was evaluated for its exertion of a therapeutic effect on psoriasis, one type of autoimmune disease, in an in vivo experimental system using imiquimod-induced psoriasis mouse models in accordance with the method described in the literature (The Journal of Dermatological Science, 2014, Vol. 76, No. 2, p. 96-103). Specifically, the evaluation was conducted by verifying the suppressive effect of the compound on auricular hypertrophy by using, as an index, the thickness of the auricle increased with the progression of symptoms in imiquimod-induced psoriasis models.

Seven-week-old BALB/c male mice (Charles River Laboratories Japan, Inc.) were preliminarily bred and then used at the age of 8 weeks. To induce psoriasis-like symptoms, 5 mg/ear of Beselna Cream 5% was applied (imiquimod dose: 0.25 mg/body/day) to both the ears of each mouse once a day for 8 days from the date of initial administration of imiquimod (hereinafter, referred to as post-induction day 0) to post-induction day 7. A dosing vehicle was prepared by adding Tween 20 to a 0.5% (w/v) aqueous methylcellulose solution to attain a final concentration of 0.025% (v/v). A test compound was suspended in the dosing vehicle to prepare a drug solution. The drug solution was orally administered (dosing volume: 10 mL/kg) twice a day (a.m. and p.m.) for 4 days from post-induction days 4 to 7. The test compound used was the compound of Example 2, and groups given the compound of Example 2 were designated as Example 2 compound administration groups. A group given only the dosing vehicle in the same way as above was established as a vehicle administration group.

The thickness of the auricle before imiquimod administration (before induction) at the date of induction and the thickness of the auricle at post-induction day 8 were measured using a digital micrometer (Mitsutoyo Corp.), and the change therebetween (the thickness of the auricle at post-induction day 8—the thickness of the auricle before induction) was used as an index for drug efficacy evaluation. Statistical analysis was carried out using statistical analysis software EXSAS (ver. 7.6). As a result of studying homoscedasticity among the groups by the Bartlett's test, the variance was homogeneous. Therefore, the parametric Dunnett test (two-tailed) was carried out. As for the drug dependence of the drug efficacy of the compound of Example 2 on auricular hypertrophy, as a result of studying homoscedasticity between the vehicle group and each compound administration group by the Bartlett's test, the variance was homogeneous. Therefore, the Williams test (two-tailed) was carried out. P<0.05 was confirmed as significant difference.

The results of evaluating the compound of Example 2 are shown in FIG. 1. The ordinate of the drawing depicts the change in the thickness of the auricle (μm), and the abscissa depicts each administration group. The term "Compound of Example 2" depicts the Example 2 compound administration groups. In the drawing, the symbol "*" shows that there was statistically significant (P<0.05) difference compared to the vehicle administration group.

The thickness of the auricle in the vehicle administration group was increased by 198 μm. By contrast, the changes in the thickness of the auricle in the groups orally given the compound of Example 2 at 7.5 mg/kg (twice a day), 15 mg/kg (twice a day), or 30 mg/kg (twice a day) were only 179 μm, 131 μm, and 118 μm increases, respectively. The changes in the thickness of the the auricle in the 15 mg/kg (twice a day) and 30 mg/kg (twice a day) administration groups were significantly decreased compared to the vehicle administration group.

The results demonstrated that the guanidine derivative (I) or the pharmacologically acceptable salt thereof exerts a therapeutic effect on psoriasis.

Example 100 Suppressive Effect on Auricular Hypertrophy in Oxazolone-Induced Atopic Dermatitis Mouse Model The guanidine derivative (I) or the pharmacologically acceptable salt thereof was evaluated for its exertion of a therapeutic effect on atopic dermatitis, one type of allergic disease, in an in vivo experimental system using oxazolone-induced atopic dermatitis mouse models in accordance with the method described in the literature (Plos One, Vol. 8, No. 7, e6614). Specifically, the evaluation was conducted by verifying the suppressive effect of the compound on auricular hypertrophy by using, as an index, the thickness of the auricle increased with the progression of symptoms in oxazolone-induced atopic dermatitis models.

Seven-week-old BALB/c male mice (Charles River Laboratories Japan, Inc.) were preliminarily bred and then used at the age of 8 weeks. To induce atopic dermatitis-like symptoms, 20 μL of a solution of oxazolone added at 0.5 w/v % to an acetone/olive oil 1:1 mixed solution was applied to the right ear of each mouse at a single dose at the date of initial administration (post-induction day 0; hereinafter, referred to as the date of induction) and three times a week from post-induction days 7 to 27. A dosing vehicle was prepared by adding Tween 20 to a 0.5% (w/v) aqueous methylcellulose solution to attain a final concentration of 0.025% (v/v). A test compound was suspended in the dosing vehicle to prepare a drug solution. The drug solution was orally administered (dosing volume: 10 mL/kg) twice a day (a.m. and p.m.) for 7 days from post-induction days 21 to 27. The test compound used was the compound of Example 2, and a group given the compound of Example 2 was designated as an Example 2 compound administration group. A group given the dosing vehicle in the same way as above was established as a vehicle administration group.

The thickness of the auricle before oxazolone administration (before induction) at the date of induction and the thickness of the auricle at post-induction day 28 were measured using a digital micrometer (Mitsutoyo Corp.), and the change therebetween (the thickness of the auricle at post-induction day 28—the thickness of the auricle before induction) was used as an index for drug efficacy evaluation. Statistical analysis was carried out by the t test using statistical analysis software EXSAS (ver. 7.6).

Figure 2:
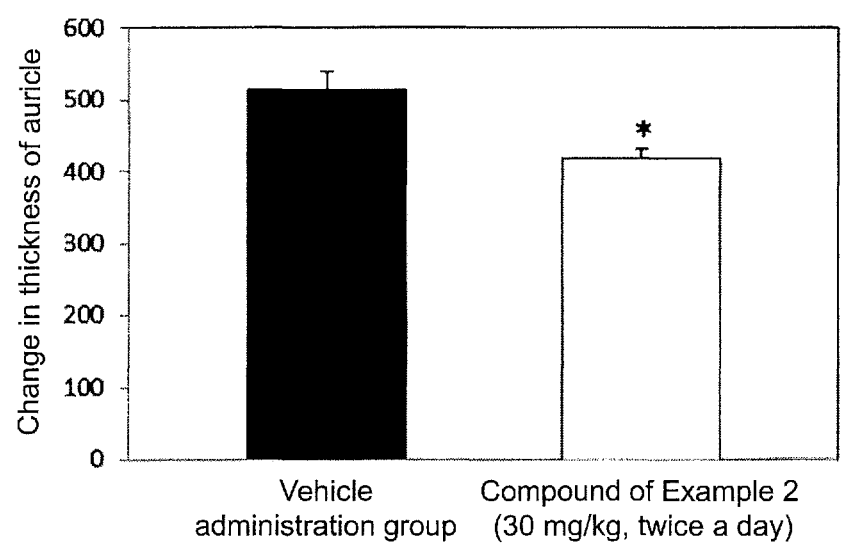
FIG. 2 is a diagram showing the effect of the compound of Example 2 on the thickness of the auricle in oxazolone-induced atopic dermatitis mouse models.

The results of evaluating the compound of Example 2 are shown in FIG. 2. The ordinate of the drawing depicts the change in the thickness of the auricle (μm), and the abscissa depicts each administration group. The term "Compound of Example 2" depicts the Example 2 compound administration group. In the drawing, the symbol "*" shows that there was statistically significant (P<0.05) difference compared to the vehicle administration group.

The thickness of the auricle in the vehicle administration group was increased by 515 μm. By contrast, the change in the thickness of the auricle in the group orally given the compound of Example 2 at 30 mg/kg (twice a day) was only 419 μm increase. The change in the thickness of the the auricle in the Example 2 compound administration group was statistically significantly decreased compared to the vehicle administration group.

The results demonstrated that the guanidine derivative (I) or the pharmacologically acceptable salt thereof exerts a therapeutic effect on atopic dermatitis.

INDUSTRIAL APPLICABILITY

The guanidine derivative (I) or the pharmacologically acceptable salt thereof has an effect of strongly inhibiting the protease activity of MALT1 and as such, can be used as a therapeutic or prophylactic agent for autoimmune disease such as psoriasis or allergic disease such as atopic dermatitis.

The invention claimed is:
1. A guanidine derivative represented by general formula (I) or a pharmacologically acceptable salt thereof:

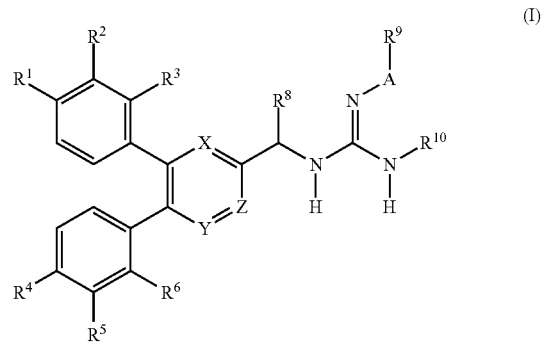

wherein
$R^1$ to $R^6$ each independently represent a hydrogen atom, a halogen atom, an alkyl group having 1 to 3 carbon atoms, an alkoxy group having 1 to 3 carbon atoms, a cyano group, a methoxycarbonyl group or a hydroxy group, wherein
in each of the alkyl group having 1 to 3 carbon atoms and the alkoxy group having 1 to 3 carbon atoms, 1 to 5 hydrogen atoms are optionally replaced, each independently, with a halogen atom;
X and Y each independently represent N or CH, and Z represents N or $CR^7$, with the proviso that X, Y and Z neither represent N at the same time nor represent the group other than N at the same time;
$R^7$ represents a hydrogen atom, a halogen atom, an alkyl group having 1 to 3 carbon atoms, an alkoxy group having 1 to 3 carbon atoms or a hydroxy group;
$R^8$ represents a hydrogen atom or an alkyl group having 1 to 3 carbon atoms;
A represents $S(=O)_2$, $C(=O)$ or $CH_2$;
$R^9$ represents an alkoxy group having 1 to 3 carbon atoms; an amino group; a dimethylamino group; an alkyl group having 1 to 6 carbon atoms in which 1 to 3 hydrogen atoms are optionally replaced, each independently, with a halogen atom, a methoxy group or a phenyl group; a cycloalkyl group having 3 to 6 carbon atoms in which 1 to 3 hydrogen atoms are optionally replaced, each independently, with a halogen atom; an aryl group in which 1 or 2 hydrogen atoms are optionally replaced, each independently, with a halogen atom, a trifluoromethyl group, an alkoxy group having 1 to 3 carbon atoms, a hydroxy group or a cyano group; or a heteroaryl group in which one hydrogen atom is optionally replaced with a halogen atom, a methyl group or a cyano group; and
$R^{10}$ represents a hydrogen atom, an alkyl group having 1 to 3 carbon atoms, a hydroxy group or an amino group.
2. The guanidine derivative or the pharmacologically acceptable salt thereof according to claim 1, wherein
$R^1$ and $R^4$ are each independently a hydrogen atom, a fluorine atom, a chlorine atom, a methyl group, a trifluoromethyl group, a methoxy group, an isopropoxy group, a trifluoromethoxy group or a cyano group;
$R^2$, $R^3$, $R^5$ and $R^6$ are each independently a hydrogen atom, a fluorine atom or a chlorine atom;
a combination of X to Z is X=CH, Y=N, and Z=$CR^7$, X=CH, Y=CH, and Z=N, X=N, Y=CH, and Z=CH, or X=N, Y=CH, and Z=N;
$R^7$ is a hydrogen atom, a fluorine atom, a methyl group, a methoxy group or a hydroxy group;
$R^8$ is a hydrogen atom or a methyl group;

A is $S(=O)_2$;

$R^9$ is a dimethylamino group; a benzyl group; a cycloalkyl group having 3 to 6 carbon atoms; a phenyl group in which one hydrogen atom is optionally replaced with a halogen atom, an alkoxy group having 1 to 3 carbon atoms, a hydroxy group or a cyano group; or a heteroaryl group in which one hydrogen atom is optionally replaced with a halogen atom, a methyl group or a cyano group; and $R^{10}$ is a hydrogen atom, a methyl group, a hydroxy group or an amino group.

3. The guanidine derivative or the pharmacologically acceptable salt thereof according to claim 1, wherein $R^1$ and $R^4$ are each independently a hydrogen atom, a fluorine atom, a chlorine atom, a methyl group, a trifluoromethyl group, a methoxy group, a trifluoromethoxy group or a cyano group;

each of $R^2$, $R^3$, $R^5$ and $R^6$ is a hydrogen atom;

a combination of X to Z is X=CH, Y=N, and Z=CR$^7$, X=CH, Y=CH, and Z=N, X=N, =CH, and Z=CH, or X=N, Y=CH, and Z=N;

$R^7$ is a hydrogen atom, a fluorine atom, a methyl group, a methoxy group or a hydroxy group;

$R^8$ is a hydrogen atom;

A is $S(=O)_2$;

$R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group; and $R^{10}$ is a hydrogen atom, a methyl group, a hydroxy group or an amino group.

4. The guanidine derivative or the pharmacologically acceptable salt thereof according to claim 1, wherein each of $R^1$ and $R^4$ is a chlorine atom;

each of $R^2$, $R^3$, $R^5$ and $R^6$ is a hydrogen atom;

a combination of X to Z is X=CH, Y=N, and Z=CR$^7$, X=CH, Y=CH, and Z=N, X=N, Y=CH, and Z=CH, or X=N, Y=CH, and Z=N;

$R^7$ is a hydrogen atom, a fluorine atom, a methyl group, a methoxy group or a hydroxy group;

$R^8$ is a hydrogen atom;

A is $S(=O)_2$;

$R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, an alkoxy group having 1 to 3 carbon atoms, a hydroxy group or a cyano group; and $R^{10}$ is a hydrogen atom, a methyl group, a hydroxy group or an amino group.

5. The guanidine derivative or the pharmacologically acceptable salt thereof according to claim 1, wherein $R^1$ and $R^4$ are each independently a hydrogen atom, a fluorine atom, a chlorine atom, a methyl group, a trifluoromethyl group, a methoxy group, a trifluoromethoxy group or a cyano group;

each of $R^2$, $R^3$, $R^5$ and $R^6$ is a hydrogen atom;

X is CH;

Y is N;

Z is CR$^7$;

$R^7$ is a hydrogen atom or a fluorine atom;

$R^8$ is a hydrogen atom;

A is $S(=O)_2$;

$R^9$ is a dimethylamino group; a cycloalkyl group having 3 to 6 carbon atoms; a 2-thienyl group; a 5-chloro-2-thienyl group; a 3-thienyl group; a 2-furyl group; a 3-furyl group; a 2-benzothienyl group; or a phenyl group in which one hydrogen atom is optionally replaced with a halogen atom, a methoxy group, an ethoxy group, a hydroxy group or a cyano group; and $R^{10}$ is a hydrogen atom.

6. The guanidine derivative or the pharmacologically acceptable salt thereof according to claim 1, wherein $R^1$ and $R^4$ are each independently a hydrogen atom, a fluorine atom, a chlorine atom, a methyl group, a trifluoromethyl group, a methoxy group, a trifluoromethoxy group or a cyano group;

each of $R^2$, $R^3$, $R^5$ and $R^6$ is a hydrogen atom;

a combination of X to Z is X=CH, Y=N, and Z=CR$^7$, or X=CH, Y=CH, and Z=N;

$R^7$ is a hydrogen atom;

$R^8$ is a hydrogen atom;

A is $C(=O)$;

$R^9$ is an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group; and $R^{10}$ is a hydrogen atom.

7. The guanidine derivative or the pharmacologically acceptable salt thereof according to claim 1, wherein each of $R^1$ and $R^4$ is a chlorine atom;

each of $R^2$, $R^3$, $R^5$ and $R^6$ is a hydrogen atom;

a combination of X to Z is X=CH, Y=N, and Z=CR$^7$, or X=CH, Y=CH, and Z=N;

$R^7$ is a hydrogen atom;

$R^8$ is a hydrogen atom;

A is $C(=O)$;

$R^9$ is an ethoxy group; an amino group; a dimethylamino group; a 2-thiazolyl group; a 4-thiazolyl group; a 2-thienyl group; a 3-thienyl group; a 2-pyridyl group; a 2-furyl group; an alkyl group having 2 to 5 carbon atoms in which 1 to 3 hydrogen atoms are optionally replaced, each independently, with a fluorine atom, a methoxy group or a phenyl group; a cycloalkyl group having 3 to 6 carbon atoms in which 1 or 2 hydrogen atoms are optionally replaced with fluorine atom(s); or a phenyl group in which one hydrogen atom is optionally replaced with a fluorine atom, a chlorine atom, a trifluoromethyl group, a methoxy group or a cyano group; and $R^{10}$ is a hydrogen atom.

8. A medicament comprising the guanidine derivative or the pharmacologically acceptable salt thereof according to claim 1 as an active ingredient.

9. A mucosa-associated lymphoid tissue lymphoma translocation protein 1 inhibitor comprising the guanidine derivative or the pharmacologically acceptable salt thereof according to claim 1 as an active ingredient.

10. A therapeutic or prophylactic agent for autoimmune disease comprising the guanidine derivative or the pharmacologically acceptable salt thereof according to claim 1 as an active ingredient.

11. A therapeutic or prophylactic agent for psoriasis comprising the guanidine derivative or the pharmacologically acceptable salt thereof according to claim 1 as an active ingredient.

12. A therapeutic or prophylactic agent for allergic disease comprising the guanidine derivative or the pharmacologically acceptable salt thereof according to claim 1 as an active ingredient.

13. A therapeutic or prophylactic agent for atopic dermatitis comprising the guanidine derivative or the pharmacologically acceptable salt thereof according to claim 1 as an active ingredient.

* * * * *